US012509452B2

(12) United States Patent
Lian et al.

(10) Patent No.: US 12,509,452 B2
(45) Date of Patent: Dec. 30, 2025

(54) SUBSTITUTED-ISOXAZOLINE-CONTAINING AROMATIC COMPOUND, PREPARATION METHOD THEREFOR, HERBICIDAL COMPOSITION AND USE THEREOF

(71) Applicant: QINGDAO KINGAGROOT CHEMICAL COMPOUND CO., LTD., Shandong (CN)

(72) Inventors: Lei Lian, Shandong (CN); Xuegang Peng, Shandong (CN); Rongbao Hua, Shandong (CN); De Zhao, Shandong (CN); Qi Cui, Shandong (CN)

(73) Assignee: QINGDAO KINGAGROOT CHEMICAL COMPOUND CO., LTD., Shandong (CN)

( * ) Notice: Subject to any disclaimer, the term of this patent is extended or adjusted under 35 U.S.C. 154(b) by 871 days.

(21) Appl. No.: 17/774,814

(22) PCT Filed: Nov. 4, 2020

(86) PCT No.: PCT/CN2020/126434
§ 371 (c)(1),
(2) Date: May 5, 2022

(87) PCT Pub. No.: WO2021/088856
PCT Pub. Date: May 14, 2021

(65) Prior Publication Data

US 2023/0053699 A1 Feb. 23, 2023

(30) Foreign Application Priority Data

Nov. 7, 2019 (CN) ......................... 201911082204.3
Feb. 28, 2020 (CN) ......................... 202010131605.X

(51) Int. Cl.
*C07D 413/10* (2006.01)
*A01N 43/74* (2006.01)

(52) U.S. Cl.
CPC ........... *C07D 413/10* (2013.01); *A01N 43/74* (2013.01)

(58) Field of Classification Search
CPC ..................................................... C07D 413/10
USPC ........................................................... 548/240
See application file for complete search history.

(56) References Cited

U.S. PATENT DOCUMENTS 5,013,659 A 5/1991 Bedbrook et al.
5,612,481 A 3/1997 Crews, Jr. et al.
6,380,134 B1 4/2002 Kunz et al.
6,602,825 B1 8/2003 Menke et al.
2003/0130122 A1 7/2003 Gupta et al.
2004/0019209 A1 1/2004 Kelly et al.
2004/0110749 A1 6/2004 Nakatani et al.
2011/0166143 A1 7/2011 Bretschneider et al.
(Continued)

FOREIGN PATENT DOCUMENTS

CN 1061966 A 6/1992
CN 1341105 A 3/2002
(Continued)

OTHER PUBLICATIONS

Braun et al., The general mitochondrial processing peptidase from potato is an integral part of cytochrome c reductase of the respiratory chain, *The EMBO Journal* (1992)11:3219-3227.
(Continued)

*Primary Examiner* — Taofiq A Solola
(74) *Attorney, Agent, or Firm* — Leydig, Voit & Mayer, Ltd.

(57) ABSTRACT

The invention belongs to the technical field of pesticides, and specifically relates to a type of substituted-isoxazoline-containing aromatic compound, preparation method therefor, herbicidal composition and use thereof. The compound is as shown in general formula I:

I

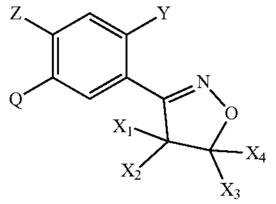

Wherein, Q represents

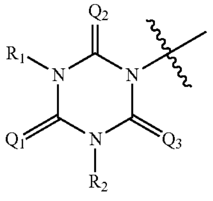

or

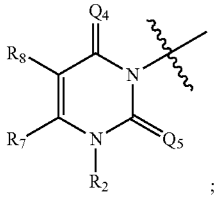

;

Y represents halogen, halogenated alkyl or cyano; Z represents halogen; $X_1$, $X_2$ each independently represent hydrogen, halogen, alkyl, etc.; $X_3$ represents halogen, cyano, etc.; $X_4$ each independently represents —$COOR_5$ or -alkyl-$COOR_5$; $R_5$ each independently represents hydrogen, alkyl, etc. The compound has excellent herbicidal activity against gramineous weeds, broadleaf weeds, and so on even at low application rates, and has high selectivity for crops.

19 Claims, No Drawings

(56) References Cited

U.S. PATENT DOCUMENTS

| | | | |
|---|---|---|---|
| 2015/0218140 A1 | 8/2015 | Dochnahl et al. |
| 2018/0230139 A1 | 8/2018 | Liu et al. |
| 2022/0227744 A1 | 7/2022 | Whittingham |

FOREIGN PATENT DOCUMENTS

| | | | | |
|---|---|---|---|---|
| CN | 1474694 | A | | 2/2004 |
| CN | 1599727 | A | | 3/2005 |
| CN | 1729177 | A | | 2/2006 |
| CN | 102875569 | A | | 1/2013 |
| CN | 105753853 | A | | 7/2016 |
| CN | 108570041 | A | | 9/2018 |
| CN | 105777733 | B | | 12/2018 |
| CN | 109293640 | A | | 2/2019 |
| CN | 109864067 | A | | 6/2019 |
| CN | 110150302 | A | | 8/2019 |
| CN | 111961041 | A | | 11/2020 |
| EP | 0 013 111 | A2 | | 7/1980 |
| EP | 0 131 624 | A1 | | 1/1985 |
| EP | 0 142 924 | A2 | | 5/1985 |
| EP | 0 193 259 | A1 | | 9/1986 |
| EP | 0 221 044 | A1 | | 5/1987 |
| EP | 0 242 236 | A1 | | 10/1987 |
| EP | 0 242 246 | A1 | | 10/1987 |
| EP | 0 257 993 | A2 | | 3/1988 |
| EP | 0 489 480 | A1 | | 6/1992 |
| JP | 3-204865 | A | | 9/1991 |
| JP | 9-25270 | A | | 1/1997 |
| JP | 2001-288175 | A | | 10/2001 |
| JP | 2002-537387 | A | | 11/2002 |
| JP | 2005-508929 | A | | 4/2005 |
| JP | 2015-526437 | A | | 9/2015 |
| JP | 2022-534105 | A | | 7/2022 |
| RU | 2 286 989 | C2 | | 11/2006 |
| RU | 2550352 | C2 | | 5/2015 |
| WO | WO 84/02919 | A1 | | 8/1984 |
| WO | WO 91/13972 | A1 | | 9/1991 |
| WO | WO 91/19806 | A1 | | 12/1991 |
| WO | WO 92/00377 | A1 | | 1/1992 |
| WO | WO 92/11376 | A1 | | 7/1992 |
| WO | WO 92/14827 | A1 | | 9/1992 |
| WO | WO 99/52892 | A2 | | 10/1999 |
| WO | WO 00/50409 | A1 | | 8/2000 |
| WO | 03/029225 | A1 | | 4/2003 |
| WO | WO 2004/056785 | A2 | | 7/2004 |
| WO | WO 2010/129497 | A1 | | 11/2010 |
| WO | WO 2011/045224 | A1 | | 4/2011 |
| WO | 2016/095768 | | * | 6/2016 |
| WO | 2018/118781 | A1 | | 6/2018 |

OTHER PUBLICATIONS

Sonnewald et al., Transgenic tobacco plants expressing yeast-derived invertase in either the cytosol, vacuole or apoplast: a powerful tool for studying sucrose metabolism and sink/source interactions, *The Plant Journal*, vol. 1(1), pp. 95-106 Jul. 1991.

Wolter et al., rbcS genes in Solanum tuberosum: conservation of transit peptide and exon shuffling during evolution, *PNAS*, vol. 85, pp. 846-850, Feb. 1988.

World Intellectual Property Organization, International Search Report and Written Opinion in counterpart International Patent Application No. PCT/CN2020/126434, mailed on Feb. 3, 2021.

European Patent Office, Extended European Search Report issued in counterpart European Patent Application No. 20884168, mailed on Nov. 22, 2023.

Russian Federal Service On Intellectual Property, Office Action and Search Report issued in counterpart Russian Patent Application No. 2022115158/04, mailed on Dec. 22, 2023.

Pérez-Perarnau et al., "A Trifluorinated Thiazoline Scaffold Leading to Pro-apoptotic Agents Targeting Prohibitins", *Angew. Chem. Int. Ed.*, 53: 10150-10154 (2014).

Zuo et al., "Synthesis, Herbicidal Activity, and QSAR of Novel N-Benzothiazolyl-pyrimidine-2,4-diones as Protoporphyrinogen Oxidase Inhibitors", *J. Agric. Food Chem.*, 64(3): 552-562 (2016), doi: 10.1021/acs.jafc.5b05378.

Brazilian Institute of Intellectual Property, Search Report and Written Opinion issued in Brazilian Patent Application No. BR112022008867-1, mailed on Dec. 15, 2023.

Indian Patent Office, Office Action issued in Indian Patent Application No. 202247028068, mailed on Feb. 1, 2024.

African Regional Intellectual Property Organization (ARIPO), Notification of Decision to Grant or Register issued in corresponding African Application No. AP/P/2022/014240, dated May 21, 2024.

Chilean National Institute of Industrial Property—INAPI, Second Office Action issued in corresponding Chilean Application No. 2022-01899, dated Jun. 19, 2024.

Intellectual Property Office of Vietnam(IP Viet Nam), First Office Action issued in corresponding Vietnam Application No. 1-2022-03431, dated Jun. 20, 2024.

Japanese Patent Office, First Office Action issued in corresponding Japanese Patent Application No. 2022-526303, mailed May 31, 2024.

Russian Federal Service On Intellectual Property, First Office Action and Search Report issued in counterpart Russian Patent Application No. 2021134383/04(072692), mailed on May 17, 2024.

Wang et al., Discovery of Novel N-Isoxazolinylphenyltriazinones as Promising Protoporphyrinogen IX Oxidase Inhibitors, J. Agric. Food Chem. (2019), 67, 45, 12382-12392.

Yang et al., Design, synthesis and herbicidal evaluation of novel uracil derivatives containing an isoxazoline moiety, Pest Manag Sci., (Oct. 2020.), 76(10), 3395-3402.

Intellectual Property Office of the Philippines, First Office Action issued in corresponding Philippines Application No. 1/2021/552589, dated Mar. 20, 2024.

Zhang et al., "Design, Synthesis, and Molecular Mechanism Studies of N-Phenylisoxazoline-thiadiazolo[3,4-alpha] pyridazine Hybrids as Protoporphyrinogen IX Oxidase Inhibitors", J. Agric. Food. Chem., 68: 13672-13684 (2020).

Jeschke, "The Unique Role of Fluorine in the Design of Active Ingredients for Modern Crop Protection", ChemBioChem, 5: 570-789 (2004).

* cited by examiner

SUBSTITUTED-ISOXAZOLINE-CONTAINING AROMATIC COMPOUND, PREPARATION METHOD THEREFOR, HERBICIDAL COMPOSITION AND USE THEREOF

CROSS-REFERENCE TO RELATED APPLICATIONS

This patent application is the U.S. National Stage of International Patent Application No. PCT/CN2020/126434, filed Nov. 4, 2020, which claims the benefit of Chinese Patent Application No. 202010131605.X, filed Feb. 28, 2020, and Chinese Patent Application No. 201911082204.3, filed Nov. 7, 2019, which are each incorporated by reference.

TECHNICAL FIELD

The invention relates to the technical field of pesticides, and in particular a type of substituted-isoxazoline-containing aromatic compound, preparation method therefor, herbicidal composition and use thereof.

TECHNICAL BACKGROUND

Weed control is one of the most important links in the course of achieving high-efficiency agriculture. Various herbicides are available in the market, for example, patents WO00/50409 etc. disclose the use of a compound of general formula 1-aryl-4-thiotriazine as a herbicide, and CN105753853A discloses an isoxazoline-containing uracil compound and the herbicidal use thereof. However, the herbicidal properties of these known compounds against harmful plants and their selectivities to crops are not completely satisfactory. And scientists still need to do continuously research and develop new herbicides with high efficacy, safety, economics and different modes of action due to problems such as the growing market, weed resistance, the service life and economics of pesticides as well as people's increasing concern on environment.

INVENTION CONTENTS

The invention provides a type of substituted-isoxazoline-containing aromatic compound, preparation method therefor, herbicidal composition and use thereof. The compound has excellent herbicidal activity against gramineous weeds, broadleaf weeds, and so on even at low application rates, and has high selectivity for crops.

The technical solution adopted by the invention is as follows:

A substituted-isoxazoline-containing aromatic compound, as shown in general formula I:

I

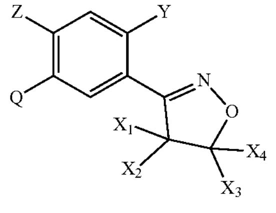

wherein,

Q represents

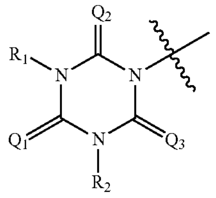

or

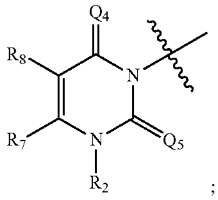

;

Y represents halogen, halogenated alkyl or cyano;

Z represents halogen;

$Q_1$, $Q_2$, $Q_3$, $Q_4$, $Q_5$ each independently represent O or S;

$R_1$, $R_2$, $R_6$ each independently represent hydrogen, alkyl, alkenyl, alkynyl, cycloalkyl or cycloalkylalkyl;

$R_7$, $R_8$ each independently represent hydrogen, alkyl, halogen, halogenated alkyl or amino;

$X_1$, $X_2$ each independently represent hydrogen, halogen, alkyl, alkenyl, alkynyl, cycloalkyl, cycloalkylalkyl, —$OR_3$, —(CO)$OR_3$ or phenyl; wherein, the "alkyl", "alkenyl", "alkynyl", "cycloalkyl" or "cycloalkylalkyl" is each independently unsubstituted or substituted with at least one substituent selected from the group consisting of halogen;

$X_3$ represents halogen, cyano, formyl, alkyl, alkenyl, alkynyl, cycloalkyl, cycloalkylalkyl, —$OR_3$, —(CO)$OR_3$, —$SR_3$, heterocyclyl, heterocyclylalkyl, aryl, arylalkyl or amino, and $X_3$ does not represent methyl; wherein, the "alkyl", "alkenyl" or "alkynyl" is each independently unsubstituted or substituted with at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O-alkyl-(CO)$OR_3$ or —O(CO)(CO)$OR_3$;

the "cycloalkyl", "cycloalkylalkyl", "heterocyclyl", "heterocyclylalkyl", "aryl" or "arylalkyl" is each independently unsubstituted or substituted with at least one substituent selected from the group consisting of oxo, halogen, cyano, nitro, alkyl, alkenyl, alkynyl, cycloalkyl, halogenated alkyl, halogenated alkenyl, halogenated alkynyl, halogenated cycloalkyl, cycloalkyl substituted with alkyl, —$OR_4$, —$SR_4$, —(CO)$OR_4$, —($SO_2$)$R_4$ or —N($R_4$) 2;

the "amino" is unsubstituted or substituted with one or two substituents selected from the group consisting of —$R_3$;

$X_4$ each independently represents —$COOR_5$ or -alkyl-$COOR_5$;

$R_3$ each independently represents hydrogen, alkyl, alkenyl, alkynyl, cycloalkyl or cycloalkylalkyl;

$R_4$ each independently represents hydrogen, alkyl or halogenated alkyl;

$R_5$ each independently represents hydrogen, alkyl, alkenyl, alkynyl, cycloalkyl or cycloalkylalkyl; wherein, the "alkyl", "alkenyl", "alkynyl", "cycloalkyl" or "cycloalkylalkyl" is each independently unsubstituted or substituted with at least one substituent selected from the group consisting of halogen.

Preferably, Y represents halogen, halogenated C1-C8 alkyl or cyano;

$R_1$, $R_2$, $R_6$ each independently represent hydrogen, C1-C8 alkyl, C2-C8 alkenyl, C2-C8 alkynyl, C3-C8 cycloalkyl or C3-C8 cycloalkyl C1-C8 alkyl;

$R_7$, $R_8$ each independently represent hydrogen, C1-C8 alkyl, halogen, halogenated C1-C8 alkyl or amino;

$X_1$, $X_2$ each independently represent hydrogen, halogen, C1-C8 alkyl, C2-C8 alkenyl, C2-C8 alkynyl, C3-C8 cycloalkyl, C3-C8 cycloalkyl C1-C8 alkyl, —$OR_3$, —(CO)$OR_3$ or phenyl; wherein, the "C1-C8 alkyl", "C2-C8 alkenyl", "C2-C8 alkynyl", "C3-C8 cycloalkyl" or "C3-C8 cycloalkyl C1-C8 alkyl" is each independently unsubstituted or substituted with at least one substituent selected from the group consisting of halogen;

$X_3$ represents halogen, cyano, formyl, C1-C8 alkyl, C2-C8 alkenyl, C2-C8 alkynyl, C3-C8 cycloalkyl, C3-C8 cycloalkyl C1-C8 alkyl, —$OR_3$, —(CO)$OR_3$, —$SR_3$, heterocyclyl, heterocyclyl C1-C8 alkyl, aryl, aryl C1-C8 alkyl or amino; wherein, the "C1-C8 alkyl", "C2-C8 alkenyl" or "C2-C8 alkynyl" is each independently unsubstituted or substituted with at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O—(C1-C8 alkyl)-(CO)$OR_3$ or —O(CO)(CO)$OR_3$;

the "C3-C8 cycloalkyl", "C3-C8 cycloalkyl C1-C8 alkyl", "heterocyclyl", "heterocyclyl C1-C8 alkyl", "aryl" or "aryl C1-C8 alkyl" is each independently unsubstituted or substituted with at least one substituent selected from the group consisting of oxo, halogen, cyano, nitro, C1-C8 alkyl, C2-C8 alkenyl, C2-C8 alkynyl, C3-C8 cycloalkyl, halogenated C1-C8 alkyl, halogenated C2-C8 alkenyl, halogenated C2-C8 alkynyl, halogenated C3-C8 cycloalkyl, C3-C8 cycloalkyl substituted with C1-C8 alkyl, —$OR_4$, —$SR_4$, —(CO)$OR_4$, —($SO_2$)$R_4$ or —N($R_4$)$_2$;

the "amino" is unsubstituted or substituted with one or two substituents selected from the group consisting of —$R_3$;

$X_4$ each independently represents-COOR$_5$ or -(C1-C8 alkyl)-COOR$_5$;

$R_3$ each independently represents hydrogen, C1-C8 alkyl, C2-C8 alkenyl, C2-C8 alkynyl, C3-C8 cycloalkyl or C3-C8 cycloalkyl C1-C8 alkyl;

$R_4$ each independently represents hydrogen, C1-C8 alkyl or halogenated C1-C8 alkyl;

$R_5$ each independently represents hydrogen, C1-C8 alkyl, C2-C8 alkenyl, C2-C8 alkynyl, C3-C8 cycloalkyl or C3-C8 cycloalkyl C1-C8 alkyl; wherein, the "C1-C8 alkyl", "C2-C8 alkenyl", "C2-C8 alkynyl", "C3-C8 cycloalkyl" or "C3-C8 cycloalkyl C1-C8 alkyl" is each independently unsubstituted or substituted with at least one substituent selected from the group consisting of halogen.

More preferably, Y represents halogen, halogenated C1-C6 alkyl or cyano;

$R_1$, $R_2$, $R_6$ each independently represent hydrogen, C1-C6 alkyl, C2-C6 alkenyl, C2-C6 alkynyl, C3-C6 cycloalkyl or C3-C6 cycloalkyl C1-C6 alkyl;

$R_7$, $R_8$ each independently represent hydrogen, C1-C6 alkyl, halogen, halogenated C1-C6 alkyl or amino;

$X_1$, $X_2$ each independently represent hydrogen, halogen, C1-C6 alkyl, C2-C6 alkenyl, C2-C6 alkynyl, C3-C6 cycloalkyl, C3-C6 cycloalkyl C1-C6 alkyl, —$OR_3$, —(CO)$OR_3$ or phenyl; wherein, the "C1-C6 alkyl", "C2-C6 alkenyl", "C2-C6 alkynyl", "C3-C6 cycloalkyl" or "C3-C6 cycloalkyl C1-C6 alkyl" is each independently unsubstituted or substituted with at least one substituent selected from the group consisting of halogen;

$X_3$ represents halogen, cyano, formyl, C1-C6 alkyl, C2-C6 alkenyl, C2-C6 alkynyl, C3-C6 cycloalkyl, C3-C6 cycloalkyl C1-C6 alkyl, —$OR_3$, —(CO)$OR_3$, —$SR_3$, heterocyclyl, heterocyclyl C1-C6 alkyl, aryl, aryl C1-C6 alkyl or amino; wherein, the "C1-C6 alkyl", "C2-C6 alkenyl" or "C2-C6 alkynyl" is each independently unsubstituted or substituted with at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O—(C1-C6 alkyl)-(CO)$OR_3$ or —O(CO)(CO)$OR_3$;

the "C3-C6 cycloalkyl", "C3-C6 cycloalkyl C1-C6 alkyl", "heterocyclyl", "heterocyclyl C1-C6 alkyl", "aryl" or "aryl C1-C6 alkyl" is each independently unsubstituted or substituted with at least one substituent selected from the group consisting of oxo, halogen, cyano, nitro, C1-C6 alkyl, C2-C6 alkenyl, C2-C6 alkynyl, C3-C6 cycloalkyl, halogenated C1-C6 alkyl, halogenated C2-C6 alkenyl, halogenated C2-C6 alkynyl, halogenated C3-C6 cycloalkyl, C3-C6 cycloalkyl substituted with C1-C6 alkyl, —$OR_4$, —$SR_4$, —(CO)$OR_4$, —($SO_2$)$R_4$ or —N($R_4$)$_2$;

the "amino" is unsubstituted or substituted with one or two substituents selected from the group consisting of —$R_3$;

$X_4$ each independently represents-COOR$_5$ or -(C1-C6 alkyl)-COOR$_5$;

$R_3$ each independently represents hydrogen, C1-C6 alkyl, C2-C6 alkenyl, C2-C6 alkynyl, C3-C6 cycloalkyl or C3-C6 cycloalkyl C1-C6 alkyl;

$R_4$ each independently represents hydrogen, C1-C6 alkyl or halogenated C1-C6 alkyl;

$R_5$ each independently represents hydrogen, C1-C6 alkyl, C2-C6 alkenyl, C2-C6 alkynyl, C3-C6 cycloalkyl or C3-C6 cycloalkyl C1-C6 alkyl; wherein, the "C1-C6 alkyl", "C2-C6 alkenyl", "C2-C6 alkynyl", "C3-C6 cycloalkyl" or "C3-C6 cycloalkyl C1-C6 alkyl" is each independently unsubstituted or substituted with at least one substituent selected from the group consisting of halogen.

Further preferably, Y represents halogen;

$R_1$, $R_2$, $R_6$ each independently represent C1-C6 alkyl;

$R_7$, $R_8$ each independently represent hydrogen or halogenated C1-C6 alkyl;

$X_1$, $X_2$ each independently represent hydrogen;

$X_3$ represents halogen, formyl, C1-C6 alkyl, C2-C6 alkenyl, C2-C6 alkynyl, C3-C6 cycloalkyl, C3-C6 cycloalkyl C1-C3 alkyl, —$OR_3$, phenyl or benzyl; wherein, the "C1-C6 alkyl", "C2-C6 alkenyl" or "C2-C6 alkynyl" is each independently unsubstituted or substituted with one, two or three substituents selected from the group consisting of halogen, —$OR_3$, —(CO)$R_3$, —O(CO)$R_3$, —O—(C1-C3 alkyl)-(CO)$OR_3$ or —O(CO)(CO)$OR_3$;

the "C3-C6 cycloalkyl", "C3-C6 cycloalkyl C1-C3 alkyl", "phenyl" or "benzyl" is each independently unsubstituted or substituted with one, two or three substituents selected from the group consisting of halogen, C1-C6 alkyl, C2-C6 alkenyl, C2-C6 alkynyl, C3-C6 cycloalkyl, halogenated C1-C6 alkyl, halogenated C2-C6 alkenyl, halogenated C2-C6 alkynyl, halogenated C3-C6 cycloalkyl, C3-C6 cycloalkyl substituted with C1-C6 alkyl, —$OR_4$ or —(CO)$OR_4$;

$X_4$ each independently represents-COOR$_5$;

$R_3$ each independently represents hydrogen, C1-C6 alkyl, C2-C6 alkenyl, C2-C6 alkynyl, C3-C6 cycloalkyl or C3-C6 cycloalkyl C1-C3 alkyl;

$R_4$ each independently represents hydrogen, C1-C6 alkyl or halogenated C1-C6 alkyl;

$R_5$ each independently represents hydrogen, C1-C6 alkyl, C2-C6 alkenyl, C2-C6 alkynyl or C3-C6 cycloalkyl.

Further preferably, Y represents chlorine;

Z represents fluorine;

$R_7$ represents C1-C6 alkyl;

$R_8$ represents hydrogen;

$X_3$ represents halogen, formyl, C1-C6 alkyl, C3-C6 cycloalkyl, C3-C6 cycloalkyl C1-C3 alkyl, —$OR_3$, —(C1-C3 alkyl)-$OR_3$, —(C1-C3 alkyl)-O(CO)$R_3$, —(C1-C3 alkyl)-(CO)$OR_3$, —(C1-C3 alkyl-O—(C1-C3 alkyl)-(CO)$OR_3$, —(C1-C3 alkyl)-O(CO)(CO)$OR_3$, phenyl or benzyl; wherein, the "C1-C6 alkyl" is each independently unsubstituted or substituted with one, two or three substituents selected from the group consisting of halogen;

$R_3$ each independently represents hydrogen or C1-C6 alkyl;

$R_5$ each independently represents hydrogen or C1-C6 alkyl;

Further preferably, Q represents

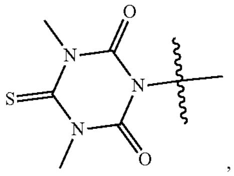
,
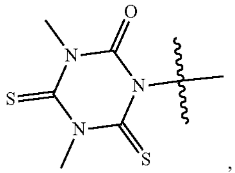
,
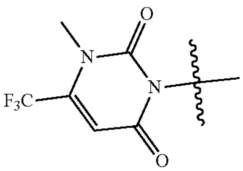
,
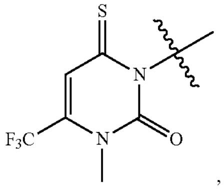
,
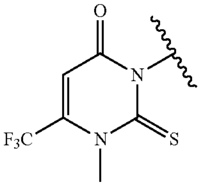
or
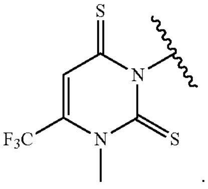
.

In the definition of the compound represented by the above Formula and all of the following structural formulas, the technical terms used, whether used alone or used in compound word, represent the following substituents: an alkyl having more than two carbon atoms may be linear or branched. For example, the alkyl in the compound word "-alkyl-(CO)$OR_{11}$" may be —$CH_2$—, —$CH_2CH_2$—, —CH($CH_3$)—, —C($CH_3$)$_2$—, and the like. The alkyl is, for example, $C_1$ alkyl: methyl; $C_2$ alkyl: ethyl; $C_3$ alkyl: propyl such as n-propyl or isopropyl; $C_4$ alkyl: butyl such as n-butyl, isobutyl, tert-butyl or 2-butyl; $C_5$ alkyl: pentyl such as n-pentyl; $C_6$ alkyl: hexyl such as n-hexyl, isohexyl and 1,3-dimethylbutyl. Similarly, the alkenyl is, for example, vinyl, allyl, 1-methylprop-2-en-1-yl, 2-methylprop-2-en-1-yl, but-2-en-1-yl, butyl-3-en-1-yl, 1-methylbut-3-en-1-yl and 1-methylbut-2-en-1-yl. The alkynyl is, for example, ethynyl, propargyl, but-2-yn-1-yl, but-3-yn-1-yl, 1-methylbut-3-yn-1-yl. The multiple bond(s) may be placed at any position of each unsaturated group. The cycloalkyl is a carbocyclic saturated ring system having, for example, three to six carbon atoms, such as cyclopropyl, cyclobutyl, cyclopentyl or cyclohexyl. Similarly, the cycloalkenyl is monocycloalkenyl having, for example, three to six carbon ring members, such as cyclopropenyl, cyclobutenyl, cyclopentenyl, and cyclohexenyl, wherein double bond can be at any position. Halogen is fluorine, chlorine, bromine or iodine.

Unless otherwise specified, the "aryl" of the present invention includes, but is not limited to, phenyl, naphthyl,

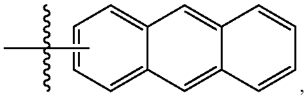
, or
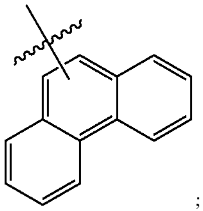
;

the "heterocyclyl" not only includes, but is not limited to, saturated or unsaturated non-aromatic cyclic group,

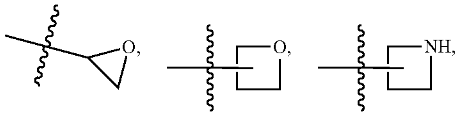
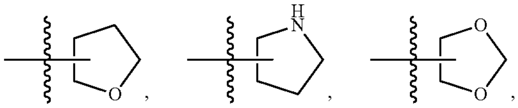
,
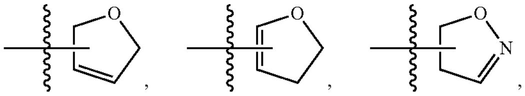
,
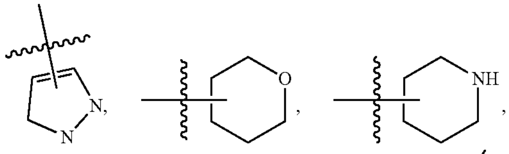
,
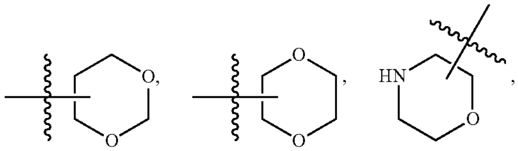
,
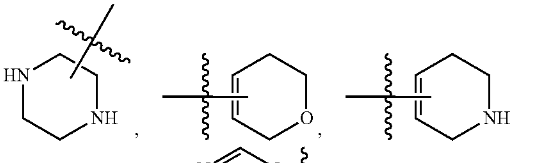
or
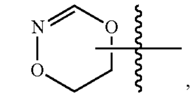
, etc., but also includes, but is not limited to, "heteroaryl", which is an aromatic cyclic group having, for example, 3 to 6 ring atoms and optionally being fused with a benzo ring, and 1 to 4 (for example, 1, 2, 3 or 4) heteroatoms of the ring are selected from the group consisting of oxygen, nitrogen and sulfur. For example,

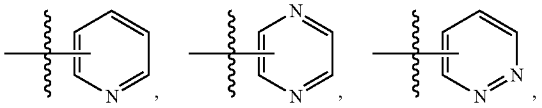
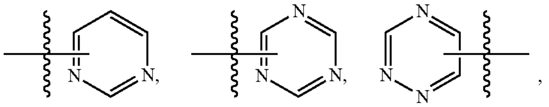
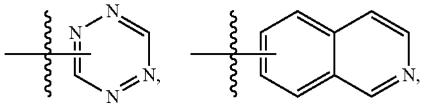
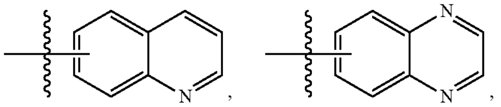
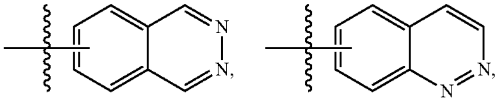
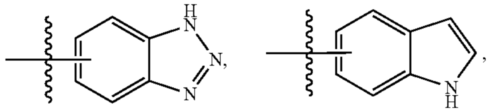
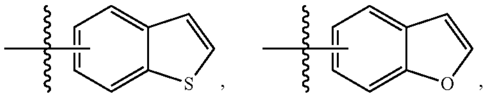
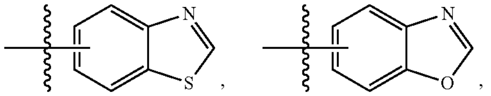
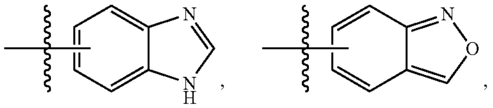
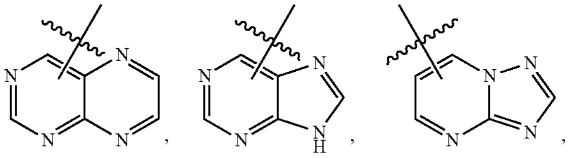
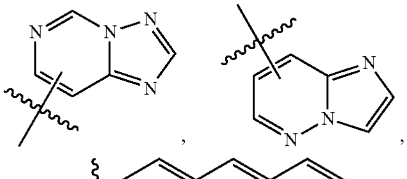
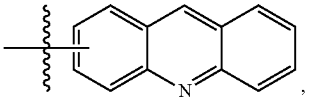
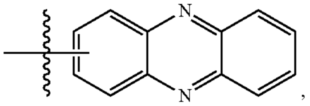
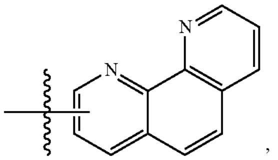
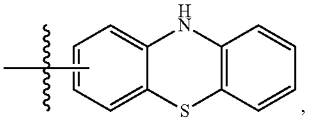
-continued
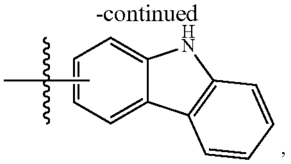
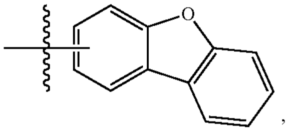
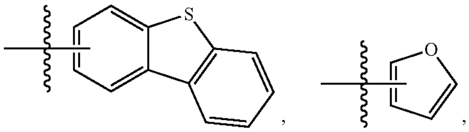
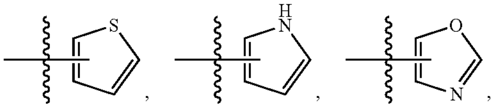
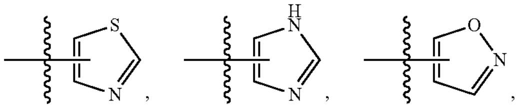
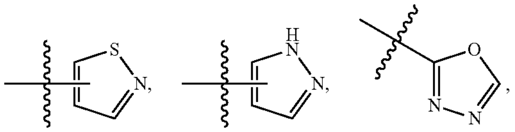
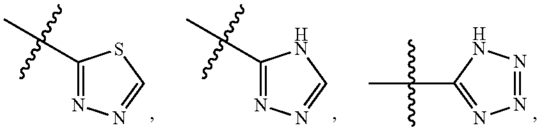
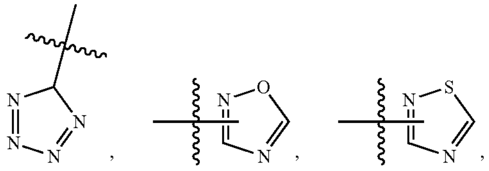
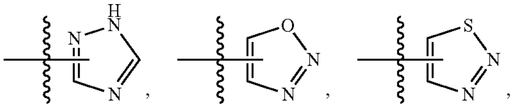
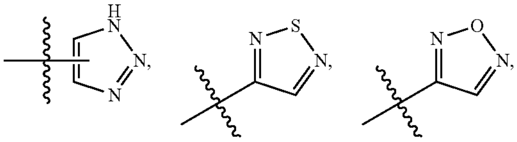
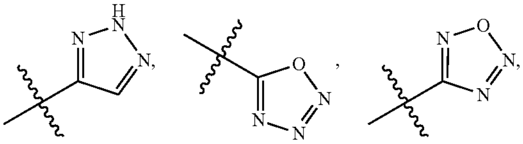
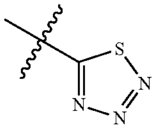
or
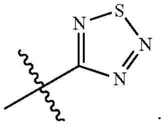
If a group is substituted by a group, which should be understood to mean that the group is substituted by one or more groups, which are same or different groups, selected from the mentioned groups. In addition, the same or different substitution characters contained in the same or different substituents are independently selected, and may be the same or different. This is also applicable to ring systems formed with different atoms and units. Meanwhile, the scope of the claims will exclude those compounds chemically unstable under standard conditions known to those skilled in the art.

In addition, unless specifically defined, "substituted with at least one group" in the present invention means substituted with, for example, 1, 2, 3, 4 or 5 groups; a group (including heterocyclyl, aryl, etc.) without being specified a linking site may be attached at any site, including a C or N site; if it is substituted, the substituent may be substituted at any site as long as it comply with the valence bond theory. For example, if the heteroaryl

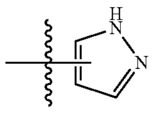

is substituted with one methyl, it can be etc.

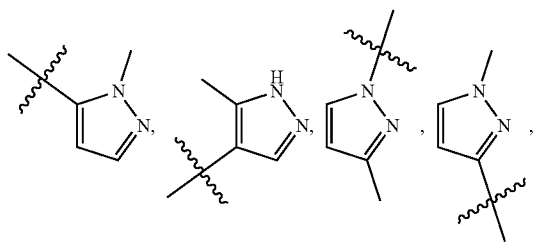

It should be pointed out that, when the carbon atom (C*) connected to $X_3$ and $X_4$ in the general formula I

I

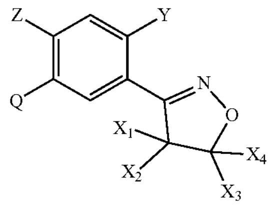

is a chiral center (i.e., $X_3$ and $X_4$ are not the same), it is in R configuration or S configuration, preferably S configuration, and based on the content of stereoisomers having R and S configurations at this position, it has a stereochemical purity of 60-100% (S), preferably 70-100% (S), more preferably 80-100% (S), still more preferably 90-100% (S), still more preferably 95-100% (S). Wherein, "stereochemical purity" means the amount of the stated stereoisomer expressed as a percentage of the total amount of stereoisomers having the given chiral centre.

In addition, the present invention also provides a substituted-isoxazoline-containing aromatic compound with S configuration, as shown in general formula I':

I'

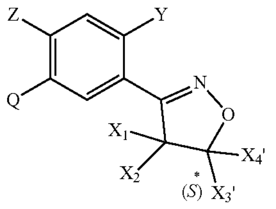

Wherein, $X_3'$ represents hydrogen, methyl or $X_3$, the substituents $X_1$, $X_2$, $X_3$, $X_4$, Q, Y and Z are defined as mentioned above, and $X_3$ and $X_4$ are different.

In the present invention the stereochemical configuration at the marked * position of formula I and I' is fixed as being predominantly(S) according to the Cahn-Ingold-Prelog system, however is the subject matter of the invention is also directed to all stereoisomers at other locants which are encompassed by formula I and I', and their mixtures. Such compounds of the formula I and I' contain, e.g. one or more additional asymmetric carbon atoms or else double bonds which are not stated specifically in the formula I and I'. It will be understood that the present invention embraces both the pure isomers and more or less enriched mixtures thereof, where the asymmetric carbon atom in marked * position is in the S-configuration or, in mixtures, a compound or compounds of same chemical constitution have the S-configuration in marked * position or are present in a ratio that compounds having the S-configuration are predominantly present (at least 60% S-configuration) whilst the other asymmetric carbon atom(s) may be present in racemic form or are more or less resolved too. Provided the condition for the stereochemical configuration at marked * position is met, the possible stereoisomers which are defined by their specific spatial form, such as enantiomers, diastereomers, Z- and E-isomers, are all encompassed by formula I and I' and can be obtained by customary methods from mixtures of the stereoisomers, or else be prepared by stereoselective reactions in combination with the use of stereochemically pure raw materials.

The invention also encompasses any keto and enol tautomer forms and mixtures and salts thereof, if respective functional groups are present.

Stereoisomers can be obtained by optical resolution from the mixture obtained in the preparation. The stereoisomers may also be prepared selectively by using stereoselective reactions and using optically active raw materials and/or auxiliaries. It is generally possible to use customary methods for optical resolutions (cf. Textbooks of Stereochemistry), for example following processes for separating mixtures into diastereomers, for example physical processes, such as crystallization, chromatographic processes, in particular column chromatography and high pressure liquid chromatography, distillation, if appropriate under reduced pressure, extraction and other processes, it is possible to separate the remaining mixtures of enantiomers, generally by chromatographic separation on chiral solid phases. Suitable for preparative amounts or use on an industrial scale are processes such as the crystallization of diastereomeric salts which can be obtained from the compounds using optically active acids and, if appropriate, provided that acidic groups are present, using optically active bases.

A method for preparing the substituted-isoxazoline-containing aromatic compound comprises the following steps:

when Q represents

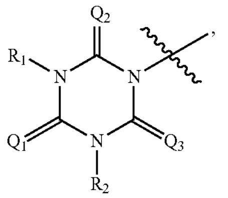

(1) subjecting a compound as shown in general formula II-1 and a compound as shown in general formula III-1 to cyclization reaction to obtain a compound as shown in general formula I-1, with the chemical reaction equation shown as follows:

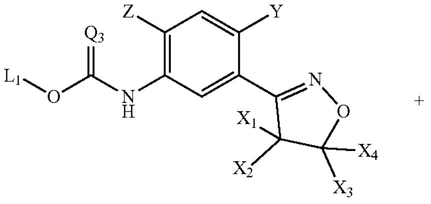

II-1

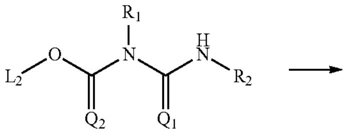

III-1

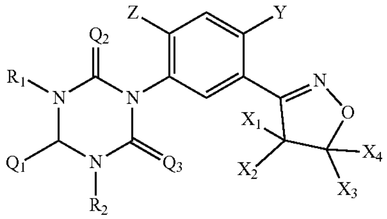

I-1 when Q represents

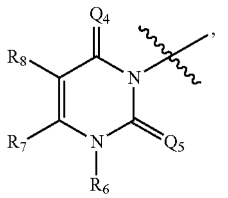

(2) subjecting a compound as shown in general formula II-2 and a compound as shown in general formula III-2 to cyclization reaction to obtain a compound as shown in general formula I-2, with the chemical reaction equation shown as follows:

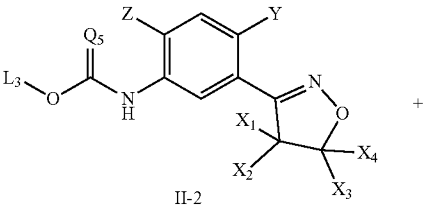

II-2

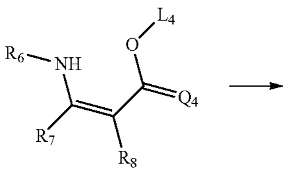

III-2

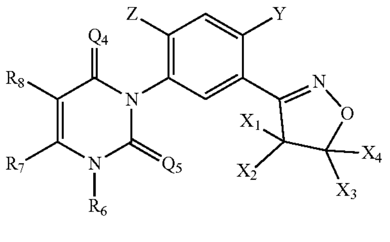

I-2

(3) subjecting a compound as shown in general formula II-3 and a compound as shown in general formula III-3 to reaction to obtain a compound as shown in general formula I-3;

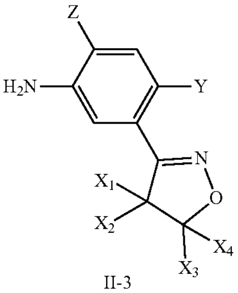

II-3

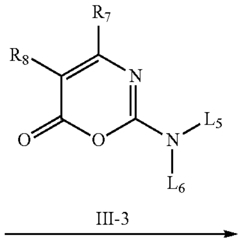

III-3

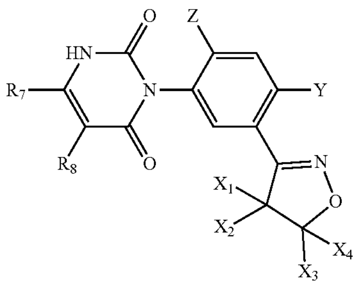

I-3

(4) subjecting a compound as shown in general formula II-4 and a compound as shown in general formula III-4 to reaction to obtain a compound as shown in general formula I-4;

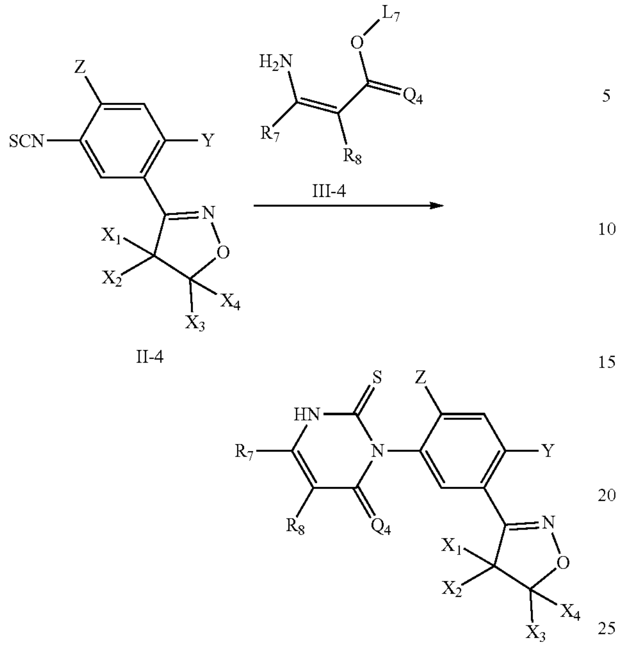

II-4

III-4

I-4 or, (5) subjecting a compound as shown in general formula I-5 and $R_6$'-Hal to substitution reaction to obtain a compound as shown in general formula I-6, with the chemical reaction equation shown as follows:

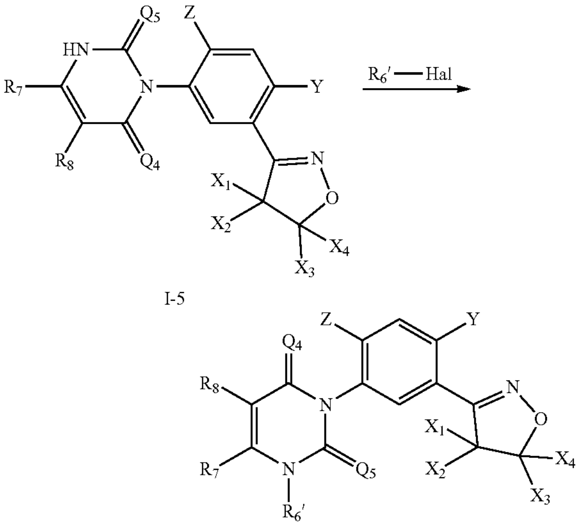

I-5

I-6 wherein, $L_1$, $L_2$, $L_3$, $L_4$, $L_5$, $L_6$ and $L_7$ each independently represent C1-C6 alkyl or aryl, preferably methyl, ethyl or phenyl; Hal represents halogen, preferably iodine; $R_6$' represents groups in $R_6$ other than hydrogen; other substituents $R_1$, $R_2$, $R_6$, $R_7$, $R_8$, $X_1$, $X_2$, $X_3$, $X_4$, $Q_1$, $Q_2$, $Q_3$, $Q_4$, $Q_5$, Y and Z are defined as above.

Preferably, the steps (1), (2), (4) and (5) are all carried out in the presence of a base and a solvent.

The base is at least one selected from inorganic bases (e.g. $K_2CO_3$, $Na_2CO_3$, $Cs_2CO_3$, $NaHCO_3$, KF, CsF, KOAc, AcONa, $K_3PO_4$, t-BuONa, EtONa, NaOH, KOH, NaOMe, etc.) or organic bases (e.g. pyrazol, triethylamine, DIEA, etc.).

The solvent is at least one selected from a group consisting of DMF, DMA, methanol, ethanol, acetonitrile, dichloroethane, DMSO, dioxane, dichloromethane or ethyl acetate.

Preferably, the step (3) is carried out in the presence of an acid.

The acid is selected from acetic acid, hydrochloric acid or sulfuric acid.

In addition, when at least one of the substituents $Q_1$, $Q_2$ and $Q_3$ in Q

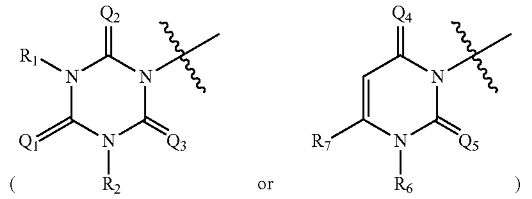

( or )

is S or at least one of $Q_4$ and $Q_5$ is S, such compound can also be prepared by conventional sulfur substitution reaction in the presence of Lawesson reagent

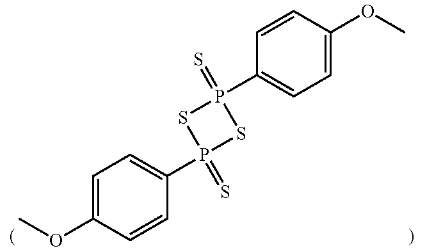

( )

or phosphorus pentasulfide by using the corresponding compound wherein Q represents

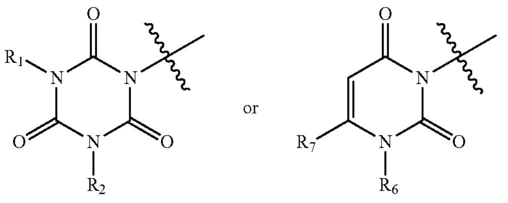

or as raw material.

The compounds of the present invention are also prepared by referring to the relevant methods described in patents WO00/50409, CN105753853A, etc.

An herbicidal composition, which comprises at least one of the substituted-isoxazoline-containing aromatic compound in a herbicidally effective amount; preferably, further comprises a formulation auxiliary.

A method for controlling a weed, which comprises applying at least one of the substituted-isoxazoline-containing aromatic compound or the herbicidal composition in a herbicidally effective amount on a plant or a weed area.

Use of at least one of the substituted-isoxazoline-containing aromatic compound or the herbicidal composition for controlling a weed; preferably, the substituted-isoxazoline-containing aromatic compound is used to control a weed in a useful crop, the useful crop is a transgenic crop or a crop treated by genome editing technique.

The compounds of the formula I and I' according to the invention have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is generally immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, *Avena, Lolium, Alopecurus, Phalaris, Echinochloa, Digitaria, Setaria* and also *Cyperus* species from the annual sector and from amongst the perennial species *Agropyron, Cynodon, Imperata* and Sorghum, and also perennial *Cyperus* species.

In the case of the dicotyledonous weed species, the spectrum of action extends to species such as, for example, Galium, Viola, Veronica, *Lamium, Stellaria, Amaranthus, Sinapis, Ipomoea, Sida, Matricaria* and *Abutilon* from amongst the annuals, and *Convolvulus, Cirsium, Rumex* and *Artemisia* in the case of the perennial weeds. The active compounds according to the invention also effect outstanding control of harmful plants which occur under the specific conditions of rice growing such as, for example, *Echinochloa, Sagittaria, Alisma, Eleocharis, Scirpus* and *Cyperus*. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely. In particular, the compounds according to the invention exhibit excellent activity against *Apera* spica venti, *Chenopodium album, Lamium purpureum, Polygonum convulvulus, Stellaria media, Veronica hederifolia, Veronica persica*, Viola tricolor and against *Amaranthus, Galium* and *Kochia* species.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. In particular, they have excellent compatibility in cereals, such as wheat, barley and corn, in particular wheat. For these reasons, the present compounds are highly suitable for selectively controlling undesirable plant growth in plantings for agricultural use or in plantings of ornamentals.

Owing to their herbicidal properties, these active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula I and I' according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula I and I' can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of:

- genetically engineered changes in crop plants in order to modify the starch synthesized in the plants (for example WO 92/11376, WO 92/14827, WO 91/19806),
- transgenic crop plants which are resistant to certain herbicides of the glufosinate-(cf., for example, EP-A 0 242 236, EP-A 0 242 246) or glyphosate-type (WO 92/00377), or of the sulfonylurea-type (EP-A 0 257 993, U.S. Pat. No. 5,013,659A),
- transgenic crop plants, for example cotton, having the ability to produce *Bacillus thuringiensis* toxins (Bt toxins) which impart resistance to certain pests to the plants (EP-A 0 142 924, EP-A 0 193 259),
- transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423-431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the above-mentioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106).

The transgenic plant cells can be regenerated to whole plants using known techniques. The transgenic plants can in principle be plants of any desired plant species, i.e. both monocotyledonous and dicotyledonous plants. In this manner, it is possible to obtain transgenic plants which have modified properties by overexpression, suppression or inhibition of homologous (=natural) genes or gene sequences or by expression of heterologous (=foreign) genes or gene sequences.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants. The invention therefore also provides for the use of the compounds according to the invention as herbicides for controlling harmful plants in transgenic crop plants.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

The compounds according to the invention can be applied in the customary formulations in the form of wettable powders, emulsifiable concentrates, sprayable solutions, dusts or granules. The invention therefore also provides herbicidal compositions comprising compounds of the formula I and I'. The compounds of the formula I and I' can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil dispersions (OD), oil- or water-based dispersions, oil-miscible solutions, dusts (DP), capsule suspensions (CS), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N. J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; Mccutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflüchenaktive Äthylenoxidaddkte" [Surface-active ethylene oxide adducts], Wiss. Verlagagesell. Stuttgart 1976; Winnacker-Küchler, "Chemische Technologie" [Chemical Technology], Volume 7, C. Hauser Verlag Munich, 4th Edition 1986.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutyinaphthalenesulfona-te or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth. Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers. Water-dispersible granules are generally prepared by the customary processes, such as spray-drying, fluidized-bed granulation, disk granulation, mixing using high-speed mixers, and extrusion without solid inert material.

For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8-57. For further details on the formulation of crop protection products, see for example G. C. Klingman, "Weed Control as a Science", John Wiley and Sons Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations generally contain from 0.1 to 99% by weight, in particular from 0.1 to 95% by weight, of active compound of the formula I and I'. In wettable powders the concentration of active compound is, for example, from about 10 to 99% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, the formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Suitable active compounds which can be combined with the active compounds according to the invention in mixed formulations or in a tank mix are, for example, known active compounds as described in for example World Herbicide New Product Technology Handbook, China Agricultural Science and Farming Techniques Press, 2010.9 and in the literature cited therein. For example the following active compounds may be mentioned as herbicides which can be combined with the compounds of the formula I and I' (note: the compounds are either named by the "common name" in accordance with the International Organization for Standardization (ISO) or by the chemical names, if appropriate together with a customary code number): acetochlor, butachlor, alachlor, propisochlor, metolachlor, s-metolachlor, pretilachlor, propachlor, ethachlor, napropamide, R-left handed napropamide, propanil, mefenacet, diphenamid, diflufenican, ethaprochlor, beflubutamid, bromobutide, dimethenamid, dimethenamid-P, etobenzanid, flufenacet, thenylchlor, metazachlor, isoxaben, flamprop-M-methyl, flamprop-M-propyl, allidochlor, pethoxamid, chloranocryl, cyprazine, mefluidide, monalide, delachlor, prynachlor, terbuchlor, xylachlor, dimethachlor, cisanilide, trimexachlor, clomeprop, propyzamide, pentanochlor, carbetamide, benzoylprop-ethyl, cyprazole, butenachlor, tebutam, benzipram, mogrton, dichlofluanid, naproanilide, diethatyl-ethyl, naptalam, flufenacet, EL-177, benzadox, chlorthiamid, chlorophthalimide, isocarbamide, picolinafen, atrazine, simazine, prometryn, cyanatryn, simetryn, ametryn, propazine, dipropetryn, SSH-108, terbutryn, terbuthylazine, triaziflam, cyprazine, proglinazine, trietazine, prometon, simetone, aziprotryne, desmetryn, dimethametryn, procyazine, mesoprazine, sebuthylazine, secbumeton, terbumeton, methoprotryne, cyanatryn, ipazine, chlorazine, atraton, pendimethalin, eglinazine, cyanuric acid, indaziflam, chlorsulfuron, metsulfuron-methyl, bensulfuron methyl, chlorimuron-ethyl, tribenuron-methyl, thifensulfuron-methyl, pyrazosulfuron-ethyl, mesosulfuron, iodosulfuron-methyl sodium, foramsulfuron, cinosulfuron, triasulfuron, sulfometuron methyl, nicosulfuron, ethametsulfuron-methyl, amidosulfuron, ethoxysulfuron, cyclosulfamuron, rimsulfuron, azimsulfuron, flazasulfuron, monosulfuron, monosulfuron-ester, flucarbazone-sodium, flupyrsulfuron-methyl, halosulfuron-methyl, oxasulfuron, imazosulfuron, primisulfuron, propoxycarbazone, prosulfuron, sulfosulfuron, trifloxysulfuron, triflusulfuron-methyl, tritosulfuron, sodium metsulfuron methyl, flucetosulfuron, HNPC—C, orthosulfamuron, propyrisulfuron, metazosulfuron, acifluorfen, fomesafen, lactofen, fluoroglycofen, oxyfluorfen, chlornitrofen, aclonifen, ethoxyfen-ethyl, bifenox, nitrofluorfen, chlomethoxyfen, fluorodifen, fluoronitrofen, furyloxyfen, nitrofen, TOPE, DMNP, PPG1013, AKH-7088, halosafen, chlortoluron, isoproturon, linuron, diuron, dymron, fluometuron, benzthiazuron, methabenzthiazuron, cumyluron, ethidimuron, isouron, tebuthiuron, buturon, chlorbromuron, methyldymron, phenobenzuron, SK-85, metobromuron, metoxuron, afesin, monuron, siduron, fenuron, fluothiuron, neburon, chloroxuron, noruron, isonoruron, 3-cyclooctyl-1, thiazfluron, tebuthiuron, difenoxuron, parafluron, methylamine tribunil, karbutilate, trimeturon, dimefuron, monisouron, anisuron, methiuron, chloreturon, tetrafluron, phenmedipham, phenmedipham-ethyl, desmedipham, asulam, terbucarb, barban, propham, chlorpropham, rowmate, swep, chlorbufam, carboxazole, chlorprocarb, fenasulam, BCPC, CPPC, carbasulam, butylate, benthiocarb, vernolate, molinate, triallate, dimepiperate, esprocarb, pyributicarb, cycloate, avadex, EPTC, ethiolate, orbencarb, pebulate, prosulfocarb, tiocarbazil, CDEC, dimexano, isopolinate, methiobencarb, 2,4-D butyl ester, MCPA-Na, 2,4-D isooctyl ester, MCPA isooctyl ester, 2,4-D sodium salt, 2,4-D dimethyla mine salt, MCPA-thioethyl, MCPA, 2,4-D propionic acid, high 2,4-D propionic acid salt, 2,4-D butyric acid, MCPA propionic acid, MCPA propionic acid salt, MCPA butyric acid, 2,4,5-D, 2,4,5-D propionic acid, 2,4,5-D butyric acid, MCPA amine salt, dicamba, erbon, chlorfenac, saison, TBA, chloramben, methoxy-TBA, diclofop-methyl, fluazifop-butyl, fluazifop-p-butyl, haloxyfop-methyl, haloxyfop-P, quizalofop-ethyl, quizalofop-p-ethyl, fenoxaprop-ethy, fenoxaprop-p-ethyl, propaquizafop, cyhalofop-butyl, metamifop, clodinafop-propargyl, fenthiaprop-ethyl, chloroazifop-propynyl, poppenate-methyl, trifopsime, isoxapyrifop, paraquat, diquat, oryzalin, ethalfluralin, isopropalin, nitralin, profluralin, prodinamine, benfluralin, fluchloraline, dinitramina, dipropalin, chlornidine, methalpropalin, dinoprop, glyphosate, anilofos, glufosinate ammonium, amiprophos-methyl, sulphosate, piperophos, bialaphos-sodium, bensulide, butamifos, phocarb, 2,4-DEP, H-9201, zytron, imazapyr, imazethapyr, imazaquin, imazamox, imazamox ammonium salt, imazapic, imazamethabenz-methyl, fluroxypyr, fluroxypyr isooctyl ester, clopyralid, picloram, trichlopyr, dithiopyr, haloxydine, 3,5,6-trichloro-2-pyridinol, thiazopyr, fluridone, aminopyralid, diflufenzopyr, triclopyr-butotyl, Cliodinate, sethoxydim, clethodim, cycloxydim, alloxydim, clefoxydim, butroxydim, tralkoxydim, tepraloxydim, buthidazole, metribuzin, hexazinone, metamitron, ethiozin, ametridione, amibuzin, bromoxynil, bromoxynil octanoate, ioxynil octanoate, ioxynil, dichlobenil, diphenatrile, pyraclonil, chloroxynil, iodobonil, flumetsulam, florasulam, penoxsulam, metosulam, cloransulam-methyl, diclosulam, pyroxsulam, benfuresate, bispyribac-sodium, pyribenzoxim, pyriftalid, pyriminobac-methyl, pyrithiobac-sodium, benzobicylon, mesotrione, sulcotrione, tembotrione, tefuryltrione, bicyclopyrone, ketodpiradox, isoxaflutole, clomazone, fenoxasulfone, methiozolin, fluazolate, pyraflufenethyl, pyrazolynate, difenzoquat, pyrazoxyfen, benzofenap, nipyraclofen, pyrasulfotole, topramezone, pyroxasulfone, cafenstrole, flupoxam, aminotriazole, amicarbazone, azafenidin, carfentrazone-ethyl, sulfentrazone, bencarbazone, benzfendizone, butafenacil, bromacil, isocil, lenacil, terbacil, flupropacil, cinidon-ethyl, flumiclorac-pentyl, flumioxazin, propyzamide, MK-129, flumezin, pentachlorophenol, dinoseb, dinoterb, dinoterb acetate, dinosam, DNOC, chloronitrophene, medinoterb acetate, dinofenate, oxadiargyl, oxadiazon, pentoxazone, Flufenacet, fluthiacet-methyl, fentrazamide, flufenpyr-ethyl, pyrazon, brompyrazon, metflurazon, kusakira, dimidazon, oxapyrazon, norflurazon, pyridafol, quinclorac, quinmerac, bentazone, pyridate, oxaziclomefone, benazolin, clomazone, cinmethylin, ZJ0702, pyribambenz-propyl, indanofan, sodium chlorate, dalapon, trichloroacetic acid, monochloroacetic acid, hexachloroacetone, flupropanate, cyperquat, bromofenoxim, epronaz, methazole, flurtamone, benfuresate, ethofumesate, tioclorim, chlorthal, fluorochloridone, tavron, acrolein, bentranil, tridiphane, chlorfenpropmethyl, thidiarizonaimin, phenisopham, busoxinone, methoxyphenone, saflufenacil, clacyfos, chloropon, alorac, diethamquat, etnipromid, iprymidam, ipfencarbazone, thiencarbazone-methyl, pyrimisulfan, chlorflurazole, tripropindan, sulglycapin, prosulfalin, cambendichlor, aminocyclopyrachlor, rodethanil, benoxacor, fenclorim, flurazole, fenchlorazole-ethyl, cloquintocet-mexyl, oxabetrinil, MG/91, cyometrinil, DKA-24, mefenpyr-diethyl, furilazole, fluxofenim, isoxadifen-ethyl, dichlormid, halauxifen-methyl, DOW florpyrauxifen, UBH-509, D489, LS 82-556, KPP-300, NC-324, NC-330, KH-218, DPX-N8189, SC-0744, DOWCO535, DK-8910, V-53482, PP-600, MBH-001, KIH-9201, ET-751, KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use. The application rate of the compounds of the formula I and I' required varies with the external conditions, such as temperature, humidity, the nature of the herbicide used and the like. It can vary within wide limits, for example between 0.001 and 1.0 kg a.i./ha or more of active substance, but it is preferably between 0.005 and 750 g a.i./ha, especially between 0.005 and 250 g a.i./ha.

Specific Mode for Carrying Out the Invention

The following embodiments are used to illustrate the present invention in detail and should not be taken as any limit to the present invention. The scope of the invention would be explained through the Claims.

In view of economics and variety of a compound, we preferably synthesized several compounds, part of which are listed in the following Table 1. The structure and information of a certain compound are shown in Table 1. The compounds in Table 1 are listed for further explication of the present invention, other than any limit therefor. The subject of the present invention should not be interpreted by those skilled in the art as being limited to the following compounds.

TABLE 1

Structures and $^1H$ NMR data of compounds

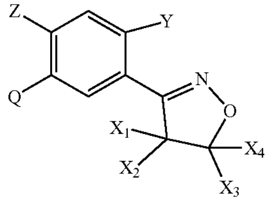

I

| NO. | 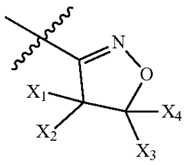 | Y | Z | Q | $^1H$ NMR |
|---|---|---|---|---|---|
| 1 | 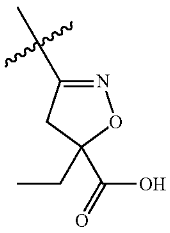 [SMILES: *C1=NOC(CC)(C(=O)O)C1] | Cl | F | 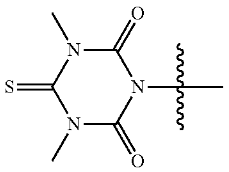 [SMILES: *n1c(=O)n(C)c(=S)n(C)c1=O] | |

TABLE 1-continued
Structures and $^1$H NMR data of compounds
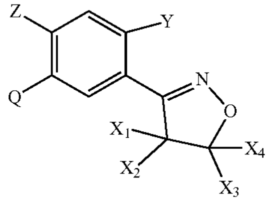
I
| NO. | 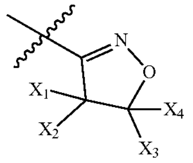 | Y | Z | Q | $^1$H NMR |
|---|---|---|---|---|---|
| 2 | 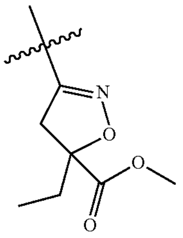 [SMILES: *C1=NOC(CC)(C(=O)OC)C1] | Cl | F | 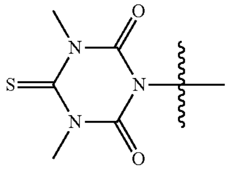 [SMILES: *n1c(=O)n(C)c(=S)n(C)c1=O] | |
| 3 | 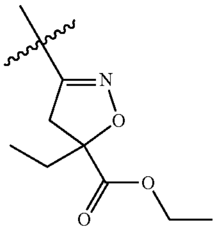 [SMILES: *C1=NOC(CC)(C(=O)OCC)C1] | Cl | F | 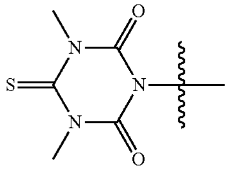 [SMILES: *n1c(=O)n(C)c(=S)n(C)c1=O] | $^1$H NMR (500 MHz, DMSO-$d_6$) δ 7.99-7.90 (m, 2H), 4.22 (q, J = 7.0 Hz, 2H), 3.86 (d, J = 17.5 Hz, 1H), 3.65 (s, 6H), 3.56 (d, J = 17.5 Hz, 1H), 2.07-1.89 (m, 2H), 1.25 (t, J = 7.0 Hz, 3H), 0.92 (t, J = 7.5 Hz, 3H). |
| 4 | 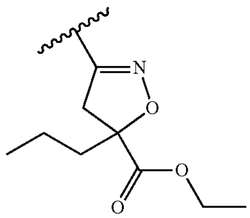 [SMILES: *C1=NOC(CCC)(C(=O)OCC)C1] | Cl | F | 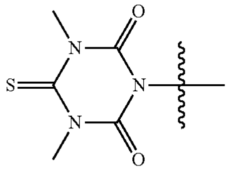 [SMILES: *n1c(=O)n(C)c(=S)n(C)c1=O] | $^1$H NMR (500 MHz, DMSO-$d_6$) δ 7.95-7.90(m, 2H), 4.21 (q, J = 7.0 Hz, 2H), 3.86 (d, J = 18.0 Hz, 1H), 3.65 (s, 6H), 3.57 (d, J = 18.0 Hz, 1H), 1.94 (t, J = 8.0 Hz, 2H), 1.40-1.28 (m, 2H), 1.24 (t, J = 7.0 Hz, 3H), 0.93 (t, J = 7.5 Hz, 3H) |
| 5 | 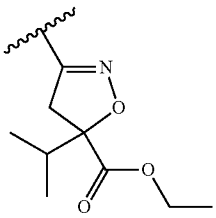 [SMILES: *C1=NOC(C(=O)OCC)(C(C)C)C1] | Cl | F | 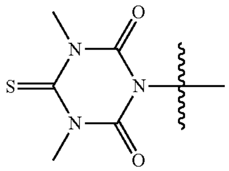 [SMILES: *n1c(=O)n(C)c(=S)n(C)c1=O] | $^1$H NMR (500 MHz, DMSO-$d_6$) δ 7.92-7.90 (m, 2H), 4.32-4.16 (m, 2H), 3.80 (d, J = 18.0 Hz, 1H), 3.55 (d, J = 18.0 Hz, 1H), 2.35-2.25 (m, 1H), 1.24-1.22 (m, 3H), 1.25-0.90 (m, 6H). |
| 6 | 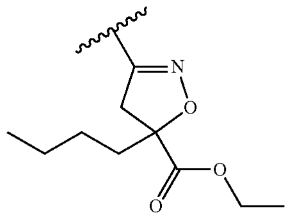 [SMILES: *C1=NOC(CCCC)(C(=O)OCC)C1] | Cl | F | 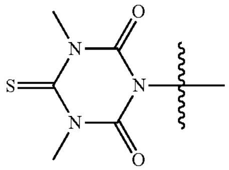 [SMILES: *n1c(=O)n(C)c(=S)n(C)c1=O] | $^1$H NMR (500 MHz, $CDCl_3$) δ 7.76 (d, J = 7.5 Hz, 1H), 7.40 (d, J = 9.0 Hz, 1H), 4.41-4.26 (m, 2H), 3.98 (d, J = 17.5 Hz, 1H), 3.81 (s, 6H), 3.47 (d, J = 17.5 Hz, 1H), 2.08-2.01 (m, 2H), 1.45-1.40 (m, 2H), 1.40-1.34 (m, 2H), 0.96 (t, J = 6.5 Hz, 3H), 0.93 (d, J = 6.5 Hz, 3H). |

TABLE 1-continued
Structures and $^1H$ NMR data of compounds
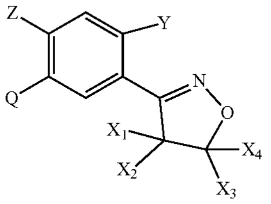
I
| NO. | 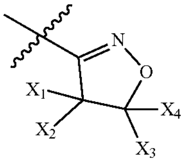 | Y | Z | Q | $^1H$ NMR |
|---|---|---|---|---|---|
| 7 | 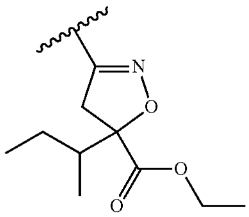 [SMILES: *C1=NOC(C(=O)OCC)(C(C)CC)C1] | Cl | F | 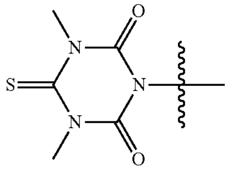 [SMILES: *n1c(=O)n(C)c(=S)n(C)c1=O] | |
| 8 | 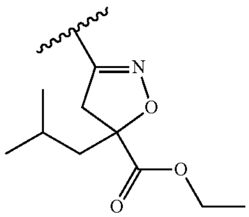 [SMILES: *C1=NOC(CC(C)C)(C(=O)OCC)C1] | Cl | F | 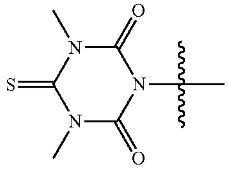 [SMILES: *n1c(=O)n(C)c(=S)n(C)c1=O] | |
| 9 | 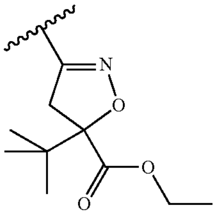 [SMILES: *C1=NOC(C(=O)OCC)(C(C)(C)C)C1] | Cl | F | 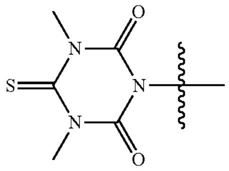 [SMILES: *n1c(=O)n(C)c(=S)n(C)c1=O] | |
| 10 | 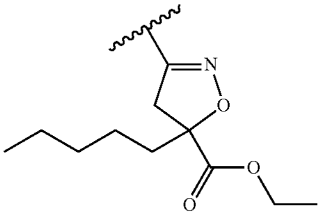 | Cl | F | 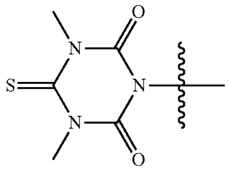 [SMILES: *n1c(=O)n(C)c(=S)n(C)c1=O] | |
| 11 | 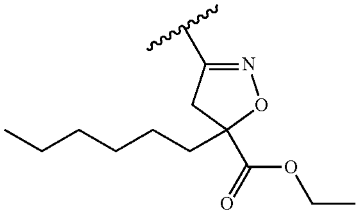 [SMILES: *C1=NOC(CCCCCC)(C(=O)OCC)C1] | Cl | F | 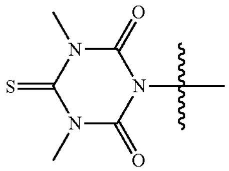 [SMILES: *n1c(=O)n(C)c(=S)n(C)c1=O] | |

TABLE 1-continued
Structures and $^{1}H$ NMR data of compounds
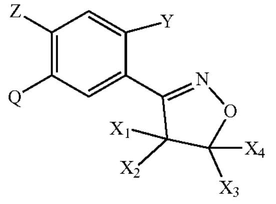
I
| NO. | 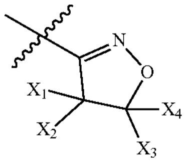 | Y | Z | Q | $^{1}H$ NMR |
|---|---|---|---|---|---|
| 12 | 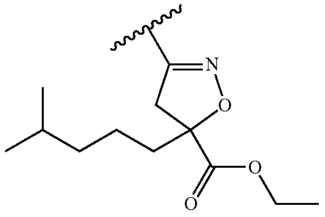 [SMILES: *C1=NOC(CCCC(C)C)(C(=O)OCC)C1] | Cl | F | 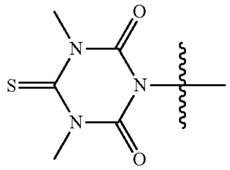 [SMILES: *n1c(=O)n(C)c(=S)n(C)c1=O] | |
| 13 | 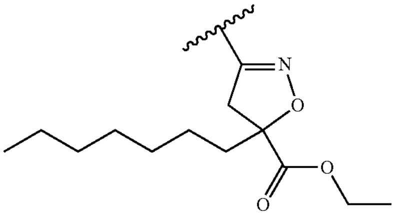 [SMILES: *C1=NOC(CCCCCCC)(C(=O)OCC)C1] | Cl | F | 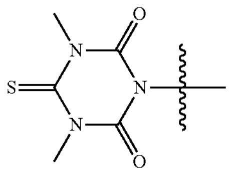 [SMILES: *n1c(=O)n(C)c(=S)n(C)c1=O] | |
| 14 | 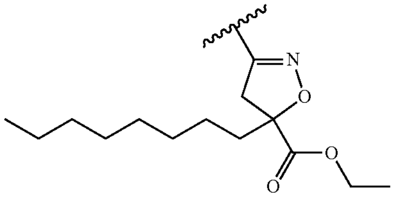 [SMILES: *C1=NOC(CCCCCCCC)(C(=O)OCC)C1] | Cl | F | 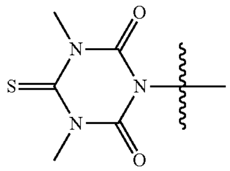 [SMILES: *n1c(=O)n(C)c(=S)n(C)c1=O] | |
| 15 | 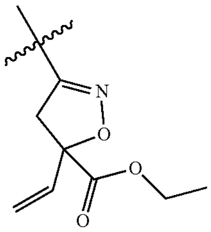 [SMILES: *C1=NOC(C=C)(C(=O)OCC)C1] | Cl | F | 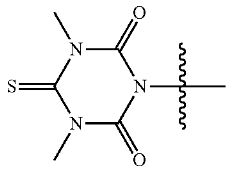 [SMILES: *n1c(=O)n(C)c(=S)n(C)c1=O] | |
| 16 | 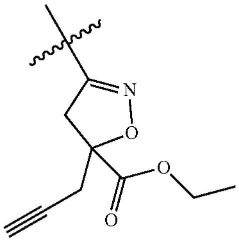 [SMILES: *C1=NOC(CC#C)(C(=O)OCC)C1] | Cl | F | 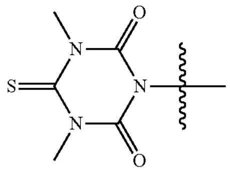 [SMILES: *n1c(=O)n(C)c(=S)n(C)c1=O] | |

TABLE 1-continued
Structures and $^{1}H$ NMR data of compounds
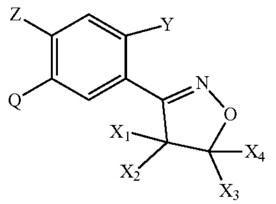
I
| NO. | 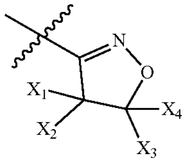 | Y | Z | Q | $^{1}H$ NMR |
|---|---|---|---|---|---|
| 17 | 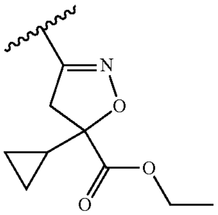 [SMILES: *C1=NOC(C(=O)OCC)(C2CC2)C1] | Cl | F | 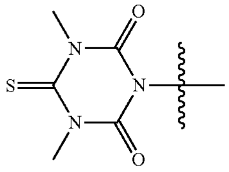 [SMILES: *n1c(=O)n(C)c(=S)n(C)c1=O] | $^{1}H$ NMR (500 MHz, DMSO-$d_6$) δ 7.94-7.91 (m, 2H), 4.23 (q, J = 7.5 Hz, 2H), 3.88 (d, J = 18.0 Hz, 1H), 3.65 (s, 6H), 3.46 (d, J = 18.0 Hz, 1H), 1.48-1.46 (m, 1H), 1.26 (1, J = 7.5 Hz, 3H), 0.60-0.50 (m, 3H), 0.37-0.34 (m, 1H). |
| 18 | 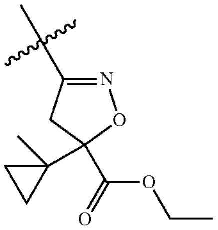 [SMILES: *C1=NOC(C(=O)OCC)(C2(C)CC2)C1] | Cl | F | 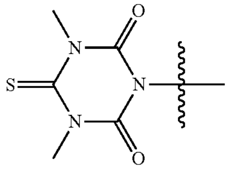 [SMILES: *n1c(=O)n(C)c(=S)n(C)c1=O] | |
| 19 | 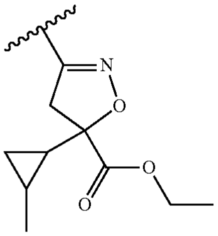 [SMILES: *C1=NOC(C(=O)OCC)(C2CC2C)C1] | Cl | F | 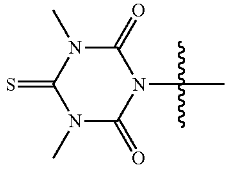 [SMILES: *n1c(=O)n(C)c(=S)n(C)c1=O] | |
| 20 | 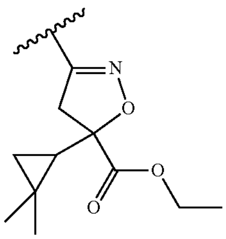 [SMILES: *C1=NOC(C(=O)OCC)(C2CC2(C)C)C1] | Cl | F | 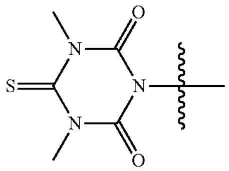 [SMILES: *n1c(=O)n(C)c(=S)n(C)c1=O] | |

TABLE 1-continued
Structures and $^1$H NMR data of compounds
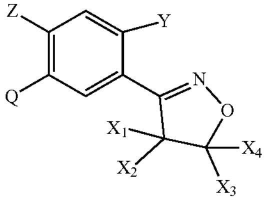
I
| NO. | 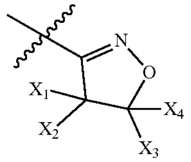 | Y | Z | Q | $^1$H NMR |
|---|---|---|---|---|---|
| 21 | 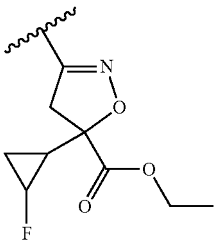 [SMILES: *C1=NOC(C(=O)OCC)(C2CC2F)C1] | Cl | F | 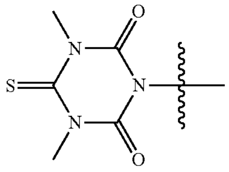 [SMILES: *n1c(=O)n(C)c(=S)n(C)c1=O] | |
| 22 | 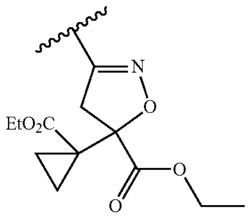 [SMILES: *C1=NOC(C(=O)OCC)(C2(C(=O)OCC)CC2)C1] | Cl | F | 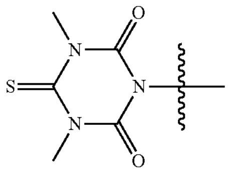 [SMILES: *n1c(=O)n(C)c(=S)n(C)c1=O] | |
| 23 | 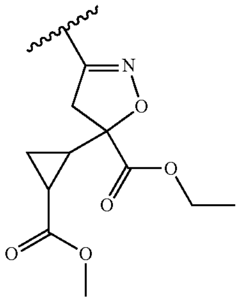 [SMILES: *C1=NOC(C(=O)OCC)(C2CC2C(=O)OC)C1] | Cl | F | 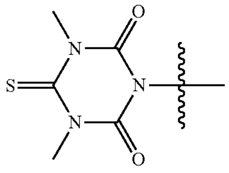 [SMILES: *n1c(=O)n(C)c(=S)n(C)c1=O] | |
| 24 | 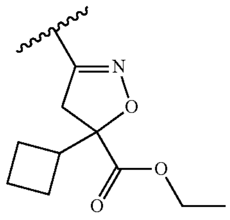 [SMILES: *C1=NOC(C(=O)OCC)(C2CCC2)C1] | Cl | F | 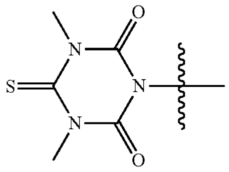 [SMILES: *n1c(=O)n(C)c(=S)n(C)c1=O] | |

TABLE 1-continued
Structures and $^1$H NMR data of compounds
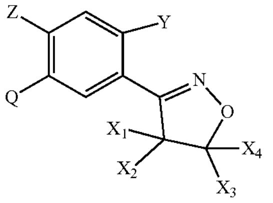
I
| NO. | 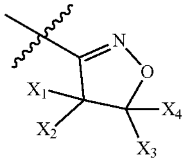 | Y | Z | Q | $^1$H NMR |
|---|---|---|---|---|---|
| 25 | 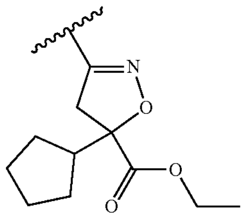 [SMILES: *C1=NOC(C(=O)OCC)(C2CCCC2)C1] | Cl | F | 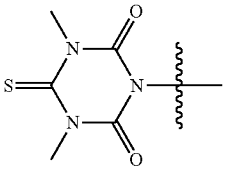 [SMILES: *n1c(=O)n(C)c(=S)n(C)c1=O] | |
| 26 | 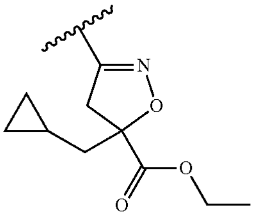 [SMILES: *C1=NOC(CC2CC2)(C(=O)OCC)C1] | Cl | F | 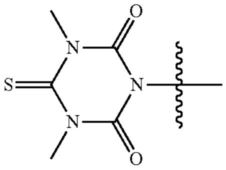 [SMILES: *n1c(=O)n(C)c(=S)n(C)c1=O] | $^1$H NMR (500 MHz, DMSO-$d_6$) δ 7.94 (d, J = 7.5 Hz, 1H), 7.90 (d, J = 9.5 Hz, 1H), 4.23-4.17 (m, 2H), 3.88 (d, J = 17.5 Hz, 1H), 3.67-3.62 (m, 7H), 1.90 (d, J = 7.0 Hz, 2H), 1.24 (t, J = 7.0 Hz, 3H), 0.76-0.68 (m, 1H), 0.45-0.41 (m, 2H), 0.16-0.12 (m, 2H). |
| 27 | 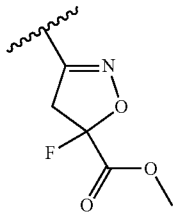 [SMILES: *C1=NOC(F)(C(=O)OC)C1] | Cl | F | 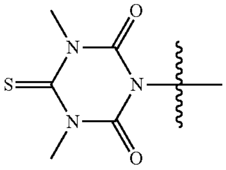 [SMILES: *n1c(=O)n(C)c(=S)n(C)c1=O] | |
| 28 | 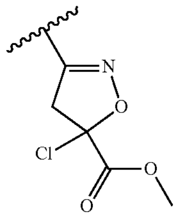 [SMILES: *C1=NOC(Cl)(C(=O)OC)C1] | Cl | F | 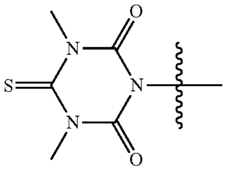 [SMILES: *n1c(=O)n(C)c(=S)n(C)c1=O] | |
| 29 | 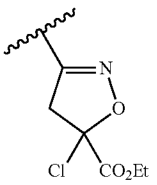 | Cl | F | 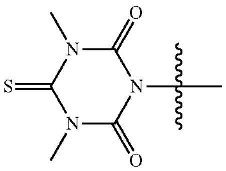 [SMILES: *n1c(=O)n(C)c(=S)n(C)c1=O] | |

TABLE 1-continued
Structures and $^1$H NMR data of compounds
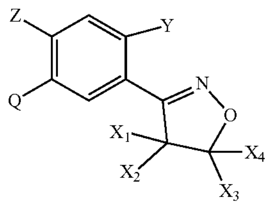
I
| NO. | 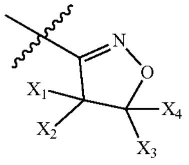 | Y | Z | Q | $^1$H NMR |
|---|---|---|---|---|---|
| 30 | 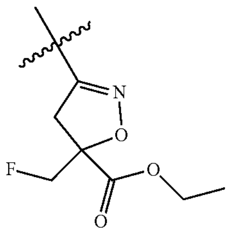 [SMILES: *C1=NOC(CF)(C(=O)OCC)C1] | Cl | F | 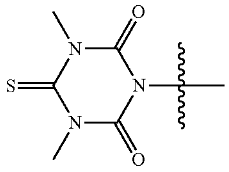 [SMILES: *n1c(=O)n(C)c(=S)n(C)c1=O] | |
| 31 | 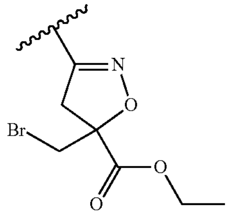 [SMILES: *C1=NOC(CBr)(C(=O)OCC)C1] | Cl | F | 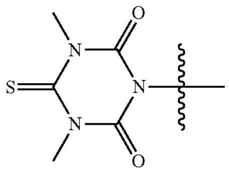 [SMILES: *n1c(=O)n(C)c(=S)n(C)c1=O] | $^1$H NMR (500 MHz, DMSO-$d_6$) δ 8.00 (d, J = 8.0 Hz, 1H), 7.94 (d, J = 9.5 Hz, 1H), 4.26 (q, J = 7.0 Hz, 2H), 4.08-4.01 (m, 2H), 3.99 (d, J = 17.5 Hz, 1H), 3.68-3.62 (m, 7H), 1.29-1.25 (m, 3H). |
| 32 | 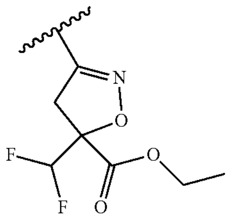 [SMILES: *C1=NOC(C(=O)OCC)(C(F)F)C1] | Cl | F | 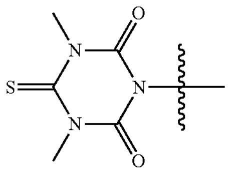 [SMILES: *n1c(=O)n(C)c(=S)n(C)c1=O] | |
| 33 | 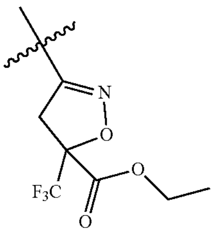 [SMILES: *C1=NOC(C(=O)OCC)(C(F)(F)F)C1] | Cl | F | 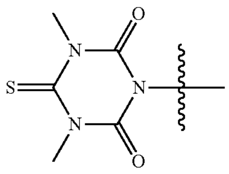 [SMILES: *n1c(=O)n(C)c(=S)n(C)c1=O] | 1H NMR (500 MHz, DMSO-$d_6$) δ 8.02 (d, J = 7.5 Hz, 1H), 7.98 (d, J = 9.5 Hz, 1H), 4.37-4.31 (m, 3H), 4.18 (d, J = 18.5 Hz, 1H), 3.65 (s, 6H), 1.28 (1, J = 7.5 Hz, 3H). |
| 34 | 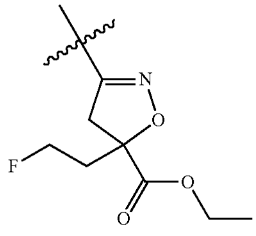 [SMILES: *C1=NOC(CCF)(C(=O)OCC)C1] | Cl | F | 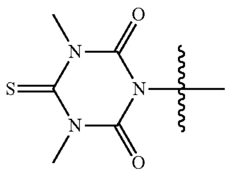 [SMILES: *n1c(=O)n(C)c(=S)n(C)c1=O] | $^1$H NMR (500 MHz, DMSO-$d_6$) δ 7.94 (d, J = 7.5 Hz, 1H), 7.91 (d, J = 9.5 Hz, 1H), 4.65 (t, J = 5.5 Hz, 1H), 4.56 (t, J = 5.5 Hz, 1H), 4.19 (q, J = 7.0 Hz, 2H), 3.90 (d, J = 17.5 Hz, 1H), 3.69 (d, J = 17.5 Hz, 1H), 3.62 (s, 6H), 2.45-2.37 (m, 2H), 1.22 (t, J = 7.0 Hz, 3H). |

TABLE 1-continued
Structures and $^1$H NMR data of compounds
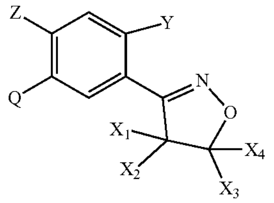
I
| NO. | 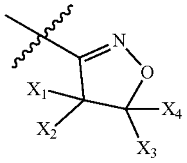 | Y | Z | Q | $^1$H NMR |
|---|---|---|---|---|---|
| 35 | 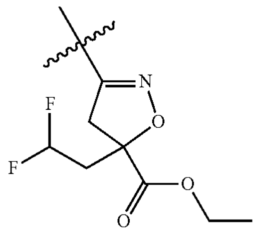 [SMILES: *C1=NOC(CC(F)F)(C(=O)OCC)C1] | Cl | F | 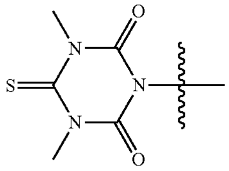 [SMILES: *n1c(=O)n(C)c(=S)n(C)c1=O] | $^1$H NMR (500 MHz, DMSO-$d_6$) δ 7.97 (d, J = 7.5 Hz, 1H), 7.93 (d, J = 9.5 Hz, 1H), 6.38-6.16 (m, 1H), 4.25-4.20 (m, 2H), 3.95 (d, J = 17.5 Hz, 1H), 3.77 (d, J = 17.5 Hz, 1H), 3.65 (s, 6H), 2.75-2.68 (m, 2H), 1.26-1.23 (m, 3H) |
| 36 | 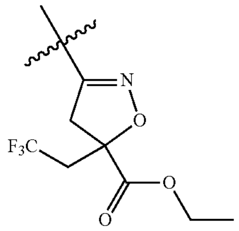 [SMILES: *C1=NOC(CC(F)(F)F)(C(=O)OCC)C1] | Cl | F | 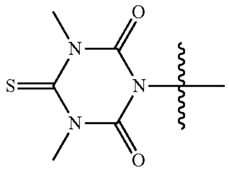 [SMILES: *n1c(=O)n(C)c(=S)n(C)c1=O] | |
| 37 | 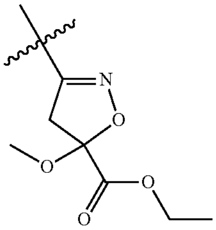 [SMILES: *C1=NOC(OC)(C(=O)OCC)C1] | Cl | F | 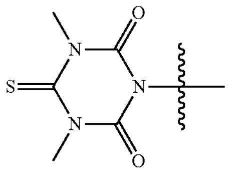 [SMILES: *n1c(=O)n(C)c(=S)n(C)c1=O] | |
| 38 | 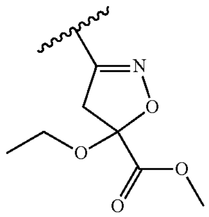 [SMILES: *C1=NOC(OCC)(C(=O)OC)C1] | Cl | F | 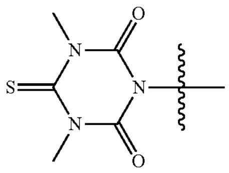 [SMILES: *n1c(=O)n(C)c(=S)n(C)c1=O] | |
| 39 | 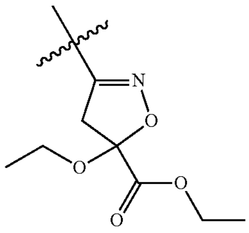 [SMILES: *C1=NOC(OCC)(C(=O)OCC)C1] | Cl | F | 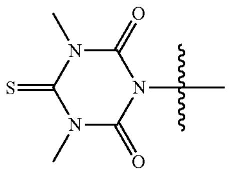 [SMILES: *n1c(=O)n(C)c(=S)n(C)c1=O] | |

TABLE 1-continued
Structures and $^1$H NMR data of compounds
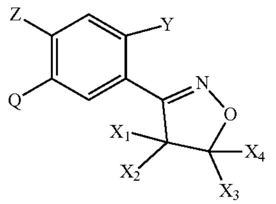
I
| NO. | 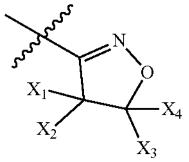 | Y | Z | Q | $^1$H NMR |
|---|---|---|---|---|---|
| 40 | 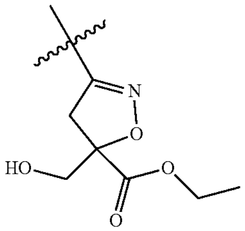 [SMILES: *C1=NOC(CO)(C(=O)OCC)C1] | Cl | F | 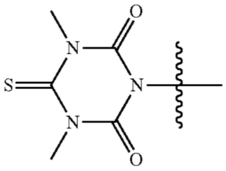 | |
| 41 | 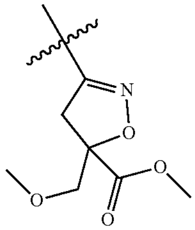 | Cl | F | 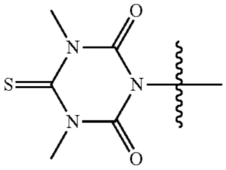 [SMILES: *n1c(=O)n(C)c(=S)n(C)c1=O] | |
| 42 | 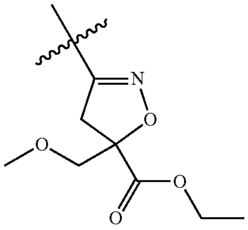 [SMILES: *C1=NOC(COC)(C(=O)OCC)C1] | Cl | F | 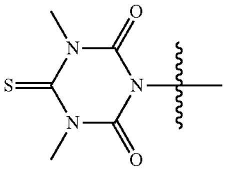 [SMILES: *n1c(=O)n(C)c(=S)n(C)c1=O] | |
| 43 | 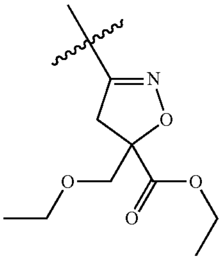 [SMILES: *C1=NOC(COCC)(C(=O)OCC)C1] | Cl | F | 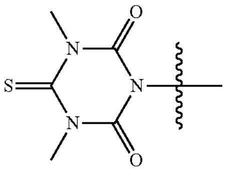 [SMILES: *n1c(=O)n(C)c(=S)n(C)c1=O] | $^1$H NMR (500 MHz, DMSO-$d_6$) δ 7.97-7.91 (m, 2H), 4.22 (q, J = 7.0 Hz, 2H), 3.90-3.75 (m, 3H), 3.67-3.64 (m, 7H), 3.56-3.53 (m, 2H), 1.24 (t, J = 7.0 Hz, 3H), 1.11 (t, J = 7.0 Hz. 3H). |

TABLE 1-continued
Structures and ¹H NMR data of compounds
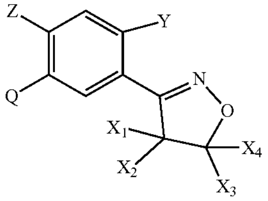
I
| NO. | 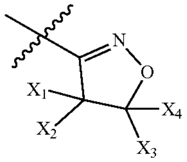 | Y | Z | Q | $^1$H NMR |
|---|---|---|---|---|---|
| 44 | 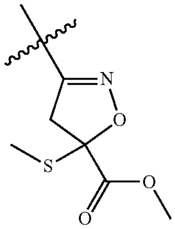 | Cl | F | 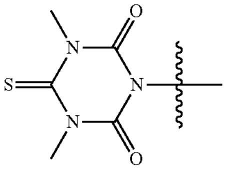 [SMILES: *n1c(=O)n(C)c(=S)n(C)c1=O] | |
| 45 | 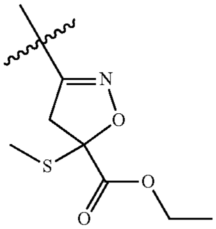 | Cl | F | 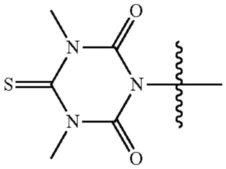 [SMILES: *n1c(=O)n(C)c(=S)n(C)c1=O] | |
| 46 | 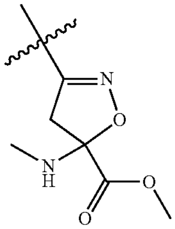 | Cl | F | 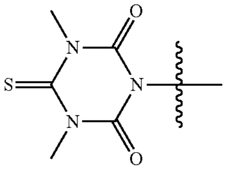 | |
| 47 | 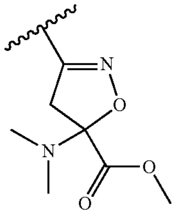 | Cl | F | 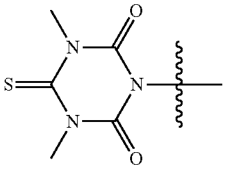 | |
| 48 | 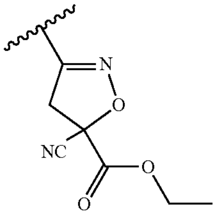 | Cl | F | 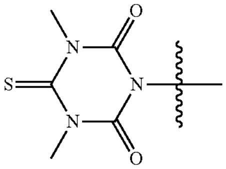 [SMILES: *n1c(=O)n(C)c(=S)n(C)c1=O] | |

TABLE 1-continued
Structures and $^1$H NMR data of compounds
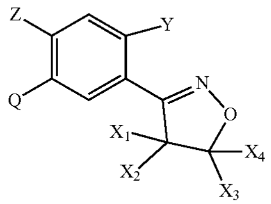
I
| NO. | 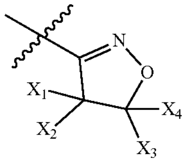 | Y | Z | Q | $^1$H NMR |
|---|---|---|---|---|---|
| 49 | 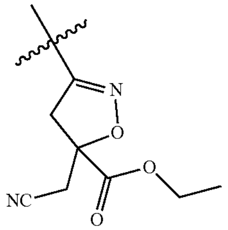 [SMILES: *C1=NOC(CC#N)(C(=O)OCC)C1] | Cl | F | 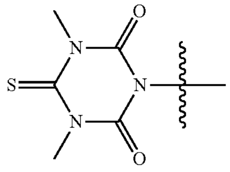 [SMILES: *n1c(=O)n(C)c(=S)n(C)c1=O] | |
| 50 | 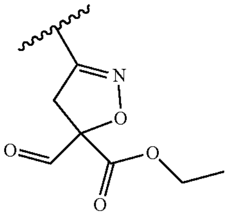 [SMILES: *C1=NOC(C=O)(C(=O)OCC)C1] | Cl | F | 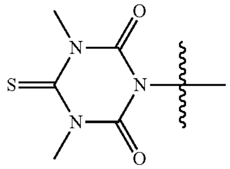 [SMILES: *n1c(=O)n(C)c(=S)n(C)c1=O] | |
| 51 | 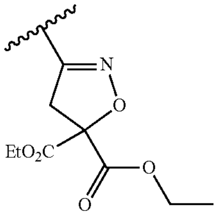 [SMILES: *C1=NOC(C(=O)OCC)(C(=O)OCC)C1] | Cl | F | 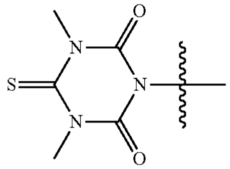 [SMILES: *n1c(=O)n(C)c(=S)n(C)c1=O] | |
| 52 | 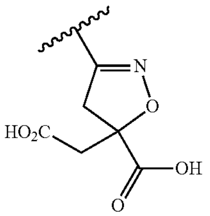 [SMILES: *C1=NOC(CC(=O)O)(C(=O)O)C1] | Cl | F | 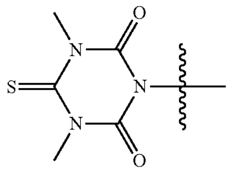 [SMILES: *n1c(=O)n(C)c(=S)n(C)c1=O] | $^1$H NMR (500 MHz, DMSO-$d_6$) δ 7.74 (d, J = 7.5 Hz, 1H), 7.40 (d, J = 9.0 Hz, 1H), 4.12-4.06 (m, 1H), 3.76 (s, 6H), 3.71-3.65 (m, 1H), 3.30-3.12 (m, 2H). |
| 53 | 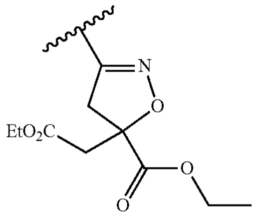 [SMILES: *C1=NOC(CC(=O)OCC)(C(=O)OCC)C1] | Cl | F | 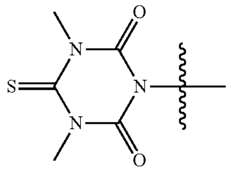 [SMILES: *n1c(=O)n(C)c(=S)n(C)c1=O] | $^1$H NMR (500 MHz, Chloroform-d) δ 7.75 (d, J = 7.5 Hz, 1H), 7.41 (d, J = 9.0 Hz, 1H), 4.36-4.28 (m, 2H), 4.23-4.15 (m, 3H), 3.81 (s, 6H), 3.69 (d, J = 17.5 Hz, 1H), 3.27 (d, J = 17.5 Hz, 1H), 3.07-2.96 (m, 1H), 1.35 (t, J = 7.0 Hz, 3H), 1.30 (t, J = 7.0 Hz, 3H). |

TABLE 1-continued
Structures and $^{1}H$ NMR data of compounds
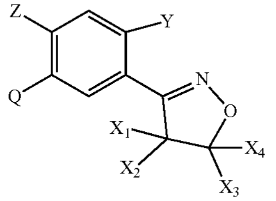
I
| NO. | 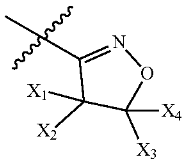 | Y | Z | Q | $^{1}H$ NMR |
|---|---|---|---|---|---|
| 54 | 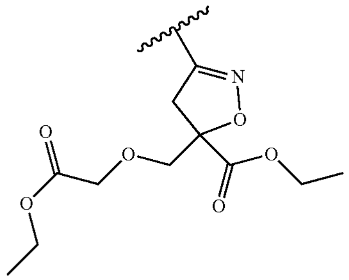 [SMILES: *C1=NOC(COCC(=O)OCC)(C(=O)OCC)C1] | Cl | F | 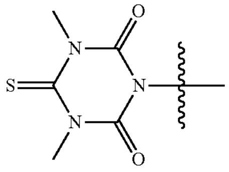 [SMILES: *n1c(=O)n(C)c(=S)n(C)c1=O] | $^{1}H$ NMR (500 MHz, DMSO-$d_6$) δ 7.99-7.91 (m, 2H), 4.26-4.20 (m, 4H), 4.15 (q, J = 7.5Hz, 2H), 3.96-3.93 (m, 2H), 3.89-3.76 (m, 2H), 3.65 (s, 6H), 1.25 (t, J = 7.5 Hz, 3H), 1.21 (t, J = 7.5 Hz, 3H). |
| 55 | 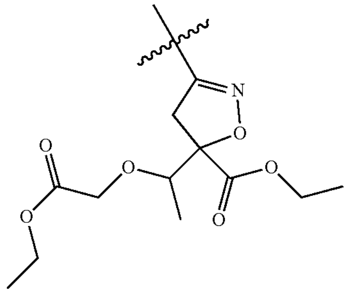 [SMILES: *C1=NOC(C(=O)OCC)(C(C)OCC(=O)OCC)C1] | Cl | F | 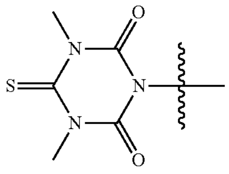 [SMILES: *n1c(=O)n(C)c(=S)n(C)c1=O] | $^{1}H$ NMR (500 MHz, DMSO-$d_6$) δ 7.97 (d, J = 7.5 Hz, 1H), 7.92 (d, J = 9.5 Hz, 1H), 4.30-4.09 (m, 4H), 3.98-3.92 (m, 1H), 3.88-3.78 (m, 3H), 3.77-3.72 (m, 1H), 3.65 (s, 6H), 1.30-1.28 (m, 3H), 1.26-1.23 (m, 3H), 1.22-1.18 (m, 3H). |
| 56 | 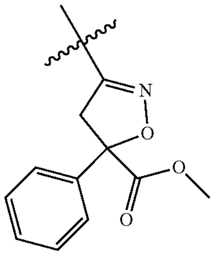 [SMILES: *C1=NOC(C(=O)OC)(c2ccccc2)C1] | Cl | F | 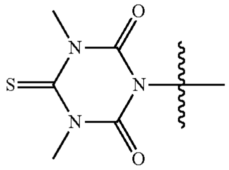 [SMILES: *n1c(=O)n(C)c(=S)n(C)c1=O] | $^{1}H$ NMR (500 MHz, DMSO-$d_6$) δ 8.01-7.90 (m, 2H), 7.55-7.39 (m, 5H), 4.43 (d, J = 17.5 Hz, 1H), 3.91 (d, J = 17.5 Hz, 1H), 3.74 (s, 3H), 3.64 (s, 6H). |
| 57 | 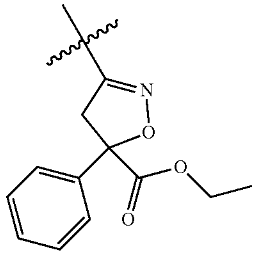 [SMILES: *C1=NOC(C(=O)OCC)(c2ccccc2)C1] | Cl | F | 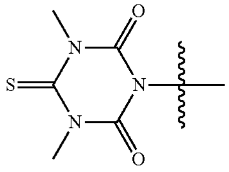 [SMILES: *n1c(=O)n(C)c(=S)n(C)c1=O] | |

TABLE 1-continued
Structures and $^1$H NMR data of compounds
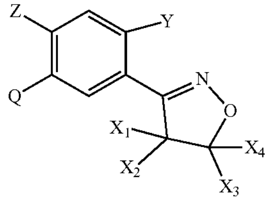
I
| NO. | 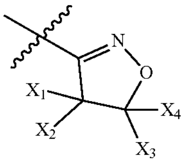 | Y | Z | Q | $^1$H NMR |
|---|---|---|---|---|---|
| 58 | 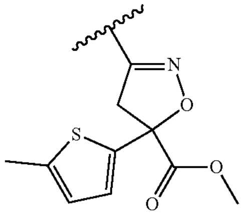 | Cl | F | 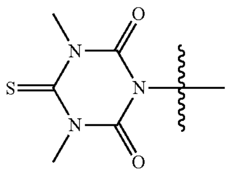 [SMILES: *n1c(=O)n(C)c(=S)n(C)c1=O] | |
| 59 | 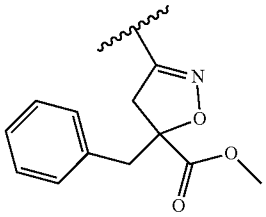 [SMILES: *C1=NOC(Cc2ccccc2)(C(=O)OC)C1] | Cl | F | 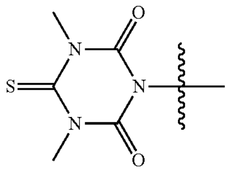 [SMILES: *n1c(=O)n(C)c(=S)n(C)c1=O] | $^1$H NMR (500 MHz, DMSO-$d_6$) δ 7.86-7.81 (m, 2H), 7.35-7.22 (m, 5H), 3.82 (d, J = 17.5 Hz, 1H), 3.71 (s, 3H), 3.62-3.59 (m, 7H), 3.34-3.24 (m, 2H). |
| 60 | 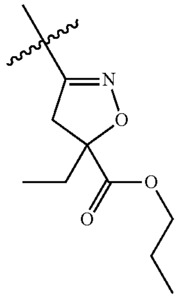 [SMILES: *C1=NOC(CC)(C(=O)OCCC)C1] | Cl | F | 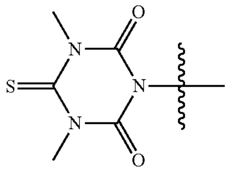 [SMILES: *n1c(=O)n(C)c(=S)n(C)c1=O] | |
| 61 | 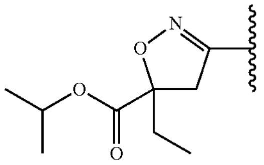 [SMILES: *C1=NOC(CC)(C(=O)OC(C)C)C1] | Cl | F | 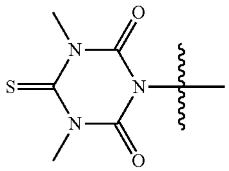 [SMILES: *n1c(=O)n(C)c(=S)n(C)c1=O] | |
| 62 | 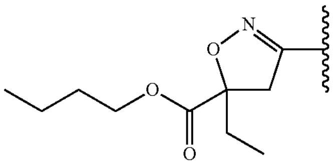 [SMILES: *C1=NOC(CC)(C(=O)OCCCC)C1] | Cl | F | 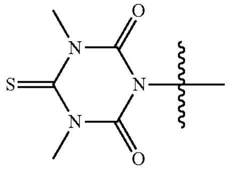 [SMILES: *n1c(=O)n(C)c(=S)n(C)c1=O] | |

TABLE 1-continued
Structures and $^1$H NMR data of compounds
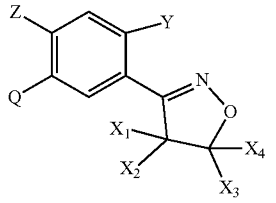
I
| NO. | 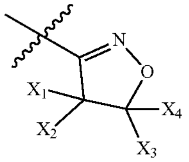 | Y | Z | Q | $^1$H NMR |
|---|---|---|---|---|---|
| 63 | 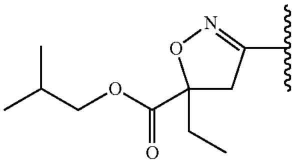 | Cl | F | 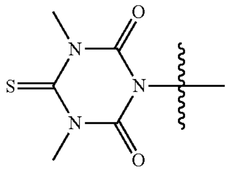 [SMILES: *n1c(=O)n(C)c(=S)n(C)c1=O] | |
| 64 | 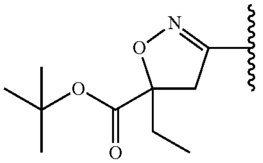 [SMILES: *C1=NOC(CC)(C(=O)OC(C)(C)C)C1] | Cl | F | 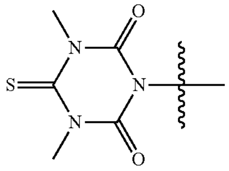 [SMILES: *n1c(=O)n(C)c(=S)n(C)c1=O] | |
| 65 | 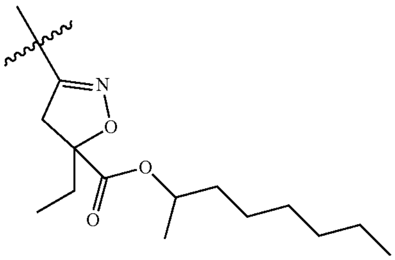 [SMILES: *C1=NOC(CC)(C(=O)OC(C)CCCCCC)C1] | Cl | F | 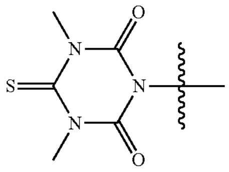 [SMILES: *n1c(=O)n(C)c(=S)n(C)c1=O] | |
| 66 | 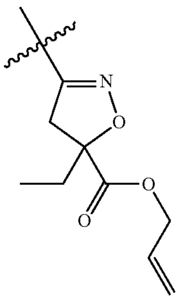 [SMILES: *C1=NOC(CC)(C(=O)OCC=C)C1] | Cl | F | 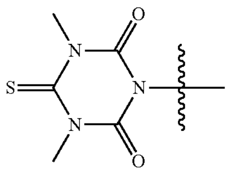 [SMILES: *n1c(=O)n(C)c(=S)n(C)c1=O] | |
| 67 | 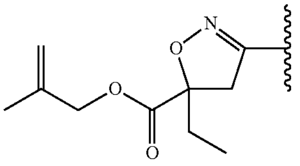 [SMILES: *C1=NOC(CC)(C(=O)OCC(=C)C)C1] | Cl | F | 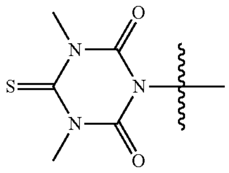 [SMILES: *n1c(=O)n(C)c(=S)n(C)c1=O] | |

TABLE 1-continued
Structures and $^1$H NMR data of compounds
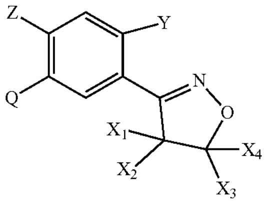
I
| NO. | 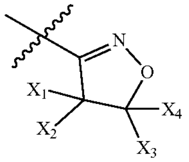 | Y | Z | Q | $^1$H NMR |
|---|---|---|---|---|---|
| 68 | 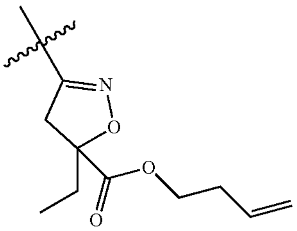 [SMILES: *C1=NOC(CC)(C(=O)OCCC=C)C1] | Cl | F | 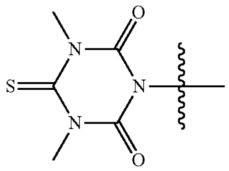 [SMILES: *n1c(=O)n(C)c(=S)n(C)c1=O] | |
| 69 | 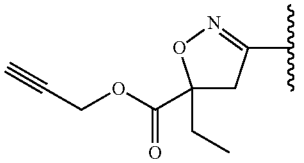 [SMILES: *C1=NOC(CC)(C(=O)OCC#C)C1] | Cl | F | 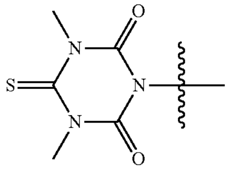 [SMILES: *n1c(=O)n(C)c(=S)n(C)c1=O] | |
| 70 | 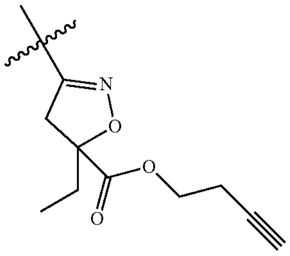 [SMILES: *C1=NOC(CC)(C(=O)OCCC#C)C1] | Cl | F | 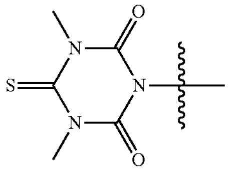 [SMILES: *n1c(=O)n(C)c(=S)n(C)c1=O] | |
| 71 | 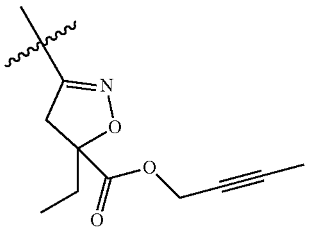 [SMILES: *C1=NOC(CC)(C(=O)OCC#CC)C1] | Cl | F | 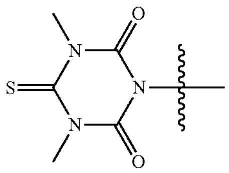 [SMILES: *n1c(=O)n(C)c(=S)n(C)c1=O] | |
| 72 | 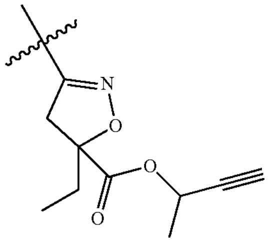 [SMILES: *C1=NOC(CC)(C(=O)OC(C)C#C)C1] | Cl | F | 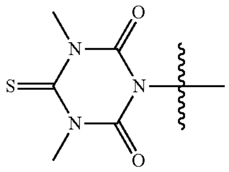 [SMILES: *n1c(=O)n(C)c(=S)n(C)c1=O] | |

TABLE 1-continued
Structures and $^1$H NMR data of compounds
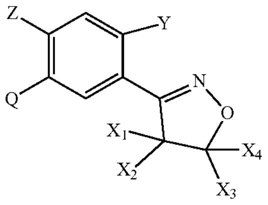
I
| NO. | 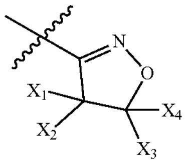 | Y | Z | Q | $^1$H NMR |
|---|---|---|---|---|---|
| 73 | 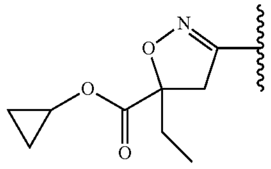 [SMILES: *C1=NOC(CC)(C(=O)OC2CC2)C1] | Cl | F | 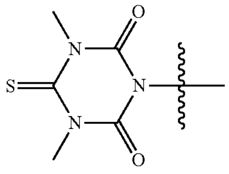 [SMILES: *n1c(=O)n(C)c(=S)n(C)c1=O] | |
| 74 | 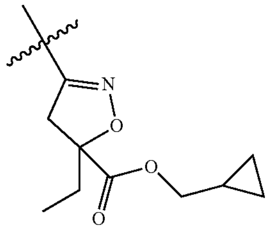 [SMILES: *C1=NOC(CC)(C(=O)OCC2CC2)C1] | Cl | F | 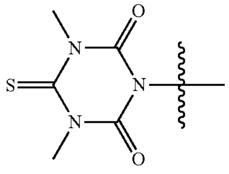 [SMILES: *n1c(=O)n(C)c(=S)n(C)c1=O] | |
| 75 | 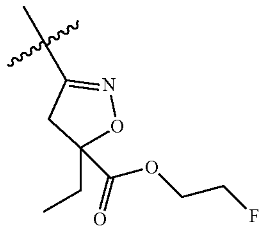 [SMILES: *C1=NOC(CC)(C(=O)OCCF)C1] | Cl | F | 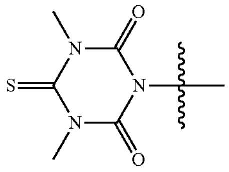 [SMILES: *n1c(=O)n(C)c(=S)n(C)c1=O] | |
| 76 | 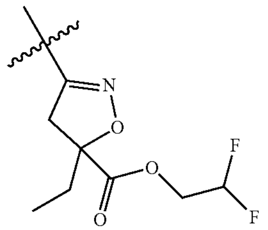 [SMILES: *C1=NOC(CC)(C(=O)OCC(F)F)C1] | Cl | F | 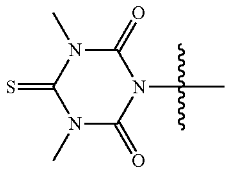 [SMILES: *n1c(=O)n(C)c(=S)n(C)c1=O] | |
| 77 | 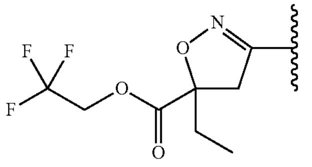 [SMILES: *C1=NOC(CC)(C(=O)OCC(F)(F)F)C1] | Cl | F | 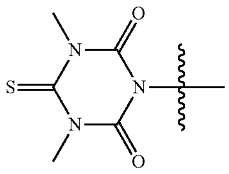 [SMILES: *n1c(=O)n(C)c(=S)n(C)c1=O] | |

TABLE 1-continued
Structures and $^{1}$H NMR data of compounds
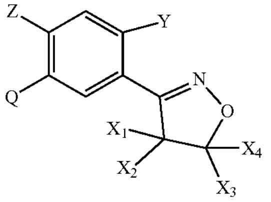
I
| NO. | 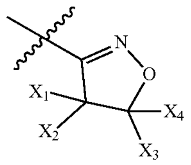 | Y | Z | Q | $^{1}$H NMR |
|---|---|---|---|---|---|
| 78 | 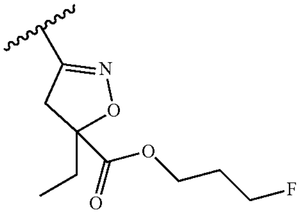 [SMILES: *C1=NOC(CC)(C(=O)OCCCF)C1] | Cl | F | 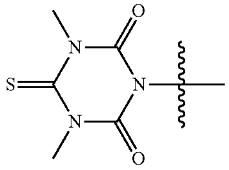 [SMILES: *n1c(=O)n(C)c(=S)n(C)c1=O] | |
| 79 | 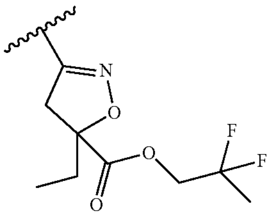 [SMILES: *C1=NOC(CC)(C(=O)OCC(C)(F)F)C1] | Cl | F | 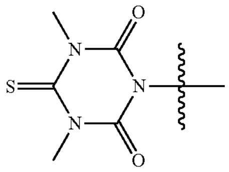 [SMILES: *n1c(=O)n(C)c(=S)n(C)c1=O] | |
| 80 | 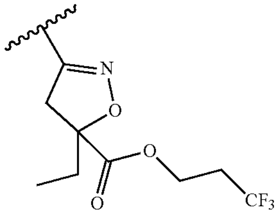 [SMILES: *C1=NOC(CC)(C(=O)OCCC(F)(F)F)C1] | Cl | F | 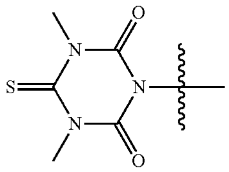 [SMILES: *n1c(=O)n(C)c(=S)n(C)c1=O] | |
| 81 | 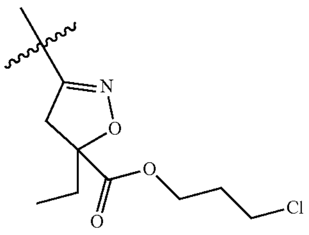 [SMILES: *C1=NOC(CC)(C(=O)OCCCCl)C1] | Cl | F | 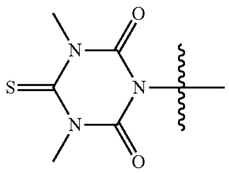 [SMILES: *n1c(=O)n(C)c(=S)n(C)c1=O] | |
| 82 | 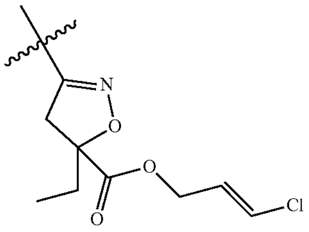 [SMILES: *C1=NOC(CC)(C(=O)OC/C=C/Cl)C1] | Cl | F | 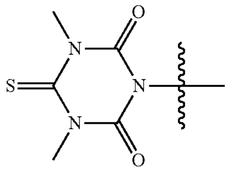 [SMILES: *n1c(=O)n(C)c(=S)n(C)c1=O] | |

TABLE 1-continued
Structures and $^{1}$H NMR data of compounds
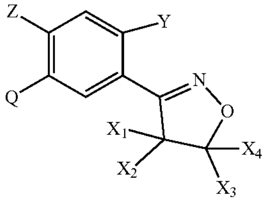
I
| NO. | 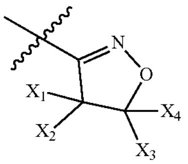 | Y | Z | Q | $^{1}$H NMR |
|---|---|---|---|---|---|
| 83 | 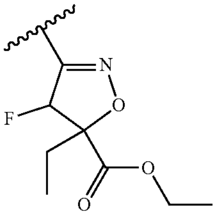 [SMILES: *C1=NOC(CC)(C(=O)OCC)C1F] | Cl | F | 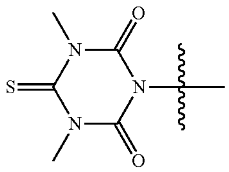 [SMILES: *n1c(=O)n(C)c(=S)n(C)c1=O] | |
| 84 | 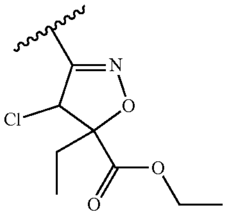 [SMILES: *C1=NOC(CC)(C(=O)OCC)C1Cl] | Cl | F | 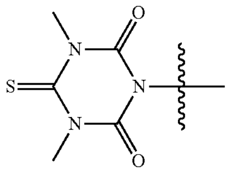 [SMILES: *n1c(=O)n(C)c(=S)n(C)c1=O] | |
| 85 | 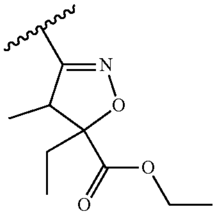 [SMILES: *C1=NOC(CC)(C(=O)OCC)C1C] | Cl | F | 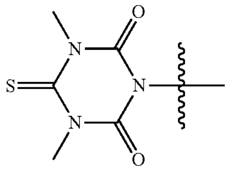 [SMILES: *n1c(=O)n(C)c(=S)n(C)c1=O] | |
| 86 | 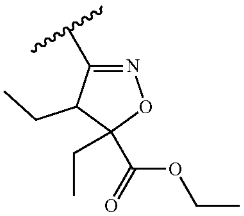 [SMILES: *C1=NOC(CC)(C(=O)OCC)C1CC] | Cl | F | 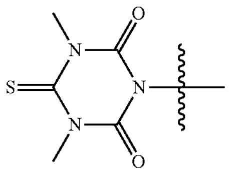 [SMILES: *n1c(=O)n(C)c(=S)n(C)c1=O] | |
| 87 | 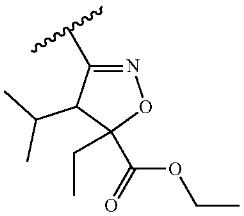 [SMILES: *C1=NOC(CC)(C(=O)OCC)C1C(C)C] | Cl | F | 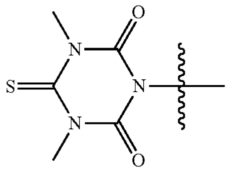 [SMILES: *n1c(=O)n(C)c(=S)n(C)c1=O] | |

TABLE 1-continued
Structures and $^1$H NMR data of compounds
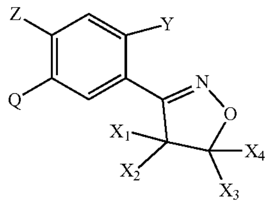
I
| NO. | 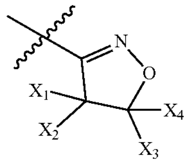 | Y | Z | Q | $^1$H NMR |
|---|---|---|---|---|---|
| 88 | 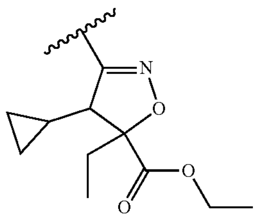 [SMILES: *C1=NOC(CC)(C(=O)OCC)C1C1CC1] | Cl | F | 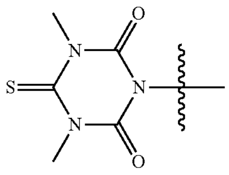 [SMILES: *n1c(=O)n(C)c(=S)n(C)c1=O] | |
| 89 | 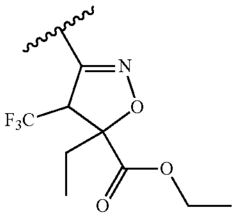 [SMILES: *C1=NOC(CC)(C(=O)OCC)C1C(F)(F)F] | Cl | F | 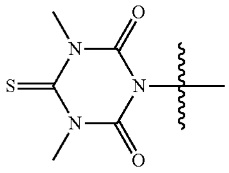 [SMILES: *n1c(=O)n(C)c(=S)n(C)c1=O] | |
| 90 | 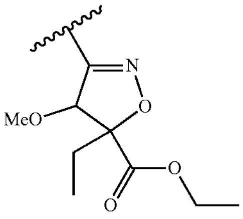 [SMILES: *C1=NOC(CC)(C(=O)OCC)C1OC] | Cl | F | 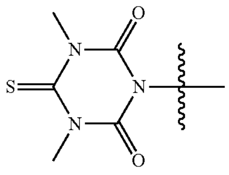 [SMILES: *n1c(=O)n(C)c(=S)n(C)c1=O] | |
| 91 | 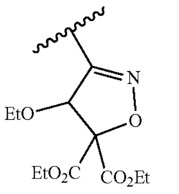 | Cl | F | 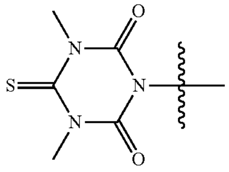 [SMILES: *n1c(=O)n(C)c(=S)n(C)c1=O] | |
| 92 | 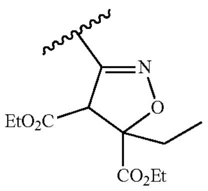 | Cl | F | 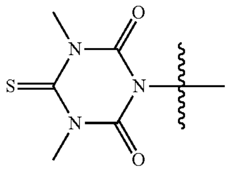 [SMILES: *n1c(=O)n(C)c(=S)n(C)c1=O] | |

TABLE 1-continued
Structures and $^{1}H$ NMR data of compounds
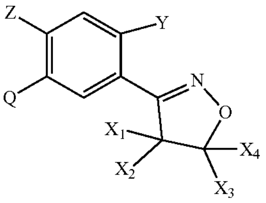
I
| NO. | 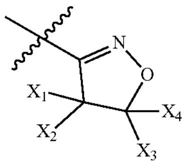 | Y | Z | Q | $^{1}H$ NMR |
|---|---|---|---|---|---|
| 93 | 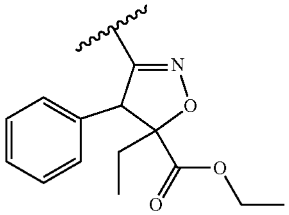 [SMILES: *C1=NOC(CC)(C(=O)OCC)C1c1ccccc1] | Cl | F | 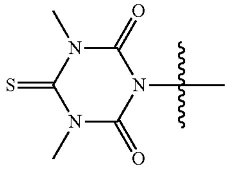 [SMILES: *n1c(=O)n(C)c(=S)n(C)c1=O] | |
| 94 | 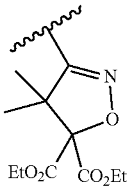 [SMILES: *C1=NOC(C(=O)OCC)(C(=O)OCC)C1(C)C] | Cl | F | 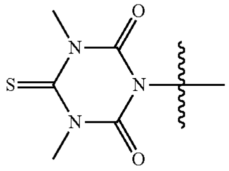 [SMILES: *n1c(=O)n(C)c(=S)n(C)c1=O] | |
| 95 | 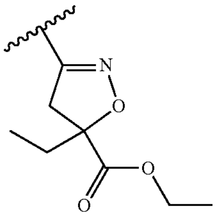 [SMILES: *C1=NOC(CC)(C(=O)OCC)C1] | Br | F | 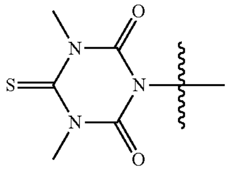 [SMILES: *n1c(=O)n(C)c(=S)n(C)c1=O] | |
| 96 | 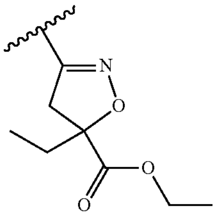 [SMILES: *C1=NOC(CC)(C(=O)OCC)C1] | $CF_3$ | F | 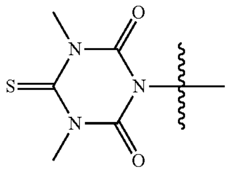 | |
| 97 | 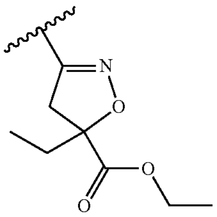 [SMILES: *C1=NOC(CC)(C(=O)OCC)C1] | CN | F | 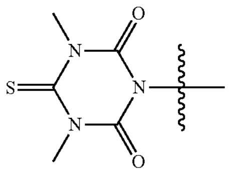 [SMILES: *n1c(=O)n(C)c(=S)n(C)c1=O] | |

TABLE 1-continued
Structures and $^1$H NMR data of compounds
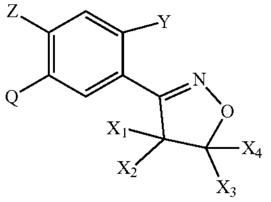
I
| NO. | 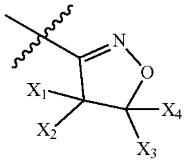 | Y | Z | Q | $^1$H NMR |
| --- | --- | --- | --- | --- | --- |
| 98 | 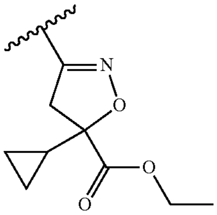 [SMILES: *C1=NOC(C(=O)OCC)(C2CC2)C1] | Br | F | 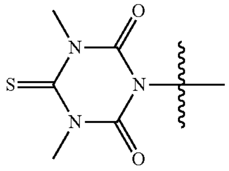 [SMILES: *n1c(=O)n(C)c(=S)n(C)c1=O] | |
| 99 | 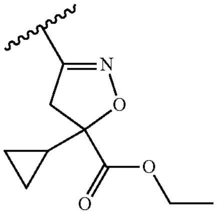 [SMILES: *C1=NOC(C(=O)OCC)(C2CC2)C1] | $CF_3$ | F | 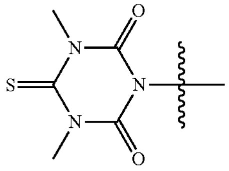 [SMILES: *n1c(=O)n(C)c(=S)n(C)c1=O] | |
| 100 | 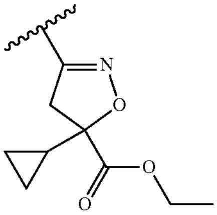 [SMILES: *C1=NOC(C(=O)OCC)(C2CC2)C1] | CN | F | 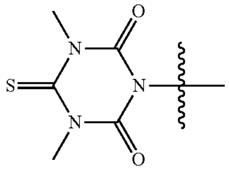 [SMILES: *n1c(=O)n(C)c(=S)n(C)c1=O] | |
| 101 | 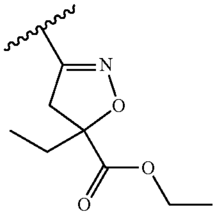 [SMILES: *C1=NOC(CC)(C(=O)OCC)C1] | Cl | F | 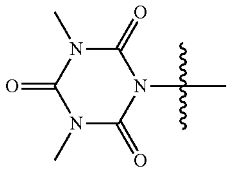 [SMILES: *n1c(=O)n(C)c(=O)n(C)c1=O] | |
| 102 | 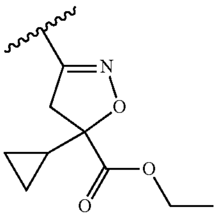 [SMILES: *C1=NOC(C(=O)OCC)(C2CC2)C1] | Cl | F | 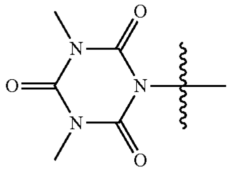 [SMILES: *n1c(=O)n(C)c(=O)n(C)c1=O] | |

TABLE 1-continued
Structures and $^1$H NMR data of compounds
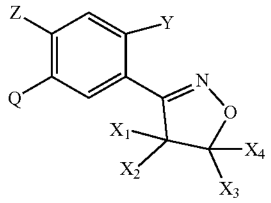
I
| NO. | 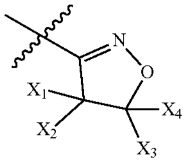 | Y | Z | Q | $^1$H NMR |
|---|---|---|---|---|---|
| 103 | 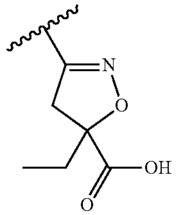 [SMILES: *C1=NOC(CC)(C(=O)O)C1] | Cl | F | 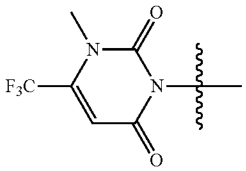 [SMILES: *n1c(=O)cc(C(F)(F)F)n(C)c1=O] | |
| 104 | 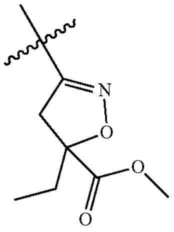 [SMILES: *C1=NOC(CC)(C(=O)OC)C1] | Cl | F | 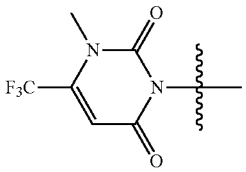 [SMILES: *n1c(=O)cc(C(F)(F)F)n(C)c1=O] | |
| 105 | 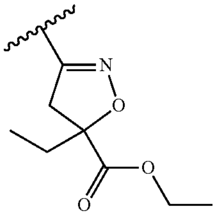 [SMILES: *C1=NOC(CC)(C(=O)OCC)C1] | Cl | F | 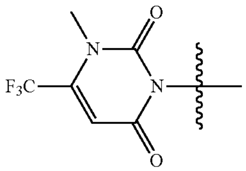 [SMILES: *n1c(=O)cc(C(F)(F)F)n(C)c1=O] | 1H NMR (500 MHz, DMSO-$d_6$) δ 7.92-7.87 (m, 2H), 6.64 (s, 1H), 4.21 (q, J = 7.0 Hz, 2H), 3.86 (dd, J = 18.0, 5.5 Hz, 1H), 3.56 (dd, J = 18.0, 5.5 Hz, 1H), 3.43 (s, 3H), 1.99-1.95 (m, 2H), 1.24 (t, J = 7.0 Hz, 3H), 0.92 (t, J = 7.0 Hz, 3H). |
| 106 | 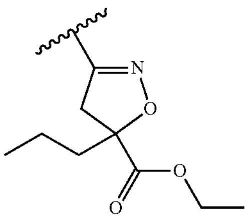 [SMILES: *C1=NOC(CCC)(C(=O)OCC)C1] | Cl | F | 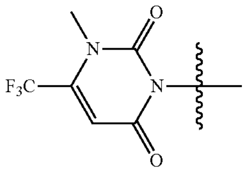 [SMILES: *n1c(=O)cc(C(F)(F)F)n(C)c1=O] | |
| 107 | 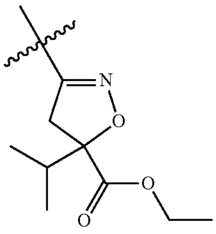 [SMILES: *C1=NOC(C(=O)OCC)(C(C)C)C1] | Cl | F | 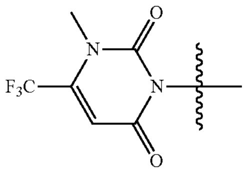 [SMILES: *n1c(=O)cc(C(F)(F)F)n(C)c1=O] | |

TABLE 1-continued
Structures and $^1H$ NMR data of compounds
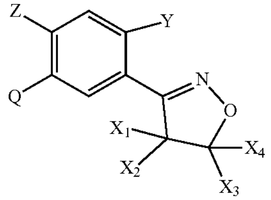
I
| NO. | 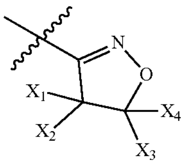 | Y | Z | Q | $^1H$ NMR |
|---|---|---|---|---|---|
| 108 | 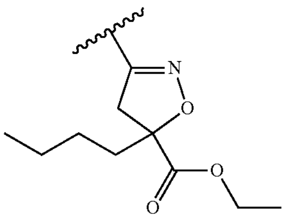 [SMILES: *C1=NOC(CCCC)(C(=O)OCC)C1] | Cl | F | 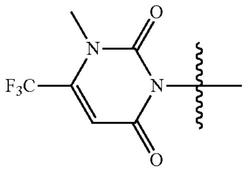 [SMILES: *n1c(=O)cc(C(F)(F)F)n(C)c1=O] | |
| 109 | 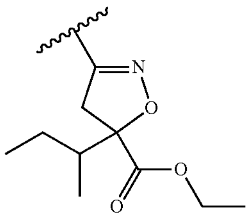 [SMILES: *C1=NOC(C(=O)OCC)(C(C)CC)C1] | Cl | F | 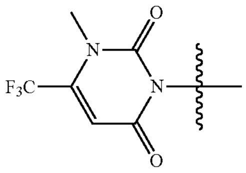 [SMILES: *n1c(=O)cc(C(F)(F)F)n(C)c1=O] | |
| 110 | 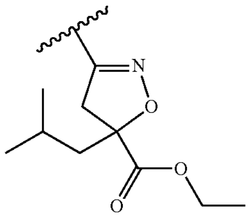 [SMILES: *C1=NOC(CC(C)C)(C(=O)OCC)C1] | Cl | F | 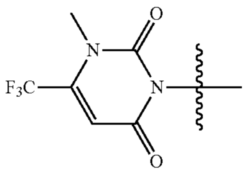 [SMILES: *n1c(=O)cc(C(F)(F)F)n(C)c1=O] | |
| 111 | 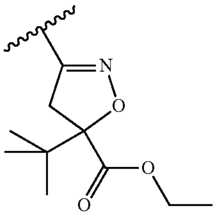 [SMILES: *C1=NOC(C(=O)OCC)(C(C)(C)C)C1] | Cl | F | 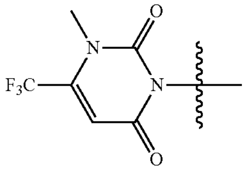 [SMILES: *n1c(=O)cc(C(F)(F)F)n(C)c1=O] | |
| 112 | 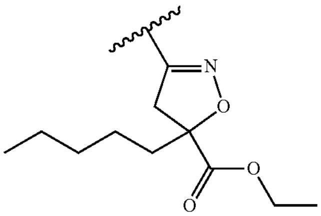 [SMILES: *C1=NOC(CCCCC)(C(=O)OCC)C1] | Cl | F | 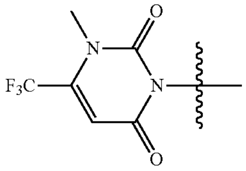 [SMILES: *n1c(=O)cc(C(F)(F)F)n(C)c1=O] | |

TABLE 1-continued
Structures and $^1$H NMR data of compounds
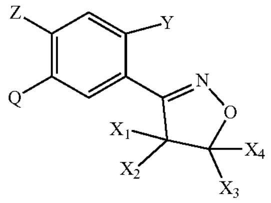
I
| NO. | 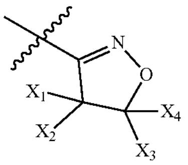 | Y | Z | Q | $^1$H NMR |
|---|---|---|---|---|---|
| 113 | 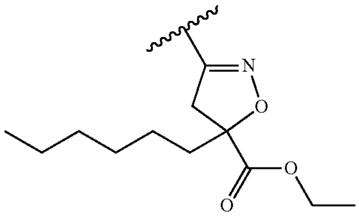 [SMILES: *C1=NOC(CCCCCC)(C(=O)OCC)C1] | Cl | F | 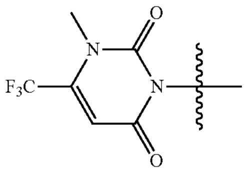 [SMILES: *n1c(=O)cc(C(F)(F)F)n(C)c1=O] | |
| 114 | 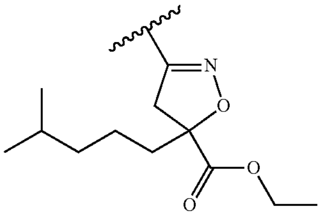 [SMILES: *C1=NOC(CCCC(C)C)(C(=O)OCC)C1] | Cl | F | 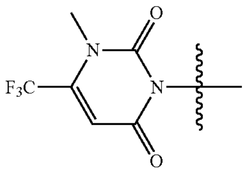 [SMILES: *n1c(=O)cc(C(F)(F)F)n(C)c1=O] | |
| 115 | 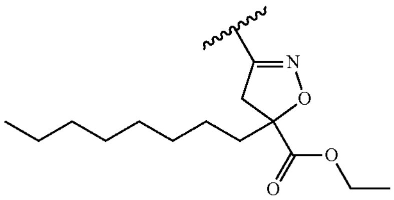 [SMILES: *C1=NOC(CCCCCCCC)(C(=O)OCC)C1] | Cl | F | 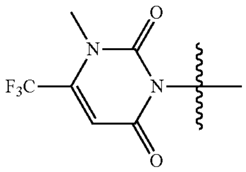 [SMILES: *n1c(=O)cc(C(F)(F)F)n(C)c1=O] | |
| 116 | 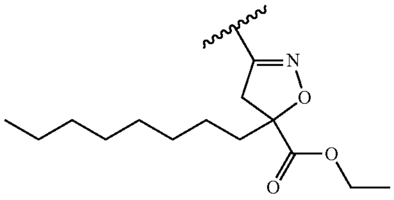 [SMILES: *C1=NOC(CCCCCCCC)(C(=O)OCC)C1] | Cl | F | 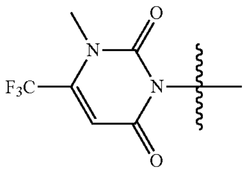 [SMILES: *n1c(=O)cc(C(F)(F)F)n(C)c1=O] | |
| 117 | 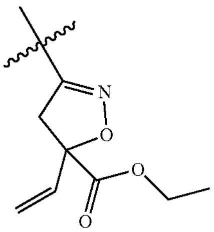 [SMILES: *C1=NOC(C=C)(C(=O)OCC)C1] | Cl | F | 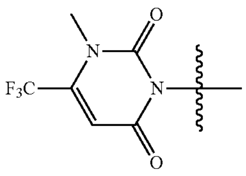 [SMILES: *n1c(=O)cc(C(F)(F)F)n(C)c1=O] | |

TABLE 1-continued
Structures and $^1$H NMR data of compounds
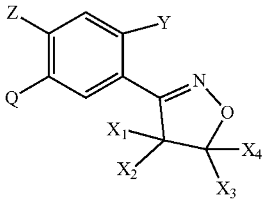
I
| NO. | 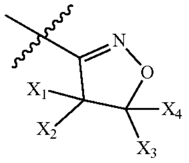 | Y | Z | Q | $^1$H NMR |
|---|---|---|---|---|---|
| 118 | 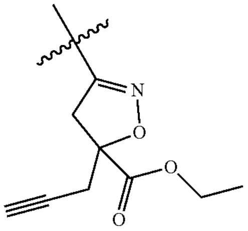 [SMILES: *C1=NOC(CC#C)(C(=O)OCC)C1] | Cl | F | 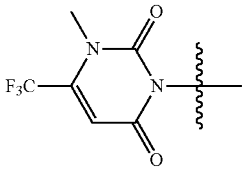 [SMILES: *n1c(=O)cc(C(F)(F)F)n(C)c1=O] | |
| 119 | 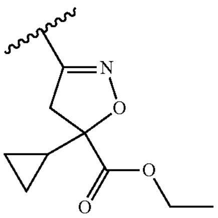 [SMILES: *C1=NOC(C(=O)OCC)(C2CC2)C1] | Cl | F | 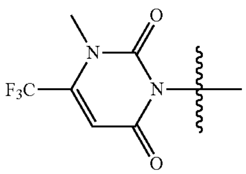 [SMILES: *n1c(=O)cc(C(F)(F)F)n(C)c1=O] | $^1$H NMR (500 MHz, DMSO-$d_6$) δ 7.91-7.86 (m, 2H), 6.64 (s, 1H), 4.23 (q, J = 7.0 Hz, 2H), 3.88 (dd, J = 17.5, 5.5 Hz, 1H), 3.48 (dd, J = 17.5, 5.5 Hz, 1H), 3.44 (s, 3H), 1.54-1.41 (m, 1H), 1.26 (t, J = 7.0 Hz, 3H), 0.57-0.52 (m, 3H), 0.37-0.34 (m, 1H). |
| 120 | 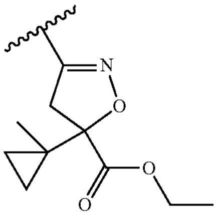 [SMILES: *C1=NOC(C(=O)OCC)(C2(C)CC2)C1] | Cl | F | 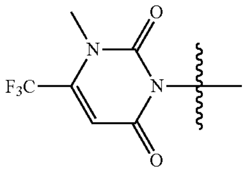 [SMILES: *n1c(=O)cc(C(F)(F)F)n(C)c1=O] | |
| 121 | 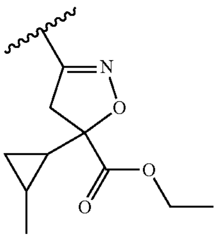 [SMILES: *C1=NOC(C(=O)OCC)(C2CC2C)C1] | Cl | F | 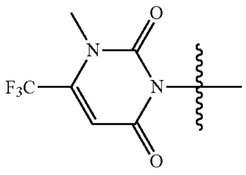 [SMILES: *n1c(=O)cc(C(F)(F)F)n(C)c1=O] | |
| 122 | 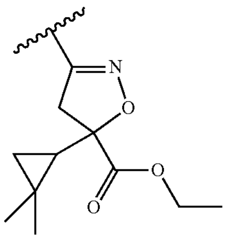 [SMILES: *C1=NOC(C(=O)OCC)(C2CC2(C)C)C1] | Cl | F | 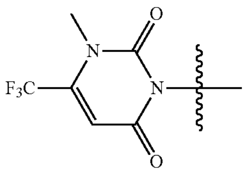 [SMILES: *n1c(=O)cc(C(F)(F)F)n(C)c1=O] | |

TABLE 1-continued
Structures and $^1$H NMR data of compounds
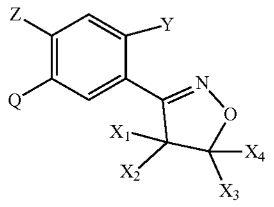
I
| NO. | 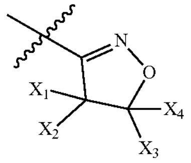 | Y | Z | Q | $^1$H NMR |
|---|---|---|---|---|---|
| 123 | 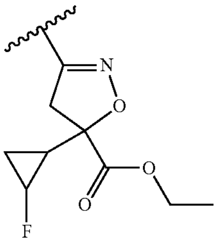 [SMILES: *C1=NOC(C(=O)OCC)(C2CC2F)C1] | Cl | F | 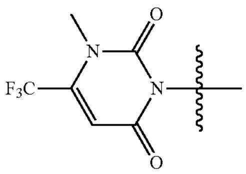 [SMILES: *n1c(=O)cc(C(F)(F)F)n(C)c1=O] | |
| 124 | 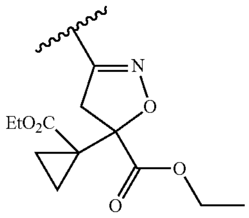 [SMILES: *C1=NOC(C(=O)OCC)(C2(C(=O)OCC)CC2)C1] | Cl | F | 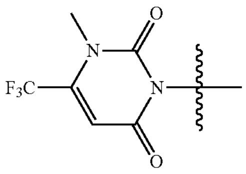 [SMILES: *n1c(=O)cc(C(F)(F)F)n(C)c1=O] | |
| 125 | 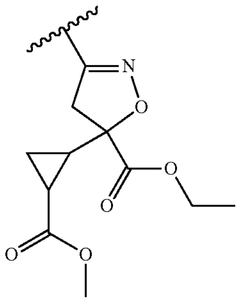 [SMILES: *C1=NOC(C(=O)OCC)(C2CC2C(=O)OC)C1] | Cl | F | 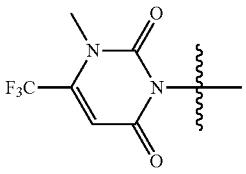 [SMILES: *n1c(=O)cc(C(F)(F)F)n(C)c1=O] | |
| 126 | 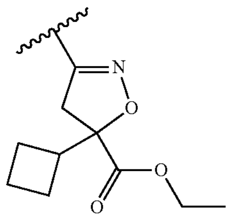 [SMILES: *C1=NOC(C(=O)OCC)(C2CCC2)C1] | Cl | F | 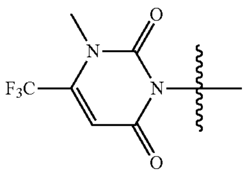 [SMILES: *n1c(=O)cc(C(F)(F)F)n(C)c1=O] | $^1$H NMR (500 MHz, DMSO) δ 7.88-7.86 (m, 2H), 6.60 (s, 1H), 4.45-4.40(m, 1H), 4.36-4.33 (m, 1H), 4.23-4.11 (m, 2H), 3.39 (s, 3H), 2.12-2.02 (m, 1H), 1.73-1.62 (m, 3H), 1.54-1.46 (m, 3H), 1.20-1.18 (m, 3H). |

TABLE 1-continued
Structures and $^1H$ NMR data of compounds
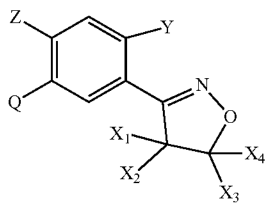
I
| NO. | 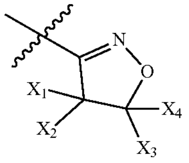 | Y | Z | Q | $^1H$ NMR |
|---|---|---|---|---|---|
| 127 | 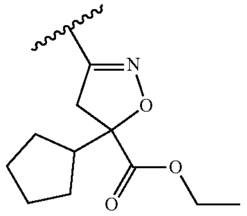 [SMILES: *C1=NOC(C(=O)OCC)(C2CCCC2)C1] | Cl | F | 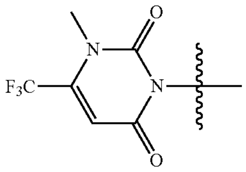 [SMILES: *n1c(=O)cc(C(F)(F)F)n(C)c1=O] | |
| 128 | 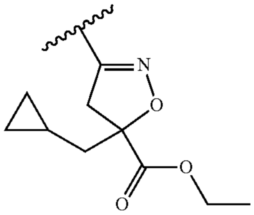 [SMILES: *C1=NOC(CC2CC2)(C(=O)OCC)C1] | Cl | F | 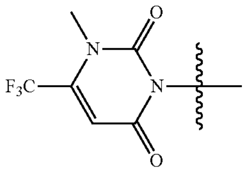 [SMILES: *n1c(=O)cc(C(F)(F)F)n(C)c1=O] | |
| 129 | 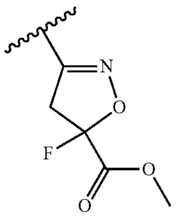 [SMILES: *C1=NOC(F)(C(=O)OC)C1] | Cl | F | 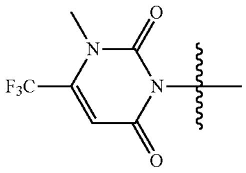 [SMILES: *n1c(=O)cc(C(F)(F)F)n(C)c1=O] | $^1H$ NMR (500 MHz, DMSO-$d_6$) δ 8.02-7.79 (m, 2H), 6.65 (s, 1H), 4.45 (m, 1H), 4.18-4.02 (m, 1H), 3.89 (s, 3H), 3.44 (s, 3H). |
| 130 | 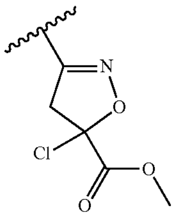 | Cl | F | 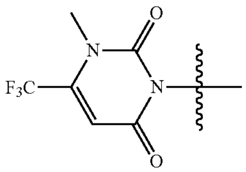 [SMILES: *n1c(=O)cc(C(F)(F)F)n(C)c1=O] | |
| 131 | 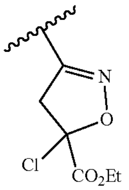 | Cl | F | 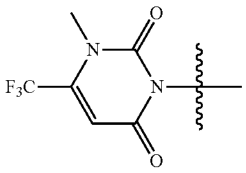 [SMILES: *n1c(=O)cc(C(F)(F)F)n(C)c1=O] | |

TABLE 1-continued
Structures and $^1$H NMR data of compounds
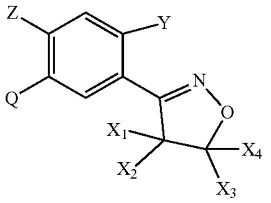
I
| NO. | 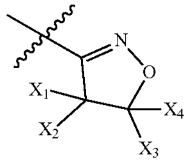 | Y | Z | Q | $^1$H NMR |
|---|---|---|---|---|---|
| 132 | 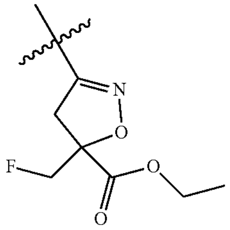 [SMILES: *C1=NOC(CF)(C(=O)OCC)C1] | Cl | F | 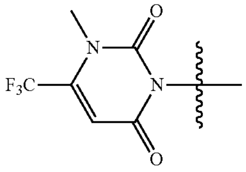 [SMILES: *n1c(=O)cc(C(F)(F)F)n(C)c1=O] | 1H NMR (500 MHz, DMSO-$d_6$) δ 7.93-7.88 (m, 2H), 6.63 (s, 1H), 4.92-4.74 (m, 2H), 4.25 (q, J = 7.0 Hz, 2H), 3.93-3.88 (m 1H), 3.77-3.70 (m, 1H), 3.44 (s, 3H), 1.25 (t, J = 7.0 Hz, 3H). |
| 133 | 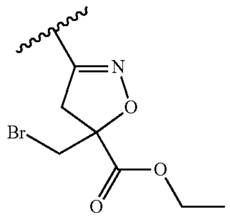 [SMILES: *C1=NOC(CBr)(C(=O)OCC)C1] | Cl | F | 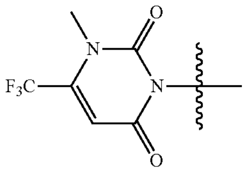 [SMILES: *n1c(=O)cc(C(F)(F)F)n(C)c1=O] | |
| 134 | 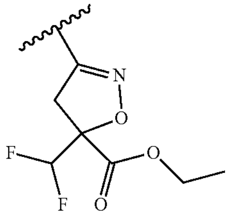 [SMILES: *C1=NOC(C(=O)OCC)(C(F)F)C1] | Cl | F | 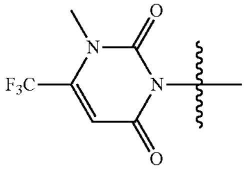 [SMILES: *n1c(=O)cc(C(F)(F)F)n(C)c1=O] | $^1$H NMR (500 MHz, DMSO-$d_6$) δ 7.93-7.91 (m, 2H), 6.72-6.45 (m, 2H), 4.28 (t, J = 7.0 Hz, 2H), 4.12-3.84 (m, 2H), 3.42 (s, 3H), 1.25 (t, J = 7.0 Hz, 3H). |
| 135 | 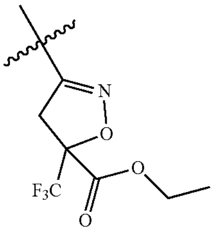 [SMILES: *C1=NOC(C(=O)OCC)(C(F)(F)F)C1] | Cl | F | 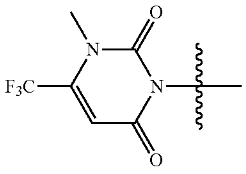 [SMILES: *n1c(=O)cc(C(F)(F)F)n(C)c1=O] | $^1$H NMR (500 MHz, DMSO-$d_6$) δ 7.99-7.93 (m, 2H), 6.65 (s, 1H), 4.37-4.32 (m, 3H), 4.23-4.17 (m, 1H), 3.44 (s, 3H), 1.27 (t, J = 7.0 Hz, 3H). |
| 136 | 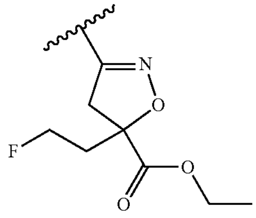 [SMILES: *C1=NOC(CCF)(C(=O)OCC)C1] | Cl | F | 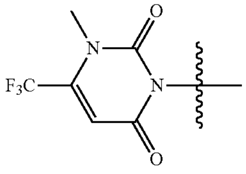 [SMILES: *n1c(=O)cc(C(F)(F)F)n(C)c1=O] | $^1$H NMR (500 MHz, DMSO-$d_6$) δ 7.90 (dd, J = 10.5, 8.5 Hz, 2H), 6.63 (s, 1H), 4.71-4.56 (m. 2H), 4.21 (q, J = 7.0 Hz, 2H), 3.97-3.88 (m, 1H), 3.70-3.68 (m, 1H), 3.44 (s, 3H), 2.43-2.40 (m, 2H), 1.24 (t, J = 7.0, 3H). |

TABLE 1-continued
Structures and $^1$H NMR data of compounds
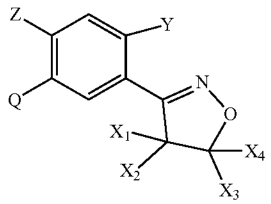
I
| NO. | 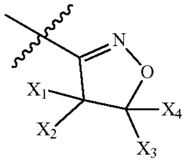 | Y | Z | Q | $^1$H NMR |
|---|---|---|---|---|---|
| 137 | 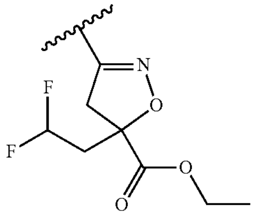 [SMILES: *C1=NOC(CC(F)F)(C(=O)OCC)C1] | Cl | F | 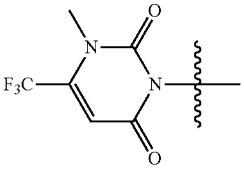 [SMILES: *n1c(=O)cc(C(F)(F)F)n(C)c1=O] | |
| 138 | 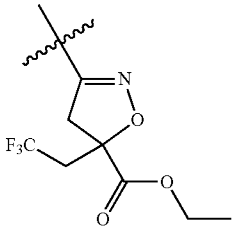 [SMILES: *C1=NOC(CC(F)(F)F)(C(=O)OCC)C1] | Cl | F | 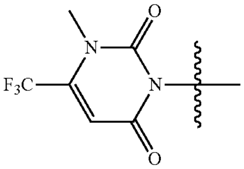 [SMILES: *n1c(=O)cc(C(F)(F)F)n(C)c1=O] | |
| 139 | 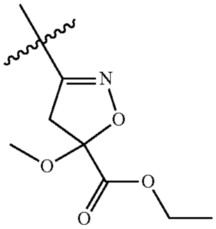 [SMILES: *C1=NOC(OC)(C(=O)OCC)C1] | Cl | F | 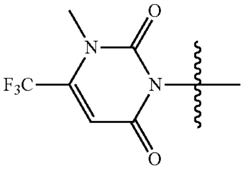 [SMILES: *n1c(=O)cc(C(F)(F)F)n(C)c1=O] | |
| 140 | 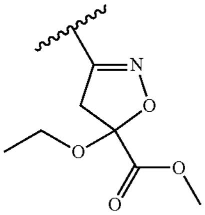 [SMILES: *C1=NOC(OCC)(C(=O)OC)C1] | Cl | F | 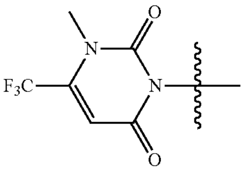 [SMILES: *n1c(=O)cc(C(F)(F)F)n(C)c1=O] | |
| 141 | 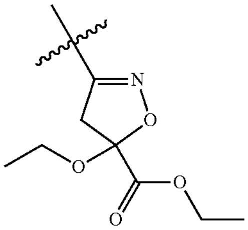 [SMILES: *C1=NOC(OCC)(C(=O)OCC)C1] | Cl | F | 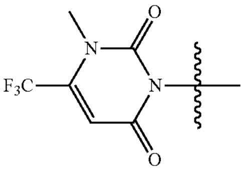 [SMILES: *n1c(=O)cc(C(F)(F)F)n(C)c1=O] | |

TABLE 1-continued
Structures and $^1$H NMR data of compounds
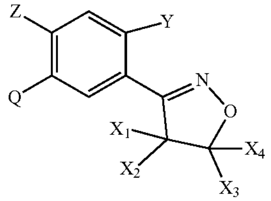
I
| NO. | 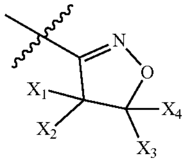 | Y | Z | Q | $^1$H NMR |
|---|---|---|---|---|---|
| 142 | 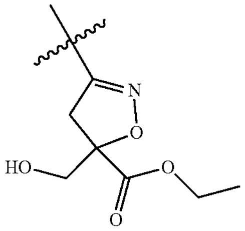 [SMILES: *C1=NOC(CO)(C(=O)OCC)C1] | Cl | F | 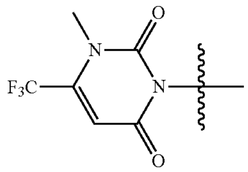 [SMILES: *n1c(=O)cc(C(F)(F)F)n(C)c1=O] | $^1$H NMR (500 MHz, DMSO) δ 7.90-7.79 (m, 2H), 6.59 (s, 1H), 5.47 (t, J = 6.0 Hz, 1H), 4.16 (q, J = 7.0 Hz, 2H), 3.79-3.66 (m, 3H), 3.63-3.61 (m, 1H), 3.39 (s, 3H), 1.20-1.18 (m, 3H). |
| 143 | 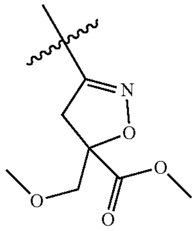 | Cl | F | 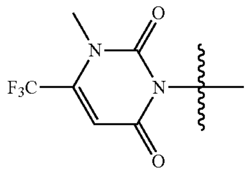 [SMILES: *n1c(=O)cc(C(F)(F)F)n(C)c1=O] | |
| 144 | 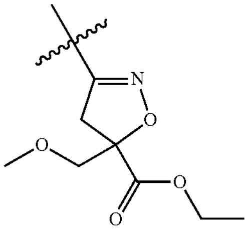 [SMILES: *C1=NOC(COC)(C(=O)OCC)C1] | Cl | F | 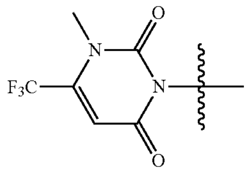 [SMILES: *n1c(=O)cc(C(F)(F)F)n(C)c1=O] | |
| 145 | 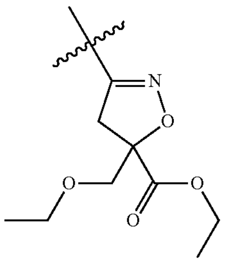 [SMILES: *C1=NOC(COCC)(C(=O)OCC)C1] | Cl | F | 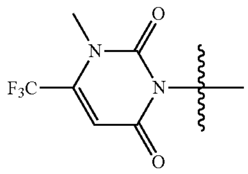 [SMILES: *n1c(=O)cc(C(F)(F)F)n(C)c1=O] | |

TABLE 1-continued
Structures and $^{1}$H NMR data of compounds
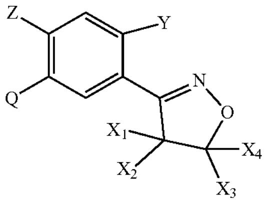
I
| NO. | 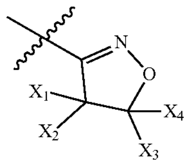 | Y | Z | Q | $^{1}$H NMR |
|---|---|---|---|---|---|
| 146 | 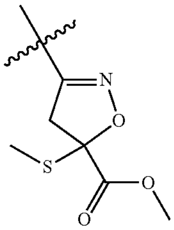 | Cl | F | 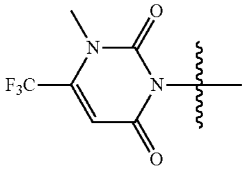 [SMILES: *n1c(=O)cc(C(F)(F)F)n(C)c1=O] | |
| 147 | 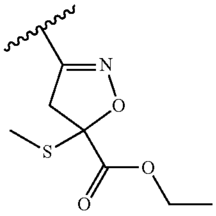 | Cl | F | 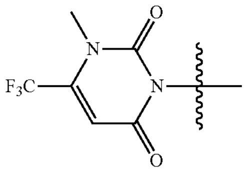 [SMILES: *n1c(=O)cc(C(F)(F)F)n(C)c1=O] | |
| 148 | 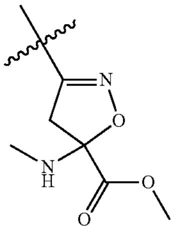 | Cl | F | 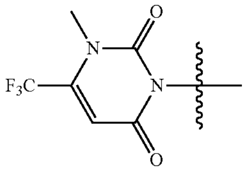 [SMILES: *n1c(=O)cc(C(F)(F)F)n(C)c1=O] | |
| 149 | 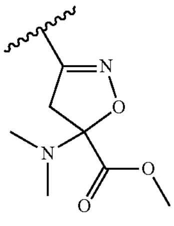 | Cl | F | 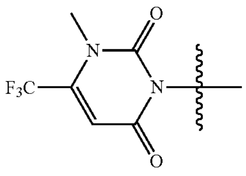 [SMILES: *n1c(=O)cc(C(F)(F)F)n(C)c1=O] | |
| 150 | 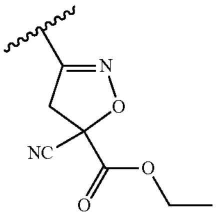 [SMILES: *C1=NOC(C#N)(C(=O)OCC)C1] | Cl | F | 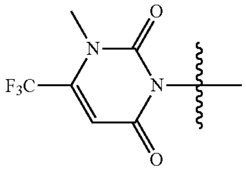 [SMILES: *n1c(=O)cc(C(F)(F)F)n(C)c1=O] | |

TABLE 1-continued
Structures and $^1$H NMR data of compounds
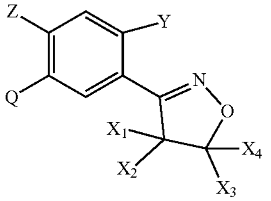
I
| NO. | 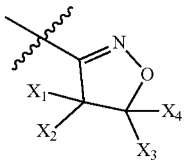 | Y | Z | Q | $^1$H NMR |
|---|---|---|---|---|---|
| 151 | 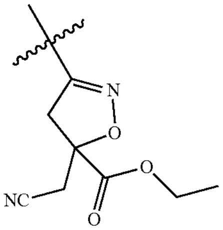 [SMILES: *C1=NOC(CC#N)(C(=O)OCC)C1] | Cl | F | 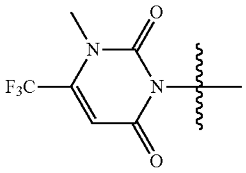 [SMILES: *n1c(=O)cc(C(F)(F)F)n(C)c1=O] | |
| 152 | 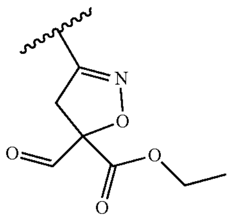 [SMILES: *C1=NOC(C=O)(C(=O)OCC)C1] | Cl | F | 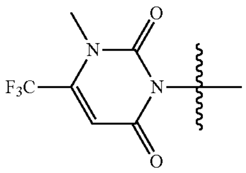 [SMILES: *n1c(=O)cc(C(F)(F)F)n(C)c1=O] | 1H NMR (500 MHz, DMSO-d6) δ 10.23 (s, 1H), 7.94-7.89 (m, 2H), 6.64 (s, 1H), 4.29-4.27 (m, 2H), 4.21-4.18 (m, 2H), 3.43 (s, 3H), 1.26-1.23 (m, 3H). |
| 153 | 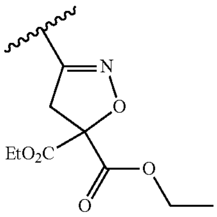 [SMILES: *C1=NOC(C(=O)OCC)(C(=O)OCC)C1] | Cl | F | 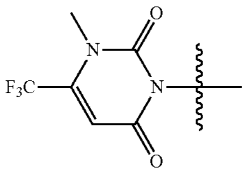 [SMILES: *n1c(=O)cc(C(F)(F)F)n(C)c1=O] | |
| 154 | 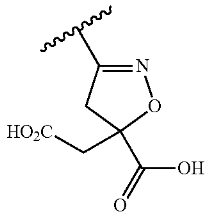 [SMILES: *C1=NOC(CC(=O)O)(C(=O)O)C1] | Cl | F | 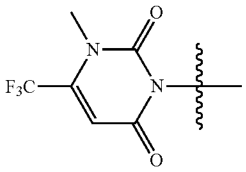 [SMILES: *n1c(=O)cc(C(F)(F)F)n(C)c1=O] | |
| 155 | 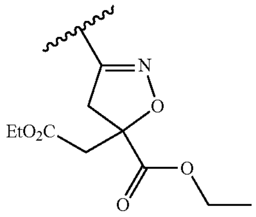 [SMILES: *C1=NOC(CC(=O)OCC)(C(=O)OCC)C1] | Cl | F | 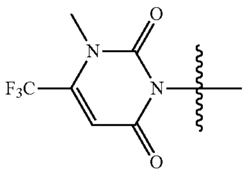 [SMILES: *n1c(=O)cc(C(F)(F)F)n(C)c1=O] | |

TABLE 1-continued
Structures and $^1$H NMR data of compounds
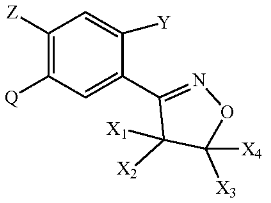
I
| NO. | 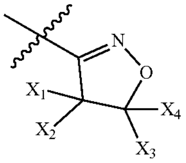 | Y | Z | Q | $^1$H NMR |
|---|---|---|---|---|---|
| 156 | 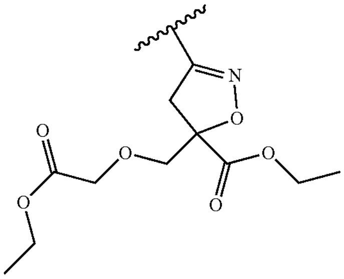 [SMILES: *C1=NOC(COCC(=O)OCC)(C(=O)OCC)C1] | Cl | F | 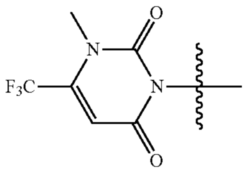 [SMILES: *n1c(=O)cc(C(F)(F)F)n(C)c1=O] | |
| 157 | 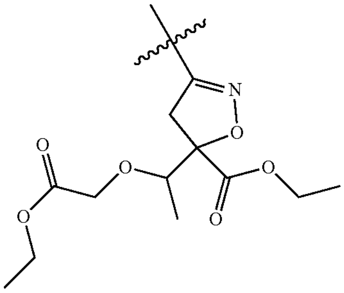 [SMILES: *C1=NOC(C(=O)OCC)(C(C)OCC(=O)OCC)C1] | Cl | F | 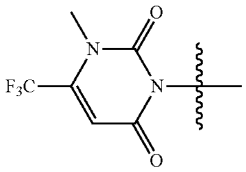 [SMILES: *n1c(=O)cc(C(F)(F)F)n(C)c1=O] | |
| 158 | 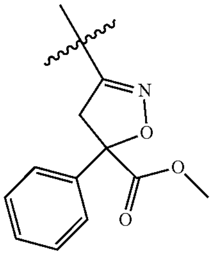 [SMILES: *C1=NOC(C(=O)OC)(c2ccccc2)C1] | Cl | F | 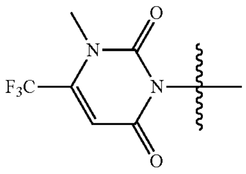 [SMILES: *n1c(=O)cc(C(F)(F)F)n(C)c1=O] | |
| 159 | 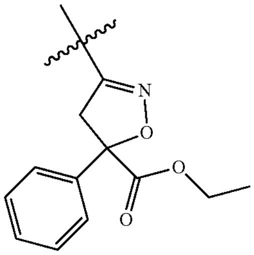 [SMILES: *C1=NOC(C(=O)OCC)(c2ccccc2)C1] | Cl | F | 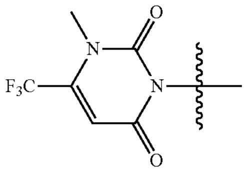 [SMILES: *n1c(=O)cc(C(F)(F)F)n(C)c1=O] | |

TABLE 1-continued
Structures and $^1$H NMR data of compounds
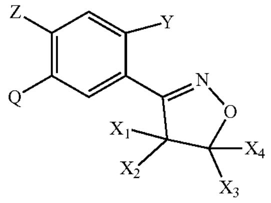
I
| NO. | 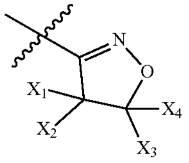 | Y | Z | Q | $^1$H NMR |
|---|---|---|---|---|---|
| 160 | 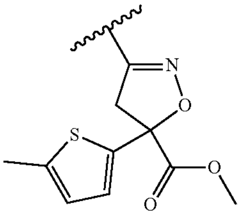 | Cl | F | 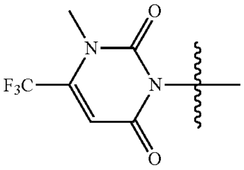 [SMILES: *n1c(=O)cc(C(F)(F)F)n(C)c1=O] | |
| 161 | 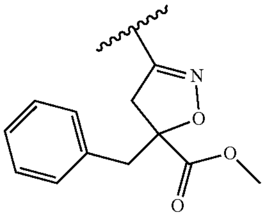 [SMILES: *C1=NOC(Cc2ccccc2)(C(=O)OC)C1] | Cl | F | 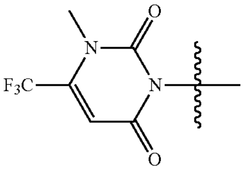 [SMILES: *n1c(=O)cc(C(F)(F)F)n(C)c1=O] | |
| 162 | 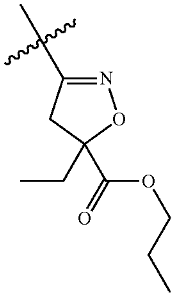 [SMILES: *C1=NOC(CC)(C(=O)OCCC)C1] | Cl | F | 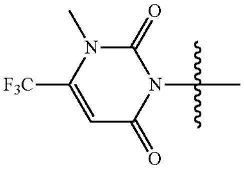 [SMILES: *n1c(=O)cc(C(F)(F)F)n(C)c1=O] | |
| 163 | 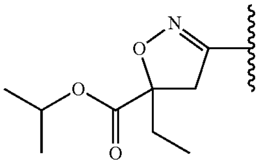 [SMILES: *C1=NOC(CC)(C(=O)OC(C)C)C1] | Cl | F | 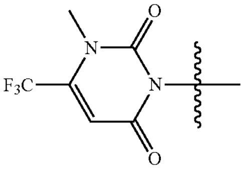 [SMILES: *n1c(=O)cc(C(F)(F)F)n(C)c1=O] | |
| 164 | 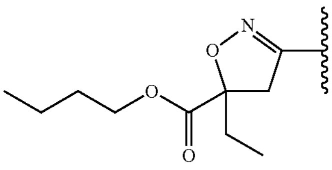 | Cl | F | 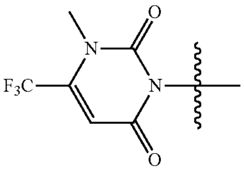 [SMILES: *n1c(=O)cc(C(F)(F)F)n(C)c1=O] | |

TABLE 1-continued
Structures and $^{1}H$ NMR data of compounds
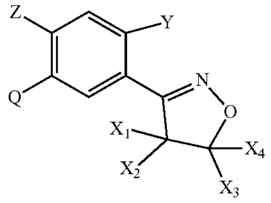
I
| NO. | 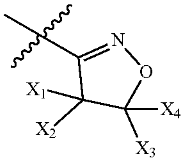 | Y | Z | Q | $^{1}H$ NMR |
|---|---|---|---|---|---|
| 165 | 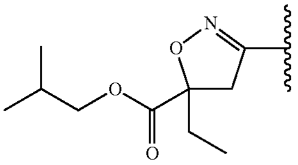 [SMILES: *C1=NOC(CC)(C(=O)OCC(C)C)C1] | Cl | F | 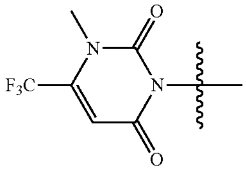 [SMILES: *n1c(=O)cc(C(F)(F)F)n(C)c1=O] | |
| 166 | 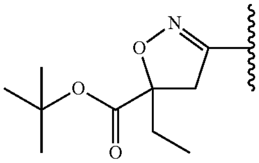 [SMILES: *C1=NOC(CC)(C(=O)OC(C)(C)C)C1] | Cl | F | 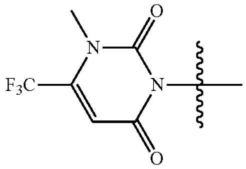 [SMILES: *n1c(=O)cc(C(F)(F)F)n(C)c1=O] | |
| 167 | 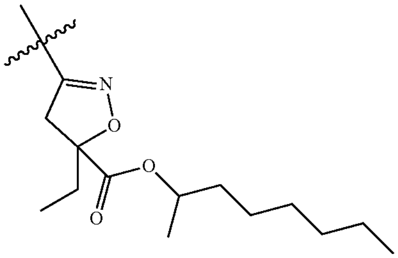 [SMILES: *C1=NOC(CC)(C(=O)OC(C)CCCCCC)C1] | Cl | F | 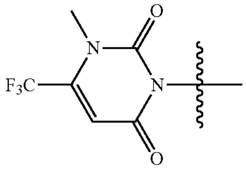 [SMILES: *n1c(=O)cc(C(F)(F)F)n(C)c1=O] | |
| 168 | 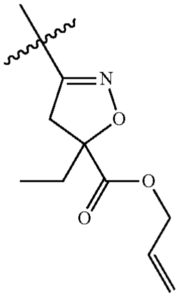 [SMILES: *C1=NOC(CC)(C(=O)OCC=C)C1] | Cl | F | 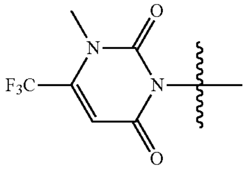 [SMILES: *n1c(=O)cc(C(F)(F)F)n(C)c1=O] | |
| 169 | 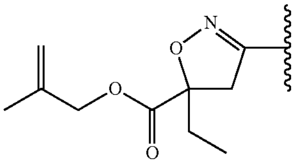 [SMILES: *C1=NOC(CC)(C(=O)OCC(=C)C)C1] | Cl | F | 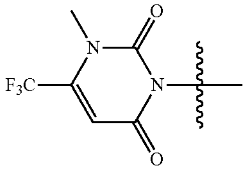 [SMILES: *n1c(=O)cc(C(F)(F)F)n(C)c1=O] | |

TABLE 1-continued
Structures and $^{1}$H NMR data of compounds
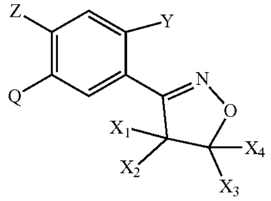
I
| NO. | 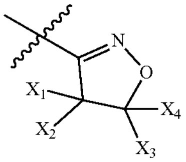 | Y | Z | Q | $^{1}$H NMR |
|---|---|---|---|---|---|
| 170 | 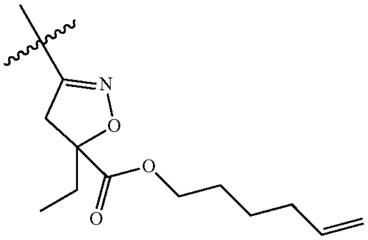 [SMILES: *C1=NOC(CC)(C(=O)OCCCCC=C)C1] | Cl | F | 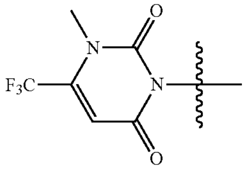 [SMILES: *n1c(=O)cc(C(F)(F)F)n(C)c1=O] | |
| 171 | 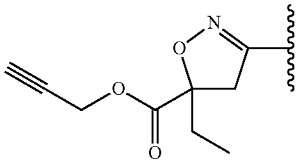 [SMILES: *C1=NOC(CC)(C(=O)OCC#C)C1] | Cl | F | 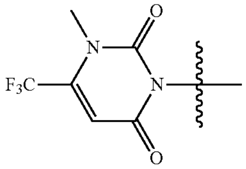 [SMILES: *n1c(=O)cc(C(F)(F)F)n(C)c1=O] | |
| 172 | 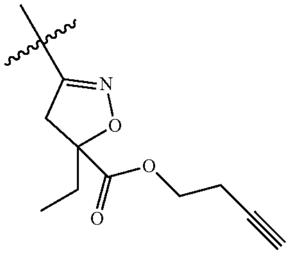 [SMILES: *C1=NOC(CC)(C(=O)OCCC#C)C1] | Cl | F | 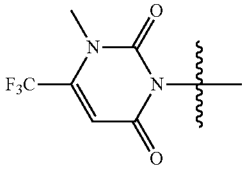 [SMILES: *n1c(=O)cc(C(F)(F)F)n(C)c1=O] | |
| 173 | 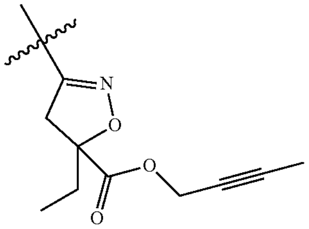 [SMILES: *C1=NOC(CC)(C(=O)OCC#CC)C1] | Cl | F | 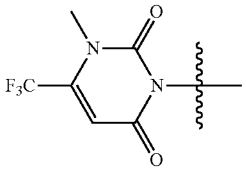 [SMILES: *n1c(=O)cc(C(F)(F)F)n(C)c1=O] | |
| 174 | 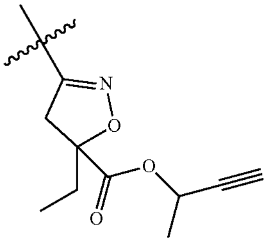 [SMILES: *C1=NOC(CC)(C(=O)OC(C)C#C)C1] | Cl | F | 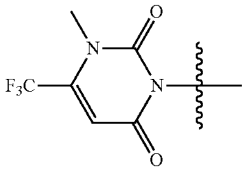 [SMILES: *n1c(=O)cc(C(F)(F)F)n(C)c1=O] | |

TABLE 1-continued
Structures and $^1H$ NMR data of compounds
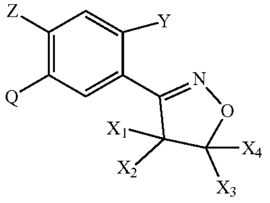
I
| NO. | 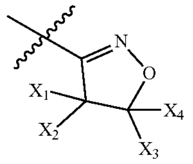 | Y | Z | Q | $^1H$ NMR |
|---|---|---|---|---|---|
| 175 | 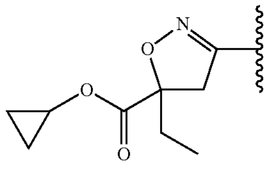 [SMILES: *C1=NOC(CC)(C(=O)OC2CC2)C1] | Cl | F | 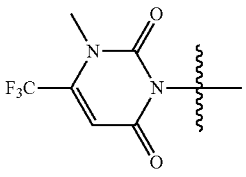 [SMILES: *n1c(=O)cc(C(F)(F)F)n(C)c1=O] | |
| 176 | 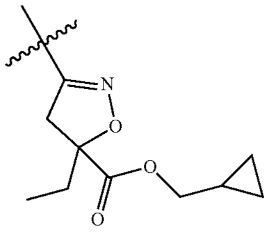 [SMILES: *C1=NOC(CC)(C(=O)OCC2CC2)C1] | Cl | F | 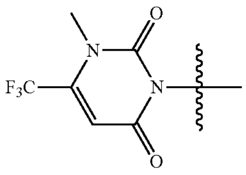 [SMILES: *n1c(=O)cc(C(F)(F)F)n(C)c1=O] | |
| 177 | 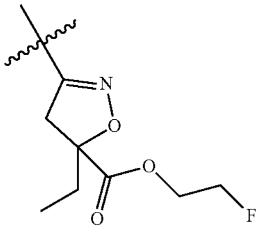 [SMILES: *C1=NOC(CC)(C(=O)OCCF)C1] | Cl | F | 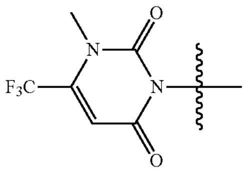 [SMILES: *n1c(=O)cc(C(F)(F)F)n(C)c1=O] | |
| 178 | 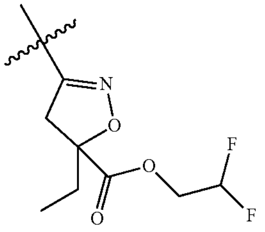 [SMILES: *C1=NOC(CC)(C(=O)OCC(F)F)C1] | Cl | F | 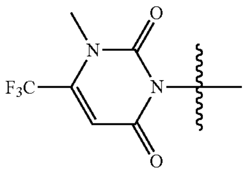 [SMILES: *n1c(=O)cc(C(F)(F)F)n(C)c1=O] | |
| 179 | 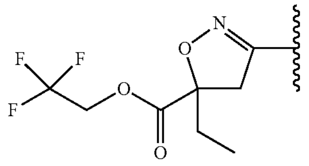 [SMILES: *C1=NOC(CC)(C(=O)OCC(F)(F)F)C1] | Cl | F | 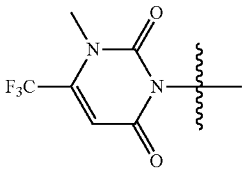 [SMILES: *n1c(=O)cc(C(F)(F)F)n(C)c1=O] | |

TABLE 1-continued
Structures and $^1$H NMR data of compounds
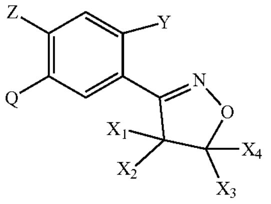
I
| NO. | 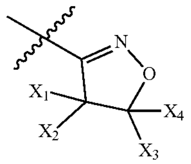 | Y | Z | Q | $^1$H NMR |
|---|---|---|---|---|---|
| 180 | 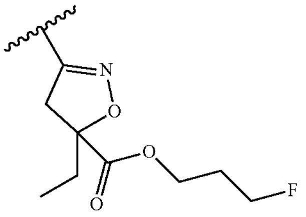 [SMILES: *C1=NOC(CC)(C(=O)OCCCF)C1] | Cl | F | 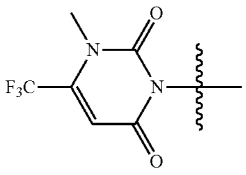 [SMILES: *n1c(=O)cc(C(F)(F)F)n(C)c1=O] | |
| 181 | 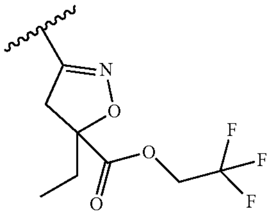 [SMILES: *C1=NOC(CC)(C(=O)OCC(F)(F)F)C1] | Cl | F | 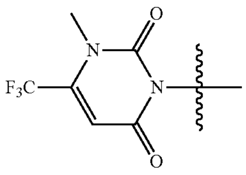 [SMILES: *n1c(=O)cc(C(F)(F)F)n(C)c1=O] | |
| 182 | 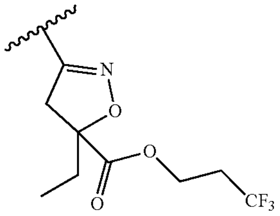 [SMILES: *C1=NOC(CC)(C(=O)OCCC(F)(F)F)C1] | Cl | F | 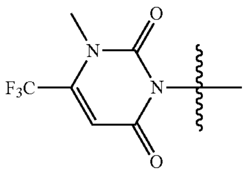 [SMILES: *n1c(=O)cc(C(F)(F)F)n(C)c1=O] | |
| 183 | 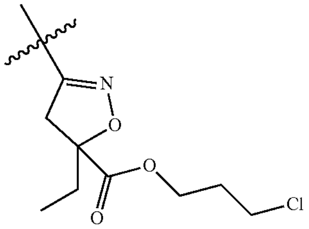 [SMILES: *C1=NOC(CC)(C(=O)OCCCCl)C1] | Cl | F | 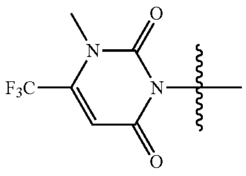 [SMILES: *n1c(=O)cc(C(F)(F)F)n(C)c1=O] | |

TABLE 1-continued
Structures and $^{1}H$ NMR data of compounds
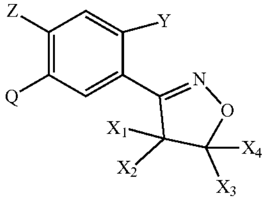
I
| NO. | 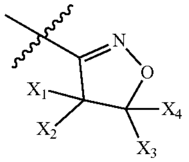 | Y | Z | Q | $^{1}H$ NMR |
|---|---|---|---|---|---|
| 184 | 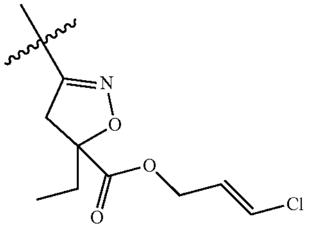 [SMILES: *C1=NOC(CC)(C(=O)OC/C=C/Cl)C1] | Cl | F | 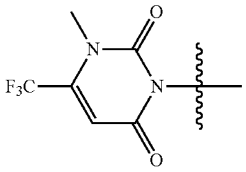 [SMILES: *n1c(=O)cc(C(F)(F)F)n(C)c1=O] | |
| 185 | 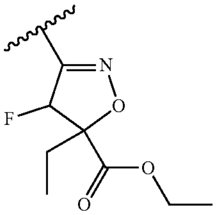 [SMILES: *C1=NOC(CC)(C(=O)OCC)C1F] | Cl | F | 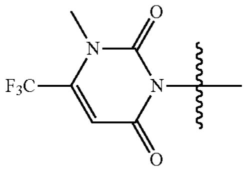 [SMILES: *n1c(=O)cc(C(F)(F)F)n(C)c1=O] | |
| 186 | 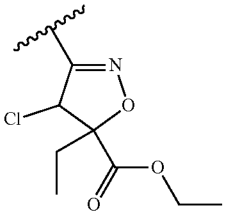 [SMILES: *C1=NOC(CC)(C(=O)OCC)C1Cl] | Cl | F | 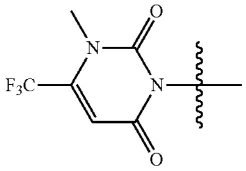 [SMILES: *n1c(=O)cc(C(F)(F)F)n(C)c1=O] | |
| 187 | 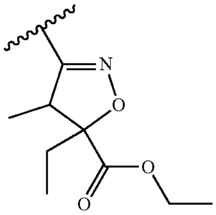 [SMILES: *C1=NOC(CC)(C(=O)OCC)C1C] | Cl | F | 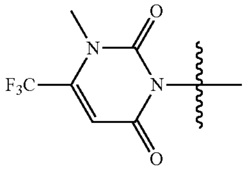 [SMILES: *n1c(=O)cc(C(F)(F)F)n(C)c1=O] | |
| 188 | 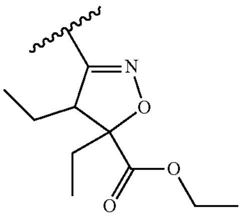 [SMILES: *C1=NOC(CC)(C(=O)OCC)C1CC] | Cl | F | 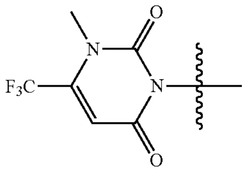 [SMILES: *n1c(=O)cc(C(F)(F)F)n(C)c1=O] | |

TABLE 1-continued
Structures and $^1$H NMR data of compounds
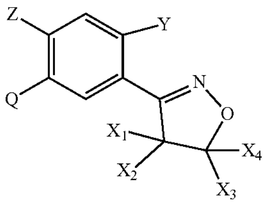
I
| NO. | 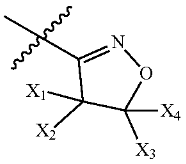 | Y | Z | Q | $^1$H NMR |
|---|---|---|---|---|---|
| 189 | 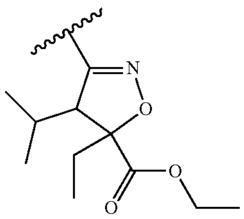 [SMILES: *C1=NOC(CC)(C(=O)OCC)C1C(C)C] | Cl | F | 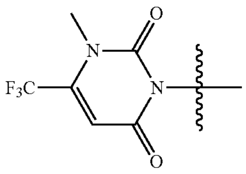 [SMILES: *n1c(=O)cc(C(F)(F)F)n(C)c1=O] | |
| 190 | 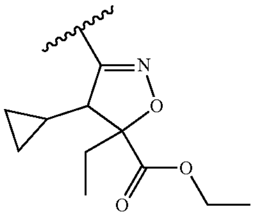 [SMILES: *C1=NOC(CC)(C(=O)OCC)C1C1CC1] | Cl | F | 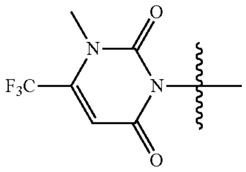 [SMILES: *n1c(=O)cc(C(F)(F)F)n(C)c1=O] | |
| 191 | 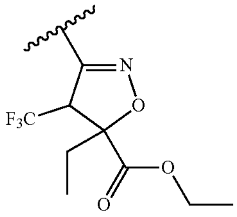 [SMILES: *C1=NOC(CC)(C(=O)OCC)C1C(F)(F)F] | Cl | F | 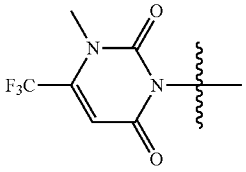 [SMILES: *n1c(=O)cc(C(F)(F)F)n(C)c1=O] | |
| 192 | 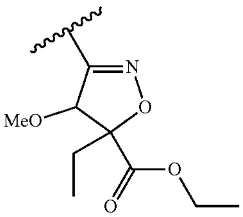 [SMILES: *C1=NOC(CC)(C(=O)OCC)C1OC] | Cl | F | 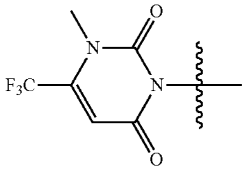 [SMILES: *n1c(=O)cc(C(F)(F)F)n(C)c1=O] | |
| 193 | 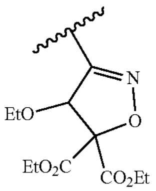 [SMILES: *C1=NOC(C(=O)OCC)(C(=O)OCC)C1OCC] | Cl | F | 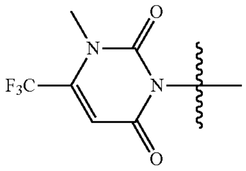 [SMILES: *n1c(=O)cc(C(F)(F)F)n(C)c1=O] | |

TABLE 1-continued
Structures and $^1$H NMR data of compounds
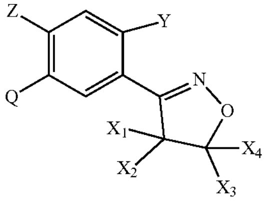
I
| NO. | 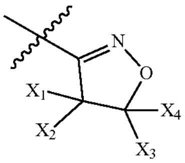 | Y | Z | Q | $^1$H NMR |
|---|---|---|---|---|---|
| 194 | 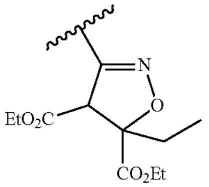 [SMILES: *C1=NOC(CC)(C(=O)OCC)C1C(=O)OCC] | Cl | F | 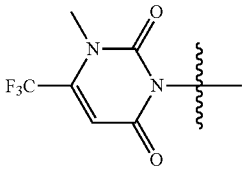 [SMILES: *n1c(=O)cc(C(F)(F)F)n(C)c1=O] | |
| 195 | 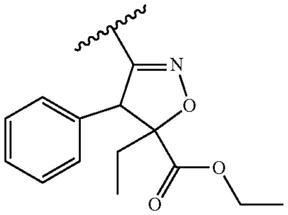 [SMILES: *C1=NOC(CC)(C(=O)OCC)C1c1ccccc1] | Cl | F | 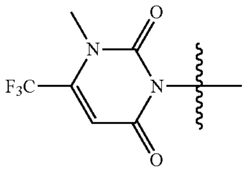 [SMILES: *n1c(=O)cc(C(F)(F)F)n(C)c1=O] | |
| 196 | 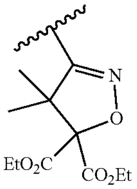 | Cl | F | 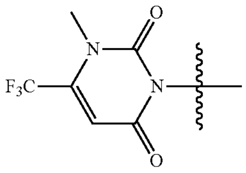 [SMILES: *n1c(=O)cc(C(F)(F)F)n(C)c1=O] | |
| 197 | 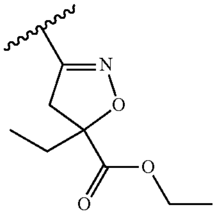 [SMILES: *C1=NOC(CC)(C(=O)OCC)C1] | Br | F | 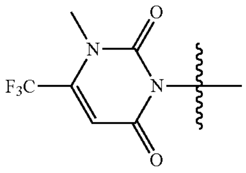 [SMILES: *n1c(=O)cc(C(F)(F)F)n(C)c1=O] | |
| 198 | 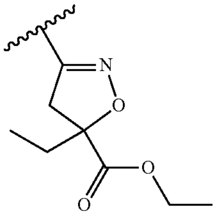 [SMILES: *C1=NOC(CC)(C(=O)OCC)C1] | $CF_3$ | F | 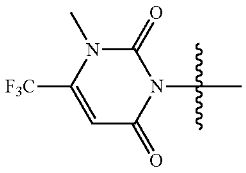 [SMILES: *n1c(=O)cc(C(F)(F)F)n(C)c1=O] | |

TABLE 1-continued
Structures and $^1$H NMR data of compounds
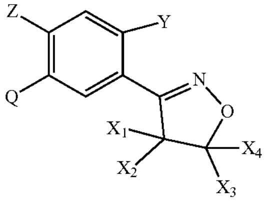
I
| NO. | 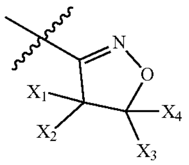 | Y | Z | Q | $^1$H NMR |
|---|---|---|---|---|---|
| 199 | 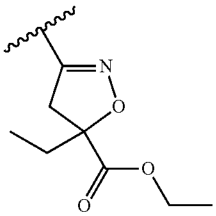 [SMILES: *C1=NOC(CC)(C(=O)OCC)C1] | CN | F | 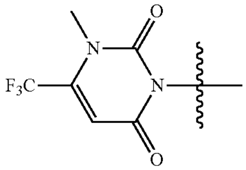 [SMILES: *n1c(=O)cc(C(F)(F)F)n(C)c1=O] | |
| 200 | 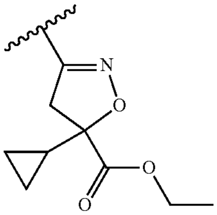 [SMILES: *C1=NOC(C(=O)OCC)(C2CC2)C1] | Br | F | 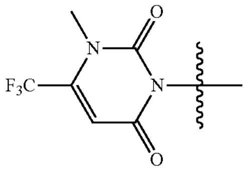 [SMILES: *n1c(=O)cc(C(F)(F)F)n(C)c1=O] | |
| 201 | 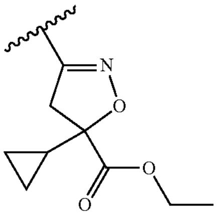 [SMILES: *C1=NOC(C(=O)OCC)(C2CC2)C1] | $CF_3$ | F | 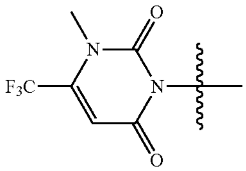 [SMILES: *n1c(=O)cc(C(F)(F)F)n(C)c1=O] | |
| 202 | 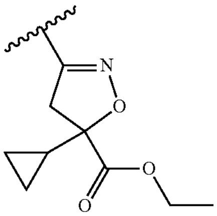 [SMILES: *C1=NOC(C(=O)OCC)(C2CC2)C1] | CN | F | 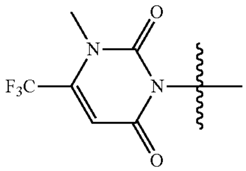 [SMILES: *n1c(=O)cc(C(F)(F)F)n(C)c1=O] | |
| 203 | 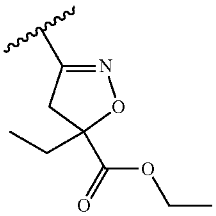 [SMILES: *C1=NOC(CC)(C(=O)OCC)C1] | Cl | F | 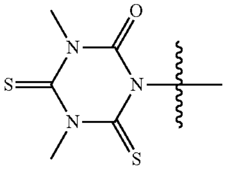 | 1H NMR (500 MHz, Chloroform-d) δ 7.72 (d, J = 7.5 Hz, 1H), 7.38 (d, J = 9.0 Hz, 1H), 4.36-4.23 (m, 5H), 4.03-3.94 (m, 1H), 3.80 (s, 3H), 3.52-3.43 (m, 1H), 2.13-2.04 (m, 2H), 1.37 (t, J = 7.0 Hz, 3H), 1.05 (t, J = 7.5 Hz, 3H). |

TABLE 1-continued
Structures and $^1$H NMR data of compounds
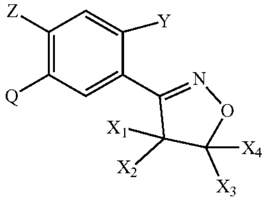
I
| NO. | 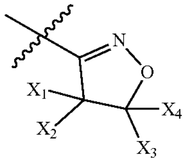 | Y | Z | Q | $^1$H NMR |
|---|---|---|---|---|---|
| 204 | 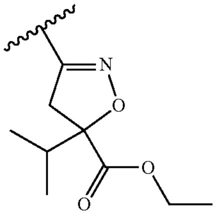 [SMILES: *C1=NOC(C(=O)OCC)(C(C)C)C1] | Cl | F | 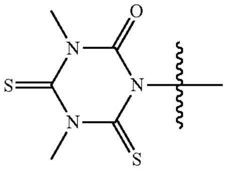 | 1H NMR (500 MHz, DMSO) δ 7.93 (d, J = 7.5 Hz, 1H), 7.90 (d, J = 9.5 Hz, 1H), 4.29-4.21 (m, 2H), 4.15 (s, 3H), 3.82-3.80 (m, 1H), 3.63 (s, 3H), 3.57-3.55 (m, 1H), 2.34-2.30 (m, 1H), 1.22 (t, J = 7.5 Hz, 3H), 0.94-0.92 (m, 6H). |
| 205 | 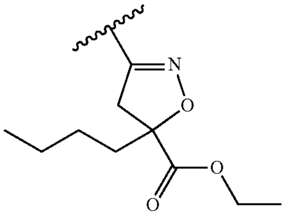 [SMILES: *C1=NOC(CCCC)(C(=O)OCC)C1] | Cl | F | 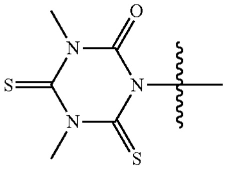 | 1H NMR (500 MHz, DMSO) δ 7.94 (d, J = 8.0 Hz, 1H), 7.89 (d, J = 9.5 Hz, 1H), 4.21 (q, J = 7.0 Hz, 2H), 4.15 (s, 3H), 3.88-3.82 (m, 1H), 3.63 (s, 3H), 3.58-3.52 (m, 1H), 1.99-1.91 (m, 2H), 1.39-1.27 (m, 4H), 1.24 (t, J = 7.0 Hz, 3H), 0.89 (t, J = 6.5 Hz, 3H). |
| 206 | 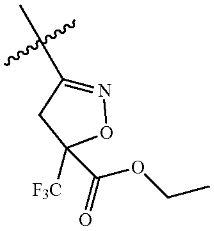 [SMILES: *C1=NOC(C(=O)OCC)(C(F)(F)F)C1] | Cl | F | 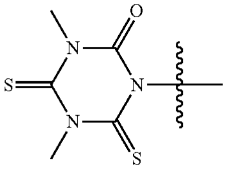 | 1H NMR (500 MHz, DMSO-d6) δ 8.02 (d, J = 7.5 Hz, 1H), 7.96 (d, J = 9.5 Hz, 1H), 4.38-4.29 (m, 3H), 4.17-4.13 (m, 4H), 3.63 (s, 3H), 1.28 (t, J = 7.0 Hz, 3H). |
| 207 | 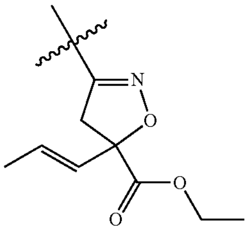 [SMILES: *C1=NOC(/C=C/C)(C(=O)OCC)C1] | Cl | F | 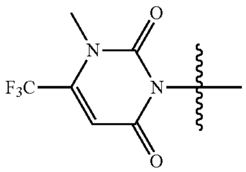 [SMILES: *n1c(=O)cc(C(F)(F)F)n(C)c1=O] | |
| 208 | 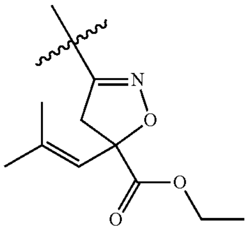 [SMILES: *C1=NOC(C=C(C)C)(C(=O)OCC)C1] | Cl | F | 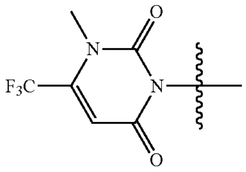 [SMILES: *n1c(=O)cc(C(F)(F)F)n(C)c1=O] | |

TABLE 1-continued
Structures and $^1$H NMR data of compounds
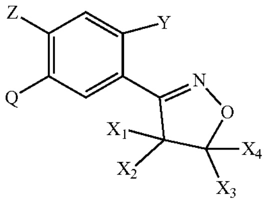
I
| NO. | 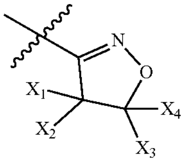 | Y | Z | Q | $^1$H NMR |
|---|---|---|---|---|---|
| 209 | 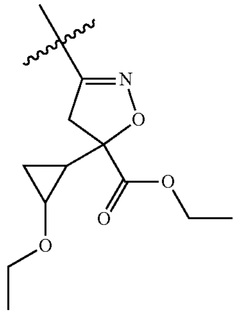 [SMILES: *C1=NOC(C(=O)OCC)(C2CC2OCC)C1] | Cl | F | 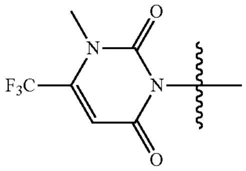 [SMILES: *n1c(=O)cc(C(F)(F)F)n(C)c1=O] | |
| 210 | 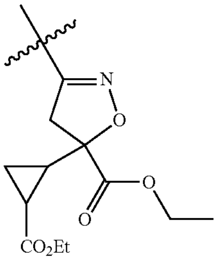 [SMILES: *C1=NOC(C(=O)OCC)(C2CC2C(=O)OCC)C1] | Cl | F | 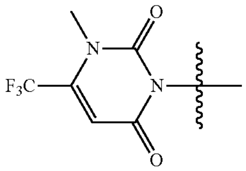 [SMILES: *n1c(=O)cc(C(F)(F)F)n(C)c1=O] | |
| 211 | 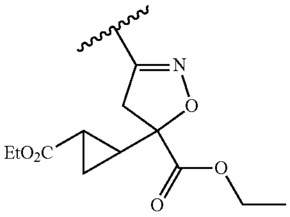 [SMILES: *C1=NOC(C(=O)OCC)(C2CC2C(=O)OCC)C1] | Cl | F | 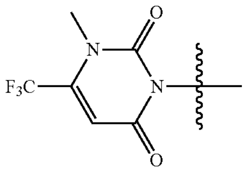 [SMILES: *n1c(=O)cc(C(F)(F)F)n(C)c1=O] | |
| 212 | 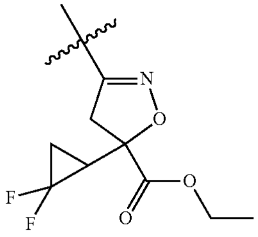 [SMILES: *C1=NOC(C(=O)OCC)(C2CC2(F)F)C1] | Cl | F | 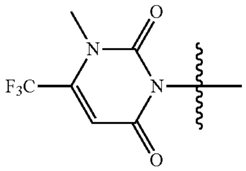 [SMILES: *n1c(=O)cc(C(F)(F)F)n(C)c1=O] | |

TABLE 1-continued
Structures and $^{1}H$ NMR data of compounds
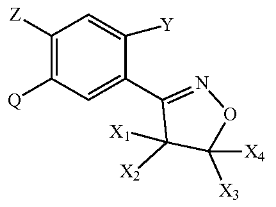
I
| NO. | 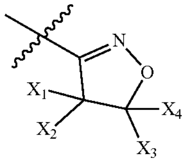 | Y | Z | Q | $^{1}H$ NMR |
|---|---|---|---|---|---|
| 213 | 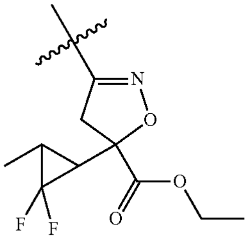 [SMILES: *C1=NOC(C(=O)OCC)(C2C(C)C2(F)F)C1] | Cl | F | 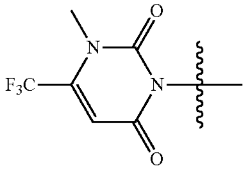 [SMILES: *n1c(=O)cc(C(F)(F)F)n(C)c1=O] | |
| 214 | 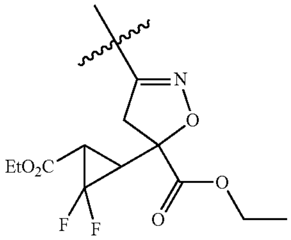 [SMILES: *C1=NOC(C(=O)OCC)(C2C(C(=O)OCC)C2(F)F)C1] | Cl | F | 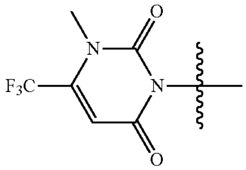 [SMILES: *n1c(=O)cc(C(F)(F)F)n(C)c1=O] | |
| 215 | 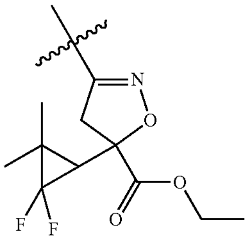 [SMILES: *C1=NOC(C(=O)OCC)(C2C(C)(C)C2(F)F)C1] | Cl | F | 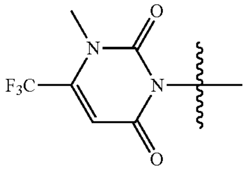 [SMILES: *n1c(=O)cc(C(F)(F)F)n(C)c1=O] | |
| 216 | 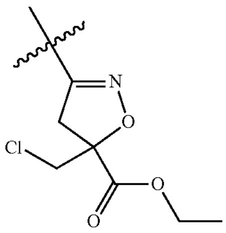 [SMILES: *C1=NOC(CCl)(C(=O)OCC)C1] | Cl | F | 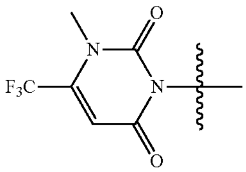 [SMILES: *n1c(=O)cc(C(F)(F)F)n(C)c1=O] | |

TABLE 1-continued
Structures and $^{1}$H NMR data of compounds
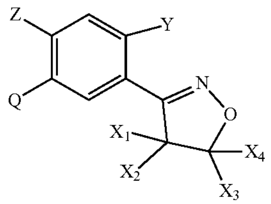
I
| NO. | 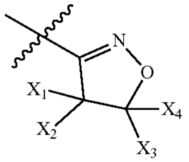 | Y | Z | Q | $^{1}$H NMR |
|---|---|---|---|---|---|
| 217 | 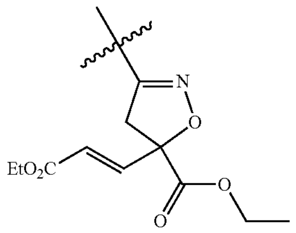 [SMILES: *C1=NOC(/C=C/C(=O)OCC)(C(=O)OCC)C1] | Cl | F | 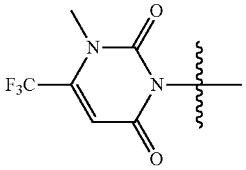 [SMILES: *n1c(=O)cc(C(F)(F)F)n(C)c1=O] | |
| 218 | 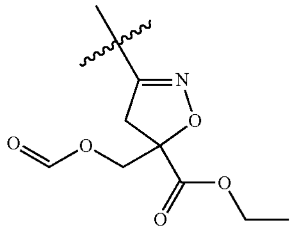 [SMILES: *C1=NOC(COC=O)(C(=O)OCC)C1] | Cl | F | 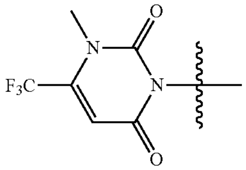 [SMILES: *n1c(=O)cc(C(F)(F)F)n(C)c1=O] | 1H NMR (500 MHz, DMSO-d6) δ 10.23 (s, 1H), 7.94-7.89 (m, 2H), 6.64 (s, 1H), 4.65-4.23 (m, 2H), 4.29-4.27 (m, 2H), 4.21-4.18 (m, 2H), 3.43 (s, 3H), 1.26-1.23 (m, 3H). |
| 219 | 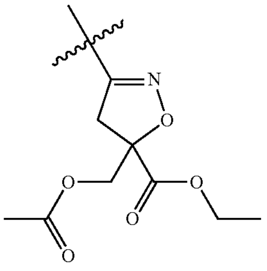 [SMILES: *C1=NOC(COC(C)=O)(C(=O)OCC)C1] | Cl | F | 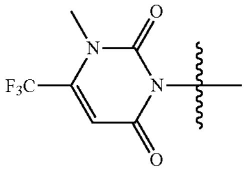 [SMILES: *n1c(=O)cc(C(F)(F)F)n(C)c1=O] | 1H NMR (500 MHz, DMSO) δ 7.88-7.86 (m, 2H), 6.60 (s, 1H), 4.45-4.40 (m, 1H), 4.36-4.33 (m, 1H), 4.23-4.11 (m, 2H), 3.86-3.84 (m, 1H), 3.75-3.68 (m, 1H), 3.39 (s, 3H), 2.01 (s, 3H), 1.20-1.18 (m, 3H). |
| 220 | 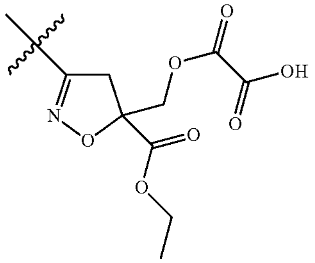 [SMILES: *C1=NOC(COC(=O)C(=O)O)(C(=O)OCC)C1] | Cl | F | 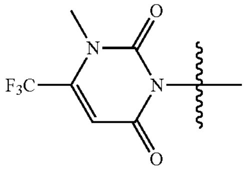 [SMILES: *n1c(=O)cc(C(F)(F)F)n(C)c1=O] | 1H NMR (500 MHz, DMSO-d6) δ 7.91-7.86 (m, 2H), 6.61 (s, 1H), 4.68 (d, J = 12.0 Hz, 1H), 4.59 (d, J = 12.0 Hz, 1H), 4.25-4.08 (m, 4H), 3.42 (s, 3H), 1.25-1.20 (m, 3H). |

TABLE 1-continued
Structures and $^1$H NMR data of compounds
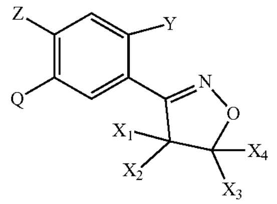
I
| NO. | 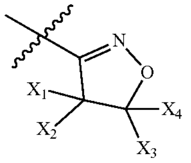 | Y | Z | Q | $^1$H NMR |
|---|---|---|---|---|---|
| 221 | 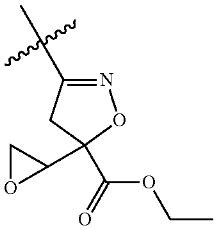 [SMILES: *C1=NOC(C(=O)OCC)(C2CO2)C1] | Cl | F | 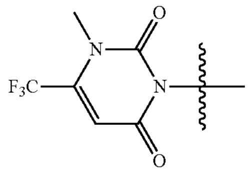 [SMILES: *n1c(=O)cc(C(F)(F)F)n(C)c1=O] | |
| 222 | 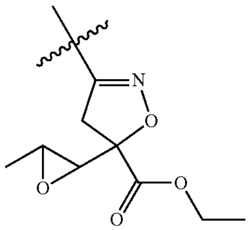 [SMILES: *C1=NOC(C(=O)OCC)(C2OC2C)C1] | Cl | F | 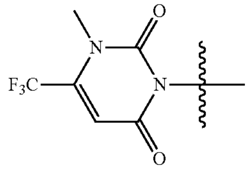 [SMILES: *n1c(=O)cc(C(F)(F)F)n(C)c1=O] | |
| 223 | 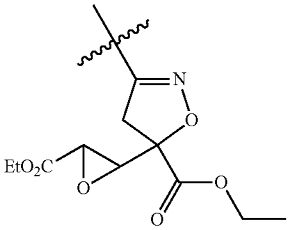 [SMILES: *C1=NOC(C(=O)OCC)(C2OC2C(=O)OCC)C1] | Cl | F | 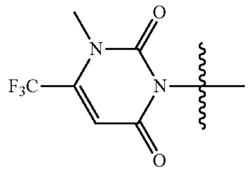 [SMILES: *n1c(=O)cc(C(F)(F)F)n(C)c1=O] | |
| 224 | 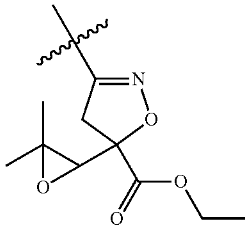 [SMILES: *C1=NOC(C(=O)OCC)(C2OC2(C)C)C1] | Cl | F | 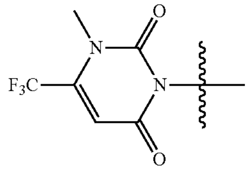 [SMILES: *n1c(=O)cc(C(F)(F)F)n(C)c1=O] | |
| 225 | 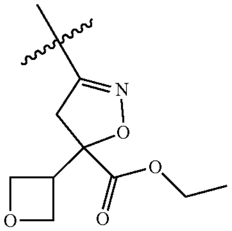 [SMILES: *C1=NOC(C(=O)OCC)(C2COC2)C1] | Cl | F | 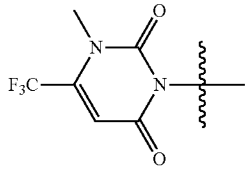 [SMILES: *n1c(=O)cc(C(F)(F)F)n(C)c1=O] | |

TABLE 1-continued
Structures and $^1$H NMR data of compounds
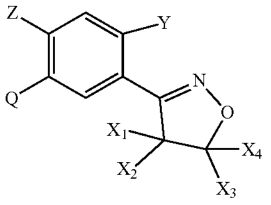
I
| NO. | 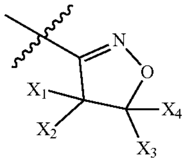 | Y | Z | Q | $^1$H NMR |
|---|---|---|---|---|---|
| 226 | 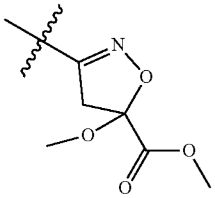 [SMILES: *C1=NOC(OC)(C(=O)OC)C1] | Cl | F | 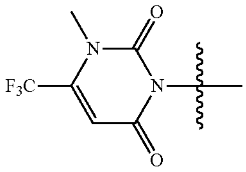 [SMILES: *n1c(=O)cc(C(F)(F)F)n(C)c1=O] | $^1$H NMR (500 MHz, DMSO-d6) δ 7.94 (dd, J = 8.5, 5.5 Hz, 2H), 6.64 (s, 1H), 4.09 (m, 1H), 3.82 (s, 3H), 3.69 (m, 1H), 3.44 (s, 3H), 3.34 (s, 3H). |
| 227 | 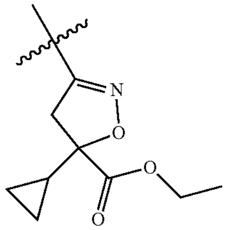 [SMILES: *C1=NOC(C(=O)OCC)(C2CC2)C1] | Cl | F | 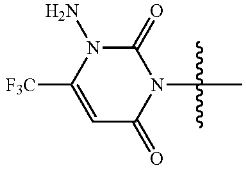 [SMILES: *n1c(=O)cc(C(F)(F)F)n(N)c1=O] | |
| 228 | 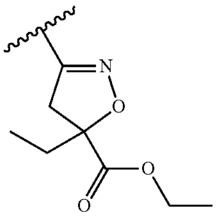 [SMILES: *C1=NOC(CC)(C(=O)OCC)C1] | Cl | F | 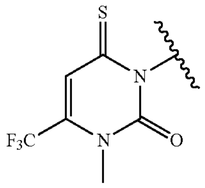 [SMILES: *n1c(=S)cc(C(F)(F)F)n(C)c1=O] | $^1$H NMR (500 MHz, DMSO-d6) δ 7.91-7.88 (m, 2H), 7.12 (s, 1H), 4.21 (q, J = 7.0 Hz, 2H), 3.85 (dd, J = 18.0, 3.0 Hz, 1H), 3.55 (dd, J = 18.0, 3.0 Hz, 1H), 3.43 (s, 3H), 2.00-1.97 (m, 2H), 1.24 (t, J = 7.0 Hz, 3H), 0.92 (t, J = 7.5 Hz, 3H). |
| 229 | 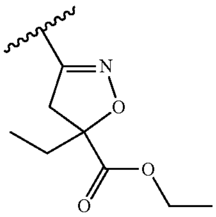 [SMILES: *C1=NOC(CC)(C(=O)OCC)C1] | Cl | F | 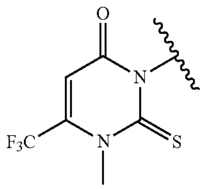 [SMILES: *n1c(=O)cc(C(F)(F)F)n(C)c1=S] | $^1$H NMR (500 MHz, DMSO-d6) δ 8.16 (d, J = 8.0 Hz, 1H), 8.06 (d, J = 9.0 Hz, 1H), 6.98 (s, 1H), 4.22 (t, J = 7.0 Hz, 2H), 3.89-3.83 (m 1H), 3.58-3.53 (m, 1H), 3.42 (s, 3H), 2.00-1.94 (m, 2H), 1.25 (t, J = 7.0 Hz, 3H), 0.92 (t, J = 7.5 Hz, 3H). |
| 230 | 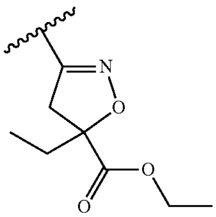 | Cl | F | 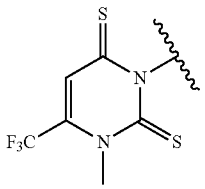 [SMILES: *n1c(=S)cc(C(F)(F)F)n(C)c1=S] | $^1$H NMR (500 MHz, DMSO-d6) δ 8.17 (d, J = 7.5 Hz, 1H), 8.08 (d, J = 9.5 Hz, 1H), 7.65 (s, 1H), 4.22 (q, J = 7.0 Hz, 2H), 3.86 (dd, J = 18.0, 7.5 Hz, 1H), 3.55 (dd, J = 18.0, 7.5 Hz, 1H), 3.42 (s, 3H),1.98 (q, J = 7.0 Hz, 2H), 1.25 (t, J = 7.0 Hz, 3H), 0.92 (t, J = 7.0 Hz, 3H). |

TABLE 1-continued
Structures and $^1$H NMR data of compounds
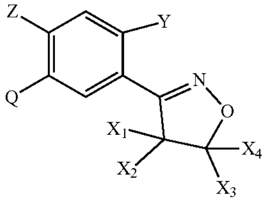
I
| NO. | 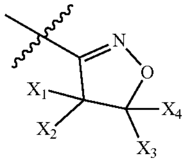 | Y | Z | Q | $^1$H NMR |
|---|---|---|---|---|---|
| 231 | 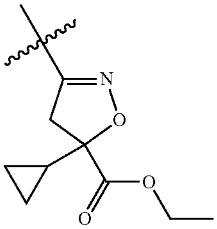 [SMILES: *C1=NOC(C(=O)OCC)(C2CC2)C1] | Cl | F | 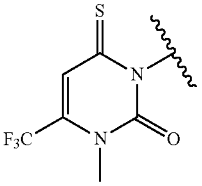 [SMILES: *n1c(=S)cc(C(F)(F)F)n(C)c1=O] | $^1$H NMR (500 MHz, DMSO-d6) δ 7.92-7.87 (m, 2H), 7.12 (s, 1H), 4.23 (q, J = 7.0 Hz, 2H), 3.88 (dd, J = 17.5, 5.5 Hz, 1H), 3.48-3.45 (m 1H), 3.43 (s, 3H), 1.49-1.46 (m, 1H), 1.25 (t, J = 7.0 Hz, 3H), 0.57-0.52 (m, 3H), 0.37-0.34 (m, 1H). |
| 232 | 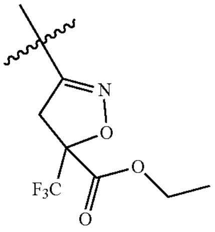 [SMILES: *C1=NOC(C(=O)OCC)(C(F)(F)F)C1] | Cl | F | 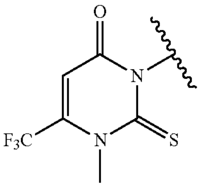 [SMILES: *n1c(=O)cc(C(F)(F)F)n(C)c1=S] | $^1$H NMR (500 MHz, DMSO-d6) δ 9.14 (d, J = 9.5 Hz, 1H), 8.53 (d, J = 7.5 Hz, 1H), 7.10 (s, 1H), 4.42-4.40 (m, 1H), 4.35 (t, J = 7.0 Hz, 2H), 4.25-4.23 (m, 1H), 2.52 (s, 3H), 1.31 (t, J = 7.0 Hz, 3H). |
| 233 | 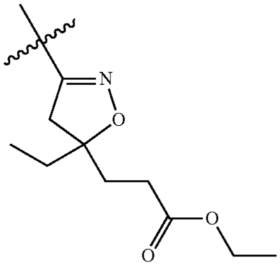 [SMILES: *C1=NOC(CC)(CCC(=O)OCC)C1] | Cl | F | 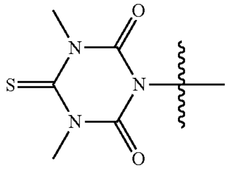 [SMILES: *n1c(=O)n(C)c(=S)n(C)c1=O] | |
| 234 | 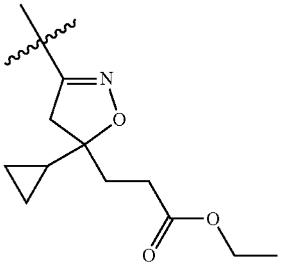 [SMILES: *C1=NOC(CCC(=O)OCC)(C2CC2)C1] | Cl | F | 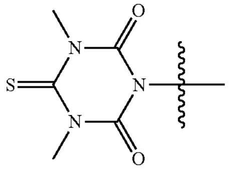 [SMILES: *n1c(=O)n(C)c(=S)n(C)c1=O] | |

TABLE 1-continued

Structures and $^1H$ NMR data of compounds

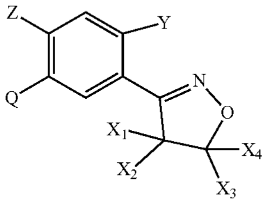

I

| NO. | 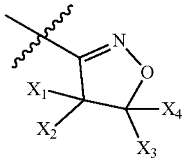 | Y | Z | Q | $^1H$ NMR |
|---|---|---|---|---|---|
| 235 | 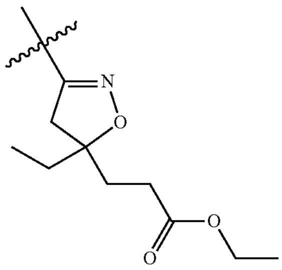 [SMILES: *C1=NOC(CC)(CCC(=O)OCC)C1] | Cl | F | 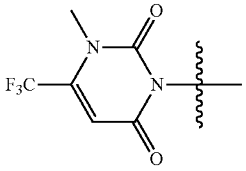 [SMILES: *n1c(=O)cc(C(F)(F)F)n(C)c1=O] | |
| 236 | 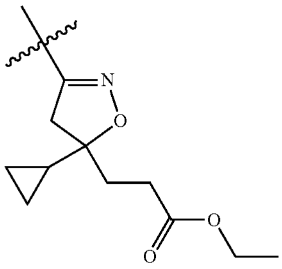 [SMILES: *C1=NOC(CCC(=O)OCC)(C2CC2)C1] | Cl | F | 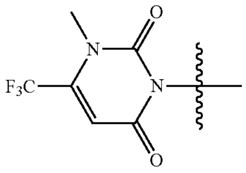 [SMILES: *n1c(=O)cc(C(F)(F)F)n(C)c1=O] | |

Table A is constructed in the same way as that of Table 1 above, except for replacing the racemate compounds having a chiral center (the carbon atom (C *) connected to $X_3$ and $X_4$ in general formula I

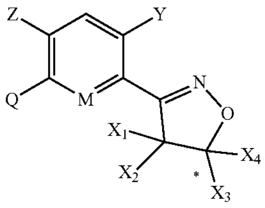

I is a chiral center, that is, $X_3$, $X_4$ are not the same) (that is, compounds 1-50, 52-90, 92-93, 95-152, 154-192, 194-195 and 197-236) with the corresponding compounds in S configuration and deleting the compounds having no chiral center at the corresponding position, and in Table A, the entries in the column "NO." are listed in sequence as "1 (S)-50 (S), 52 (S)-90 (S), 92 (S)-93 (S), 95 (S)-152 (S), 154 (S)-192 (S), 194 (S)-195 (S) and 197 (S)-236 (S)". For example, "1 (S)" corresponds to S configuration of compound "1" in Table 1, "119 (S)" corresponds to S configuration of compound "119" in Table 1.

TABLE B
Structures and $^1H$ NMR date of compounds
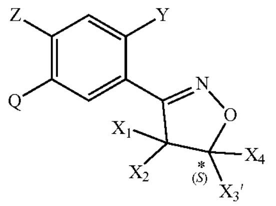
I'
| NO. | 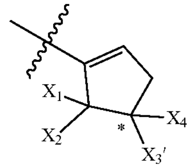 | Y | Z | Q | $^1H$ NMR |
|---|---|---|---|---|---|
| 1-1 | 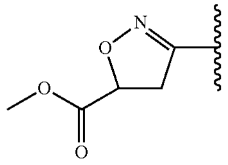 [SMILES: *C1=NOC(C(=O)OC)C1] | Cl | F | 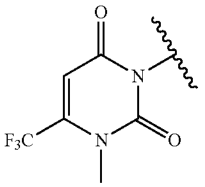 [SMILES: *n1c(=O)cc(C(F)(F)F)n(C)c1=O] | |
| 1-2 | 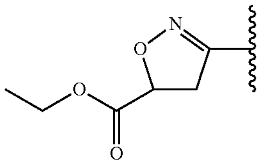 [SMILES: *C1=NOC(C(=O)OCC)C1] | Cl | F | 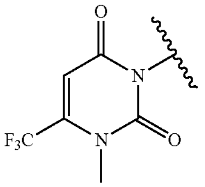 [SMILES: *n1c(=O)cc(C(F)(F)F)n(C)c1=O] | $^1H$ NMR (500 MHz, DMSO-$d_6$) δ 7.90-7.88 (m, 2H), 6.63 (s, 1H), 5.36 (dd, J = 12.0, 6.0 Hz, 1H), 4.20 (q, J = 7.0 Hz, 2H), 3.90-3.84 (m, 1H), 3.72-3.66 (m, 1H), 3.44 (s, 3H), 1.25 (t, J = 7.0 Hz, 3H). |
| 1-3 | 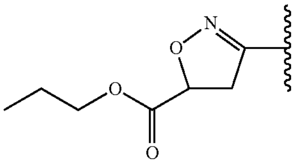 | Cl | F | 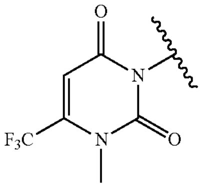 [SMILES: *n1c(=O)cc(C(F)(F)F)n(C)c1=O] | |
| 1-4 | 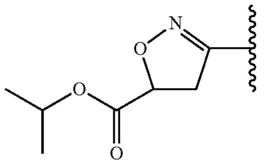 [SMILES: *C1=NOC(C(=O)OC(C)C)C1] | Cl | F | 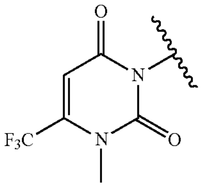 [SMILES: *n1c(=O)cc(C(F)(F)F)n(C)c1=O] | |
| 1-5 | 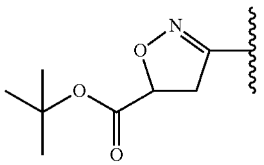 [SMILES: *C1=NOC(C(=O)OC(C)(C)C)C1] | Cl | F | 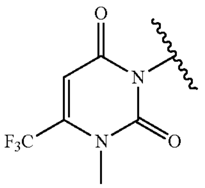 | |
| 1-6 | 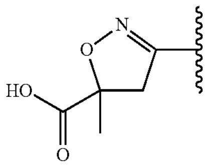 [SMILES: *C1=NOC(C)(C(=O)O)C1] | Cl | F | 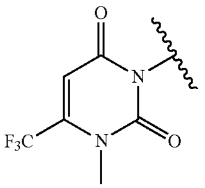 [SMILES: *n1c(=O)cc(C(F)(F)F)n(C)c1=O] | |

TABLE B-continued
Structures and $^1$H NMR date of compounds
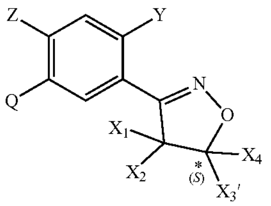
I'
| NO. | 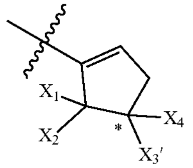 | Y | Z | Q | $^1$H NMR |
|---|---|---|---|---|---|
| 1-7 | 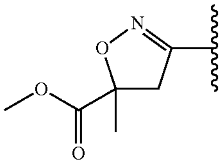 [SMILES: *C1=NOC(C)(C(=O)OC)C1] | Cl | F | 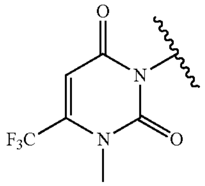 | |
| 1-8 | 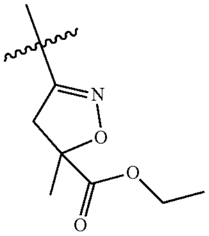 [SMILES: *C1=NOC(C)(C(=O)OCC)C1] | Cl | Cl | 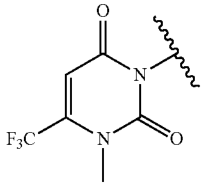 [SMILES: *n1c(=O)cc(C(F)(F)F)n(C)c1=O] | |
| 1-9 | 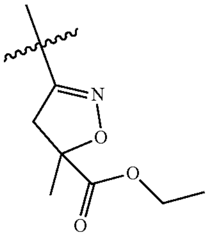 [SMILES: *C1=NOC(C)(C(=O)OCC)C1] | Cl | F | 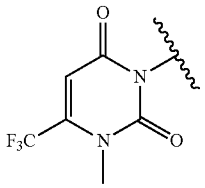 [SMILES: *n1c(=O)cc(C(F)(F)F)n(C)c1=O] | $^1$H NMR (500 MHz, Chloroform-d) δ 7.72 (d, J = 7.5 Hz, 1H), 7.39 (d, J = 9.0 Hz, 1H), 6.41 (s, 1H), 4.39-4.25 (m, 2H), 4.04-3.95 (m, 1H), 3.60 (s, 3H), 3.51-3.31 (m, 1H), 1.75 (d, J = 2.5 Hz, 3H), 1.36 (td, J = 7.1, 1.7 Hz, 3H). |
| 1-10 | 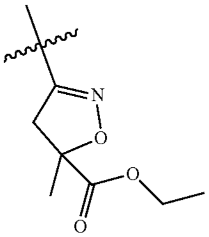 [SMILES: *C1=NOC(C)(C(=O)OCC)C1] | $CF_3$ | F | 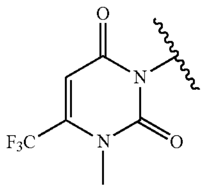 [SMILES: *n1c(=O)cc(C(F)(F)F)n(C)c1=O] | |
| 1-11 | 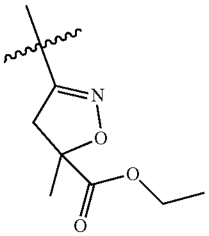 [SMILES: *C1=NOC(C)(C(=O)OCC)C1] | Br | F | 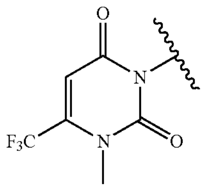 [SMILES: *n1c(=O)cc(C(F)(F)F)n(C)c1=O] | |

TABLE B-continued
Structures and $^1$H NMR date of compounds
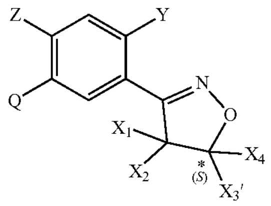
I'
| NO. | 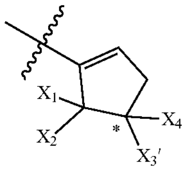 | Y | Z | Q | $^1$H NMR |
| --- | --- | --- | --- | --- | --- |
| 1-12 | 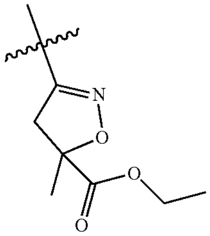 [SMILES: *C1=NOC(C)(C(=O)OCC)C1] | CN | F | 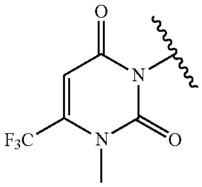 [SMILES: *n1c(=O)cc(C(F)(F)F)n(C)c1=O] | |
| 1-13 | 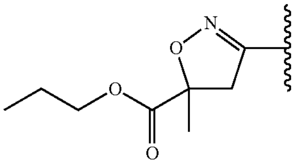 | Cl | F | 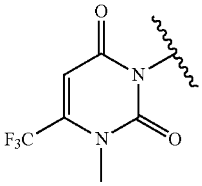 [SMILES: *n1c(=O)cc(C(F)(F)F)n(C)c1=O] | |
| 1-14 | 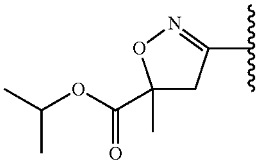 [SMILES: *C1=NOC(C)(C(=O)OC(C)C)C1] | Cl | F | 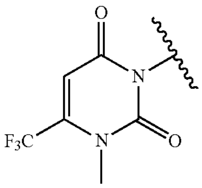 [SMILES: *n1c(=O)cc(C(F)(F)F)n(C)c1=O] | |
| 1-15 | 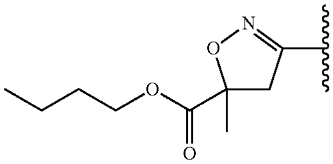 [SMILES: *C1=NOC(C)(C(=O)OCCCC)C1] | Cl | F | 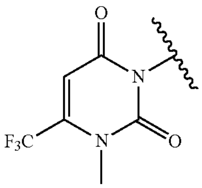 [SMILES: *n1c(=O)cc(C(F)(F)F)n(C)c1=O] | |
| 1-16 | 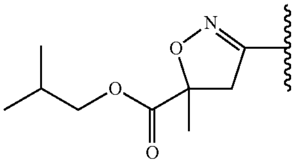 [SMILES: *C1=NOC(C)(C(=O)OCC(C)C)C1] | Cl | F | 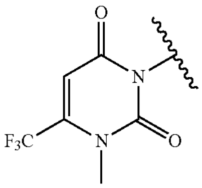 [SMILES: *n1c(=O)cc(C(F)(F)F)n(C)c1=O] | |

TABLE B-continued
Structures and $^{1}H$ NMR date of compounds
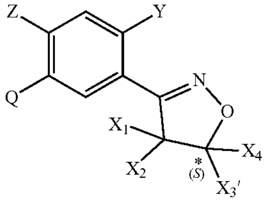
I'
| NO. | 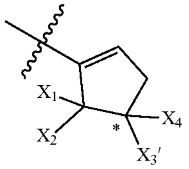 | Y | Z | Q | $^{1}H$ NMR |
|---|---|---|---|---|---|
| 1-17 | 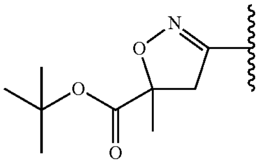 [SMILES: *C1=NOC(C)(C(=O)OC(C)(C)C)C1] | Cl | F | 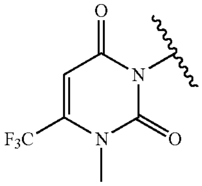 [SMILES: *n1c(=O)cc(C(F)(F)F)n(C)c1=O] | |
| 1-18 | 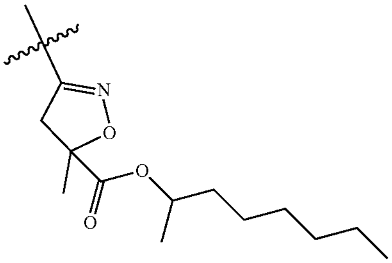 [SMILES: *C1=NOC(C)(C(=O)OC(C)CCCCCC)C1] | Cl | F | 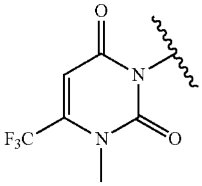 | |
| 1-19 | 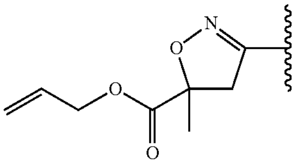 [SMILES: *C1=NOC(C)(C(=O)OCC=C)C1] | Cl | F | 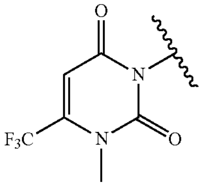 [SMILES: *n1c(=O)cc(C(F)(F)F)n(C)c1=O] | |
| 1-20 | 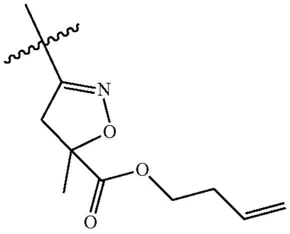 [SMILES: *C1=NOC(C)(C(=O)OCCC=C)C1] | Cl | F | 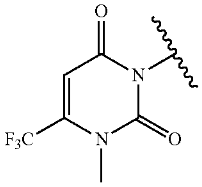 | |
| 1-21 | 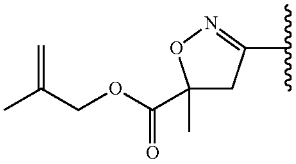 [SMILES: *C1=NOC(C)(C(=O)OCC(=C)C)C1] | Cl | F | 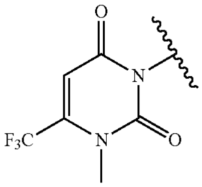 | |

TABLE B-continued
Structures and $^1$H NMR date of compounds
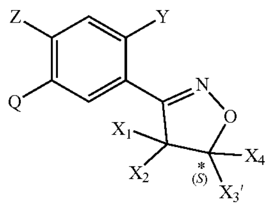
I'
| NO. | 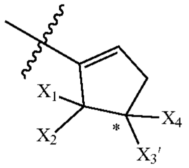 | Y | Z | Q | $^1$H NMR |
|---|---|---|---|---|---|
| 1-22 | 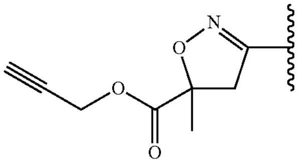 [SMILES: *C1=NOC(C)(C(=O)OCC#C)C1] | Cl | F | 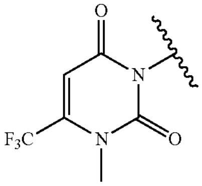 [SMILES: *n1c(=O)cc(C(F)(F)F)n(C)c1=O] | |
| 1-23 | 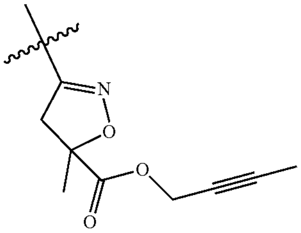 [SMILES: *C1=NOC(C)(C(=O)OCC#CC)C1] | Cl | F | 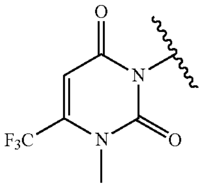 [SMILES: *n1c(=O)cc(C(F)(F)F)n(C)c1=O] | |
| 1-24 | 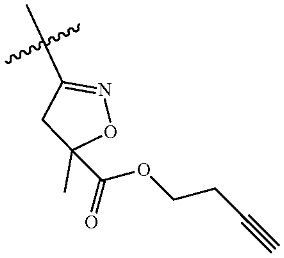 [SMILES: *C1=NOC(C)(C(=O)OCCC#C)C1] | Cl | F | 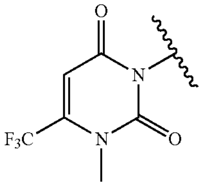 [SMILES: *n1c(=O)cc(C(F)(F)F)n(C)c1=O] | |
| 1-25 | 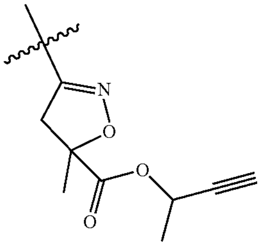 [SMILES: *C1=NOC(C)(C(=O)OC(C)C#C)C1] | Cl | F | 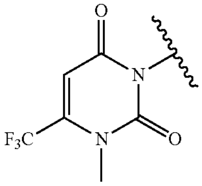 [SMILES: *n1c(=O)cc(C(F)(F)F)n(C)c1=O] | |
| 1-26 | 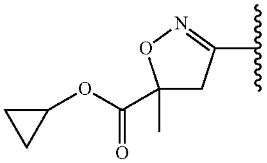 [SMILES: *C1=NOC(C)(C(=O)OC2CC2)C1] | Cl | F | 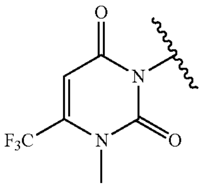 | |

TABLE B-continued
Structures and $^1$H NMR date of compounds
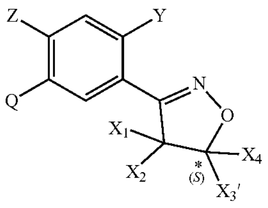
I'
| NO. | 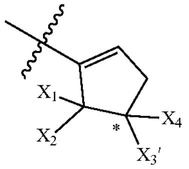 | Y | Z | Q | $^1$H NMR |
|---|---|---|---|---|---|
| 1-27 | 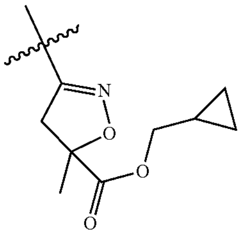 [SMILES: *C1=NOC(C)(C(=O)OCC2CC2)C1] | Cl | F | 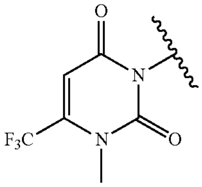 [SMILES: *n1c(=O)cc(C(F)(F)F)n(C)c1=O] | |
| 1-28 | 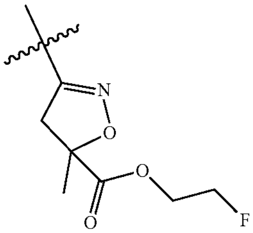 [SMILES: *C1=NOC(C)(C(=O)OCCF)C1] | Cl | F | 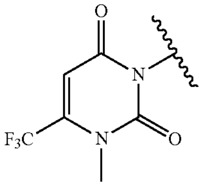 [SMILES: *n1c(=O)cc(C(F)(F)F)n(C)c1=O] | |
| 1-29 | 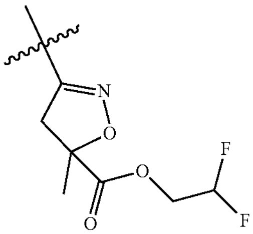 [SMILES: *C1=NOC(C)(C(=O)OCC(F)F)C1] | Cl | F | 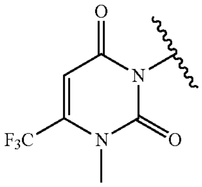 [SMILES: *n1c(=O)cc(C(F)(F)F)n(C)c1=O] | |
| 1-30 | 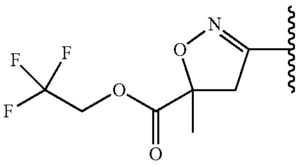 [SMILES: *C1=NOC(C)(C(=O)OCC(F)(F)F)C1] | Cl | F | 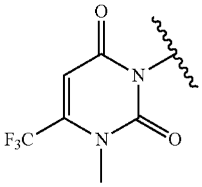 [SMILES: *n1c(=O)cc(C(F)(F)F)n(C)c1=O] | |
| 1-31 | 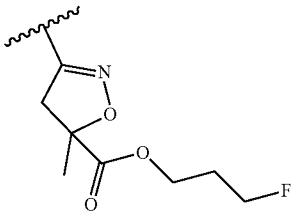 [SMILES: *C1=NOC(C)(C(=O)OCCCF)C1] | Cl | F | 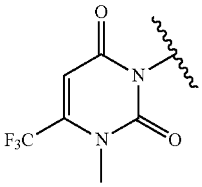 [SMILES: *n1c(=O)cc(C(F)(F)F)n(C)c1=O] | |

TABLE B-continued
Structures and $^{1}$H NMR date of compounds
| NO. | 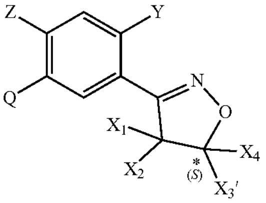 I' 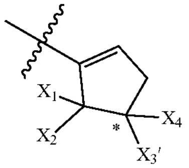 | Y | Z | Q | $^{1}$H NMR |
|---|---|---|---|---|---|
| 1-32 | 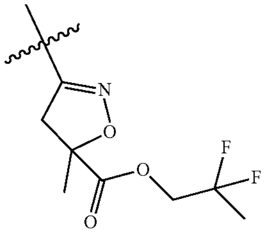 [SMILES: *C1=NOC(C)(C(=O)OCC(C)(F)F)C1] | Cl | F | 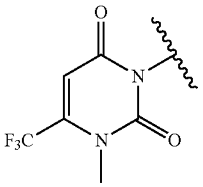 [SMILES: *n1c(=O)cc(C(F)(F)F)n(C)c1=O] | |
| 1-33 | 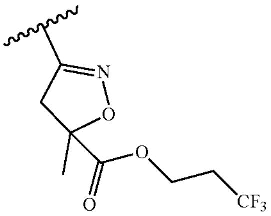 [SMILES: *C1=NOC(C)(C(=O)OCCC(F)(F)F)C1] | Cl | F | 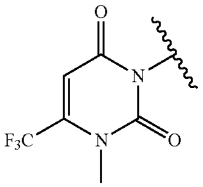 [SMILES: *n1c(=O)cc(C(F)(F)F)n(C)c1=O] | |
| 1-34 | 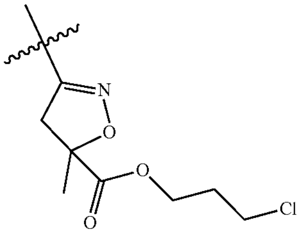 [SMILES: *C1=NOC(C)(C(=O)OCCCCl)C1] | Cl | F | 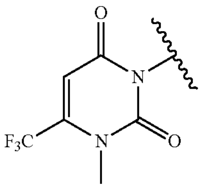 [SMILES: *n1c(=O)cc(C(F)(F)F)n(C)c1=O] | |
| 1-35 | 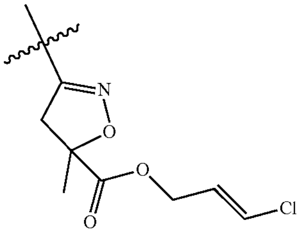 [SMILES: *C1=NOC(C)(C(=O)OC/C=C/Cl)C1] | Cl | F | 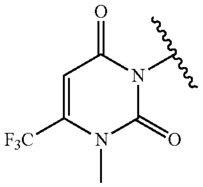 [SMILES: *n1c(=O)cc(C(F)(F)F)n(C)c1=O] | |
| 1-36 | 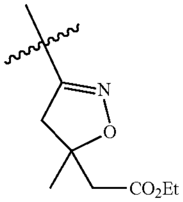 [SMILES: *C1=NOC(C)(CC(=O)OCC)C1] | Cl | F | 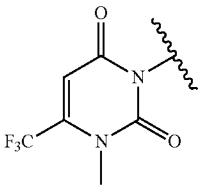 [SMILES: *n1c(=O)cc(C(F)(F)F)n(C)c1=O] | |

TABLE B-continued
Structures and $^1H$ NMR date of compounds
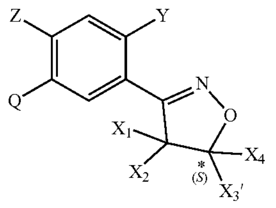
I'
| NO. | 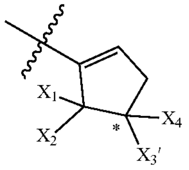 | Y | Z | Q | $^1H$ NMR |
|---|---|---|---|---|---|
| 1-37 | 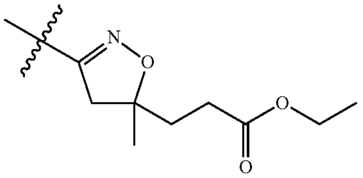 [SMILES: *C1=NOC(C)(CCC(=O)OCC)C1] | Cl | F | 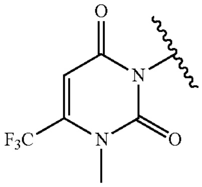 [SMILES: *n1c(=O)cc(C(F)(F)F)n(C)c1=O] | $^1H$ NMR (500 MHz, DMSO) δ 7.87 (d, J = 9.5 Hz, 1H), 7.84 (d, J = 8.0 Hz, 1H), 6.63 (s, 1H), 4.10-4.03 (m, 2H), 3.44 (s, 3H), 3.44-3.37 (m, 1H), 3.28-3.22 (m, 1H), 2.44-2.40 (m, 2H), 2.03-1.92 (m, 2H), 1.40 (s, 3H), 1.19 (t, J = 7.0 Hz, 3H). |
| 1-38 | 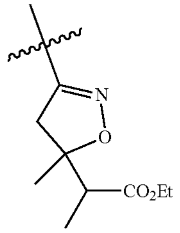 [SMILES: *C1=NOC(C)(C(C)C(=O)OCC)C1] | Cl | F | 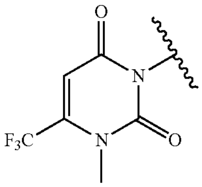 [SMILES: *n1c(=O)cc(C(F)(F)F)n(C)c1=O] | |
| 1-39 | 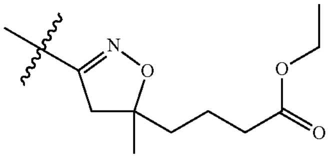 [SMILES: *C1=NOC(C)(CCCC(=O)OCC)C1] | Cl | F | 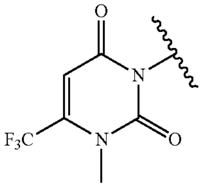 [SMILES: *n1c(=O)cc(C(F)(F)F)n(C)c1=O] | $^1H$ NMR (500 MHz, DMSO) δ 7.86-7.85 (m, 2H), 6.63 (s, 1H), 4.07 (q, J = 7.0 Hz, 2H), 3.44 (s, 3H), 3.33 (d, J = 17.0 Hz, 1H), 3.22 (d, J = 17.0 Hz, 1H), 2.35-2.34 (m, 2H), 1.73-1.58 (m, 4H), 1.38 (s, 3H), 1.19 (t, J = 7.0 Hz, 3H). |
| 1-40 | 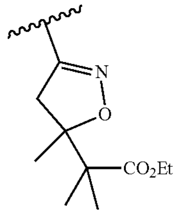 [SMILES: *C1=NOC(C)(C(C)(C)C(=O)OCC)C1] | Cl | F | 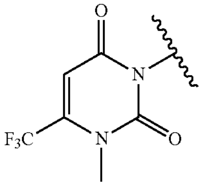 [SMILES: *n1c(=O)cc(C(F)(F)F)n(C)c1=O] | |
| 1-41 | 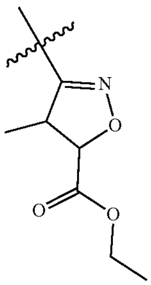 [SMILES: *C1=NOC(C(=O)OCC)C1C] | Cl | F | 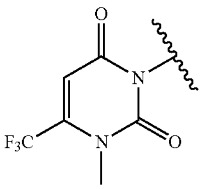 [SMILES: *n1c(=O)cc(C(F)(F)F)n(C)c1=O] | |

TABLE B-continued
Structures and $^{1}$H NMR date of compounds
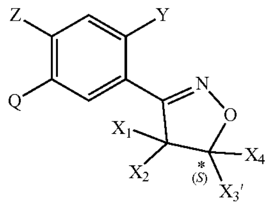
I'
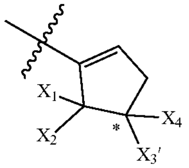
| NO. | | Y | Z | Q | $^{1}$H NMR |
| --- | --- | --- | --- | --- | --- |
| 1-42 | 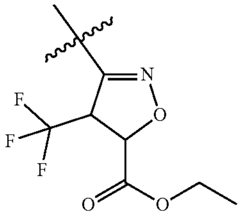 [SMILES: *C1=NOC(C(=O)OCC)C1C(F)(F)F] | Cl | F | 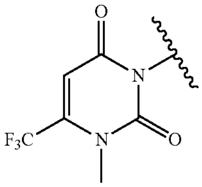 [SMILES: *n1c(=O)cc(C(F)(F)F)n(C)c1=O] | |
| 1-43 | 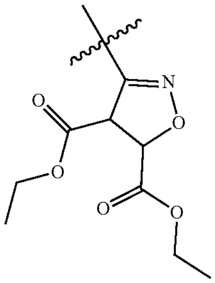 [SMILES: *C1=NOC(C(=O)OCC)C1C(=O)OCC] | Cl | F | 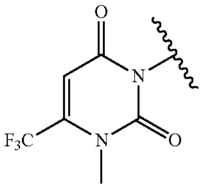 [SMILES: *n1c(=O)cc(C(F)(F)F)n(C)c1=O] | |
| 1-44 | 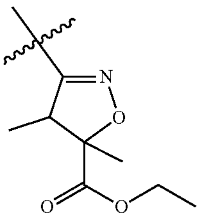 [SMILES: *C1=NOC(C)(C(=O)OCC)C1C] | Cl | F | 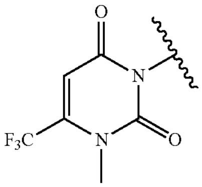 [SMILES: *n1c(=O)cc(C(F)(F)F)n(C)c1=O] | |
| 1-45 | 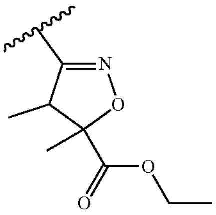 | Cl | F | 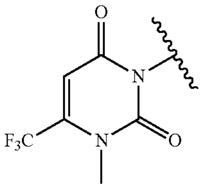 [SMILES: *n1c(=O)cc(C(F)(F)F)n(C)c1=O] | |
| 1-46 | 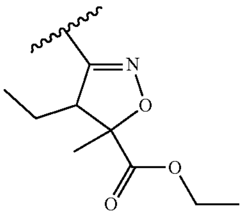 [SMILES: *C1=NOC(C)(C(=O)OCC)C1CC] | Cl | F | 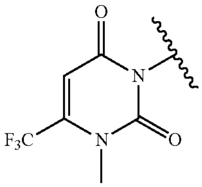 [SMILES: *n1c(=O)cc(C(F)(F)F)n(C)c1=O] | |

TABLE B-continued
Structures and $^1$H NMR date of compounds
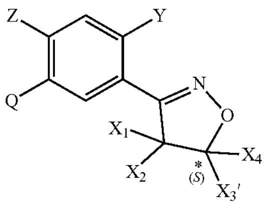
I'
| NO. | 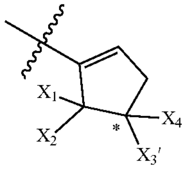 | Y | Z | Q | $^1$H NMR |
|---|---|---|---|---|---|
| 1-47 | 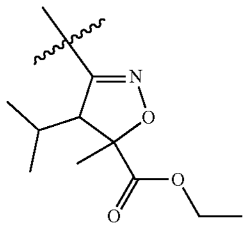 [SMILES: *C1=NOC(C)(C(=O)OCC)C1C(C)C] | Cl | F | 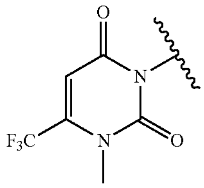 [SMILES: *n1c(=O)cc(C(F)(F)F)n(C)c1=O] | |
| 1-48 | 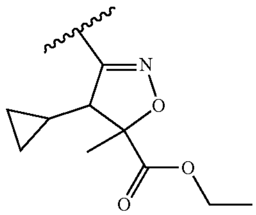 [SMILES: *C1=NOC(C)(C(=O)OCC)C1C1CC1] | Cl | F | 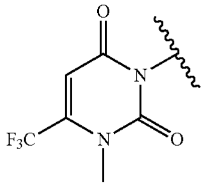 [SMILES: *n1c(=O)cc(C(F)(F)F)n(C)c1=O] | |
| 1-49 | 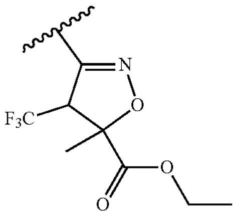 [SMILES: *C1=NOC(C)(C(=O)OCC)C1C(F)(F)F] | Cl | F | 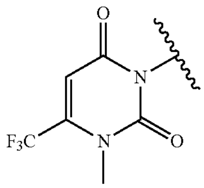 [SMILES: *n1c(=O)cc(C(F)(F)F)n(C)c1=O] | |
| 1-50 | 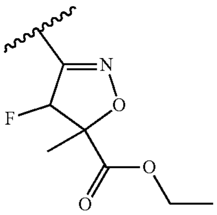 [SMILES: *C1=NOC(C)(C(=O)OCC)C1F] | Cl | F | 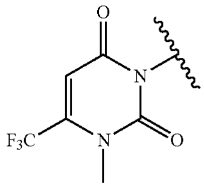 [SMILES: *n1c(=O)cc(C(F)(F)F)n(C)c1=O] | |
| 1-51 | 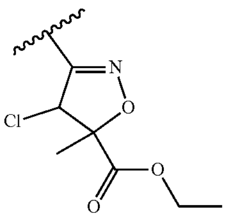 [SMILES: *C1=NOC(C)(C(=O)OCC)C1Cl] | Cl | F | 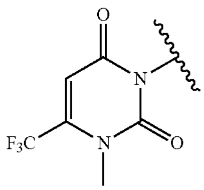 [SMILES: *n1c(=O)cc(C(F)(F)F)n(C)c1=O] | |

TABLE B-continued
Structures and $^1$H NMR date of compounds
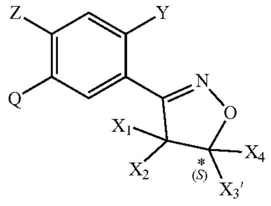
I'
| NO. | 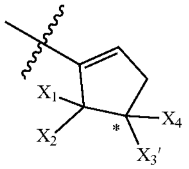 | Y | Z | Q | $^1$H NMR |
|---|---|---|---|---|---|
| 1-52 | 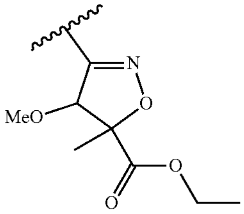 [SMILES: *C1=NOC(C)(C(=O)OCC)C1OC] | Cl | F | 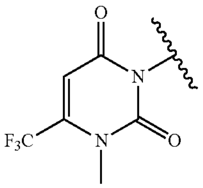 [SMILES: *n1c(=O)cc(C(F)(F)F)n(C)c1=O] | |
| 1-53 | 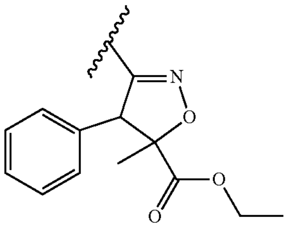 [SMILES: *C1=NOC(C)(C(=O)OCC)C1c1ccccc1] | Cl | F | 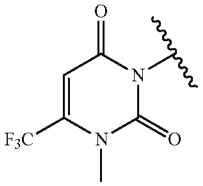 [SMILES: *n1c(=O)cc(C(F)(F)F)n(C)c1=O] | |
| 1-54 | 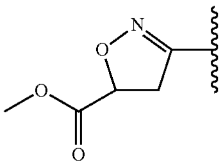 [SMILES: *C1=NOC(C(=O)OC)C1] | Cl | F | 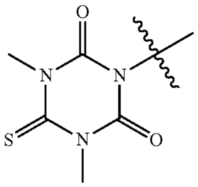 [SMILES: *n1c(=O)n(C)c(=S)n(C)c1=O] | |
| 1-55 | 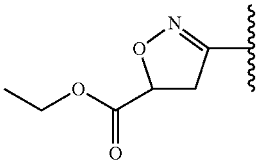 [SMILES: *C1=NOC(C(=O)OCC)C1] | Cl | F | 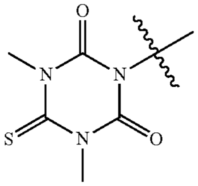 [SMILES: *n1c(=O)n(C)c(=S)n(C)c1=O] | $^1$H NMR (500 MHz, DMSO-$d_6$) δ 7.97 (d, J = 7.5 Hz, 1H), 7.92 (d, J = 9.5 Hz, 1H), 5.38-5.34 (m, 1H), 4.20 (q, J = 7.0 Hz, 2H), 3.90-3.85 (m, 1H), 3.73-3.67 (m, 1H), 3.65 (s, 6H), 1.25 (t, J = 7.0 Hz, 3H). |
| 1-56 | 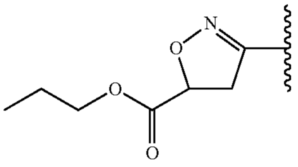 | Cl | F | 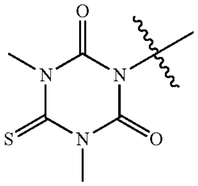 [SMILES: *n1c(=O)n(C)c(=S)n(C)c1=O] | |

TABLE B-continued
Structures and $^1$H NMR date of compounds
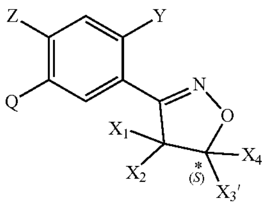
I'
| NO. | 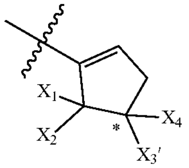 | Y | Z | Q | $^1$H NMR |
|---|---|---|---|---|---|
| 1-57 | 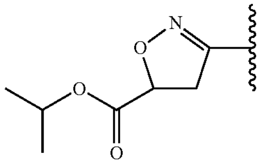 | Cl | F | 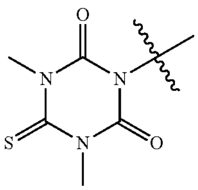 [SMILES: *n1c(=O)n(C)c(=S)n(C)c1=O] | |
| 1-58 | 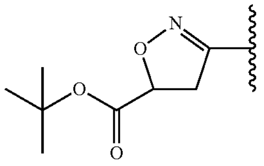 [SMILES: *C1=NOC(C(=O)OC(C)(C)C)C1] | Cl | F | 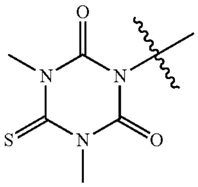 [SMILES: *n1c(=O)n(C)c(=S)n(C)c1=O] | |
| 1-59 | 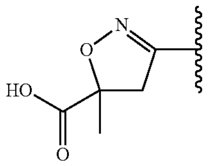 [SMILES: *C1=NOC(C)(C(=O)O)C1] | Cl | F | 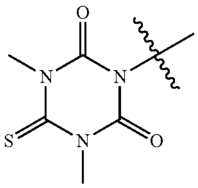 [SMILES: *n1c(=O)n(C)c(=S)n(C)c1=O] | $^1$H NMR (500 MHz, DMSO) δ 13.39 (s, 1H), 7.96 (d, J = 7.5 Hz, 1H), 7.90 (d, J = 9.5 Hz, 1H), 3.90 (d, J = 17.0 Hz, 1H), 3.65 (s, 6H), 3.49 (d, J = 17.0 Hz, 1H), 1.62 (s, 3H). |
| 1-60 | 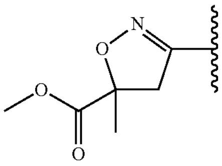 [SMILES: *C1=NOC(C)(C(=O)OC)C1] | Cl | F | 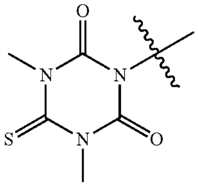 [SMILES: *n1c(=O)n(C)c(=S)n(C)c1=O] | $^1$H NMR (500 MHz, DMSO) δ 7.97 (d, J = 7.5 Hz, 1H), 7.91 (d, J = 9.5 Hz, 1H), 3.93 (d, J = 17.5 Hz, 1H), 3.75 (s, 3H), 3.65 (s, 6H), 3.53 (t, J = 17.5 Hz, 1H), 1.64 (s, 3H). |
| 1-61 | 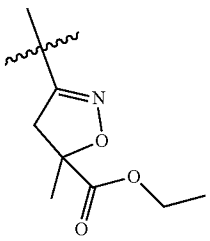 [SMILES: *C1=NOC(C)(C(=O)OCC)C1] | Cl | Cl | 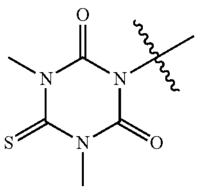 [SMILES: *n1c(=O)n(C)c(=S)n(C)c1=O] | $^1$H NMR (500 MHz, DMSO-$d_6$) δ 8.09 (s, 1H), 8.02 (s, 1H), 4.22 (q, J = 7.0 Hz, 2H), 3.94 (d, J = 17.5 Hz, 1H), 3.66 (s, 6H), 3.56 (d, J = 17.5 Hz, 1H), 1.64 (s, 3H), 1.24 (t, J = 7.0 Hz, 3H). |

TABLE B-continued

Structures and $^{1}H$ NMR date of compounds

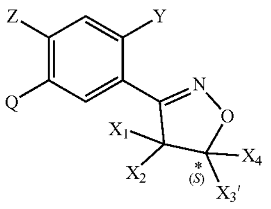

I'

| NO. | 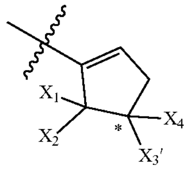 | Y | Z | Q | $^{1}H$ NMR |
|---|---|---|---|---|---|
| 1-62 | 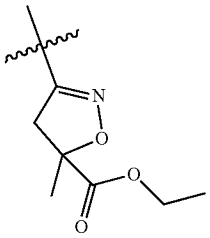 [SMILES: *C1=NOC(C)(C(=O)OCC)C1] | Cl | F | 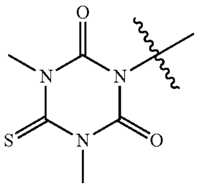 [SMILES: *n1c(=O)n(C)c(=S)n(C)c1=O] | $^{1}H$ NMR (500 MHz, DMSO-d6) δ 7.94 (d, J = 7.5 Hz, 1H), 7.90 (d, J = 9.5 Hz, 1H), 4.19 (q, J = 7.0 Hz, 2H), 3.89 (d, J = 17.5 Hz, 1H), 3.63 (s, 6H), 3.52 (d, J = 17.5 Hz, 1H), 1.62 (s, 3H), 1.23 (t, J = 7.0 Hz, 3H). |
| 1-63 | 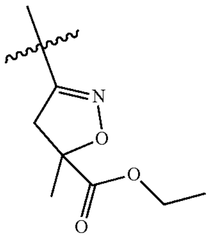 [SMILES: *C1=NOC(C)(C(=O)OCC)C1] | Cl | F | 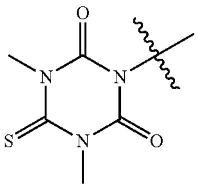 [SMILES: *n1c(=O)n(C)c(=S)n(C)c1=O] | $^{1}H$ NMR (500 MHz, DMSO) δ 7.95 (d, J = 7.5 Hz, 1H), 7.93 (d, J = 9.5 Hz, 1H), 4.20 (q, J = 7.0 Hz, 2H), 3.91 (d, J = 17.5 Hz, 1H), 3.53 (d, J = 17.5 Hz, 1H), 3.25 (s, 6H), 1.63 (s, 3H), 1.25 (t, J = 7.0 Hz, 3H). |
| 1-64 | 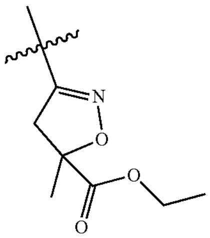 [SMILES: *C1=NOC(C)(C(=O)OCC)C1] | Cl | F | 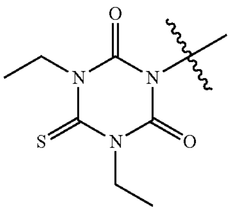 [SMILES: *n1c(=O)n(CC)c(=S)n(CC)c1=O] | $^{1}H$ NMR (500 MHz, DMSO-$d_6$) δ 8.00 (d, J = 7.5 Hz, 1H), 7.90 (d, J = 9.5 Hz, 1H), 4.40-4.32 (m, 4H), 4.19 (q, J = 7.0 Hz, 2H), 3.90 (d, J = 17.5 Hz, 1H), 3.53 (d, J = 17.5 Hz, 1H), 1.62 (s, 3H), 1.27-1.21 (m, 9H). |
| 1-65 | 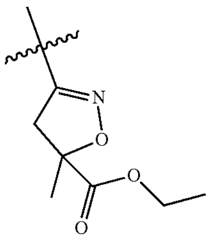 [SMILES: *C1=NOC(C)(C(=O)OCC)C1] | Cl | F | 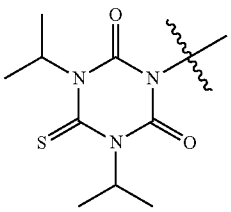 [SMILES: *n1c(=O)n(C(C)C)c(=S)n(C(C)C)c1=O] | $^{1}H$ NMR (500 MHz, DMSO-$d_6$) δ 8.00 (d, J = 7.5 Hz, 1H), 7.90 (d, J = 9.5 Hz, 1H), 6.01-5.95 (m, 2H), 4.20 (q, J = 7.0 Hz, 2H), 3.92 (d, J = 17.5 Hz, 1H), 3.56 (d, J = 17.5 Hz, 1H), 1.64 (s, 3H), 1.46-1.42 (m, 12H), 1.24 (t, J = 7.0 Hz, 3H). |

TABLE B-continued

Structures and $^1$H NMR date of compounds

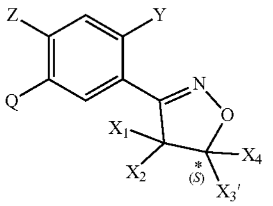

I'

| NO. | 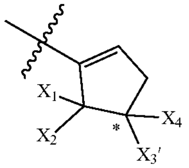 | Y | Z | Q | $^1$H NMR |
|---|---|---|---|---|---|
| 1-66 | 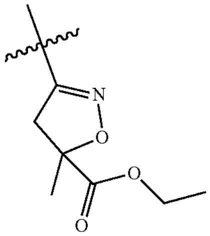 [SMILES: *C1=NOC(C)(C(=O)OCC)C1] | Cl | F | 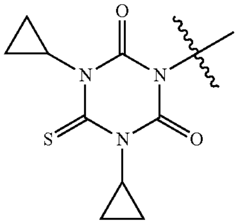 [SMILES: *n1c(=O)n(C2CC2)c(=S)n(C2CC2)c1=O] | $^1$H NMR (500 MHz, DMSO-$d_6$) δ 7.98 (d, J = 7.5 Hz 1H), 7.89 (d, J = 9.5 Hz, 1H), 4.21 (q, J = 7.0 Hz, 2H), 3.91 (d, J = 17.5 Hz, 1H), 3.54 (d, J = 17.5 Hz, 1H), 2.88-2.85 (m, 2H), 1.64 (s, 3H), 1.25 (t, J = 7.0 Hz, 3H), 1.19-1.04 (m, 4H), 0.92-0.75 (m, 4H). |
| 1-67 | 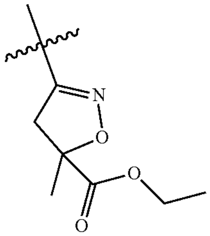 [SMILES: *C1=NOC(C)(C(=O)OCC)C1] | $CF_3$ | F | 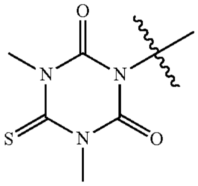 [SMILES: *n1c(=O)n(C)c(=S)n(C)c1=O] | $^1$H NMR (500 MHz, DMSO-$d_6$) δ 8.16 (d, J = 9.5 Hz, 1H), 8.00 (d, J = 7.0 Hz, 1H), 4.21 (q, J = 7.0 Hz, 2H), 3.80 (d, J = 17.5 Hz, 1H), 3.66 (s, 6H), 3.41 (d, J = 17.5 Hz, 1H), 1.63 (s, 3H), 1.25 (t, J = 7.0 Hz, 3H). |
| 1-68 | 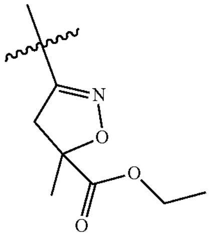 [SMILES: *C1=NOC(C)(C(=O)OCC)C1] | Br | F | 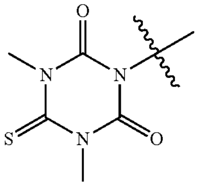 [SMILES: *n1c(=O)n(C)c(=S)n(C)c1=O] | $^1$H NMR (500 MHz, DMSO-$d_6$) δ 8.07 (d, J = 9.5 Hz, 1H), 7.86 (d, J = 7.5 Hz, 1H), 4.21 (q, J = 7.0 Hz, 2H), 3.91 (d, J = 17.5 Hz, 1H), 3.64 (s, 6H), 3.52 (d, J = 17.5 Hz, 1H), 1.64 (s, 3H), 1.25 (t, J = 7.0 Hz, 3H). |
| 1-69 | 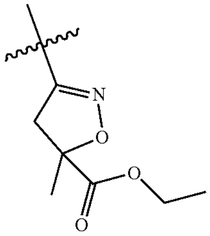 [SMILES: *C1=NOC(C)(C(=O)OCC)C1] | CN | F | 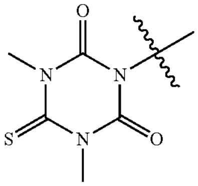 [SMILES: *n1c(=O)n(C)c(=S)n(C)c1=O] | $^1$H NMR (500 MHz, DMSO-$d_6$) δ 8.33 (d, J = 9.5 Hz, 1H), 8.12 (d, J = 7.0 Hz, 1H), 4.21 (q, J = 7.0 Hz, 2H), 3.93 (d, J = 17.0 Hz, 1H), 3.65 (s, 6H), 3.54 (d, J = 17.0 Hz, 1H), 1.66 (s, 3H), 1.25 (t, J = 7.0 Hz, 3H). |
| 1-70 | 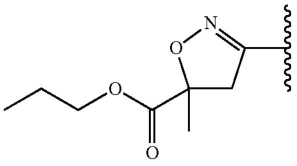 [SMILES: *C1=NOC(C)(C(=O)OCCC)C1] | Cl | F | 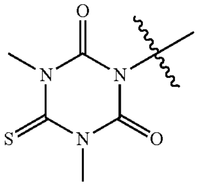 [SMILES: *n1c(=O)n(C)c(=S)n(C)c1=O] | $^1$H NMR (500 MHz, DMSO-$d_6$) δ 7.94 (d, J = 7.5 Hz, 1H), 7.90 (d, J = 9.5 Hz, 1H), 4.10 (t, J = 6.5 Hz, 2H), 3.90 (d, J = 17.5 Hz, 1H), 3.63 (s, 6H), 3.52 (d, J = 17.5 Hz, 1H), 1.63 (s, 3H), 1.62-1.58 (m, 2H), 0.88 (q, J = 7.0 Hz, 3H). |

TABLE B-continued

Structures and $^1$H NMR date of compounds

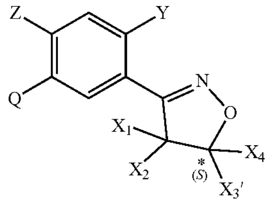

I'

| NO. | 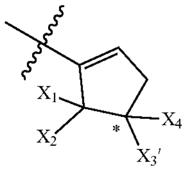 | Y | Z | Q | $^1$H NMR |
| --- | --- | --- | --- | --- | --- |
| 1-71 | 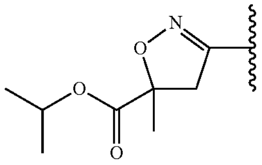 [SMILES: *C1=NOC(C)(C(=O)OC(C)C)C1] | Cl | F | 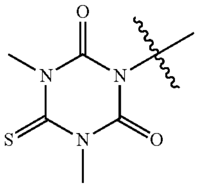 [SMILES: *n1c(=O)n(C)c(=S)n(C)c1=O] | $^1$H NMR (500 MHz, DMSO-$d_6$) δ 7.94 (d, J = 7.5 Hz, 1H), 7.90 (d, J = 9.5 Hz, 1H), 4.99 (p, J = 6.0 Hz, 1H), 4.05 (d, J = 17.5 Hz, 1H), 3.64 (s, 6H), 3.52 (d, J = 17.5 Hz, 1H), 1.62 (s, 3H), 1.30 (d, J = 6.0 Hz, 1H). |
| 1-72 | 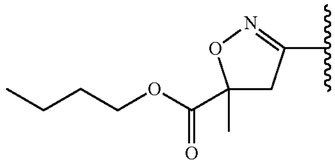 [SMILES: *C1=NOC(C)(C(=O)OCCCC)C1] | Cl | F | 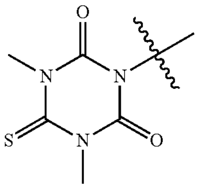 [SMILES: *n1c(=O)n(C)c(=S)n(C)c1=O] | $^1$H NMR (500 MHz, DMSO) δ 7.94 (d, J = 7.5 Hz, 1H), 7.90 (d, J = 9.5 Hz, 1H), 4.14 (t, J = 6.0 Hz, 2H), 3.89 (d, J = 17.5 Hz, 1H), 3.63 (s, 6H), 3.52 (d, J = 17.5 Hz, 1H), 1.62 (s, 3H), 1.62-1.55 (m, 2H), 1.39-1.28 (m, 2H), 0.89 (t, J = 7.0 Hz, 3H). |
| 1-73 | 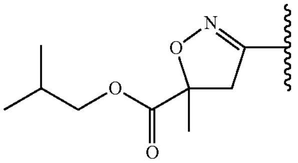 [SMILES: *C1=NOC(C)(C(=O)OCC(C)C)C1] | Cl | F | 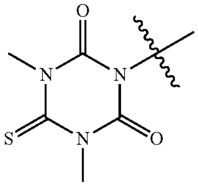 [SMILES: *n1c(=O)n(C)c(=S)n(C)c1=O] | $^1$H NMR (500 MHz, DMSO-$d_6$) δ 7.94 (d, J = 7.5 Hz, 1H), 7.90 (d, J = 9.5 Hz, 1H), 3.94 (d, J = 6.5 Hz, 2H), 3.91 (d, J = 17.5 Hz, 1H), 3.63 (s, 6H), 3.53 (d, J = 17.5 Hz, 1H), 1.97-1.88 (m, 1H), 1.64 (s, 3H), 0.90 (d, J = 6.5 Hz, 6H). |
| 1-74 | 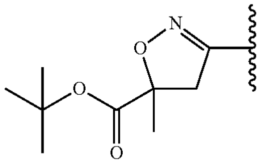 | Cl | F | 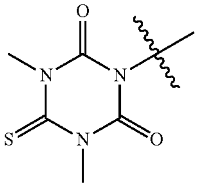 [SMILES: *n1c(=O)n(C)c(=S)n(C)c1=O] | $^1$H NMR (500 MHz, DMSO) δ 7.96-7.87 (m, 2H), 3.84 (d, J = 17.5 Hz, 1H), 3.63 (s, 6H), 3.46 (d, J = 17.5 Hz, 1H), 1.57 (s, 3H), 1.44 (s, 9H). |
| 1-75 | 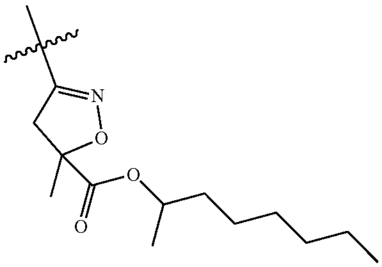 [SMILES: *C1=NOC(C)(C(=O)OC(C)CCCCCC)C1] | Cl | F | 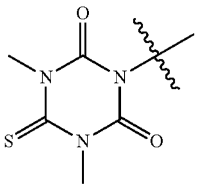 [SMILES: *n1c(=O)n(C)c(=S)n(C)c1=O] | $^1$H NMR (500 MHz, DMSO) δ 7.96-7.93 (m, 2H), 4.90-4.87 (m, 1H), 3.88 (d, J = 17.5, 1H), 3.64 (s, 6H), 3.53 (d, J = 17.5 Hz, 1H), 1.63 (s, 3H), 1.26-1.21 (m, 10H), 0.85 (t, J = 7.5 Hz, 3H). |

TABLE B-continued
Structures and $^{1}$H NMR date of compounds
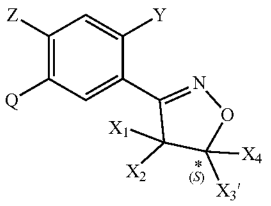
I'
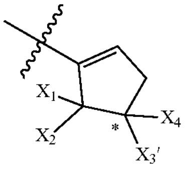
| NO. | | Y | Z | Q | $^{1}$H NMR |
|---|---|---|---|---|---|
| 1-76 | 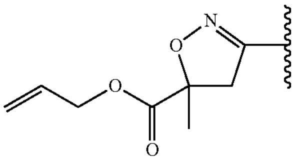 [SMILES: *C1=NOC(C)(C(=O)OCC=C)C1] | Cl | F | 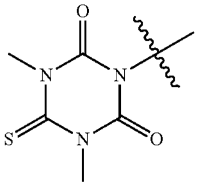 [SMILES: *n1c(=O)n(C)c(=S)n(C)c1=O] | $^{1}$H NMR (500 MHz, DMSO-$d_6$) δ 7.97 (d, J = 7.5 Hz, 1H), 7.92 (d, J = 9.5 Hz, 1H), 6.00-5.93 (m, 1H), 5.39-5.24 (m, 2H), 4.69 (dd, J = 5.0, 1.5 Hz, 2H), 3.94 (d, J = 17.5 Hz, 1H), 3.65 (s, 6H), 3.56 (d, J = 17.5 Hz, 1H), 1.66 (s, 3H). |
| 1-77 | 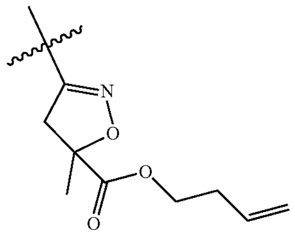 [SMILES: *C1=NOC(C)(C(=O)OCCC=C)C1] | Cl | F | 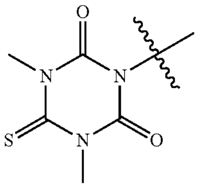 [SMILES: *n1c(=O)n(C)c(=S)n(C)c1=O] | |
| 1-78 | 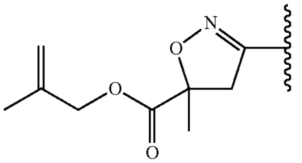 | Cl | F | 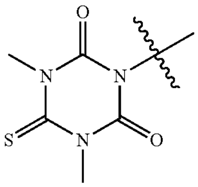 [SMILES: *n1c(=O)n(C)c(=S)n(C)c1=O] | |
| 1-79 | 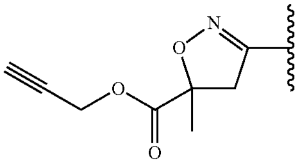 [SMILES: *C1=NOC(C)(C(=O)OCC#C)C1] | Cl | F | 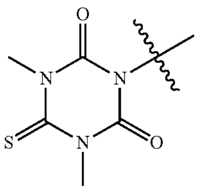 [SMILES: *n1c(=O)n(C)c(=S)n(C)c1=O] | $^{1}$H NMR (500 MHz, DMSO-$d_6$) δ 7.97 (d, J = 7.5 Hz, 1H), 7.92 (d, J = 9.5 Hz, 1H), 4.85 (s, 2H), 3.92 (d, J = 17.5 Hz, 1H), 3.58 (d, J = 17.5 Hz, 1H), 3.35 (s, 1H), 1.66 (s, 3H). |
| 1-80 | 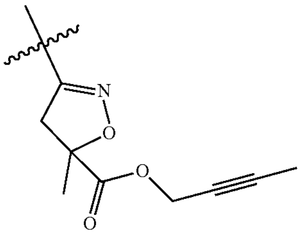 [SMILES: *C1=NOC(C)(C(=O)OCC#CC)C1] | Cl | F | 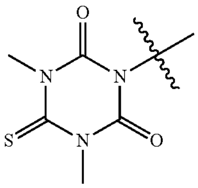 [SMILES: *n1c(=O)n(C)c(=S)n(C)c1=O] | $^{1}$H NMR (500 MHz, DMSO-$d_6$) δ 7.95 (d, J = 7.5 Hz, 1H), 7.91 (d, J = 9.5 Hz, 1H), 4.78 (q, J = 2.5 Hz, 2H), 3.89 (d, J = 17.5 Hz, 1H), 3.63 (s, 6H), 3.55 (d, J = 17.5 Hz, 1H), 1.84 (t, J = 2.5 Hz, 3H), 1.63 (s, 3H). |

TABLE B-continued
Structures and $^{1}$H NMR date of compounds
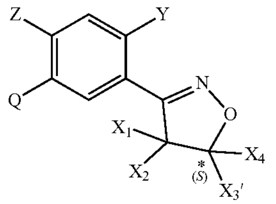
I'
| NO. | 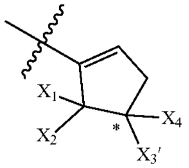 | Y | Z | Q | $^{1}$H NMR |
|---|---|---|---|---|---|
| 1-81 | 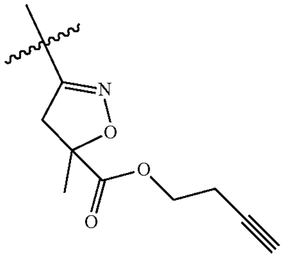 [SMILES: *C1=NOC(C)(C(=O)OCCC#C)C1] | Cl | F | 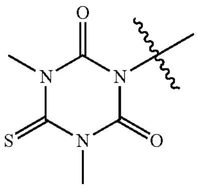 [SMILES: *n1c(=O)n(C)c(=S)n(C)c1=O] | $^{1}$H NMR (500 MHz, DMSO-$d_6$) δ 7.95 (d, J = 7.5 Hz, 1H), 7.91 (d, J = 9.5 Hz, 1H), 4.23 (t, J = 6.5 Hz, 2H), 3.93 (d, J = 18.0 Hz, 1H), 3.64 (s, 6H), 3.56 (d, J = 18.0 Hz, 1H), 2.59-2.55 (m, 2H), 2.09 (s, 1H), 1.65 (s, 3H). |
| 1-82 | 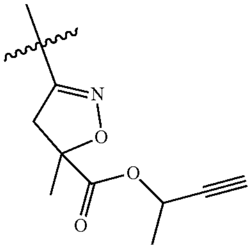 [SMILES: *C1=NOC(C)(C(=O)OC(C)C#C)C1] | Cl | F | 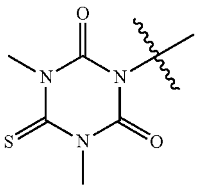 [SMILES: *n1c(=O)n(C)c(=S)n(C)c1=O] | $^{1}$H NMR (500 MHz, DMSO-$d_6$) δ 7.96 (d, J = 7.5 Hz, 1H), 7.93 (d, J = 9.5 Hz, 1H), 5.47-5.42 (m, 1H), 3.91 (d, J = 17.5 Hz, 1H), 3.65-3.62 (m, 7H), 3.56 (d, J = 17.5 Hz, 1H), 1.64 (d, J = 5.0 Hz, 3H), 1.50 (s, 3H). |
| 1-83 | 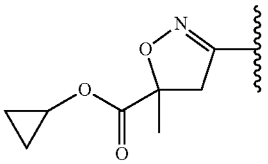 | Cl | F | 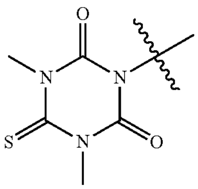 [SMILES: *n1c(=O)n(C)c(=S)n(C)c1=O] | $^{1}$H NMR (500 MHz, DMSO) δ 7.95-7.92 (m, 2H), 4.18-4.45 (m, 1H), 3.85 (d, J = 17.5 Hz, 1H), 3.64 (s, 6H), 3.52 (d, J = 17.5 Hz, 1H), 1.62 (s, 3H), 1.34-1.20 (m, 1H), 0.74-0.71 (m, 3H). |
| 1-84 | 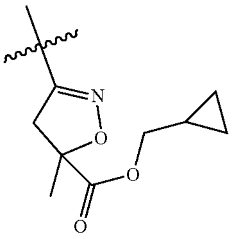 [SMILES: *C1=NOC(C)(C(=O)OCC2CC2)C1] | Cl | F | 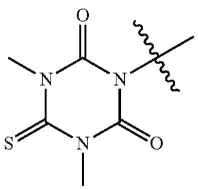 [SMILES: *n1c(=O)n(C)c(=S)n(C)c1=O] | $^{1}$H NMR (500 MHz, DMSO) δ 7.94-7.90 (m, 2H), 4.01 (d, J = 7.0 Hz, 2H), 3.92 (d, J = 17.5 Hz, 1H), 3.64 (s, 6H), 3.55 (d, J = 17.5 Hz, 1H), 1.65 (s, 3H), 1.15-1.10 (m, 1H), 0.54-0.50 (m, 2H), 0.31-0.28 (m, 2H). |

TABLE B-continued
Structures and $^1$H NMR date of compounds
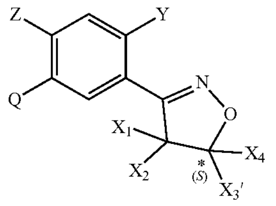
I'
| NO. | 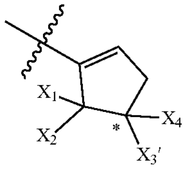 | Y | Z | Q | $^1$H NMR |
|---|---|---|---|---|---|
| 1-85 | 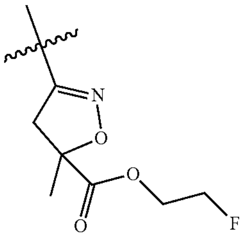 [SMILES: *C1=NOC(C)(C(=O)OCCF)C1] | Cl | F | 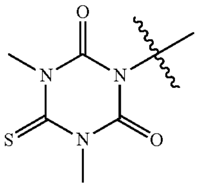 [SMILES: *n1c(=O)n(C)c(=S)n(C)c1=O] | |
| 1-86 | 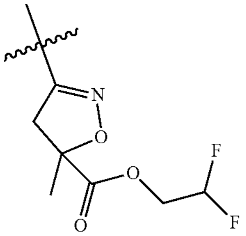 [SMILES: *C1=NOC(C)(C(=O)OCC(F)F)C1] | Cl | F | 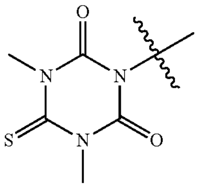 [SMILES: *n1c(=O)n(C)c(=S)n(C)c1=O] | $^1$H NMR (500 MHz, DMSO-$d_6$) δ 7.97-7.91 (m, 2H), 6.33 (t, J = 54.0 Hz, 1H), 4.51-4.45 (m, 2H), 4.07-3.92 (m, 1H), 3.64 (s, 6H), 3.34-3.30 (m, 1H), 1.67 (s, 3H). |
| 1-87 | 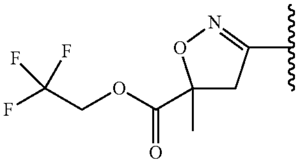 [SMILES: *C1=NOC(C)(C(=O)OCC(F)(F)F)C1] | Cl | F | 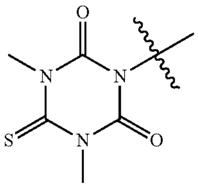 [SMILES: *n1c(=O)n(C)c(=S)n(C)c1=O] | $^1$H NMR (500 MHz, DMSO-$d_6$) δ 7.97 (d, J = 7.5 Hz, 1H), 7.92 (d, J = 9.5 Hz, 1H), 4.97-4.83 (m, 2H), 3.97 (d, J = 17.5 Hz, 1H), 3.65 (s, 6H), 3.35 (d, J = 17.5 Hz, 1H), 1.69 (s, 3H). |
| 1-88 | 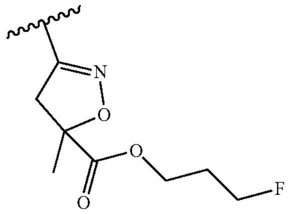 [SMILES: *C1=NOC(C)(C(=O)OCCCF)C1] | Cl | F | 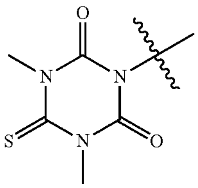 [SMILES: *n1c(=O)n(C)c(=S)n(C)c1=O] | $^1$H NMR (500 MHz, DMSO) δ 7.95 (d, J = 7.5 Hz, 1H), 7.93 (d, J = 9.5 Hz, 1H), 4.58-4.49 (m, 2H), 4.26 (t, J = 6.0 Hz, 2H), 3.93 (d, J = 17.5 Hz, 1H), 3.65 (s, 6H), 3.54 (d, J = 17.5 Hz, 1H), 2.08-1.98 (m, 2H), 1.65 (s, 3H). |
| 1-89 | 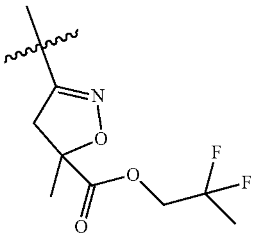 [SMILES: *C1=NOC(C)(C(=O)OCC(C)(F)F)C1] | Cl | F | 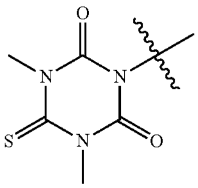 [SMILES: *n1c(=O)n(C)c(=S)n(C)c1=O] | $^1$H NMR (500 MHz, DMSO) δ 7.97 (d, J = 7.5 Hz, 1H), 7.93 (d, J = 9.5 Hz, 1H), 4.48 (t, J = 13.0 Hz, 2H), 3.95 (d, J = 17.5 Hz, 1H), 3.69-3.58 (m, 7H), 1.79-1.59 (m, 6H). |

TABLE B-continued
Structures and $^1$H NMR date of compounds
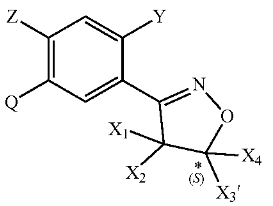
I'
| NO. | 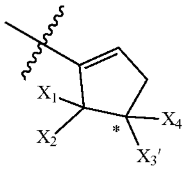 | Y | Z | Q | $^1$H NMR |
|---|---|---|---|---|---|
| 1-90 | 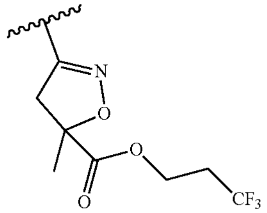 [SMILES: *C1=NOC(C)(C(=O)OCCC(F)(F)F)C1] | Cl | F | 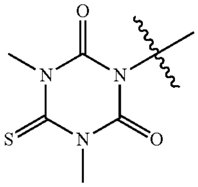 [SMILES: *n1c(=O)n(C)c(=S)n(C)c1=O] | $^1$H NMR (500 MHz, DMSO) δ 7.90 (d, J = 9.5 Hz, 1H), 7.88 (d, J = 7.5 Hz, 1H), 4.39 (t, J = 6.0 Hz, 2H), 3.93 (d, J = 17.5 Hz, 1H), 3.62 (s, 6H), 3.56 (d, J = 17.5 Hz, 1H), 2.76-2.74 (m, 2H), 1.64 (s, 3H). |
| 1-91 | 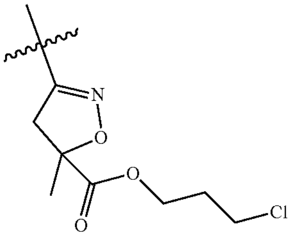 [SMILES: *C1=NOC(C)(C(=O)OCCCCl)C1] | Cl | F | 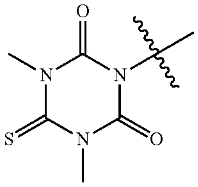 [SMILES: *n1c(=O)n(C)c(=S)n(C)c1=O] | |
| 1-92 | 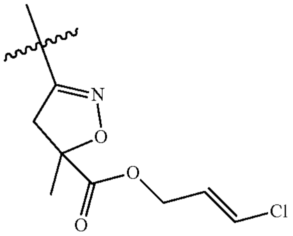 [SMILES: *C1=NOC(C)(C(=O)OC/C=C/Cl)C1] | Cl | F | 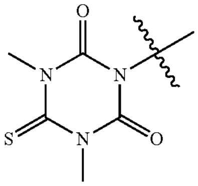 [SMILES: *n1c(=O)n(C)c(=S)n(C)c1=O] | $^1$H NMR (500 MHz, DMSO-$d_6$) δ 7.94 (d, J = 7.5 Hz, 1H), 7.90 (d, J = 9.5 Hz, 1H), 6.71-6.52 (m, 1H), 6.15-6.09 (m, 1H), 4.87-4.63 (m, 2H), 3.92 (d, J = 17.5 Hz, 1H), 3.63 (s, 6H), 3.54 (d, J = 17.5 Hz, 1H), 1.63 (s, 3H). |
| 1-93 | 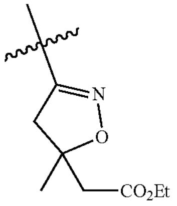 [SMILES: *C1=NOC(C)(CC(=O)OCC)C1] | Cl | F | 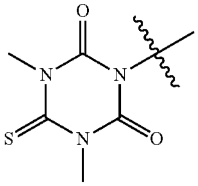 [SMILES: *n1c(=O)n(C)c(=S)n(C)c1=O] | |
| 1-94 | 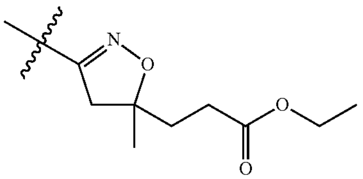 [SMILES: *C1=NOC(C)(CCC(=O)OCC)C1] | Cl | F | 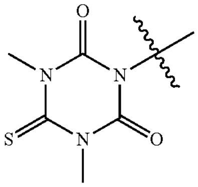 [SMILES: *n1c(=O)n(C)c(=S)n(C)c1=O] | $^1$H NMR (500 MHz, DMSO) δ 7.92 (d, J = 8.0 Hz, 1H), 7.89 (d, J = 9.5 Hz, 1H), 4.10-4.00 (m, 2H), 3.64 (s, 6H), 3.42-3.36 (m, 1H), 3.26-3.22 (m, 1H), 2.44-2.39 (m, 2H), 2.02-1.92 (m, 2H), 1.40 (s, 3H), 1.19 (t, J = 7.0 Hz, 3H). |

TABLE B-continued
Structures and $^1$H NMR date of compounds
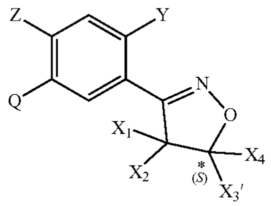
I'
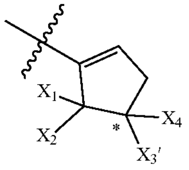
| NO. | | Y | Z | Q | $^1$H NMR |
|---|---|---|---|---|---|
| 1-95 | 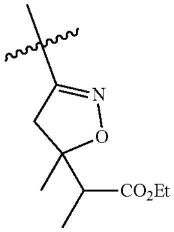 [SMILES: *C1=NOC(C)(C(C)C(=O)OCC)C1] | Cl | F | 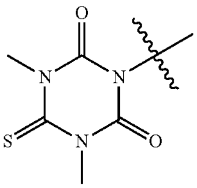 [SMILES: *n1c(=O)n(C)c(=S)n(C)c1=O] | |
| 1-96 | 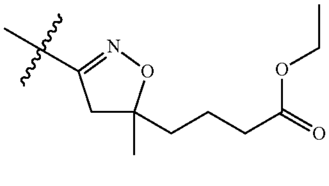 [SMILES: *C1=NOC(C)(CCCC(=O)OCC)C1] | Cl | F | 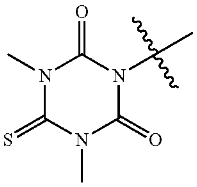 [SMILES: *n1c(=O)n(C)c(=S)n(C)c1=O] | $^1$H NMR (500 MHz, DMSO) δ 7.91-7.90 (m, 2H), 4.07-4.06 (m, 2H), 3.68-3.61 (s, 6H), 3.31 (d, J = 14.5 Hz, 1H), 3.11 (d, J = 14.5 Hz, 1H), 2.35-2.34 (m, 2H), 1.77-1.53 (m, 4H), 1.39 (s, 3H), 1.19 (t, J = 7.0 Hz, 3H) |
| 1-97 | 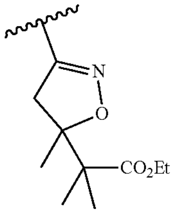 [SMILES: *C1=NOC(C)(C(C)(C)C(=O)OCC)C1] | Cl | F | 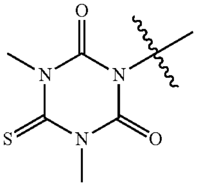 [SMILES: *n1c(=O)n(C)c(=S)n(C)c1=O] | |
| 1-98 | 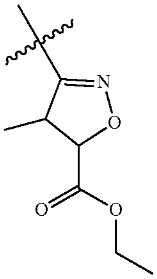 [SMILES: *C1=NOC(C(=O)OCC)C1C] | Cl | F | 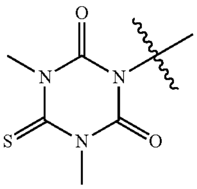 [SMILES: *n1c(=O)n(C)c(=S)n(C)c1=O] | $^1$H NMR (500 MHz, DMSO-$d_6$) δ 7.91 (d, J = 9.5 Hz, 1H), 7.83 (d, J = 7.5 Hz, 1H), 5.10-5.05 (m, 1H),4.55 (d, J = 7.0 Hz, 1H), 4.05 (q, J = 7.0 Hz, 2H), 3.62 (s, 6H), 1.43 (d, J = 6.5 Hz, 3H), 1.00 (t, J = 7.0 Hz, 3H). |
| 1-99 | 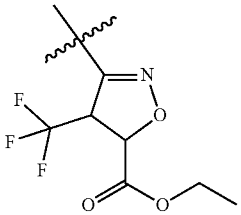 [SMILES: *C1=NOC(C(=O)OCC)C1C(F)(F)F] | Cl | F | 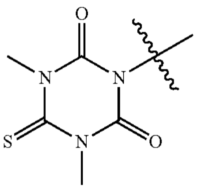 [SMILES: *n1c(=O)n(C)c(=S)n(C)c1=O] | $^1$H NMR (500 MHz, DMSO-$d_6$) δ 8.01 (d, J = 9.5 Hz, 1H), 7.95 (d, J = 7.5 Hz, 1H), 5.95-5.92 (m, 1H), 5.24 (d, J = 5.0 Hz, 1H), 4.10 (q, J = 8.0 Hz, 2H), 3.65 (s, 6H), 1.04 (t, J = 8.0 Hz, 3H). |

TABLE B-continued
Structures and $^1$H NMR date of compounds
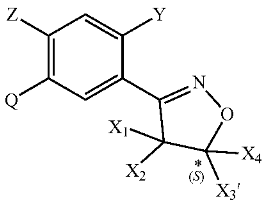
I'
| NO. | 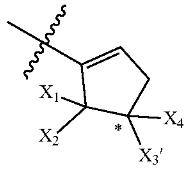 | Y | Z | Q | $^1$H NMR |
|---|---|---|---|---|---|
| 1-100 | 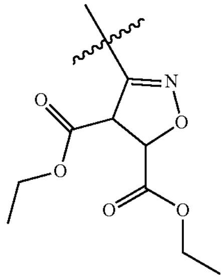 [SMILES: *C1=NOC(C(=O)OCC)C1C(=O)OCC] | Cl | F | 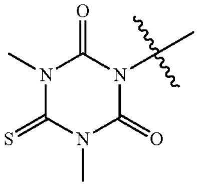 [SMILES: *n1c(=O)n(C)c(=S)n(C)c1=O] | $^1$H NMR (500 MHz, DMSO-$d_6$) δ 7.97 (d, J = 9.5 Hz, 1H), 7.90 (d, J = 7.5 Hz, 1H), 5.63 (d, J = 5.5 Hz, 1H), 5.14 (d, J = 5.5 Hz, 1H), 4.24 (q, J = 7.0 Hz, 2H), 4.09 (q, J = 7.0 Hz, 2H), 3.64 (s, 6H), 1.27 (t, J = 7.0 Hz, 3H), 1.02 (t, J = 7.0 Hz, 3H). |
| 1-101 | 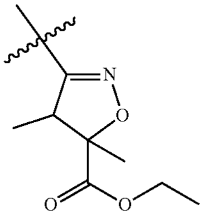 [SMILES: *C1=NOC(C)(C(=O)OCC)C1C] | Cl | F | 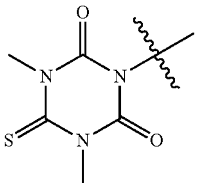 [SMILES: *n1c(=O)n(C)c(=S)n(C)c1=O] | $^1$H NMR (500 MHz, DMSO-$d_6$) δ 7.95 (d, J = 9.5 Hz, 1H), 7.86 (d, J = 7.5 Hz, 1H), 4.21 (q, J = 7.0 Hz, 2H), 4.15 (q, J = 7.5 Hz, 1H), 3.65 (s, 6H), 1.52 (s, 3H), 1.25 (t, J = 7.0 Hz, 3H), 1.04 (d, J = 7.5 Hz, 3H). |
| 1-102 | 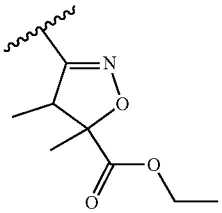 [SMILES: *C1=NOC(C)(C(=O)OCC)C1C] | Cl | F | 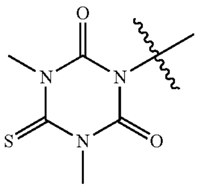 [SMILES: *n1c(=O)n(C)c(=S)n(C)c1=O] | |
| 1-103 | 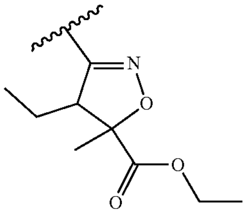 [SMILES: *C1=NOC(C)(C(=O)OCC)C1CC] | Cl | F | 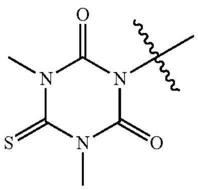 [SMILES: *n1c(=O)n(C)c(=S)n(C)c1=O] | |

TABLE B-continued
| Structures and $^1$H NMR date of compounds | | | | | |
|---|---|---|---|---|---|
| | 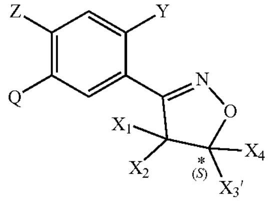 | | | | I' |
| NO. | 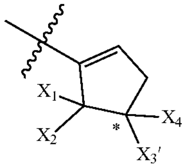 | Y | Z | Q | $^1$H NMR |
| 1-104 | 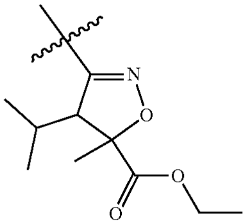 [SMILES: *C1=NOC(C)(C(=O)OCC)C1C(C)C] | Cl | F | 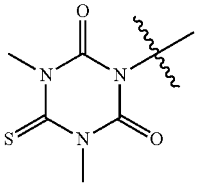 [SMILES: *n1c(=O)n(C)c(=S)n(C)c1=O] | |
| 1-105 | 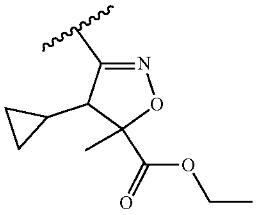 [SMILES: *C1=NOC(C)(C(=O)OCC)C1C1CC1] | Cl | F | 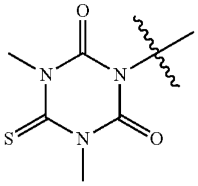 [SMILES: *n1c(=O)n(C)c(=S)n(C)c1=O] | |
| 1-106 | 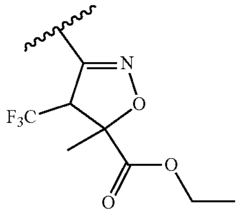 [SMILES: *C1=NOC(C)(C(=O)OCC)C1C(F)(F)F] | Cl | F | 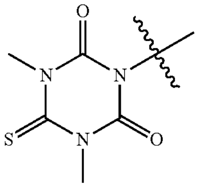 [SMILES: *n1c(=O)n(C)c(=S)n(C)c1=O] | |
| 1-107 | 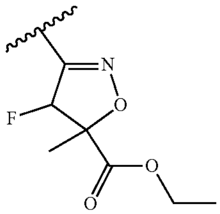 [SMILES: *C1=NOC(C)(C(=O)OCC)C1F] | Cl | F | 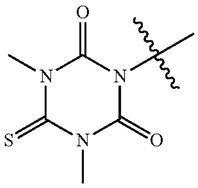 [SMILES: *n1c(=O)n(C)c(=S)n(C)c1=O] | |
| 1-108 | 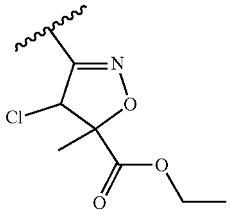 [SMILES: *C1=NOC(C)(C(=O)OCC)C1Cl] | Cl | F | 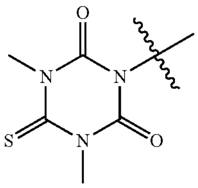 [SMILES: *n1c(=O)n(C)c(=S)n(C)c1=O] | |

TABLE B-continued

Structures and $^1$H NMR date of compounds

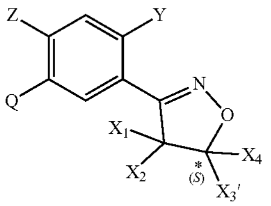

I'

| NO. | 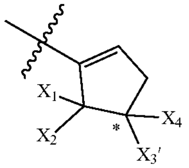 | Y | Z | Q | $^1$H NMR |
|---|---|---|---|---|---|
| 1-109 | 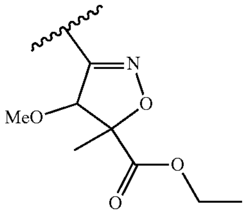 [SMILES: *C1=NOC(C)(C(=O)OCC)C1OC] | Cl | F | 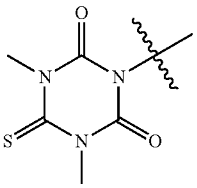 [SMILES: *n1c(=O)n(C)c(=S)n(C)c1=O] | |
| 1-110 | 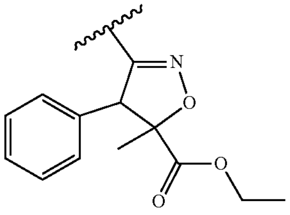 [SMILES: *C1=NOC(C)(C(=O)OCC)C1c1ccccc1] | Cl | F | 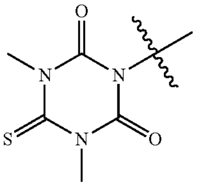 [SMILES: *n1c(=O)n(C)c(=S)n(C)c1=O] | |

The method for preparing the compound of the invention will be explained in detail in the following program and embodiment. The material is commercial available or prepared through known method reported in the literature or shown in the route. Those skilled in the art should understand that the compound of the invention can also be synthesized by other synthetic route. Although the detailed material and reaction condition in the synthetic route have been explicated in the following text, it is still easy to be replaced by other similar material and condition. Isomer of the compound, for example, that produced with the variation of the preparation method of the present invention is included in the scope of the present invention. In addition, the following preparation method can be further modified according to the disclosures of the present invention by using common chemical method known to those skilled in the art, for example, protection of suitable group in the process of the reaction, etc.

The following method of application can be used to improve further understanding of the preparation method of the present invention. The specific material, class and condition have been determined to be further explication of the present invention, not to be any limit of the reasonable scope thereof. Reagents of the following synthetic compound showed in the table can either be purchased from the market or easily prepared by those skilled in the art.

Examples of representative compounds are as follows, the synthesis methods of other compounds are similar, and will not be described in detail here.

1. Synthesis of Compound 55

(1) Compound 55-1 (1.18 g, 1.0 eq., 10 mmol) was dissolved in THF (30 mL), added with NaH (500 mg, 1.25 eq., 12.5 mmol, 60% purity) under ice-water bath. The mixture was stirred for 30 minutes under ice-water bath, then added with compound 55-2 (1.93 g, 1.0 eq, 10 mmol), slowly returned to room temperature, and stirred at room temperature for 12 hours, the reaction was tracked by TLC until the reaction was completed. After that, the reaction solution was slowly added into water (200 mL) to quench the reaction, then extracted with ethyl acetate (20 mL) for three times. The organic phase was combined, dried with anhydrous sodium sulfate, filtered, and finally concentrated to produce crude compound 55-3 (1.88 g, yield 82%, 8.2 mmol, yellow oily liquid), which was used directly in the next step.

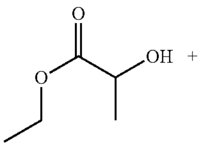

55-1

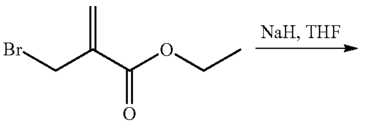

55-2

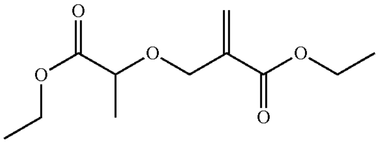

55-3

(2) Compound a (20 g, 91.5 mmol, 1.0 eq) was added to 150 mL DMF, and the reaction solution was slowly added with NCS (13.4 g, 100.7 mmol, 1.1 eq) at 35° C. After the addition, the solution was stirred at 35° C. for 1.5 hours, it was detected by LCMS that the raw material almost used up. The reaction solution was poured into 100 mL HCl (1M), then extracted by adding dichloromethane, the organic phrase was washed with saturated brine (100 ml*3), then concentrated to produce crude product 55-4 (26 g, crude product, yellow oily liquid), which was used directly for the next step.

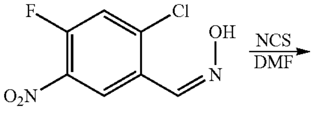

a

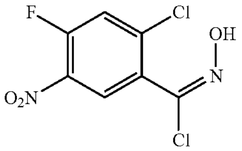

55-4

(3) Compound 55-4 (1.6 g, 6.7 mmol, 1.0 eq) and $Et_3N$ (1.01 g, 10.05 mmol, 1.5 eq) were added to 20 mL DCM. The reaction solution was added with compound 55-3 (1.84 g, 8 mmol, 1.2 eq) at 0° C. and reacted at 0° C. for 1 hour, then the product was detected by LCMS. The reaction solution was added with 100 ml water, and then extracted with dichloromethane (100 ml*3). The organic phrase was dried with anhydrous sodium sulfate and concentrated, the crude product was purified by column chromatography to produce compound 55-5 (1.94 g, yield 65%, 4.35 mmol, yellow solid).

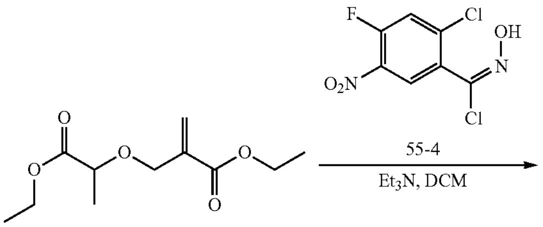

55-3

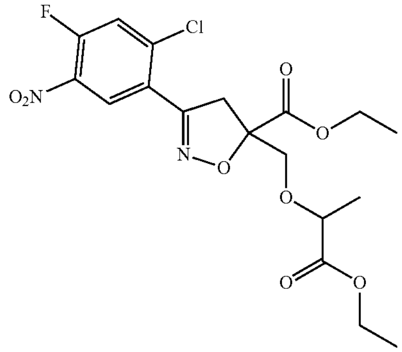

55-5

(4) Compound 55-5 (1.80 g, 4.0 mmol, 1.0 eq), Fe powder (672 mg, 12.0 mmol, 3 eq), $NH_4Cl$ (530 mg, 10.0 mmol, 2.0 eq) and water (5 ml) were successively added to 20 mL EtOH. Then after the reaction solution was reacted at 80° C. for 2 hours, it was detected by LCMS that the raw material used up, and the principle peak was the product peak. The reaction solution was filtered with diatomite and concentrated to remove ethanol, and then added with water (100 ml), extracted with ethyl acetate and concentrated to produce black crude product. Such crude product was separated and purified by column chromatography to produce compound 55-6 (1.41 g, yield 85%, 3.4 mmol, yellow solid).

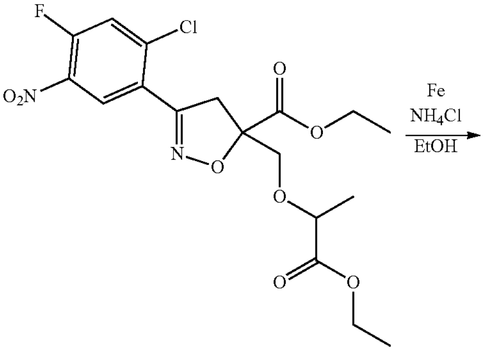

55-5

-continued

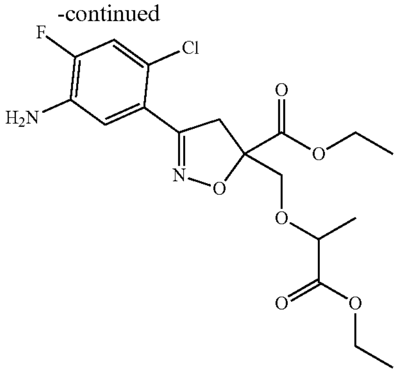

55-6

-continued

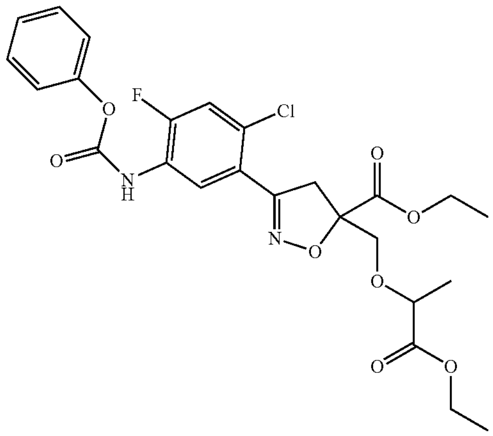

55-8

(5) Compound 55-6 (1.2 g, 2.89 mmol, 1.0 eq) and compound 55-7 (0.50 g, 3.18 mmol, 1.1 eq) were added to 10 ml toluene, and the reaction solution was heated for 1 hour at 110° C. It was detected by LCMS that the raw material almost used up, the principal peak belonged to the product. After concentrating the solvent, the crude product was separated by column chromatography to produce compound 55-8 (1.29 g, yield 83.4%, 2.41 mmol, yellow solid).

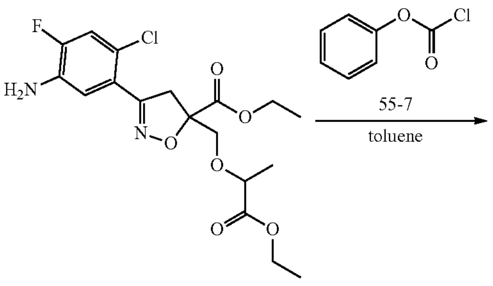

55-6

(6) Compound 55-9 (0.48 g, 2.1 mmol, 1.5 eq) and AcONa (58 mg, 0.7 mmol, 0.5 eq) were added to 10 ml DMF, and the reaction solution was added with compound 55-8 (0.75 g, 1.4 mmol, 1.0 eq) at 60° C., then reacted at 60° C. for 1 hour. The product was detected by LCMS. The reaction solution was added with water (10 ml) and extracted with ethyl acetate, the organic phase was washed with saturated brine (20 ml*1), after concentrating the organic phase, the crude product was separated by column chromatography to produce compound 55 (0.58 g, yield 72%, 1.0 mmol, yellow solid).

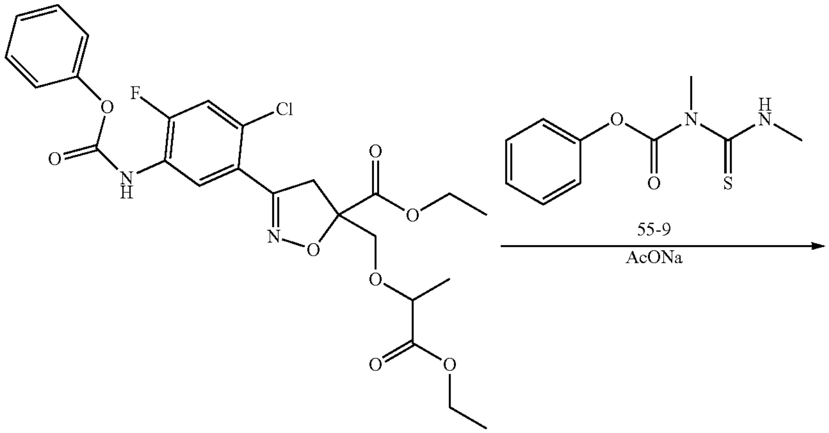

55-8

-continued

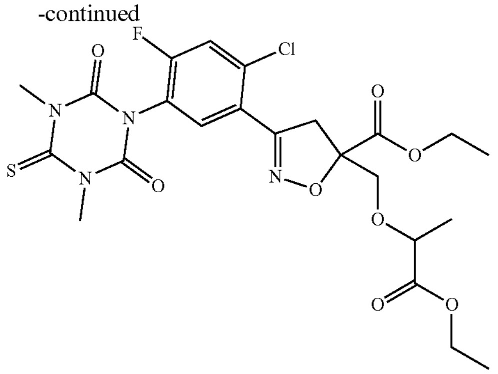

2. Synthesis of Compound 119

(1) Diethyl oxalate (5.0 g, 34.2 mmol, 1.0 eq) was dissolved in anhydrous THF (80 mL). The mixture was cooled to −60° C. through dry-ice ethanol bath under nitrogen protection, slowly added dropwise with cyclopropylmagnesium bromide (1M in THF) (37.6 mL, 37.6 mmol, 1.1 eq), then reacted at low temperature for 1 hour, it was detected by LCMS that the raw material almost used up, and a new peak emerged. The reaction solution was heated to room temperature, slowly added dropwise with saturated ammonium chloride aqueous solution to quench the reaction, and diluted with 100 ml water. The aqueous phase was extracted with ethyl acetate (EA, 3×100 mL), and the organic phase was combined, dried with anhydrous sodium sulfate, concentrated under reduced pressure to remove the solvent, the crude product 119-1 was obtained (4.9 g, quantitative), directly used in the next step without purification.

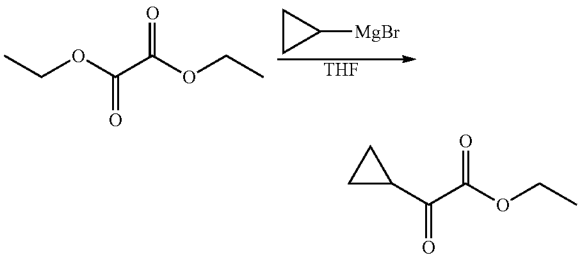

119-1

(2) Methyltriphenylphosphonium bromide (12.2 g, 34.2 mmol, 1.0 eq) was dissolved in anhydrous THF (100 mL). The mixture was cooled to −60° C. through dry-ice ethanol bath under nitrogen protection, slowly added with LiHMDS (1M in THF) (34.2 mL, 34.2 mmol, 1.0 eq), then reacted at low temperature for 1 hour. The reaction solution was slowly added with the THF solution of product 119-1 (4.9 g, 34.2 mmol, 1.0 eq) obtained from the last step, then reacted at low temperature for 2 hours. It was detected by LCMS that the raw material used up, and a new peak emerged. The reaction solution was heated to room temperature, slowly added dropwise with saturated ammonium chloride aqueous solution to quench the reaction. Most of solvent was removed by concentration under reduced pressure. The residual was diluted with 100 ml water. The aqueous phase was extracted with ether (2×100 mL), and the organic phase was combined, dried with anhydrous sodium sulfate, concentrated under reduced pressure to remove the solvent, the product 119-2 was obtained (3.2 g, crude product yield 67%), directly used in the next step without purification.

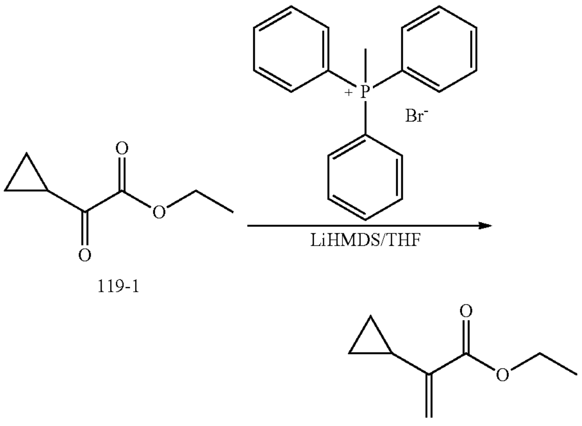

119-1

119-2

(3)Raw material 55-4 (2.8 g, 11.4 mmol, 0.5 eq) and $Et_3N$ (1.7 g, 17.1 mmol, 1.5 eq) were added to 60 mL DCM, and the reaction solution was added with product 119-2 (3.2 g, 22.8 mmol, 1.0 eq) obtained from the last step at 0° C., reacted at 0° C. for 1 hour, then the product was detected by LCMS. The reaction solution was added with 50 ml water, then extracted with dichloromethane (50 ml*3). The organic phrase was dried with anhydrous sodium sulfate and concentrated, the crude product was purified by column chromatography to produce compound 119-3 (320 mg, yield 8%, yellow oil).

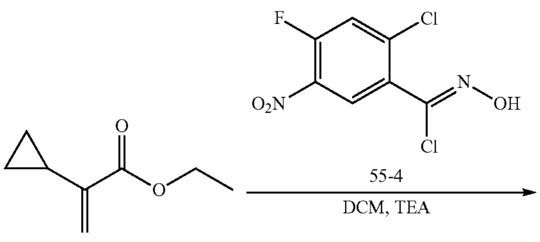

55-4

119-2

-continued

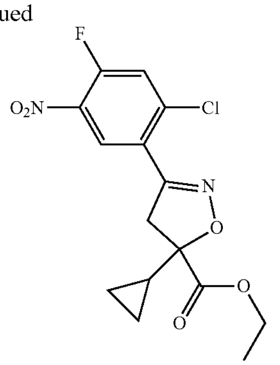

119-3

(4) Product 119-3 (320 mg, 0.9 mmol, 1.0 eq) obtained from the last step, Fe powder (151 mg, 2.7 mmol, 3 eq), $NH_4Cl$ (95 mg, 1.8 mmol, 2 eq) and water (5 ml) were successively added to 20 mL EtOH. After the reaction solution was reacted at 80° C. for 0.5 hour, it was detected by LCMS that the raw material used up, and the principle peak was the product peak. The reaction solution was filtered with diatomite and concentrated to remove ethanol, then added with water (100 ml), extracted with ethyl acetate and concentrated to produce black crude product. Such crude product was separated and purified by column chromatography to produce compound 119-4 (190 mg, yield 65%, yellow oil).

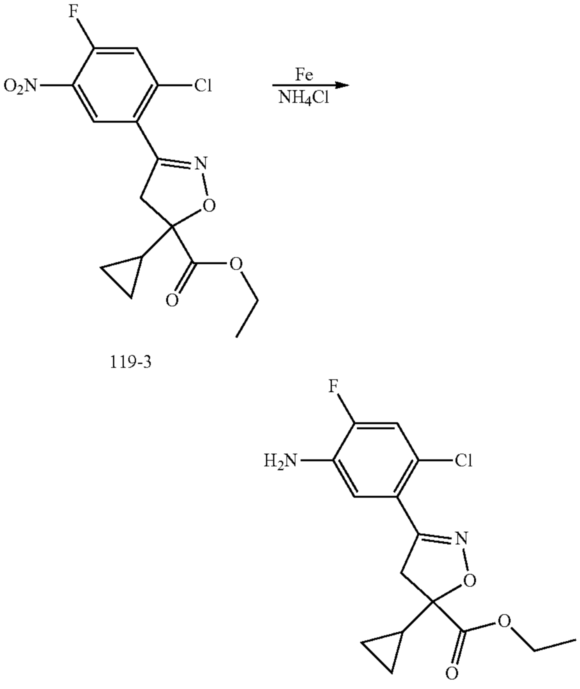

119-3

119-4

(5) Product 119-4 (190 mg, 0.6 mml, 1.0 eq) obtained from the last step, 10 mL acetic acid and raw material 119-5 (125 mg, 0.6 mml, 1.0 eq) were added into a 50 mL round mouth flask. The mixture was heated to 125° C. and reacted for 20 minutes. It was detected by LCMS that the product was formed. The reaction solution was cooled to room temperature, concentrated under reduced pressure to remove acetic acid, the residue was purified through silica gel column chromatography, then concentrated to produce compound 119-6 (160 mg, yield 56%, light-yellow oil).

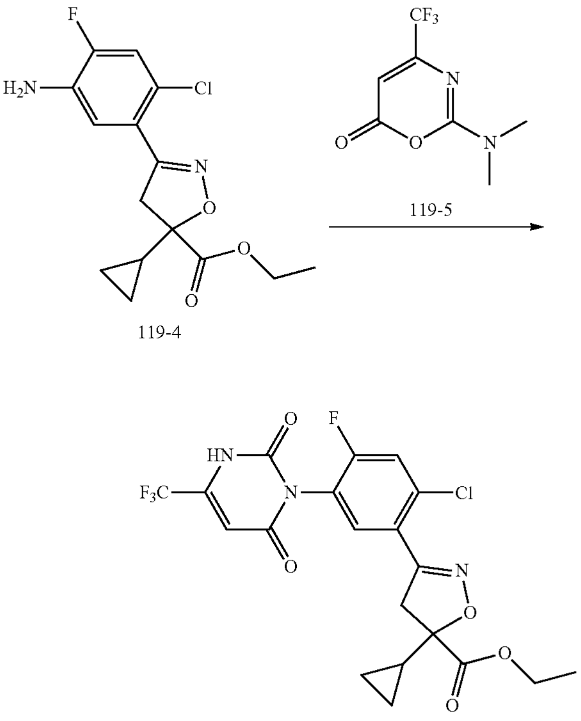

119-4

119-5

119-6

(6) Product 119-6 (160 mg, 0.33 mmol, 1.0 eq) obtained from the last step, potassium carbonate (228 mg, 1.65 mmol, 5.0 eq) and methyl iodide (140 mg, 0.99 mmol, 3.0 eq) was added to 10 mL anhydrous DMF. The mixture was reacted for 3 hours at room temperature. It was detected by LCMS that the raw material used up, and the product was formed. The reaction solution was diluted with ethyl acetate (EA, 60 ml), and the organic phase was washed with water (2×30 mL), then washed with saturated brine (30 mL), dried with anhydrous sodium sulfate, then filtered and concentrated, the crude product was separated and purified by column chromatography to produce compound 119 (100 mg, yield 60%, yellow oil).

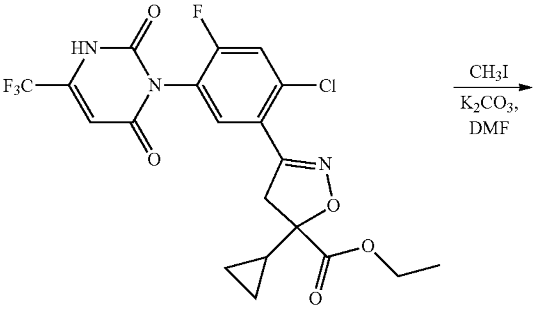

119-6

-continued

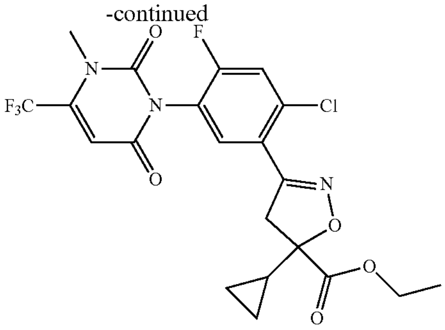

119

(7) Compound 119 was subjected to chiral HPLC separation (Chromatographic column type: AD-5H 5 μm 21.2×250 mm; Mobile phase: N-hexane: ethanol=7:3; Flow rate: 20 ml/min; Wavelength: 220 nm) to produce compound 119 (S) (liquid purity: 98%, 93% ee).

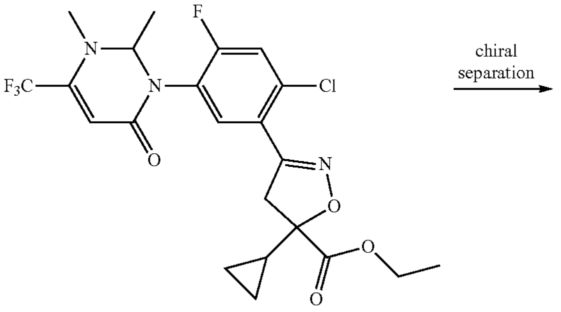

119

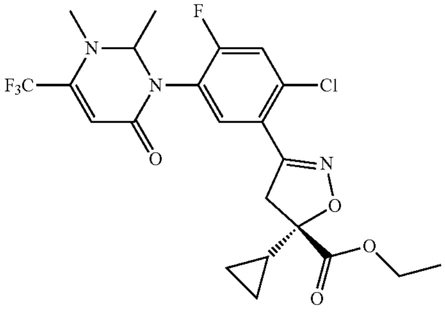

119(S)

3. Synthesis of Compound 206

(1) Compound 206-1 was prepared by referring to the above preparation method of compound 119-4. Then 10 ml 1,4-dioxane was added with compound 206-1 (0.6 g, 2.0 mmol, 1.0 eq) and 206-2 (0.38 g, 2.2 mmol, 1.1 eq). The reaction solution was heated at 110° C. for 1 hour. It was detected by LCMS that the raw material almost used up, the principal peak belonged to the product. The solvent was concentrated, and the crude product was separated by column chromatography to produce compound 206-3 (0.7 g, yield 83.4%, white solid).

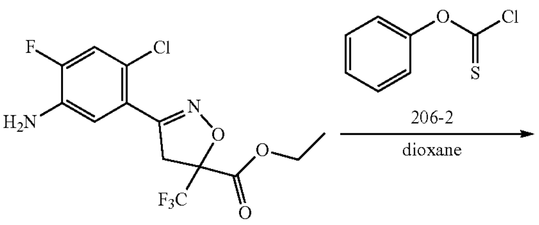

206-1

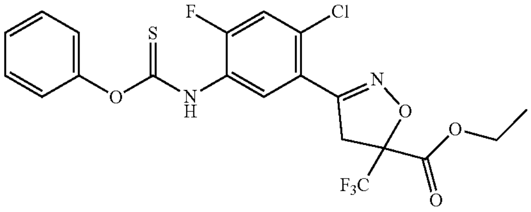

206-3

(2) Compound 206-4 (0.47 g, 2.1 mmol, 1.5 eq) and AcONa (58 mg, 0.7 mmol, 0.5 eq) was added to 10 ml DMF. The reaction solution was added with 206-3 (0.6 g, 1.4 mmol, 1.0 eq) at 60° C., then reacted at 60° C. for 1 hour. The product was detected by LCMS. The reaction solution was added with water (10 ml), then extracted with ethyl acetate. The organic phase was washed with saturated brine (20 ml*1), then concentrated, the crude product was separated by column chromatography to produce compound 206 (0.4 g, yield 61.4%, white solid).

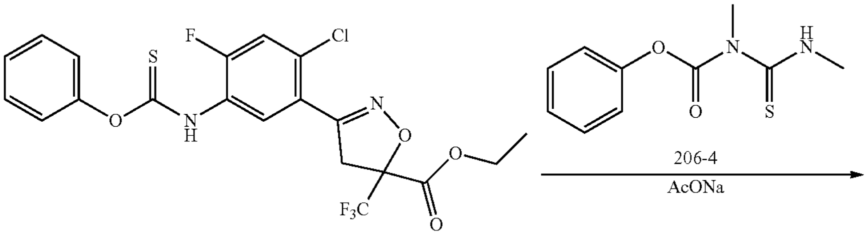

206-3

-continued

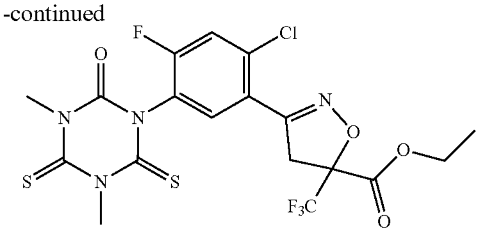

206

4. Synthesis of Compound 229

(1) Compound 55-4 (2 g, 7.94 mmol, 1.0 eq) and $Et_3N$ (1.2 g, 11.88 mmol, 1.5 eq) was added to 200 ml DCM. The reaction solution was then added with compound 229-1 (1.02 g, 7.97 mmol, 1.0 eq) at 0° C., slowly heated to 20° C. and reacted for 2-4 hours, the product was detected by LCMS. The reaction solution was added with 100 ml water, extracted with dichloromethane (50 ml*3). The organic phase was dried with anhydrous sodium sulfate and then concentrated, the crude product was purified by column chromatography to produce compound 229-2 (860 mg, yield 32%).

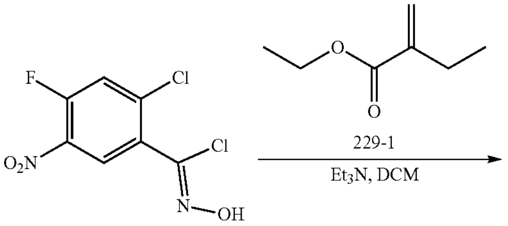

55-4

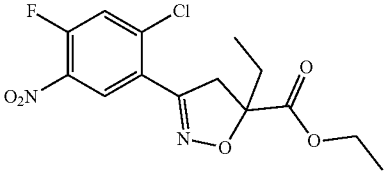

229-2

(2) Compound 229-2 (860 mg, 2.5 mmol, 1.0 eq), Fe powder (420 mg, 7.5 mmol, 3.0 eq), $NH_4Cl$ (265 mg, 5.0 mmol, 2 eq) and water (12.5 ml) was successively added to 50 mL EtOH. After the reaction solution was reacted at 80° C. for 2 hours, it was detected by LCMS that the raw material used up, the principal peak belonged to the product. The reaction solution was cooled, filtered with diatomite, concentrated to remove EtOH, then added with water, extracted with ethyl acetate and concentrated to produce black crude product 229-3 (720 mg, yield 90%), which was directly used in the next step.

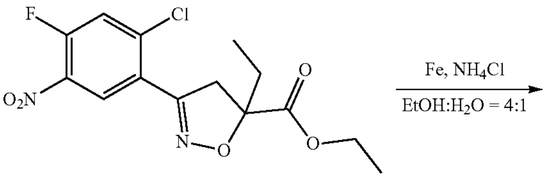

229-2

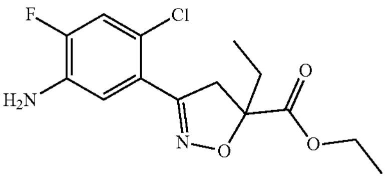

229-3

(3) Compound 229-3 (450 mg, 1.43 mmol, 1.0 eq), DMAP (17 mg, 0.14 mmol, 0.01 eq), triethylamine (217 mg, 2.15 mmol, 1.5 eq) and thiocarbonyldiimidazole CDI-S (306 mg, 1.72 mmol, 1.2 eq) were added to 20 ml toluene. The reaction solution was reacted at room temperature for 1 hour. After toluene was removed by rotary evaporation, added with water and extracted with ethyl acetate, the organic phase was mixed with silica gel, the crude product was purified by column chromatography to produce compound 229-4 (270 mg, yield 53%).

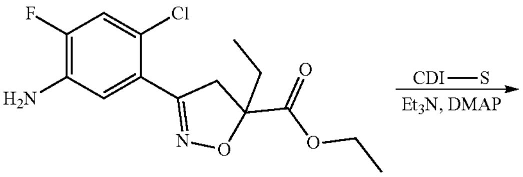

229-3

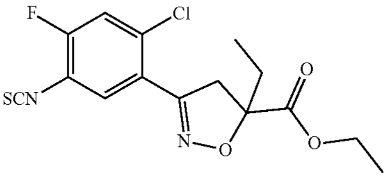

229-4

(4) Compound 229-4 (270 mg, 0.76 mmol, 1.0 eq), cesium carbonate (739 mg, 2.27 mmol, 3.0 eq) and compound 229-5 (153 mg, 0.84 mmol, 1.1 eq) were added to 10 ml DMF. After the reaction solution was stirred at 0° C. for 2-3 hours, it was detected by LCMS that the raw material used up, the principal peak belonged to the product. The reaction solution was added with water, extracted with ethyl acetate, and washed with saturated brine. The organic phase was mixed with silica gel, and the crude product was purified by column chromatography to produce 229-6 (102 mg, yield 27%).

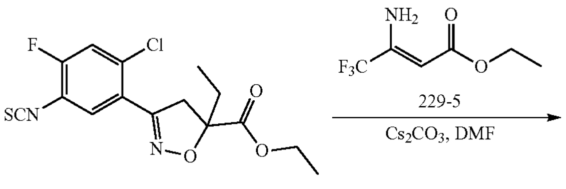

229-4

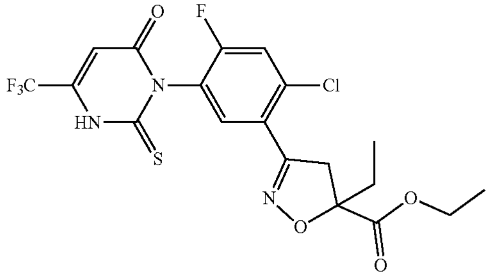

229-6

(5) Compound 229-6 (102 mg, 0.21 mmol, 1.0 eq), methyl iodide (118 mg, 0.83 mmol, 4.0 eq) and potassium carbonate (57 mg, 0.41 mmol, 2.0 eq) were successively added to 10 mL DMF. The reaction solution was reacted for 4-6 hours at 25-30° C. depending on LCMS detection until the reaction was completed. The reaction solution was added with water, extracted with ethyl acetate, and washed with saturated brine. The organic phase was mixed with silica gel, and the crude product was purified by column chromatography to produce 229 (70 mg, yield 77%).

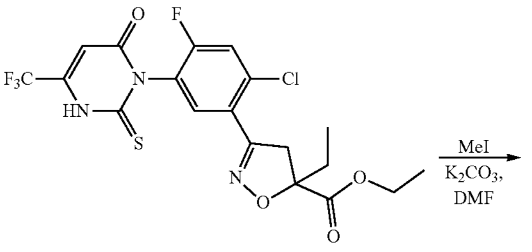

229-6

-continued

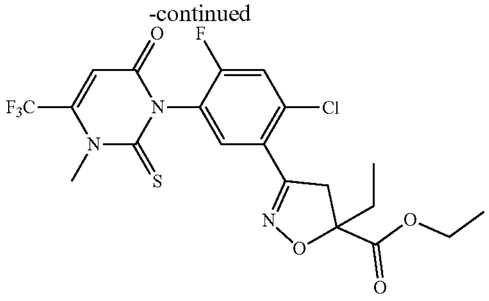

229

5. Synthesis of Compound 1-62

(1) Compound 1-62-1 was prepared by referring to the above synthesis method of compound 229-3. Then compound 1-62-1 (0.6 g, 2.0 mmol, 1.0 eq) and phenyl chloroformate (0.34 g, 2.2 mmol, 1.1 eq) were added to 10 ml toluene. The reaction solution was heated at 110° C. for 1 hour. It was detected by LCMS that the raw material almost used up, the principal peak belonged to the product. The solvent was concentrated, and the crude product was separated by column chromatography to produce compound 1-62-2 (0.7 g, yield 83.4%, white solid).

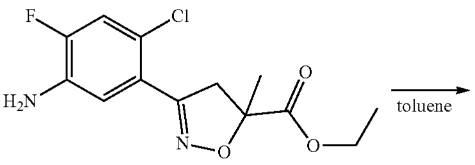

1-62-1

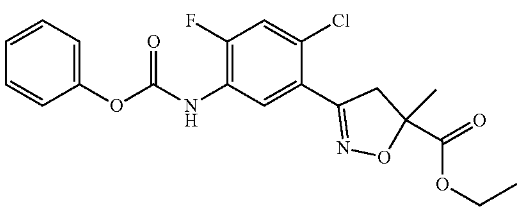

1-62-2

(2) Compound 206-4 (0.48 g, 2.1 mmol, 1.5 eq) and AcONa (58 mg, 0.7 mmol, 0.5 eq) were added to 10 ml DMF. The reaction solution was added with compound 1-62-2 (0.6 g, 1.4 mmol, 1.0 eq) at 60° C., then reacted at 60° C. for 1 hour. The product was detected by LCMS. The reaction solution was added with water (10 ml), then extracted with ethyl acetate. The organic phase was washed with saturated brine (20 ml*1), then concentrated, the crude product was separated by column chromatography to produce 1-62-racemate (0.4 g, yield 61.4%, white solid).

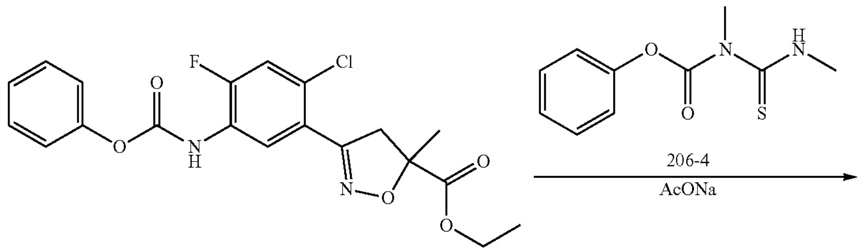

1-62-2

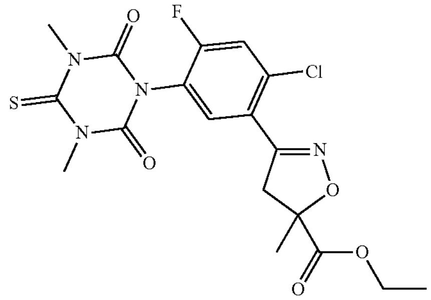

1-62-racemate (3) Compound 1-62-racemate (0.5 g, 98% purity) was subjected to chiral HPLC separation (Column: AD-5H; Column Size: 3 cm×25 cm, 5 μm; Injection: 2.0 ml; Mobile phase: Hex: i-PrOH (20% EtOH)=6:4; Flow rate: 20 ml/min; Wavelength: UV 254 nm; Temperature: 25° C.; Sample solution: 50 mg/2 ml in EtOH; Run time=60 mins), then concentrated to produce compound 1-62 (0.16 g, Rt=10.51 min, 100% ee, white solid) and 1-62-R configuration (0.13 g, Rt=30.81 min 99.8% ee, white solid).

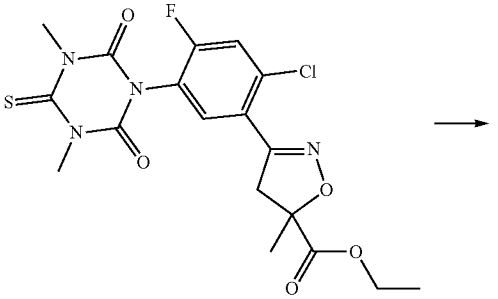

1-62-racemate

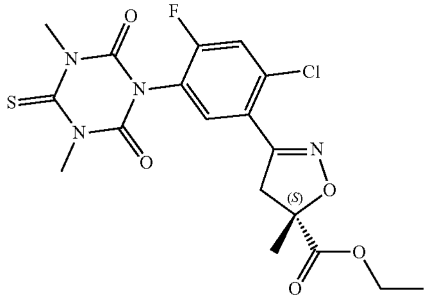

+

1-62

-continued

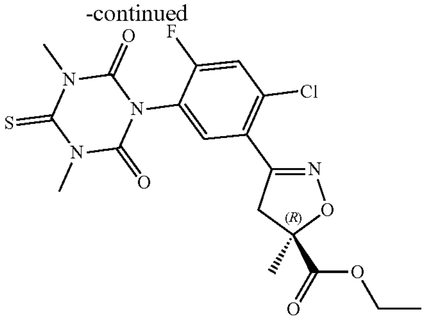

1-62-Rconfiguration

Biological Activity Evaluation:

The activity level criteria for plant damage (i.e., growth control rate) are as follows:

Level 5: growth control rate is above 85%;

Level 4: growth control rate is greater than or equal to 60% and less than 85%;

Level 3: growth control rate is greater than or equal to 40% and less than 60%;

Level 2: growth control rate is greater than or equal to 20% and less than 40%;

Level 1: growth control rate is greater than or equal to 5% and less than 20%;

Level 0: growth control rate is less than 5%.

The above growth control rates are fresh weight control rates.

Experiment on weeding effect in post-emergence stage:

Monocotyledonous and dicotyledonous weed seeds (*Descurainia sophia, Capsella bursa-pastoris, Abutilon theophrasti, Galium aparine, Stellaria media, Lithospermum arvense, Rorippa indica, Alopecurus aequalis, Alopecurus japonicus, Beckmannia syzigachne, Sclerochloa dura, Conyza Canadensis, Phleum paniculatum, Veronica didyma Tenore, Bromus japonicus, Aegilops tauschii, Phalaris arundinacea, Amaranthus retroflexus, Chenopodium album, Commelina communis, Sonchus arvensis, Convolvulus*

*arvensis, Cirsium setosum, Solanum nigrum, Acalypha australis, Digitaria sanguinalis, Echinochloa crusgalli, Setaria viridis, Setaria glauca, Leptochloa chinensis, Monochoria vaginalis, Sagittaria trifolia, Scirpus juncoides, Cyperus rotundus, Cyperus iria, Cyperus difformis, Fimbristylis, Portulaca oleracea, Xanthium sibiricum, Pharbitis nil, Conyza japonica*, etc.) and major crop seeds (wheat, corn, rice, soybean, cotton, oilseed rape, millet, sorghum, potato, sesame, *ricinus*, etc.) were placed in plastic pots filled with soil, then covered with 0.5-2 cm of soil, allowed to grow in a good greenhouse environment. After 2 weeks of sowing, the test plants were treated in the 2-3 leaf stage. The tested compounds of the present invention were respectively dissolved in acetone, then added with Tween 80 and 1.5 liter/ha of emulsifiable concentrate of methyl oleate as synergist, diluted with a certain amount of water to obtain a solution with a certain concentration, and sprayed with a spray tower onto the plants. After the application, the plants were cultured for 3 weeks in the greenhouse, and then the experimental results of the weeding were counted. The doses of the used compounds were 500, 250, 125, 60, 15, 7.5 g a.i./ha, and the averages were obtained by repeating for three times. Representative data are listed in Tables 2-6.

TABLE 2

Results on weeding effect in post-emergence stage

| Compound NO. | *Alopecurus japonicus* | *Beckmannia syzigachne* | *Rorippa indica* | *Conyza japonica* | Dose (g a.i./ha) |
|---|---|---|---|---|---|
| 3 | 5 | 5 | 5 | 5 | 125 |
| 3(S) | 5 | 5 | 5 | 5 | 125 |
| 4 | 5 | 5 | 5 | 5 | 125 |
| 4(S) | 5 | 5 | 5 | 5 | 125 |
| 5 | 5 | 5 | 5 | 5 | 125 |
| 6 | 5 | 5 | 5 | 5 | 125 |
| 17 | 5 | 5 | 5 | 5 | 125 |
| 17(S) | 5 | 5 | 5 | 5 | 125 |
| 26 | 5 | 5 | 5 | 5 | 125 |
| 31 | 5 | 5 | 5 | 5 | 125 |
| 33 | 5 | 5 | 5 | 5 | 125 |
| 34 | 5 | 5 | 5 | 5 | 125 |
| 34(S) | 5 | 5 | 5 | 5 | 125 |
| 35 | 5 | 5 | 5 | 5 | 125 |
| 43 | 5 | 5 | 5 | 5 | 125 |
| 53 | 5 | 5 | 5 | 5 | 125 |
| 54 | 5 | 5 | 5 | 5 | 125 |
| 55 | 5 | 5 | 5 | 5 | 125 |
| 56 | 5 | 5 | 5 | 5 | 125 |
| 59 | 5 | 5 | 5 | 5 | 125 |
| 203 | 5 | 5 | 5 | 5 | 125 |
| 204 | 5 | 5 | 5 | 5 | 125 |
| 205 | 5 | 5 | 5 | 5 | 125 |
| 206 | 5 | 5 | 5 | 5 | 125 |

TABLE 3

Results of comparison experiment on weeding effect in post-emergence stage

| Compound No. | *Alopecurus japonicus* | *Beckmannia syzigachne* | *Rorippa indica* | *Conyza japonica* | Dose (g a.i./ha) |
|---|---|---|---|---|---|
| 3 | 5 | 5 | 5 | 5 | 15 |
| 3(S) | 5 | 4 | 5 | 4 | 7.5 |
| 4 | 5 | 4 | 5 | 4 | 15 |
| 4(S) | 5 | 5 | 5 | 5 | 15 |
| 5 | 5 | 4 | 5 | 4 | 15 |
| 6 | 5 | 5 | 5 | 5 | 15 |
| 17 | 5 | 5 | 5 | 5 | 15 |
| 26 | 5 | 5 | 5 | 5 | 15 |

TABLE 3-continued

Results of comparison experiment on weeding effect in post-emergence stage

| Compound No. | *Alopecurus japonicus* | *Beckmannia syzigachne* | *Rorippa indica* | *Conyza japonica* | Dose (g a.i./ha) |
|---|---|---|---|---|---|
| 31(S) | 5 | 5 | 5 | 5 | 15 |
| 33(S) | 5 | 5 | 5 | 5 | 15 |
| 34 | 5 | 5 | 5 | 5 | 15 |
| 35 | N | N | 5 | 4 | 15 |
| 43 | N | N | 5 | 4 | 15 |
| 53 | N | N | 5 | 5 | 15 |
| 54(S) | 5 | 5 | 5 | 5 | 15 |
| 55(S) | 5 | 5 | 5 | 5 | 15 |
| 56(S) | 5 | 5 | 5 | 5 | 15 |
| 59(S) | 5 | 5 | 5 | 5 | 15 |
| 203 | N | N | 5 | 4 | 15 |
| 204(S) | 5 | 5 | 5 | 5 | 15 |
| 205(S) | 5 | 5 | 5 | 5 | 15 |
| 206(S) | 5 | 5 | 5 | 5 | 15 |
| Control compound A | 3 | 2 | 2 | 2 | 15 |

TABLE 4

Results on weeding effect in post-emergence stage

| Compound No. | *Alopecurus japonicus* | *Beckmannia syzigachne* | *Rorippa indica* | *Conyza japonica* | Dose (g a.i./ha) |
|---|---|---|---|---|---|
| 105 | 5 | 5 | 5 | 5 | 125 |
| 105(S) | 5 | 5 | 5 | 5 | 125 |
| 119 | 5 | 5 | 5 | 5 | 125 |
| 119(S) | 5 | 5 | 5 | 5 | 125 |
| 126 | 5 | 5 | 5 | 5 | 125 |
| 129 | 5 | 5 | 5 | 5 | 125 |
| 132 | 5 | 5 | 5 | 5 | 125 |
| 134 | 5 | 5 | 5 | 5 | 125 |
| 135 | 5 | 5 | 5 | 5 | 125 |
| 136 | 5 | 5 | 5 | 5 | 125 |
| 142 | 5 | 5 | 5 | 5 | 125 |
| 152 | 5 | 5 | 5 | 5 | 125 |
| 218 | 5 | 5 | 5 | 5 | 125 |
| 219 | 5 | 5 | 5 | 5 | 125 |
| 220 | 5 | 5 | 5 | 5 | 125 |
| 226 | 5 | 5 | 5 | 5 | 125 |
| 228 | 5 | 5 | 5 | 5 | 125 |
| 228(S) | 5 | 5 | 5 | 5 | 125 |
| 229 | 5 | 5 | 5 | 5 | 125 |
| 230 | 5 | 5 | 5 | 5 | 125 |
| 231 | 5 | 5 | 5 | 5 | 125 |

TABLE 5

Results of comparison experiment on weeding effect in post-emergence stage

| Compound No. | *Alopecurus japonicus* | *Beckmannia syzigachne* | *Rorippa indica* | *Conyza japonica* | Dose (g a.i./ha) |
|---|---|---|---|---|---|
| 105 | 5 | 5 | 5 | 5 | 15 |
| 119 | 5 | 5 | 5 | 5 | 15 |
| 119(S) | 5 | 5 | 4 | 4 | 7.5 |
| 126(S) | 5 | 5 | 5 | 5 | 15 |
| 129(S) | 5 | 5 | 5 | 5 | 15 |
| 132(S) | 5 | 5 | 5 | 5 | 15 |
| 134(S) | 5 | 5 | 5 | 5 | 15 |
| 135(S) | 5 | 5 | 5 | 5 | 15 |
| 136(S) | 5 | 5 | 5 | 5 | 15 |
| 142(S) | 5 | 5 | 5 | 5 | 15 |
| 152(S) | 5 | 5 | 5 | 5 | 15 |
| 218(S) | 5 | 5 | 5 | 5 | 15 |

TABLE 5-continued

| Results of comparison experiment on weeding effect in post-emergence stage | | | | | |
|---|---|---|---|---|---|
| Compound No. | *Alopecurus japonicus* | *Beckmannia syzigachne* | *Rorippa indica* | *Conyza japonica* | Dose (g a.i./ha) |
| 219 | N | N | 4 | N | 15 |
| 220(S) | 5 | 5 | 5 | 5 | 15 |
| 226(S) | 5 | 5 | 5 | 5 | 15 |
| 228 | 5 | 4 | 5 | 5 | 15 |
| 229(S) | 5 | 5 | 5 | 5 | 15 |
| 230(S) | 5 | 5 | 5 | 5 | 15 |
| 231 | N | 4 | 5 | 5 | 15 |
| Control compound B | 4 | 3 | 3 | 4 | 15 |
| Control compound B | 3 | 2 | 2 | 3 | 7.5 |

TABLE 6

| Results of comparison experiment on weeding effect in post-emergence stage | | | | | |
|---|---|---|---|---|---|
| Compound No. | *Alopecurus japonicus* | *Beckmannia syzigachne* | *Rorippa indica* | *Conyza japonica* | Dose (g a.i./ha) |
| 1-2 | 5 | 5 | 5 | 5 | 15 |
| 1-9 | 5 | 5 | 5 | 5 | 15 |
| 1-37 | 5 | 5 | 5 | 5 | 15 |
| 1-39 | 5 | 5 | 5 | 5 | 15 |
| Control compound B | 4 | 3 | 3 | 4 | 15 |
| 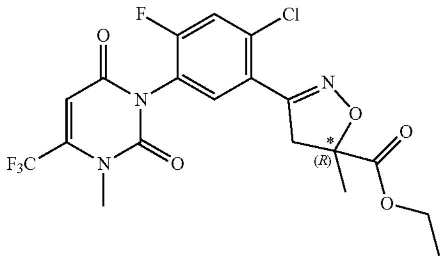 | 2 | 1 | 1 | 1 | 15 |
| 1-55 | 5 | 5 | 5 | 5 | 15 |
| 1-60 | 5 | 5 | 5 | 5 | 15 |
| 1-61 | 5 | 5 | 5 | 5 | 15 |
| 1-62 | 5 | 5 | 5 | 5 | 15 |
| 1-63 | 5 | 5 | 5 | 5 | 15 |
| 1-64 | 5 | 5 | 5 | 5 | 15 |
| 1-65 | 5 | 5 | 5 | 5 | 15 |
| 1-66 | 5 | 5 | 5 | 5 | 15 |
| 1-67 | 5 | 5 | 5 | 5 | 15 |
| 1-68 | 5 | 5 | 5 | 5 | 15 |
| 1-69 | 5 | 5 | 5 | 5 | 15 |
| 1-70 | 5 | 5 | 5 | 5 | 15 |
| 1-71 | 5 | 5 | 5 | 5 | 15 |
| 1-72 | 5 | 5 | 5 | 5 | 15 |
| 1-73 | 5 | 5 | 5 | 5 | 15 |
| 1-74 | 5 | 5 | 5 | 5 | 15 |
| 1-75 | 5 | 5 | 5 | 5 | 15 |
| 1-76 | 5 | 5 | 5 | 5 | 15 |
| 1-79 | 5 | 5 | 5 | 5 | 15 |
| 1-80 | 5 | 5 | 5 | 5 | 15 |
| 1-81 | 5 | 5 | 5 | 5 | 15 |
| 1-82 | 5 | 5 | 5 | 5 | 15 |
| 1-83 | 5 | 5 | 5 | 5 | 15 |
| 1-84 | 5 | 5 | 5 | 5 | 15 |
| 1-86 | 5 | 5 | 5 | 5 | 15 |
| 1-87 | 5 | 5 | 5 | 5 | 15 |
| 1-88 | 5 | 5 | 5 | 5 | 15 |
| 1-89 | 5 | 5 | 5 | 5 | 15 |
| 1-90 | 5 | 5 | 5 | 5 | 15 |
| 1-92 | 5 | 5 | 5 | 5 | 15 |
| 1-94 | 5 | 5 | 5 | 5 | 15 |
| 1-96 | 5 | 5 | 5 | 5 | 15 |
| 1-98 | 5 | 5 | 5 | 5 | 15 |
| 1-99 | 5 | 5 | 5 | 5 | 15 |
| 1-100 | 5 | 5 | 5 | 5 | 15 |
| 1-101 | 5 | 5 | 5 | 5 | 15 |

TABLE 6-continued

Results of comparison experiment on weeding effect in post-emergence stage

| Compound No. | *Alopecurus japonicus* | *Beckmannia syzigachne* | *Rorippa indica* | *Conyza japonica* | Dose (g a.i./ha) |
|---|---|---|---|---|---|
| Control compound A | 3 | 2 | 2 | 2 | 15 |
| 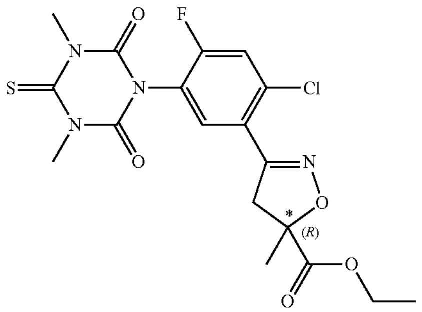 | 2 | 1 | 1 | 1 | 15 |

Note:
N represents no data; Control compound A:

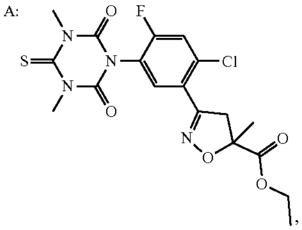,

Control compound B:

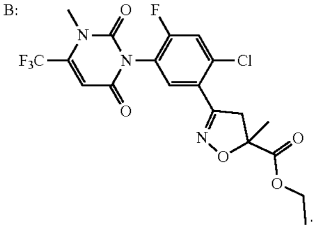.

Experiment on weed effect in pre-emergence stage:

The seeds of monocotyledonous and dicotyledonous weeds and main crops (wheat, corn, rice, soybean, cotton, oilseed rape, millet and sorghum) were put into a plastic pot loaded with soil and covered with 0.5-2 cm soil. The test compounds of the present invention was dissolved with acetone, then added with tween 80, diluted by a certain amount of water to reach a certain concentration, and sprayed immediately after sowing. The obtained seeds were incubated for 4 weeks in the greenhouse after spraying and the test results were observed. It was observed that the herbicide mostly had excellent effect at the application rate of 250 g a.i./ha, especially to weeds such as *Echinochloa crusgalli, Digitaria sanguinalis* and *Abutilon theophrasti*, etc. And many compounds had good selectivity for corn, wheat, rice, and soybean.

It is indicated from the experiment of main weeds in wheat and rice fields that the compound of the present invention generally have good weed control efficacy. Above all, it is noted that the compound of the invention have extremely high activity to broad-leaved weeds and cyperaceae weeds, which are resistant to ALS inhibitor, like *Sagittaria trifolia, Scirpus juncoides, Cyperus difformis, Descurainia sophia, Capsella bursa*-pastoris, *Lithospermum arvense, Galium aparine* L., and *Cyperus rotundus* L., etc., and have excellent commercial value.

Transplanted rice safety evaluation and weed control effect evaluation in rice field:

Rice field soil was loaded into a 1/1,000,000 ha pot. The seeds of *Echinochloa crusgalli, Scirpus juncoides*, and *Bidens tripartita* L. were sowed and gently covered with soil, then left to stand still in greenhouse in the state of 0.5-1 cm of water storage. The tuber of *Sagittaria trifolia* was planted in the next day or 2 days later. It was kept at 3-4 cm of water storage thereafter. The weeds were treated by dripping the WP or SC water diluents prepared according to the common preparation method of the compounds of the present invention with pipette homogeneously to achieve specified effective amount when *Echinochloa crusgalli, Scirpus juncoides*, and *Bidens tripartita* L. reached 0.5 leaf stage and *Sagittaria trifolia* reached the time point of primary leaf stage.

In addition, the rice field soil that loaded into the 1/1,000,000 ha pot was leveled to keep water storage at 3-4 cm depth. The 3 leaf stage rice (*japonica* rice) was transplanted at 3 cm of transplanting depth the next day. The compound of the present invention was treated by the same way after 5 days of transplantation.

The fertility condition of *Echinochloa crusgalli, Scirpus juncoides, Bidens tripartita* L. and *Sagittaria trifolia* 14 days after the treatment of the compound of the invention and the fertility condition of rice 21 days after the treatment of the compound of the invention respectively with the naked eye.

Evaluate the weed control effect with the above activity standard level. Many compounds show excellent activity and selectivity.

Note: The seeds of *Echinochloa crusgalli, Scirpus juncoides* and *Bidens tripartita* L. were collected from Heilongjiang Province of China. The tests indicated that the weeds were resistant to the common doses of Pyrazosulfuron-ethyl.

At the same time, it is found after several tests that the compounds and compositions of the present invention have good selectivity to many gramineae grasses such as *zoysia japonica*, bermuda grass, tall fescue, bluegrass, ryegrass and seashore *paspalum* etc, and are able to control many important grass weeds and broad-leaved weeds. The compounds also show excellent selectivity and commercial value in the tests on sugarcane, soybean, cotton, oil sunflower, potato, orchards and vegetables in different herbicide application methods.

The invention claimed is:

1. A substituted-isoxazoline-containing aromatic compound, as shown in general formula I:

I

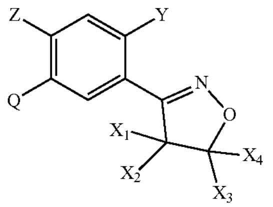

wherein,

Q represents

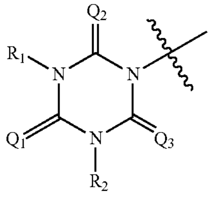

or

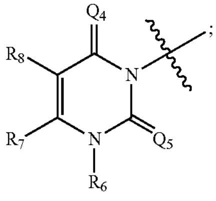

;

Y represents halogen, halogenated alkyl or cyano;

Z represents halogen;

$Q_1$, $Q_2$, $Q_3$, $Q_4$, $Q_5$ each independently represent O or S;

$R_1$, $R_2$, $R_6$ each independently represent hydrogen, alkyl, alkenyl, alkynyl, cycloalkyl or cycloalkylalkyl;

$R_7$, $R_8$ each independently represent hydrogen, alkyl, halogen, halogenated alkyl or amino;

$X_1$, $X_2$ each independently represent hydrogen, halogen, alkyl, alkenyl, alkynyl, cycloalkyl, cycloalkylalkyl, —$OR_3$, —(CO)$OR_3$ or phenyl; wherein, the "alkyl", "alkenyl", "alkynyl", "cycloalkyl" or "cycloalkylalkyl" is each independently unsubstituted or substituted with at least one substituent selected from the group consisting of halogen;

$X_3$ represents halogen, cyano, formyl, substituted alkyl, alkenyl, alkynyl, substituted alkenyl, substituted alkynyl, cycloalkyl, cycloalkylalkyl, —$OR_3$, —(CO)$OR_3$, —$SR_3$, heterocyclyl, heterocyclylalkyl, aryl, arylalkyl or amino; wherein, the "substituted alkyl", "substituted alkenyl" or "substituted alkynyl" each independently has at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O-alkyl-(CO)$OR_3$ and —O(CO)(CO)$OR_3$;

the "cycloalkyl", "cycloalkylalkyl", "heterocyclyl", "heterocyclylalkyl", "aryl" or "arylalkyl" is each independently unsubstituted or substituted with at least one substituent selected from the group consisting of oxo, halogen, cyano, nitro, alkyl, alkenyl, alkynyl, cycloalkyl, halogenated alkyl, halogenated alkenyl, halogenated alkynyl, halogenated cycloalkyl, cycloalkyl substituted with alkyl, —$OR_4$, —$SR_4$, —(CO)$OR_4$, —($SO_2$)$R_4$ and —$N(R_4)_2$;

the "amino" is unsubstituted or substituted with one or two substituents selected from the group consisting of —$R_3$;

$X_4$ each independently represents-$COOR_5$ or -alkyl-$COOR_5$;

$R_3$ each independently represents hydrogen, alkyl, alkenyl, alkynyl, cycloalkyl or cycloalkylalkyl;

$R_4$ each independently represents hydrogen, alkyl or halogenated alkyl;

$R_5$ each independently represents hydrogen, alkyl, alkenyl, alkynyl, cycloalkyl or cycloalkylalkyl; wherein, the "alkyl", "alkenyl", "alkynyl", "cycloalkyl" or "cycloalkylalkyl" is each independently unsubstituted or substituted with at least one substituent selected from the group consisting of halogen.

2. The substituted-isoxazoline-containing aromatic compound according to claim 1, which is characterized in that, Y represents halogen, halogenated C1-C8 alkyl or cyano;

$R_1$, $R_2$, $R_6$ each independently represent hydrogen, C1-C8 alkyl, C2-C8 alkenyl, C2-C8 alkynyl, C3-C8 cycloalkyl or C3-C8 cycloalkyl C1-C8 alkyl;

$R_7$, $R_8$ each independently represent hydrogen, C1-C8 alkyl, halogen, halogenated C1-C8 alkyl or amino;

$X_1$, $X_2$ each independently represent hydrogen, halogen, C1-C8 alkyl, C2-C8 alkenyl, C2-C8 alkynyl, C3-C8 cycloalkyl, C3-C8 cycloalkyl C1-C8 alkyl, —$OR_3$, —(CO)$OR_3$ or phenyl; wherein, the "C1-C8 alkyl", "C2-C8 alkenyl", "C2-C8 alkynyl", "C3-C8 cycloalkyl" or "C3-C8 cycloalkyl C1-C8 alkyl" is each independently unsubstituted or substituted with at least one substituent selected from the group consisting of halogen;

$X_3$ represents halogen, cyano, formyl, substituted C1-C8 alkyl, C2-C8 alkenyl, C2-C8 alkynyl, substituted C2-C8 alkenyl, substituted C2-C8 alkynyl, C3-C8 cycloalkyl, C3-C8 cycloalkyl C1-C8 alkyl, —$OR_3$, —(CO)$OR_3$, —$SR_3$, heterocyclyl, heterocyclyl C1-C8 alkyl, aryl, aryl C1-C8 alkyl or amino; wherein, the "substituted C1-C8 alkyl", "substituted C2-C8 alkenyl" or "substituted C2-C8 alkynyl" each independently has at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O—(C1-C8 alkyl)-(CO)$OR_3$ and —O(CO)(CO)$OR_3$;

the "C3-C8 cycloalkyl", "C3-C8 cycloalkyl C1-C8 alkyl", "heterocyclyl", "heterocyclyl C1-C8 alkyl", "aryl" or "aryl C1-C8 alkyl" is each independently unsubstituted or substituted with at least one substituent selected from the group consisting of oxo, halogen, cyano, nitro, C1-C8 alkyl, C2-C8 alkenyl, C2-C8 alkynyl, C3-C8 cycloalkyl, halogenated C1-C8 alkyl, halogenated C2-C8 alkenyl, halogenated C2-C8 alkynyl, halogenated C3-C8 cycloalkyl, C3-C8 cycloalkyl substituted with C1-C8 alkyl, —$OR_4$, —$SR_4$, —(CO)$OR_4$, —($SO_2$)$R_4$ and —$N(R_4)_2$;

the "amino" is unsubstituted or substituted with one or two substituents selected from the group consisting of —$R_3$;

$X_4$ each independently represents-$COOR_5$ or -(C1-C8 alkyl)-$COOR_5$;

$R_3$ each independently represents hydrogen, C1-C8 alkyl, C2-C8 alkenyl, C2-C8 alkynyl, C3-C8 cycloalkyl or C3-C8 cycloalkyl C1-C8 alkyl;

$R_4$ each independently represents hydrogen, C1-C8 alkyl or halogenated C1-C8 alkyl;

$R_5$ each independently represents hydrogen, C1-C8 alkyl, C2-C8 alkenyl, C2-C8 alkynyl, C3-C8 cycloalkyl or C3-C8 cycloalkyl C1-C8 alkyl; wherein, the "C1-C8 alkyl", "C2-C8 alkenyl", "C2-C8 alkynyl", "C3-C8 cycloalkyl" or "C3-C8 cycloalkyl C1-C8 alkyl" is each independently unsubstituted or substituted with at least one substituent selected from the group consisting of halogen.

3. The substituted-isoxazoline-containing aromatic compound according to claim 1, which is characterized in that, Y represents halogen, halogenated C1-C6 alkyl or cyano;

$R_1$, $R_2$, $R_6$ each independently represent hydrogen, C1-C6 alkyl, C2-C6 alkenyl, C2-C6 alkynyl, C3-C6 cycloalkyl or C3-C6 cycloalkyl C1-C6 alkyl;

$R_7$, $R_8$ each independently represent hydrogen, C1-C6 alkyl, halogen, halogenated C1-C6 alkyl or amino;

$X_1$, $X_2$ each independently represent hydrogen, halogen, C1-C6 alkyl, C2-C6 alkenyl, C2-C6 alkynyl, C3-C6 cycloalkyl, C3-C6 cycloalkyl C1-C6 alkyl, —$OR_3$, —(CO)$OR_3$ or phenyl; wherein, the "C1-C6 alkyl", "C2-C6 alkenyl", "C2-C6 alkynyl", "C3-C6 cycloalkyl" or "C3-C6 cycloalkyl C1-C6 alkyl" is each independently unsubstituted or substituted with at least one substituent selected from the group consisting of halogen;

$X_3$ represents halogen, cyano, formyl, substituted C1-C6 alkyl, C2-C6 alkenyl, C2-C6 alkynyl, substituted C2-C6 alkenyl, substituted C2-C6 alkynyl, C3-C6 cycloalkyl, C3-C6 cycloalkyl C1-C6 alkyl, —$OR_3$, —(CO)$OR_3$, —$SR_3$, heterocyclyl, heterocyclyl C1-C6 alkyl, aryl, aryl C1-C6 alkyl or amino; wherein, the "substituted C1-C6 alkyl", "substituted C2-C6 alkenyl" or "substituted C2-C6 alkynyl" each independently has at least one substituent selected from the group consisting of halogen, cyano, —$OR_3$, —(CO)$R_3$, —$SR_3$, —($SO_2$)$R_3$, —O(CO)$R_3$, —O—($SO_2$)$R_3$, —(CO)$OR_3$, —O(CO)$OR_3$, —O—(C1-C6 alkyl)-(CO)$OR_3$ and —O(CO)(CO)$OR_3$;

the "C3-C6 cycloalkyl", "C3-C6 cycloalkyl C1-C6 alkyl", "heterocyclyl", "heterocyclyl C1-C6 alkyl", "aryl" or "aryl C1-C6 alkyl" is each independently unsubstituted or substituted with at least one substituent selected from the group consisting of oxo, halogen, cyano, nitro, C1-C6 alkyl, C2-C6 alkenyl, C2-C6 alkynyl, C3-C6 cycloalkyl, halogenated C1-C6 alkyl, halogenated C2-C6 alkenyl, halogenated C2-C6 alkynyl, halogenated C3-C6 cycloalkyl, C3-C6 cycloalkyl substituted with C1-C6 alkyl, —$OR_4$, —$SR_4$, —(CO)$OR_4$, —($SO_2$)$R_4$ and —$N(R_4)_2$;

the "amino" is unsubstituted or substituted with one or two substituents selected from the group consisting of —$R_3$;

$X_4$ each independently represents-$COOR_5$ or -(C1-C6 alkyl)-$COOR_5$;

$R_3$ each independently represents hydrogen, C1-C6 alkyl, C2-C6 alkenyl, C2-C6 alkynyl, C3-C6 cycloalkyl or C3-C6 cycloalkyl C1-C6 alkyl;

$R_4$ each independently represents hydrogen, C1-C6 alkyl or halogenated C1-C6 alkyl;

$R_5$ each independently represents hydrogen, C1-C6 alkyl, C2-C6 alkenyl, C2-C6 alkynyl, C3-C6 cycloalkyl or C3-C6 cycloalkyl C1-C6 alkyl; wherein, the "C1-C6 alkyl", "C2-C6 alkenyl", "C2-C6 alkynyl", "C3-C6 cycloalkyl" or "C3-C6 cycloalkyl C1-C6 alkyl" is each independently unsubstituted or substituted with at least one substituent selected from the group consisting of halogen.

4. The substituted-isoxazoline-containing aromatic compound according to claim 1, which is characterized in that, Y represents halogen;

$R_1$, $R_2$, $R_6$ each independently represent C1-C6 alkyl;

$R_7$, $R_8$ each independently represent hydrogen or halogenated C1-C6 alkyl;

$X_1$, $X_2$ each independently represent hydrogen;

$X_3$ represents halogen, formyl, substituted C1-C6 alkyl, C2-C6 alkenyl, C2-C6 alkynyl, substituted C2-C6 alkenyl, substituted C2-C6 alkynyl, C3-C6 cycloalkyl, C3-C6 cycloalkyl C1-C3 alkyl, —$OR_3$, phenyl or benzyl; wherein, the "substituted C1-C6 alkyl", "substituted C2-C6 alkenyl" or "substituted C2-C6 alkynyl" each independently has one, two or three substituents selected from the group consisting of halogen, —$OR_3$, —(CO)$R_3$, —O(CO)$R_3$, —(CO)$OR_3$, —O—(C1-C3 alkyl)-(CO)$OR_3$ and —O(CO)(CO)$OR_3$;

the "C3-C6 cycloalkyl", "C3-C6 cycloalkyl C1-C3 alkyl", "phenyl" or "benzyl" is each independently unsubstituted or substituted with one, two or three substituents selected from the group consisting of halogen, C1-C6 alkyl, C2-C6 alkenyl, C2-C6 alkynyl, C3-C6 cycloalkyl, halogenated C1-C6 alkyl, halogenated C2-C6 alkenyl, halogenated C2-C6 alkynyl, halogenated C3-C6 cycloalkyl, C3-C6 cycloalkyl substituted with C1-C6 alkyl, —$OR_4$ and —(CO)$OR_4$;

$X_4$ each independently represents-$COOR_5$;

$R_3$ each independently represents hydrogen, C1-C6 alkyl, C2-C6 alkenyl, C2-C6 alkynyl, C3-C6 cycloalkyl or C3-C6 cycloalkyl C1-C3 alkyl;

$R_4$ each independently represents hydrogen, C1-C6 alkyl or halogenated C1-C6 alkyl;

$R_5$ each independently represents hydrogen, C1-C6 alkyl, C2-C6 alkenyl, C2-C6 alkynyl or C3-C6 cycloalkyl;

Z represents fluorine.

5. A substituted-isoxazoline-containing aromatic compound with S configuration, as shown in general formula I':

I'

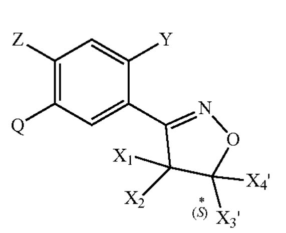

wherein, $X_3$' represents $X_3$, the substituents $X_1$, $X_2$, $X_3$, $X_4$, Q, Y and Z are defined as shown in claim 1, and $X_3$ and $X_4$ are different; based on the content of stereoisomers having R and S configurations at this position, it has a stereochemical purity of 60-100% (S).

6. The compound according to claim 1, which is selected from any one of the following compounds or the S configuration thereof:
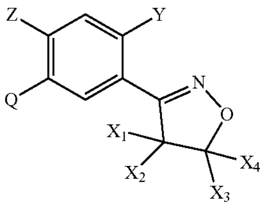
I
| NO. | 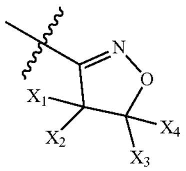 | Y | Z | Q |
|---|---|---|---|---|
| 3 | 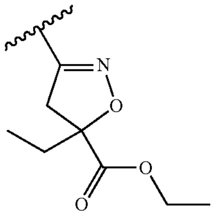 [SMILES: *C1=NOC(CC)(C(=O)OCC)C1] | Cl | F | 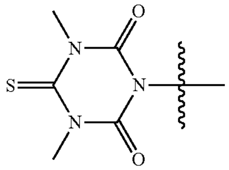 [SMILES: *n1c(=O)n(C)c(=S)n(C)c1=O] |
| 4 | 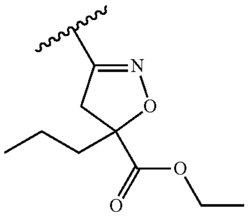 [SMILES: *C1=NOC(CCC)(C(=O)OCC)C1] | Cl | F | 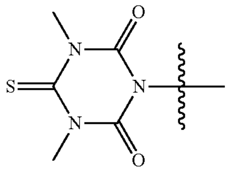 |
| 5 | 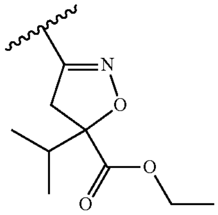 [SMILES: *C1=NOC(C(=O)OCC)(C(C)C)C1] | Cl | F | 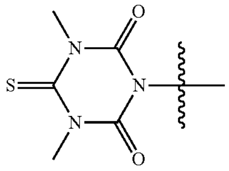 |
| 6 | 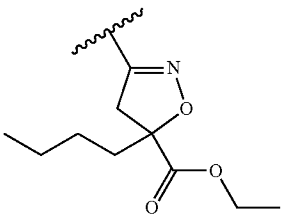 [SMILES: *C1=NOC(CCCC)(C(=O)OCC)C1] | Cl | F | 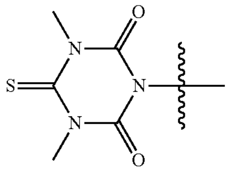 |
| 17 | 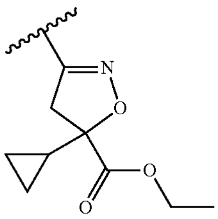 [SMILES: *C1=NOC(C(=O)OCC)(C2CC2)C1] | Cl | F | 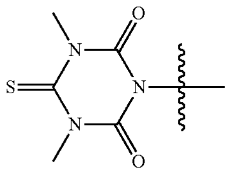 |

-continued
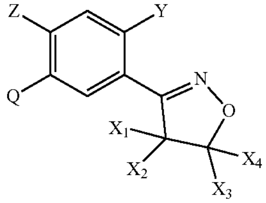
I
| NO. | 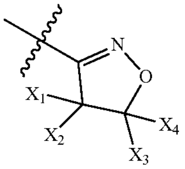 | Y | Z | Q |
|---|---|---|---|---|
| 26 | 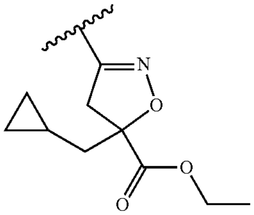 | Cl | F | 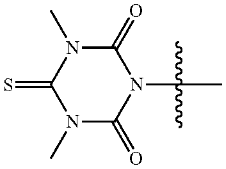 |
| 31 | 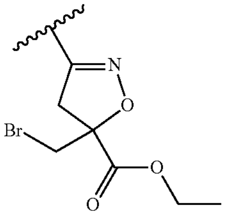 [SMILES: *C1=NOC(CBr)(C(=O)OCC)C1] | Cl | F | 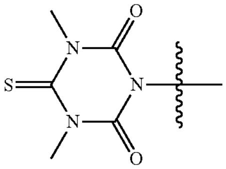 |
| 33 | 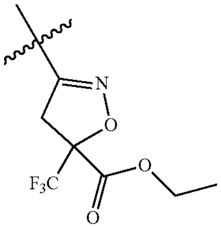 [SMILES: *C1=NOC(C(=O)OCC)(C(F)(F)F)C1] | Cl | F | 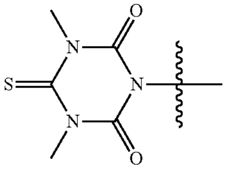 |
| 34 | 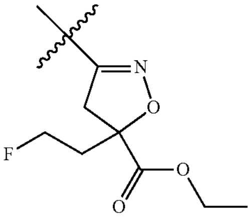 [SMILES: *C1=NOC(CCF)(C(=O)OCC)C1] | Cl | F | 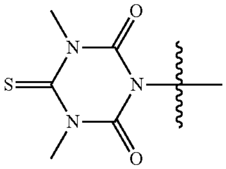 |
| 35 | 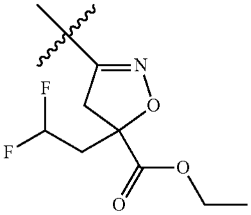 [SMILES: *C1=NOC(CC(F)F)(C(=O)OCC)C1] | Cl | F | 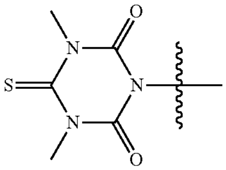 |

-continued
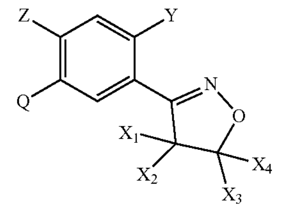
I
| NO. | 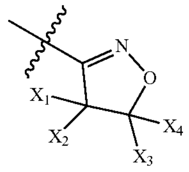 | Y | Z | Q |
|---|---|---|---|---|
| 43 | 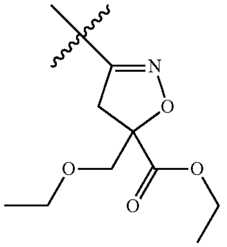 [SMILES: *C1=NOC(COCC)(C(=O)OCC)C1] | Cl | F | 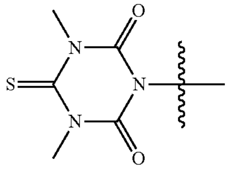 [SMILES: *n1c(=O)n(C)c(=S)n(C)c1=O] |
| 52 | 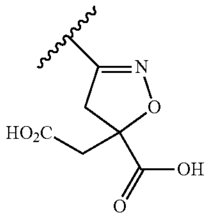 [SMILES: *C1=NOC(CC(=O)O)(C(=O)O)C1] | Cl | F | 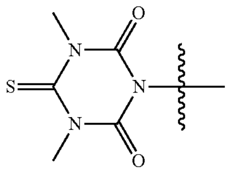 |
| 53 | 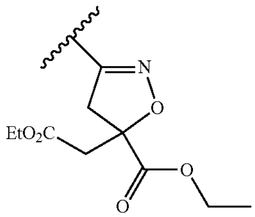 [SMILES: *C1=NOC(CC(=O)OCC)(C(=O)OCC)C1] | Cl | F | 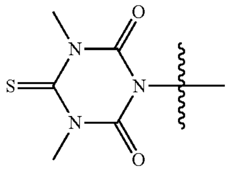 |
| 54 | 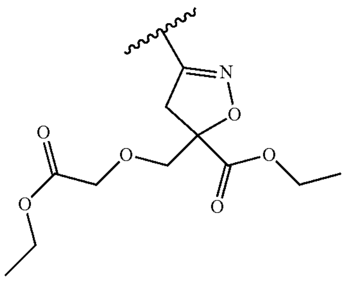 [SMILES: *C1=NOC(COCC(=O)OCC)(C(=O)OCC)C1] | Cl | F | 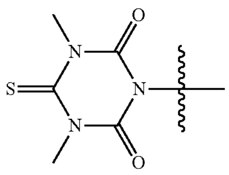 |

-continued
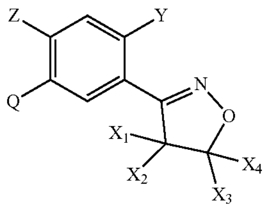
I
| NO. | 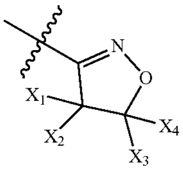 | Y | Z | Q |
|---|---|---|---|---|
| 55 | 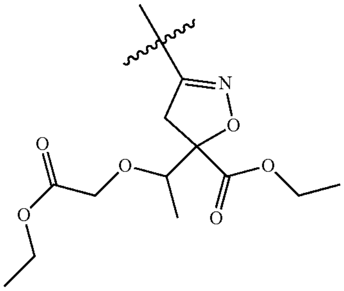 [SMILES: *C1=NOC(C(=O)OCC)(C(C)OCC(=O)OCC)C1] | Cl | F | 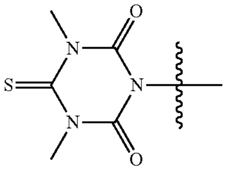 [SMILES: *n1c(=O)n(C)c(=S)n(C)c1=O] |
| 56 | 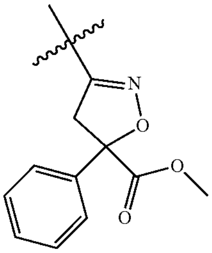 [SMILES: *C1=NOC(C(=O)OC)(c2ccccc2)C1] | Cl | F | 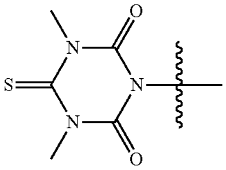 |
| 59 | 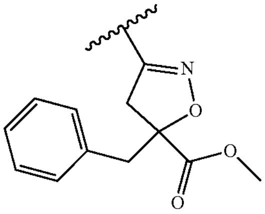 [SMILES: *C1=NOC(Cc2ccccc2)(C(=O)OC)C1] | Cl | F | 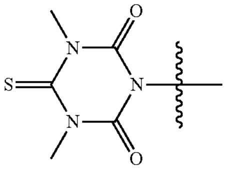 |
| 119 | 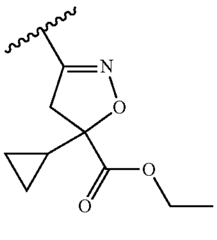 [SMILES: *C1=NOC(C(=O)OCC)(C2CC2)C1] | Cl | F | 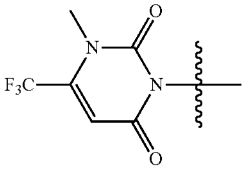 [SMILES: *n1c(=O)cc(C(F)(F)F)n(C)c1=O] |

-continued
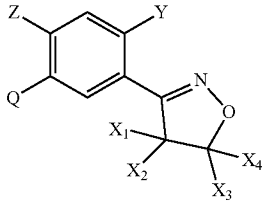
I
| NO. | 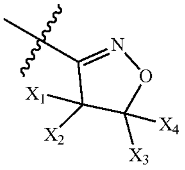 | Y | Z | Q |
|---|---|---|---|---|
| 126 | 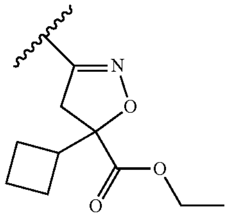 [SMILES: *C1=NOC(C(=O)OCC)(C2CCC2)C1] | Cl | F | 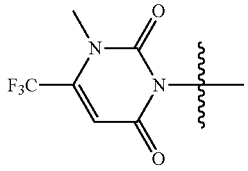 [SMILES: *n1c(=O)cc(C(F)(F)F)n(C)c1=O] |
| 129 | 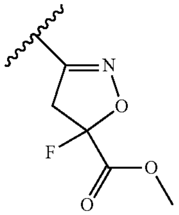 [SMILES: *C1=NOC(F)(C(=O)OC)C1] | Cl | F | 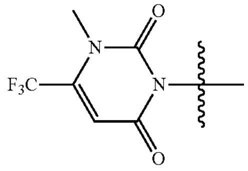 [SMILES: *n1c(=O)cc(C(F)(F)F)n(C)c1=O] |
| 132 | 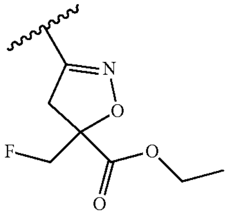 [SMILES: *C1=NOC(CF)(C(=O)OCC)C1] | Cl | F | 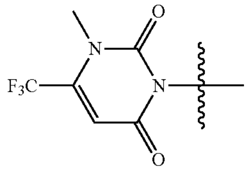 [SMILES: *n1c(=O)cc(C(F)(F)F)n(C)c1=O] |
| 134 | 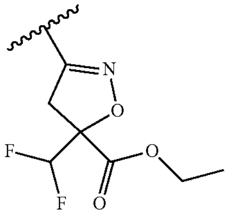 [SMILES: *C1=NOC(C(=O)OCC)(C(F)F)C1] | Cl | F | 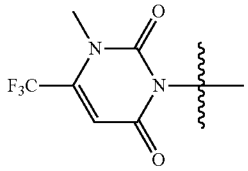 [SMILES: *n1c(=O)cc(C(F)(F)F)n(C)c1=O] |
| 135 | 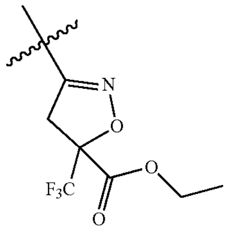 [SMILES: *C1=NOC(C(=O)OCC)(C(F)(F)F)C1] | Cl | F | 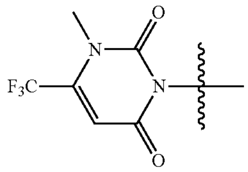 [SMILES: *n1c(=O)cc(C(F)(F)F)n(C)c1=O] |

-continued
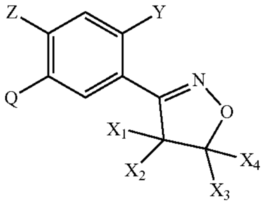
I
| NO. | 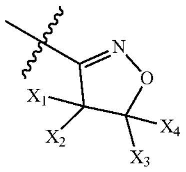 | Y | Z | Q |
| --- | --- | --- | --- | --- |
| 136 | 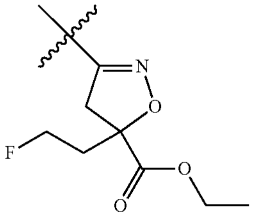 [SMILES: *C1=NOC(CCF)(C(=O)OCC)C1] | Cl | F | 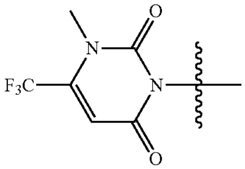 [SMILES: *n1c(=O)cc(C(F)(F)F)n(C)c1=O] |
| 142 | 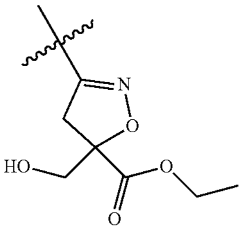 [SMILES: *C1=NOC(CO)(C(=O)OCC)C1] | Cl | F | 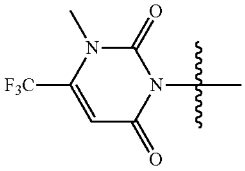 [SMILES: *n1c(=O)cc(C(F)(F)F)n(C)c1=O] |
| 152 | 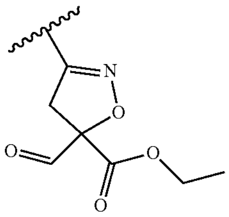 [SMILES: *C1=NOC(C=O)(C(=O)OCC)C1] | Cl | F | 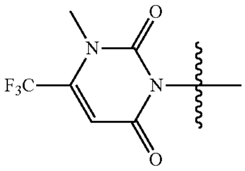 [SMILES: *n1c(=O)cc(C(F)(F)F)n(C)c1=O] |
| 203 | 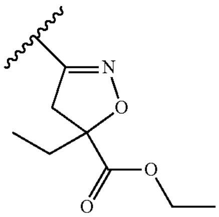 [SMILES: *C1=NOC(CC)(C(=O)OCC)C1] | Cl | F | 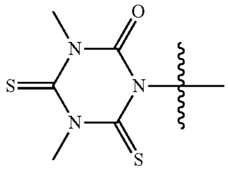 |
| 204 | 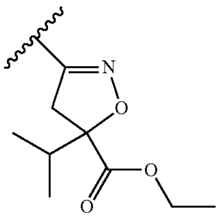 [SMILES: *C1=NOC(C(=O)OCC)(C(C)C)C1] | Cl | F | 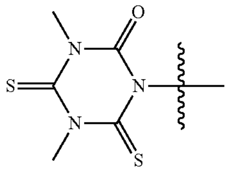 |

-continued
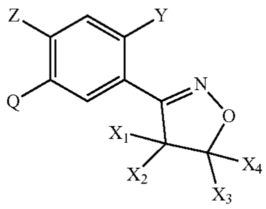
I
| NO. | 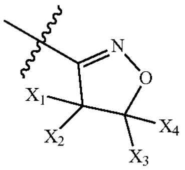 | Y | Z | Q |
|---|---|---|---|---|
| 205 | 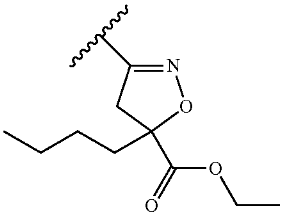 [SMILES: *C1=NOC(CCCC)(C(=O)OCC)C1] | Cl | F | 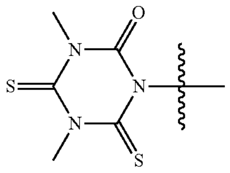 |
| 206 | 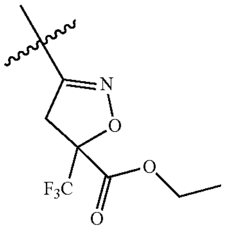 [SMILES: *C1=NOC(C(=O)OCC)(C(F)(F)F)C1] | Cl | F | 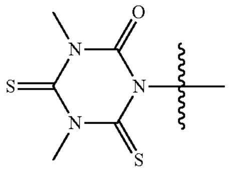 |
| 218 | 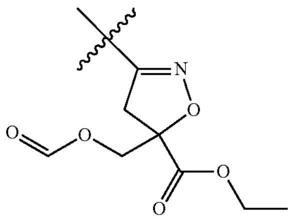 [SMILES: *C1=NOC(COC=O)(C(=O)OCC)C1] | Cl | F | 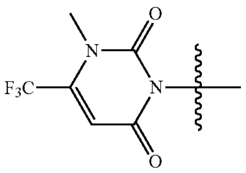 [SMILES: *n1c(=O)cc(C(F)(F)F)n(C)c1=O] |
| 219 | 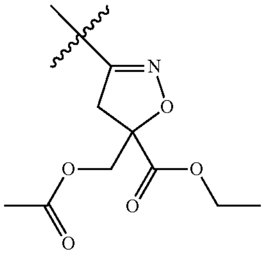 [SMILES: *C1=NOC(COC(C)=O)(C(=O)OCC)C1] | Cl | F | 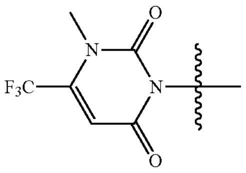 [SMILES: *n1c(=O)cc(C(F)(F)F)n(C)c1=O] |

-continued
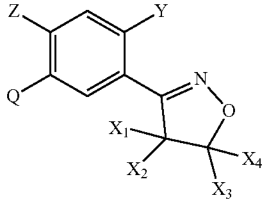
I
| NO. | 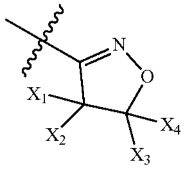 | Y | Z | Q |
|---|---|---|---|---|
| 220 | 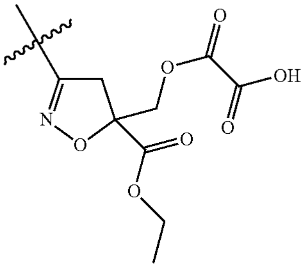 [SMILES: *C1=NOC(COC(=O)C(=O)O)(C(=O)OCC)C1] | Cl | F | 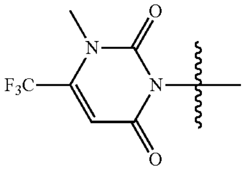 [SMILES: *n1c(=O)cc(C(F)(F)F)n(C)c1=O] |
| 226 | 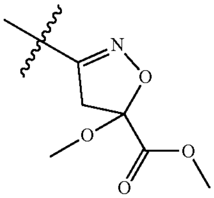 [SMILES: *C1=NOC(OC)(C(=O)OC)C1] | Cl | F | 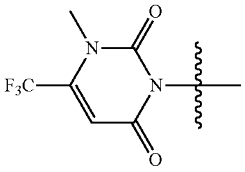 [SMILES: *n1c(=O)cc(C(F)(F)F)n(C)c1=O] |
| 228 | 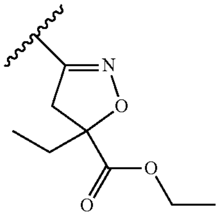 [SMILES: *C1=NOC(CC)(C(=O)OCC)C1] | Cl | F | 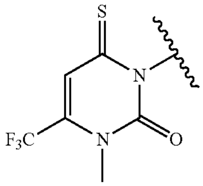 |
| 229 | 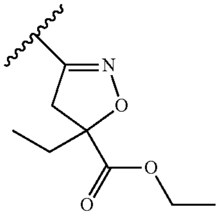 [SMILES: *C1=NOC(CC)(C(=O)OCC)C1] | Cl | F | 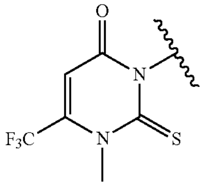 |
| 230 | 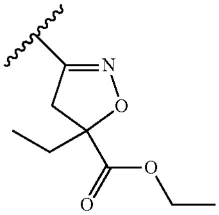 [SMILES: *C1=NOC(CC)(C(=O)OCC)C1] | Cl | F | 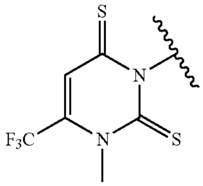 |

-continued

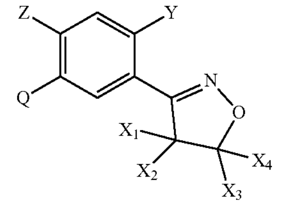

I

| NO. | 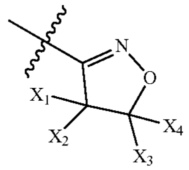 | Y | Z | Q |
|---|---|---|---|---|
| 231 | 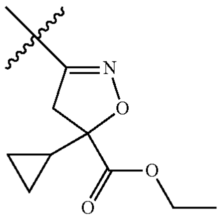 [SMILES: *C1=NOC(C(=O)OCC)(C2CC2)C1] | Cl | F | 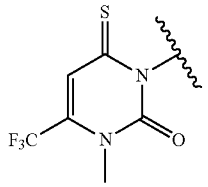 |
| 232 | 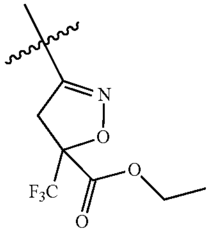 [SMILES: *C1=NOC(C(=O)OCC)(C(F)(F)F)C1] | Cl | F | 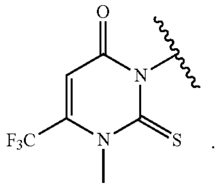 [SMILES: *n1c(=O)cc(C(F)(F)F)n(C)c1=S] . |

7. A method for preparing the substituted-isoxazoline-containing aromatic compound according to claim 1, which is characterized by comprising the following steps:

when Q represents

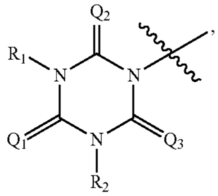, (1) subjecting a compound as shown in general formula II-1 and a compound as shown in general formula III-1 to cyclization reaction to obtain a compound as shown in general formula I-1, with the chemical reaction equation shown as follows:

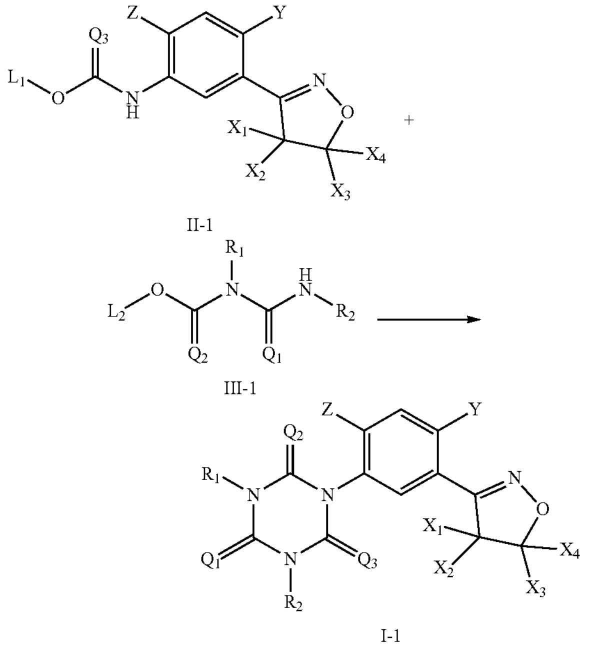

II-1 + III-1 → I-1 when Q represents

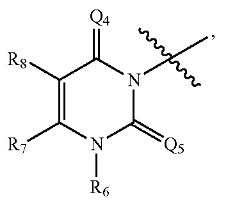

(2) subjecting a compound as shown in general formula II-2 and a compound as shown in general formula III-2 to cyclization reaction to obtain a compound as shown in general formula I-2, with the chemical reaction equation shown as follows:

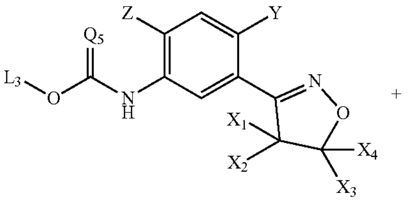

II-2

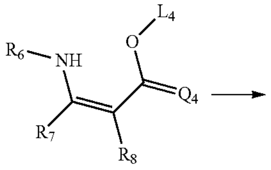

III-2

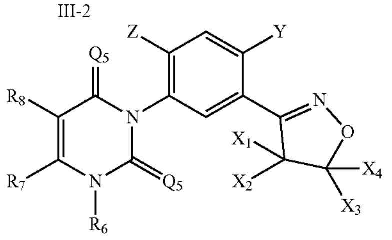

I-2

(3) subjecting a compound as shown in general formula II-3 and a compound as shown in general formula III-3 to reaction to obtain a compound as shown in general formula I-3;

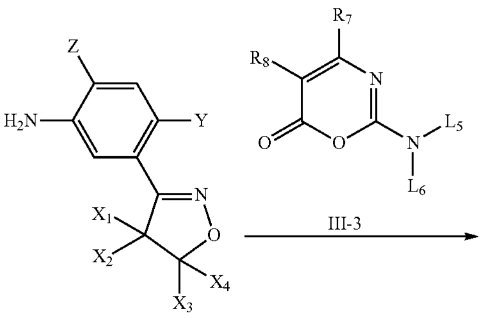

II-3

-continued

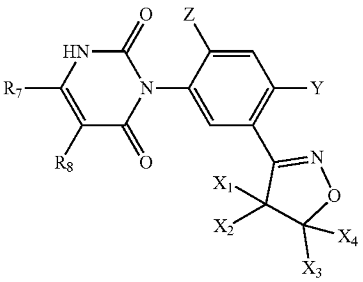

I-3

(4) subjecting a compound as shown in general formula II-4 and a compound as shown in general formula III-4 to reaction to obtain a compound as shown in general formula I-4;

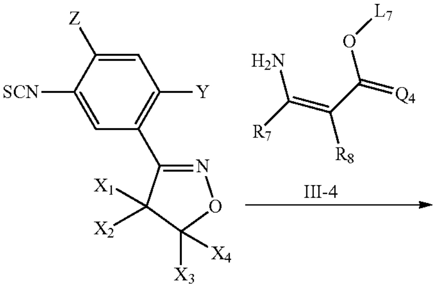

II-4

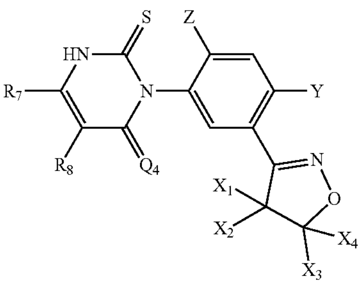

I-4 or, (5) subjecting a compound as shown in general formula I-5 and $R_6$'-Hal to substitution reaction to obtain a compound as shown in general formula I-6, with the chemical reaction equation shown as follows:

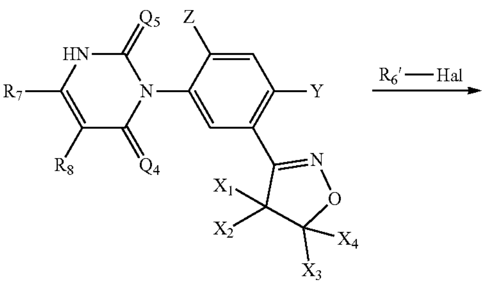

I-5

-continued

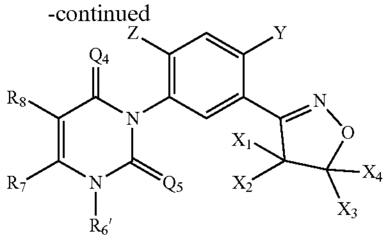

I-6 wherein, $L_1$, $L_2$, $L_3$, $L_4$, $L_5$, $L_6$ and $L_7$ each independently represent C1-C6 alkyl or aryl; Hal represents halogen; $R_6$' represents groups in $R_6$ other than hydrogen; other substituents $R_1$, $R_2$, $R_6$, $R_7$, $R_8$, $X_1$, $X_2$, $X_3$, $X_4$, $Q_1$, $Q_2$, $Q_3$, $Q_4$, $Q_5$, Y and Z are defined as shown in claim 1.

8. An herbicidal composition, which is characterized in that it comprises at least one of the substituted-isoxazoline-containing aromatic compound according to claim 1 in a herbicidally effective amount.

9. A method of controlling a weed, which is characterized in that it comprises applying at least one of the substituted-isoxazoline-containing aromatic compound according to claim 1 or a herbicidal composition in a herbicidally effective amount on a plant or a weed area, wherein the herbicidal composition comprises at least one of the substituted-isoxazoline-containing aromatic compound according to claim 1 in a herbicidally effective amount.

10. The method of claim 9, wherein the herbicidal composition further comprises a formulation auxiliary.

11. The method of claim 9, wherein the weed is a weed in a useful crop, and the useful crop is a transgenic crop or a crop treated by genome editing technique.

12. The substituted-isoxazoline-containing aromatic compound according to claim 4, which is characterized in that, Y represents chlorine;

$R_7$ represents C1-C6 alkyl;

$R_8$ represents hydrogen;

$X_3$ represents halogen, formyl, substituted C1-C6 alkyl, C3-C6 cycloalkyl, C3-C6 cycloalkyl C1-C3 alkyl, —$OR_3$, —(C1-C3 alkyl)-$OR_3$, —(C1-C3 alkyl)-O(CO)$R_3$, —(C1-C3 alkyl)-(CO)$OR_3$, —(C1-C3 alkyl-O—(C1-C3 alkyl)-(CO)$OR_3$, —(C1-C3 alkyl)-O(CO)(CO)$OR_3$, phenyl or benzyl; wherein, the "substituted C1-C6 alkyl" each independently has one, two or three substituents selected from the group consisting of halogen;

$R_3$ each independently represents hydrogen or C1-C6 alkyl;

$R_5$ each independently represents hydrogen or C1-C6 alkyl.

13. The substituted-isoxazoline-containing aromatic compound according to claim 4, which is characterized in that, Q represents

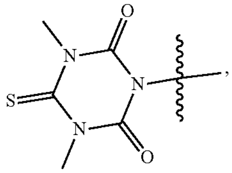,
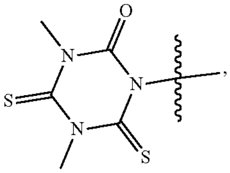,
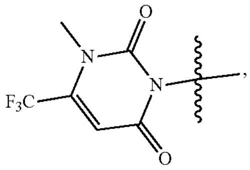,
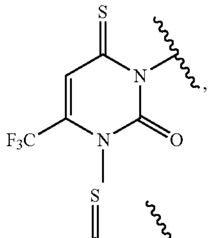,
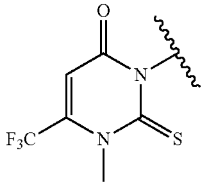 or
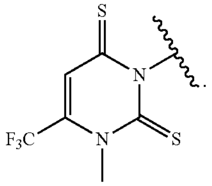.

14. The substituted-isoxazoline-containing aromatic compound according to claim 5, wherein it has a stereochemical purity of 80-100% (S).

15. The substituted-isoxazoline-containing aromatic compound according to claim 5, wherein it has a stereochemical purity of 95-100% (S).

16. The method according to claim 7, wherein, $L_1$, $L_2$, $L_3$, $L_4$, $L_5$, $L_6$ and $L_7$ each independently represent methyl, ethyl or phenyl; and/or Hal represents iodine.

17. The method according to claim 7, wherein, the steps (1), (2), (4) and (5) are all carried out in the presence of a base and a solvent; the step (3) is carried out in the presence of an acid.

18. The method according to claim 17, which has one or more of the following features:

(1) the base is at least one selected from inorganic bases and organic bases;

(2) the solvent is at least one selected from a group consisting of DMF, DMA, methanol, ethanol, acetonitrile, dichloroethane, DMSO, dioxane, dichloromethane and ethyl acetate, (3) the acid is selected from acetic acid, hydrochloric acid and sulfuric acid.

19. The herbicidal composition according to claim 8, which further comprises a formulation auxiliary.

* * * * *